(12) United States Patent
Kinsella

(10) Patent No.: US 7,105,341 B2
(45) Date of Patent: Sep. 12, 2006

(54) IN VIVO PRODUCTION OF CYCLIC PEPTIDES

(75) Inventor: Todd M. Kinsella, Mountain View, CA (US)

(73) Assignee: Rigel Pharmaceuticals. Inc., South San Francisco, CA (US)

( * ) Notice: Subject to any disclaimer, the term of this patent is extended or adjusted under 35 U.S.C. 154(b) by 441 days.

(21) Appl. No.: 09/800,770

(22) Filed: Mar. 6, 2001

(65) Prior Publication Data

US 2005/0233456 A1   Oct. 20, 2005

Related U.S. Application Data

(60) Provisional application No. 60/187,130, filed on Mar. 6, 2000.

(51) Int. Cl.
*C12N 15/867*   (2006.01)

(52) U.S. Cl. .................. 435/320.1; 435/4; 435/5; 435/6; 435/7.1

(58) Field of Classification Search ............. 435/320.1, 435/7.1, 6, 4, 5; 536/23.1, 23.4; 530/317
See application file for complete search history.

(56) References Cited

U.S. PATENT DOCUMENTS 6,153,380 A * 11/2000 Nolan et al. ................. 435/6
6,531,316 B1 * 3/2003 Patten et al. ................ 435/455

FOREIGN PATENT DOCUMENTS

WO   WO 00/36093 A3   6/2000
WO   01/57183          8/2001

OTHER PUBLICATIONS

Evans, T.C. et al., "Protein trans-Splicing and Cyclization by a Naturally Split Intein from the dnaE Gene of *Synechocystis* Species PCC6803," *J Biol Chem* 275(13):9091-9094 (2000).
Brennand, D.M. et al. "Identification of a cyclic peptide inhibitor of platelet-derived growth factor-BB receptor-binding and mitogen-induced DNA synthesis in human fibroblasts." *FEBS Lett.* Aug. 11, 1997;413(1):70-4.
Camarero et al., "Chemical Synthesis of a Circular Protein Domain: Evidence for Folding-Assis," *Angew. Chem.* 37(3):347-349 (1998).
Camarero and Muir, "Biosynthesis of a Head-to-Tail Cyclized Protein with Improved Biological Activity," *J Am Chem Soc*; 1999; 121(23); 5597-5598.
Camarero and Muir, "Chemoselective backbone cyclization of unprotected peptides," *Chem Commun* 1997(15):1369-1370 (1997).
Eriksson, J.E. et al. "Rapid microfilament reorganization induced in isolated rat hepatocytes by microcystin-LR, a cyclic peptide toxin." *Exp Cell Res.* Nov. 1989;185(1):86-100.

(Continued)

*Primary Examiner*—T. D. Wessendorf
(74) *Attorney, Agent, or Firm*—James S. Keddie; Carol L. Francis; James J. Diehl

(57) ABSTRACT

The compositions relate to retroviral vectors encoding intein containing polypeptides which, when expressed in an eukaryotic cell, are capable of generating cyclic peptides. The retroviral vectors are used in methods for producing cyclic peptides and for identifying peptides capable of altering cellular phenotypes.

7 Claims, 52 Drawing Sheets

OTHER PUBLICATIONS

Evans, T.C. Jr, et al., "Semisynthesis of cytotoxic proteins using a modified protein splicing element." *Protein Sci.* Nov. 1998;7(11):2256-64.

Evans, T.C. Jr, et al., "The cyclization and polymerization of bacterially expressed proteins using modified self-splicing inteins." *J Biol Chem.* Jun. 25, 1999;274(26):18359-63.

Friedler, A., et al., "Backbone cyclic peptide, which mimics the nuclear localization signal of human immunodeficiency virus type 1 matrix protein, inhibits nuclear import and virus production in nondividing cells." Biochemistry, Apr. 21, 1998;37(16):5616-22.

Goldenberg, D.P. and Creighton, T.E. "Circular and circularly permuted forms of bovine pancreatic trypsin inhibitor." *J Mol Biol.* Apr. 5,1983;165(2):407-13.

Hruby, V.J., et al., "Emerging approaches in the molecular design of receptor-selective peptide ligands: conformational, topographical and dynamic considerations." *Biochem J.* Jun. 1, 1990;268(2):249-62.

Hruby, V.J. "Conformational restrictions of biologically active peptides via amino acid side chain groups." *Life Sci.* Jul. 19, 1982;31(3):189-99.

Iwai, H. and Pluckthun, A: "Circular beta-lactamase: stability enhancement by cyclizing the backbone." *FEBS Lett.* Oct. 8, 1999;459(2):166-72.

Jackson, D.Y. et al., "Enzymatic Cyclization of Linear Peptide Esters Using Subtiligase," *J Am Chem Soc* 117(2):819-820 (1995).

Jois, S.D. et al., "A Ca2+ binding cyclic peptide derived from the alpha-subunit of LFA-1: inhibitor of ICAM-1/LFA-1-mediated T-cell adhesion." *J Pept Res.* Jan. 1999;53(1):18-29.

Kimura, K., et al. "Propeptin, a new inhibitor of prolyl endopeptidase produced by Microbispora. I. Fermentation, isolation and biological properties." *J Antibiot* (Tokyo). May 1997;50(5):373-8.

Koivunen, E., et al., "Phage libraries displaying cyclic peptides with different ring sizes: ligand specificities of the RGD-directed integrins." *Biotechnology* (N Y). Mar. 1995;13(3):265-70.

Scott, C.P., et al. "Production of cyclic peptides and proteins in vivo." *Proc Natl Acad Sci USA.* Nov. 23, 1999;96(24):13638-43.

Southworth, M.W. et al., "Control of protein splicing by intein fragment reassembly." *EMBO J.* Feb. 16, 1998;17(4):918-26.

Tam, J.P. and Lu, Y.A. "A biomimetic strategy in the synthesis and fragmentation of cyclic protein." *Protein Sci.* Jul. 1998;7(7):1583-92.

Wood, D.W., et al. "A genetic system yields self-cleaving inteins for bioseparations." *Nat Biotechnol.* Sep. 1999;17(9):889-92.

Zhang, L. and Tam, J.P., "Synthesis and Application of Unprotected Cyclic Peptides as Building Blocks," *J Am Chem Soc* 119(10):2363-2370 (1997).

Evans et al., The in Vitro Ligation of Bacterially Expressed Proteins Using an Intein From Methanobacterium Thermoautotorophicum, J. of Biol. Chem., 1999, 274(7): 3923-3926.

Wu et al., Protein Trans-Splicing and Functional Mini-Inteins of a Cyanobacterial DNAB Intein, Biochimica et Biophysica Acta, 1998, 1387.

Lew et al., Protein Splicing in Vitro With a Semisynthetic Two-Component Minimal Intein, J. of Biol. Chem., 1998, 273(26), 15887-015890.

Lew et al., Characteristics of Protein Splicing in Trans Mediated by a Semisynthetic Split Intein, Biopolymers, 1999, 51(5): 355-62.

Wu et al., Protein Trans-Splicing by a Split Intein Encoded in a Split DNAE Gene of Synechocystis SP. PCC6803, Proc. Natl. Acad. Sci., 1998, 95: 9226-9231.

Southworth et al., Control of Protein Splicing by Intein Fragment Reassembly, EMBO Journal, 1998, 17(4): 918-926.

* cited by examiner

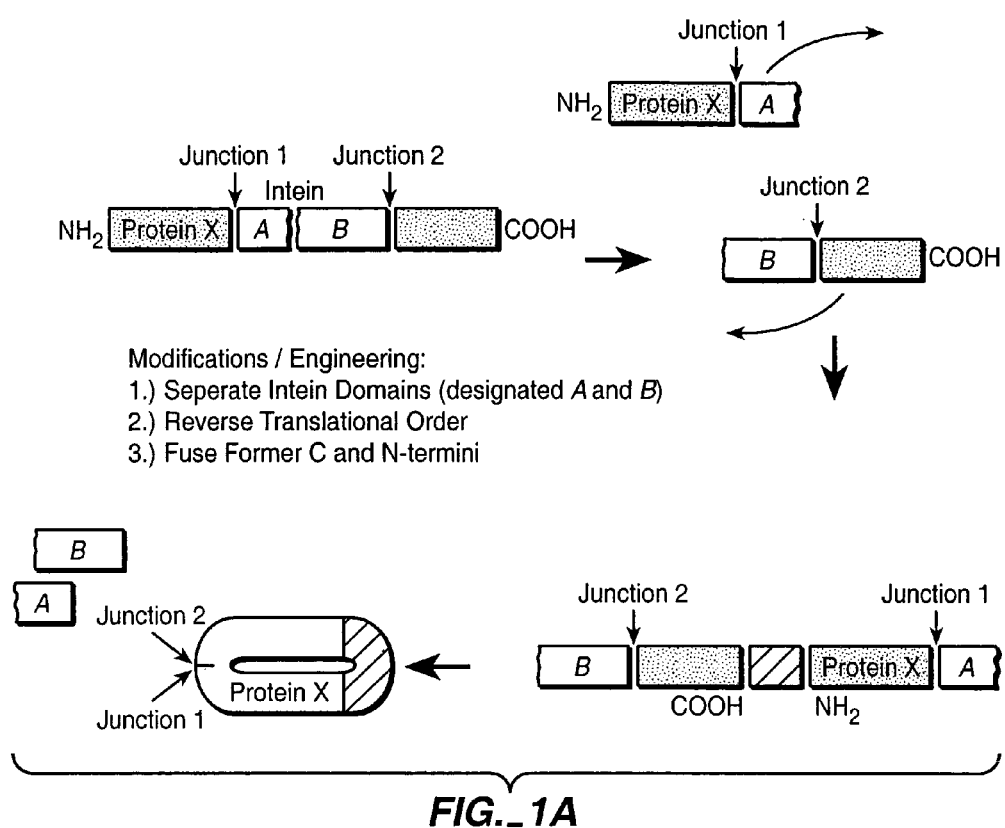
FIG._1A

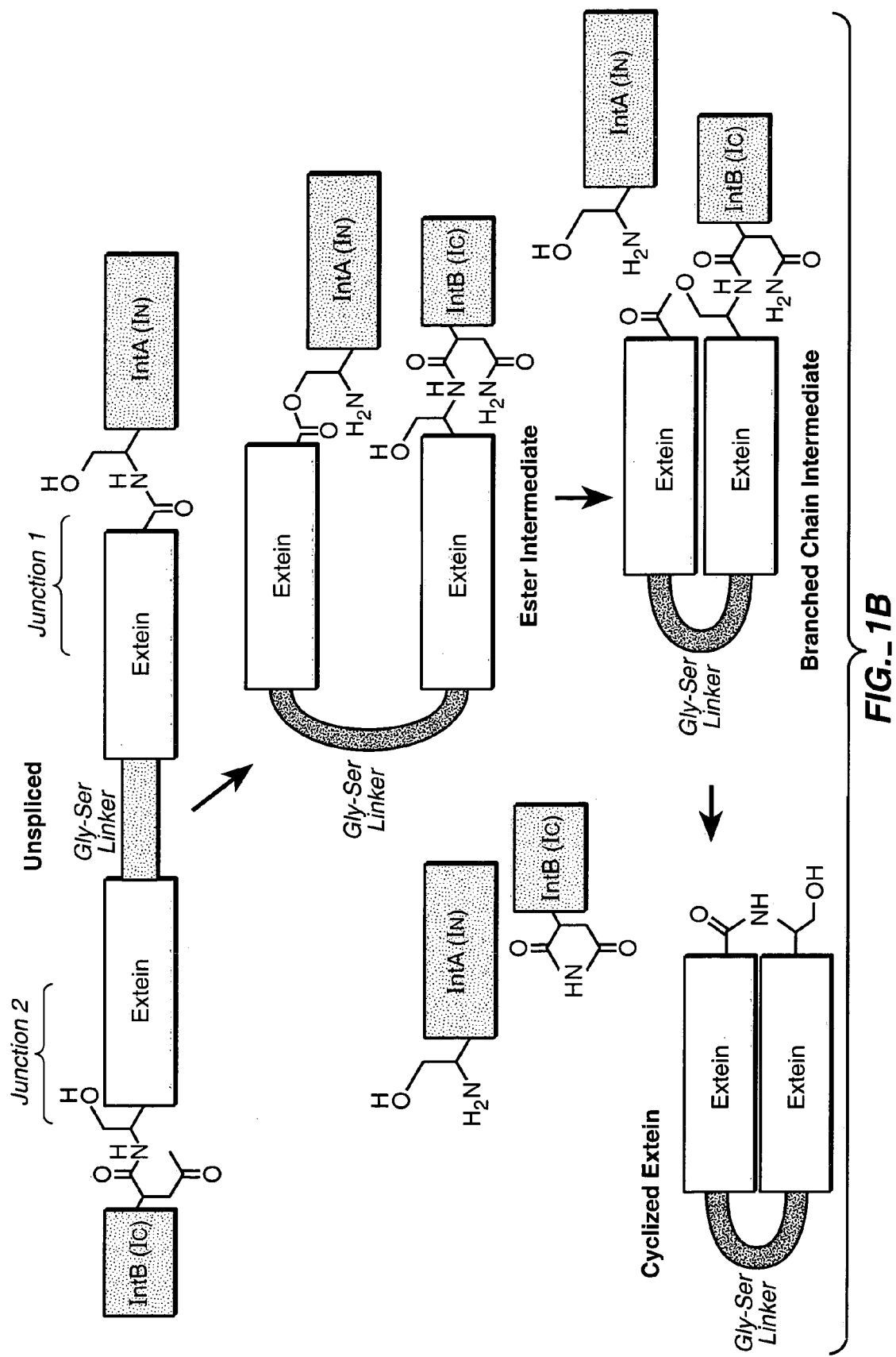
FIG._1B

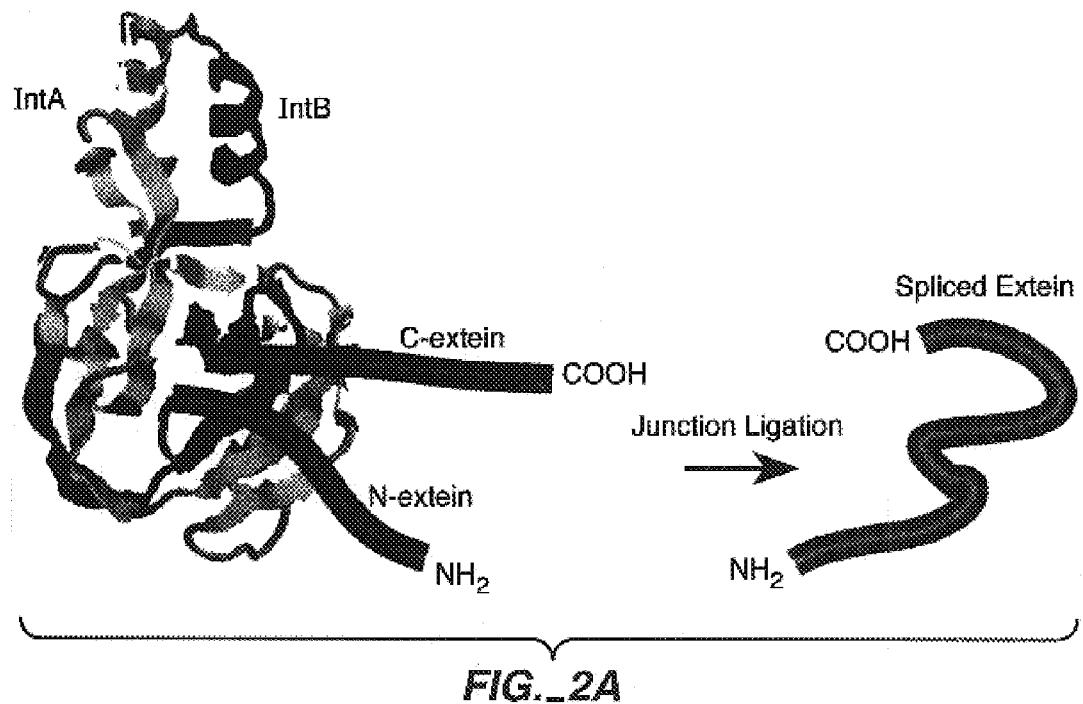
FIG._2A
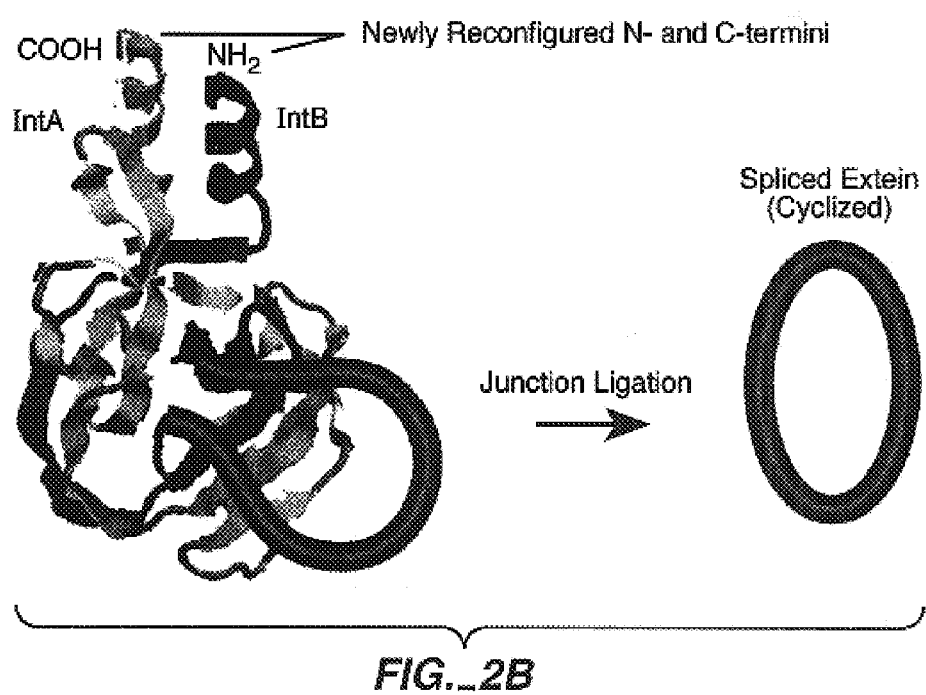
FIG._2B

GCISGDSLISLASTGKRVSIKDLLDEKDFEIWAINEQTMKLESAKVSRVFCTGKKLVYILKT
RLGRTIKATANHRFLTIDGWKRLDELSLKEHIALPRKLESSSLQLMSDEELGLLGHLIGDGC
TLPRHAIQYTSNKIELAEKVVELAKAVFGDQINPRISQERQWYQVYIPASYRLTHNKKNPIT
KWLENLDVFGLRSYEKFVPNQVFEQPQRAIAIFLRHLWSTDGCVKLIVEKSSRPVAYYATSS
EKLAKDVQSLLLKLGINARLSKISQNGKGRDNYHVTITGQADLQIFVDQIGAVDKDKQASVE
EIKTHIAQHQANTNRDVIPKQIWKTYVLPQIQIKGITTRDLQMRLGNAYCGTALYKHNLSRE
RAAKIATITQSPEIEKLSQSDIYWDSIVSITETGVEEVFDLTVPGPHNFVANDIIVHNS

FIG._3A

YCITGDALVALPEGESVRIADIVPGARPNSDNAIDLKVLDRHGNPVLADRLFHSGEHPVYTV
RTVEGLRVTGTANHPLLCLVDVAGVPTLLWKLIDEIKPGDYAVIQRSAFSVDCAGFARGKPE
FAPTTYTVGVPGLVRFLEAHHRDPDAQAIADELTDGRFYYAKVASVTDAGVQPVYSLRVDTA
DHAFITNGFVSHNT

FIG._3B

ECLTSDHTVLTTRGWIPIADVTLDDKVAVLDNNTGEMSYQNPQKVHKYDYEGPMYEVKTAGV
DLFVTPNHRMYVNTTNNTTNQNYNLVEASSIFGKKVRYKNDAIWNKTDYQFILPETATLTGH
TNKISSTPAIQPEMNAWLTFFGLWIANGHTTKIAEKTAENNQQKQRYKVILTQVKEDVCDII
EQTLNKLGFNFIRSGKDYTIENKQLWSYLNPFDNGALNKYLPDVVWELSSQQCKILLNSLCL
GNCLFTKNDDTLHYFSTSERFANDVSRLALHAGTTSTIQLEAAPSNLYDTIIGLPVEVNTTL
WRVIINQSSFYSYSTDKSSALNLSNNVACYVNAQSALTLEQNSQKINKNTLVLTKNNVKSQT
MHSQRAERVDTALLTQKELDNSLNHEILINKNPGTSQLECVVNPEVNNTSTNDRFVYYKGPV
YCLTGPNNVFYVQRNGKAVWTGNS

FIG._3C

LCVAPETMILTEDGQFPIKDLEGKIIKVWNGNEFSSVTVVKTGTEKELLEVELSNGCTLSCT
PEHKFIIVKSYTEAKKQKTDDNAIANAERVDAQDLKPRMKLIKFDLPTLFGNSEHDIKYPYT
HGFFCGDGTYTKYGKPQLSLYGDKKELLTYLDVRTMTGLEDASGRLNTWLPLDLAPKFDVPI
NSSLECRMEWLAGYLDADGCVFRNGTNESIQVSCIHLDFLKRIQLLLIGMGVTSKITKLHDE
KITTMPDGKGGQKPYSCKPIWRLFISSSGLYHLSEQGFETRRLKWEPRQPQRNAERFVEVLK
VNKTGRVDDTYCFTEPINHAGVFNGILTGQC

FIG._3D

GCFTKGTQVMMADGADKSIESIEVGDKVMGKDGMPREVVGLPRGYDDMYKVRQLSSTRRNAK
SEGLMDFTVSADHKLILKTQDVKIATRKIGGNTYGVTFYVLEKTKTGIELVKAKTKVFGH
HIHGQNGAEEKAATFAAGIDSKEYIDWIIEARDYVQVDEIVKTSTTQMINPVHFESGKLGNW
LHEHKQNKSLAPQLGYLLGTWAGIGNVKSSAFTMNSKDDVKLATRIMNYSSKLGMTCSSTES
GELNVAENEEEFFNNLGAEKDEAGDFTFDEFTDAMDELTINVHGAAASKKNNLLWNALKSLG
FRAKSTDIVKSIPQHIAVDDIVVRESLIAGLVDAAGNVETKSNGSIEAVVRTSFRHVARGLV
KIAHSLGIESSINIKDTHIDAAGVRQEFACIVNLTGAPLAGVLSKCALARNQTPVVKFTRDP
VLFNFDLIKSAKENYYGITLAEETDHQFLLSNMALVHNC

FIG._3E

```
GCLSYATNQPYFLKSDNVNFSKLTSLKVSNHYILSATLELLIPFQYNRIYPIVSLIKRELQT
GYKVVYELDFYISVIVSTVEHYVLTLNGWKRILELTVDDLVATLDIQYLIYNNTEVDLFSSN
VIFSSVINLICMNRINVYDFWIPKTNNFFVNALLVHNS
```
FIG._3F

```
GCISKFSHIMWSHVSKPLFNFSIKKSHMHNFNKNIYQLLDQGEAFISRQDKKTTYKIRTNSE
KYLELTSNHKILTLRGWQRCDQLLCNDMITTQIGFELSRKKKYLLNCIPFSLCNFETLANIN
ISNFQNVFDFAANPIPNFIANNIIVHNS
```
FIG._3G

```
GCFAKGTNVLMADGSIECIENIEVGNKVMGKDGRPREVIKLPRGRETMYSVVQKSQHRAHKS
DSSREVPELLKFTCNATHELVVRTPRSVRRLSRTIKGVEYFEVITFEMGQKKAPDGRIVELV
KEVSKSYPISEGPERANELVESYRKASNKAYFEWTIEARDLSLLGSHVRKATYQTYAPILYE
NDHFFDYMQKSKFHLTIEGPKVLAYLLGLWIGDGLSDRATFSVDSRDTSLMERVTEYAEKLN
LCAEYKDRKEPQVAKTVNLYSKVVRGNGIRNNLNTENPLWDAIVGLGFLKDGVKNIPSFLST
DNIGTRETFLAGLIDSDGYVTDEHGIKATIKTIHTSVRDGLVSLARSLGLVVSVNAEPAKVD
MNGTKHKISYAIYMSGGDVLLNVLSKCAGSKKFRPAPAAAFARECRGFYFELQELKEDDYYG
ITLSDDSDHQFLLANQVVVHNC
```
FIG._3H

```
GCFAYGTRGALADGTTEKIGKIVNQKMDVEVMSYDPDTDQVVPRKVVNWFNNGPAEQFLQFT
VEKSGGNGKSQFAATPNHLIRTPAGWTEAGDLVAGDRVMAAEPHRLSDQQFQVVLGSLMGDG
NLSPNRRDRNGVRFRMGHGAKQVDYLQWKTALLGNIKHSTHVNDKGATFVDFTPLPELAELQ
RAVYLGDGKKFLSEENFKALTPLALVFWYMDDGPFTVRSKGLQERTAGGSGRIEICVEAMSE
GNRIRLRDYLRDTHGLDVRLRLSGAAGKSVLVFSTASSAKFQELVAPYITPSMEYKLLPRFR
GQGAVTPQFVEPTQRLVPARVLDVHVKPHTRSMNRFDIEVEGNHNYFVDGVMVHNS
```
FIG._3I

```
YCLSFGTEILTVEYGPLPIGKIVSEEINCSVYSVDPEGRVYTQAIAQWHDRGEQEVLEYELE
DGSVIRATSDHRFLTTDYQLLAIEEIFARQLDLLTLENIKQTEEALDNHRLPFPLLDAGTIK
```
FIG._3J

```
KALALDTPLPTPTGWTAMGDVAVGDELLAVDEAPTRVVAATEVMLGRPCYEIEFSDGTVIVA
DAQHQWPTSYGIRTSAQLRCGLDIIAAAGSTPRHAGRLTTAAFMAPVLCIDSVRRVRSVPVR
CVEVDNAAHLYLAGRGMVPTHNS
```
FIG._3K

```
GALAYDEPIYLSDGNIINIGEFVDKFFKKYKNSIKKEDNGFGWIDIGNENIYIKSFNKLSLI
IEDKRILRVWRKKYSGKLIKITTKNRREITLTHDHPVYISKTGEVLEINAEMVKVGDYIYIP
KNNTINLDEVIKVETVDYNGHIYDLTVEDNHTYIAGKNEGFAVSNC
```
FIG._3L

GALYDFSVIQLSNGRFVLIGDLVEELFKKYAEKIKTYKDLEYIELNEEDRFEVVSVSPD1KA
NKHVVSRVWRRKVREGEKLIRIKTRTGNEIILTRNHPLFAFSNGDVVRKEAEKLKVGDRVAV
MMRPPSPPQTKAVVDPAIYVKISDYYLVPNGKGMIKVPNDGIPPEKAQYLLSVNSYPVKLVR
EVDEKLSYLAGVILGDGYISSNGYYISATFDDEAYMDAFVSVVSDFIPNYVPSIRKNGDYTI
VTVGSKIFAEMLSRIFGIPRGRKSMWDIPDVVLSNDDLMRYFIAGLFDADGYVDENGPSIVL
VTKSETVARKIWYVLQR1GIISTVSRVKSRGFKEGELFRVIISGVEDLAKFAKFIPLRHSRK
RAKLMEILRTKKPYRGRRTYRVPISSDMIAPLRQMLGLTVAELSKLASYYAGEKVSESLIRH
IEKGRVKEIRRSTLKGIALALQQIAKDVGNEEAWVRAKRLQ1IAEGDVYWDEVVSVEEVDPK
ELGIEYVYDLTVEDDHNYVANGILVSNC

FIG._3M

PCVSGDTIVMTSGGPRTVAELEGKPFTALIRGSGYPCPSGFFRTCERDVYDLRTREGHCLRL
THDHRVLVMDGGLEWRAAGELERGDRLVMDDAAGEFPALATFRGLRGAGRQDVYDATVYGAS
AFTANGFIVHNC

FIG._3N

GCIDGKAKIIFENEGEEHLTTMEEMYERYKHLGEFYDEEYNRWGIDVSNVPIYVKSFDPESK
RVVKGKVNVIWKYELGKDVTKYEIITNKGTKILTSPWHPFFVLTPDFKIVEKRADELKEGDI
LIGGMPDGEDYKFIFDYWLAGFIAGDGCFDKYHSHVKGHEYIYDRLRIYDYRIETFEIINDY
LEKTFGRKYSIQKDRNIYYIDIKARNITSHYLKLLEGIDNGIPPQILKEGKNAVLSFIAGLF
DAEGHVSNKPGIELGMVNKRLIEDVTHYLNALGIKARIREKLRKDGIDYVLHVEEYSSLLRF
YELIGKNLQNEEKREKLEKVLSNHKGGNFGLPLNFNAFKEWASEYGVEFKTNGSQTIAIIND
ERISLGQWHTRNRVSKAVLVKMLRKLYEATKDEEVKRMLHLIEGLEVVRHITTTNEPRTFYD
LTVENYQNYLAGENGMIFVHNT

FIG._3O

NSILPEEWVPLIKNGKVKIFRIGDFVDGLMKANQGKVKKTGDTEVLEVAGIHAFSFDRKSKK
ARVMAVKAVIRHRYSGNVYRIVLNSGRKITITEGHSLFVYRNGDLVEATGEDVKIGDLLAVP
RSVNLPEKRERLNIVELLLNLSPEETEDIILTIPVKGRKNFFKGMLRTLRWIFGEEKRVRTA
SRYLRHLENLGYIRLRKIGYDIIDKEGLEKYRTLYEKLVDVVRYNGNKREYLVEFNAVRDVI
SLMPEEELKEWRIGTRNGFRMGTFVDIDEDFAKLLGYYVSEGSARKWKNQTGGWSYTVRLYN
ENDEVLDDMEHLAKKFFGKVKRGKNYVEIPKKMAYIIFESLCGTLAENKRVPEVIFTSSKGV
RWAFLEGYFIGDGDVHPSKRVRLSTKSELLVNGLVLLLNSLGVSAIKLGYDSGVYRVYVNEE
LKFTEYRKKKNVYHSHIVPKDILKETFGKVFQKNISYKKFRELVENGKLDREKAKRIEWLLN
GDIVLDRVVEIKREYYDGYVYDLSVDEDENFLAGFGFLYAHNS

FIG._3P

DSVTGETEIIIKRNGKVEFVAIEELFQRVDYRIGEKEYCVLEGVEALTLDNRGRLVWKSVPY
VMRHRTNKRIYRVWFTNSWYLDVTEDHSLIGYMNTSKVKPGKPLKERLVEVKPGELGESVKS
LITPNRAIAHGIRVNPIAVKLWELIGLLVGDGNWGGQSNWAKYNVGLSLGLDKEEIEEKILK
PLKNTGIISNYYDKSKKGDVSILSKWLARFMVRYFKDESGSKRIPEFMFNLPREYIEAFLRG
LFSADGTVSLRKGVPEVRLTSVNPELSSSVRKLLWLVGVSNSMFVETNPNRYLGKESGTHSV
HVRIKDKHRFAERIGFLLDRKATKLSENLGGHTSKKRAYKYDFDLVYPKKVEEIAYDGYVYD
IEVEGTHRFFANGILVHNT

FIG._3Q

KCLLPEEKVVLPEIGLVTLRELFELANEVVVKDEEKEVRKLGKMLTGVDERGNVKLLNALYV
WRVAHKGEMIRVKVNGWYSVTVTPEHPFLTNRGWVKAGELKEGDYIAIPRRVYGNED1MKFS
KIAKELGIKGDEKEFYLAGAS1DIPIKVLFLAPSKLVSAFLRGYFDAKGVVRENYIEVPLFE
DLPLL1LRFGIVSRIEKSTLKISGKRNLELFRKHVGFTDSEKAKALDELISKAKESERYPI1
EELRRLGLLFGFTRNELRIEENPTYEV1MEILERIERGSPNLAEKIAVLEGRIKEENYLRIL
EEEGLIENGKLTELGKELLEVWRNREFDSKDVDYVRNIVENLVFLPVEKVERIEYEGYVYDV
TTETHNFVANGILVHNT

FIG._3R

QCFSGEEVIIVEKGKDRKVVKLREFVEDALKEPSGEGMDGDIKVTYKDLRGEDVRILTKDGF
VKLLYVNKREGKQKLRKIVNLDKDYWLAVTPDHKVFTSEGLKEAGEITEKDEIIRVPLVILD
GPKIASTYGEDGKFDDYIRWKKYYEKTGNGYKRAAKELNIKESTLRWWTQGAKPNSLKMIEE
LEKLNLLPLTSEDSRLEKVAIILGALFSDGNIDRNFNTLSFISSERKAIERFVETLKELFGE
FNYEIRDNHESLGKSILFRTWDRRIIRFFVALGAPVGNKTKVKLELPWWIKLKPSLFLAFMD
GLYSGDGSVPRFARYEEGIKFNGTFEIAQLTDDVEKKLPFFEEIAWYLSFFGIKAKVRVDKT
GDKYKVRLIFSQSIDNVLNFLEFIPISLSPAKREKFLREVESYLAAVPESSLAGRIEELREH
FNRIKKGERRSFIETWEVVNVTYNVTTETGNLLANGLFVKNS

FIG._3S

LCLTPDTYVVLGDGRIETIEDIVNAKERNVLSLDLDNLSIKIDTAIKFWKLRYNGNLSKITL
SNNYELKATPDHCLLVLRDNQLKWIPAKDIKENDYIAMPFNYKVERKPISLLNLLKYLDITD
VLIEFDENSTIFEKIAEYIRNNIKTSTKYKYLRNRRVPLKYLIEWNFDLDEIEKEAKYIYKS
VAGTKKIPLFKLDERFWYFAGLVLGDGSIQDSKIRIAQTPLKDVKSILDETFPFLHNWISGN
QVIISNPIIAEILEKLGMRNGKLNGIIFSLPESYINALIAGYFDTDGCFSLLYDKKAKKHNL
RMVLTSKRRDVLEKIGIYLNSIGILNTLHKSREVYSLIISNKSLETFKEKIAKYLKIRKEAF
INGYKTYKKEHEERFECDLLPVKEVFKKLTFEKGRKEILKDSKIHIENWYKEKTNNIPREKL
KTVLRYANNSEHKEFLEKIVNGDISFVRVKKVENIPYDGYVYDLSIKHNQNFISNGVISHNC

FIG._3T

KCLTGDTKVIANGQLFELRELVEKISGGKFGPTPVKGLKVIGIDEDGKLREFEVQYVYKDKT
ERLIRIRTRLGRELKVTPYHPLLVNRRNGEIKWVKAEELKPGDKLAVPRFLPIVTGEDPLAE
WLGYFLGGGYADSKENLIMFTNEDPLLRQRFMELTEKLFSDARIREITHENGTSKVYVNSKK
ALKLVNSLGNAHIPKECWRGIRSFLRAYFDCNGGVKGNAIVLATASKEMSQEIAYALAGFGI
ISRIQEYRVIISGSDNVKKFLNEIGFINRNKLEKALKLVKKDDPGHDGLEINYELISYVKDR
LRLSFFNDKRSWSYREAKEISWELMKEIYYRLDELEKLKESLSRGILIDWNEVAKRIEEVAE
ETGIRADELLEYIEGKRKLSFKDYIKIAKVLGIDVEHTIEAMRVFARKYSSYAEIGRRLGTW
NSSVKTILESNAVNVEILERIRKIELELIEEILSDEKLKEGIAYLIFLSQNELYWDEITKVE
ELRGEFIIYDLHVPGYHNFIAGNMPTVVHNT

FIG._3U

SCVTGDTKVYTPDEREVKIRDFMNYFENGLIKEVSNRIGRDTVIAAVSFNSRIVGHPVYRLT
LESGRIIEATGDHMFLTPEGWKQTYDIKEGSEVLVKPTLEGTPYEPDPRVIIDIKEFYNFLE
KIEREHNLKPLKEAKTFRELITKDKEKILRRALELRAEIENGLTKREAEILELISADTWIPR
AELEKKARISRTRLNQILQRLEKKGYIERRIEGRKQFVRKIRNGKILRNAMDIKRILEEEFG
IKISYTTVKKLLSGNVDGMAYRILKEVKEKWLVRYDDEKAGILARVVGFILGDGHLARNGRI
WFNSSKEELEMLANDLRKLGLKPSEIIERDSSSEIQGRKVKGRIYMLYVDNAAFHALLRFWK
VEVGNKTKKGYTVPEWIKKGNLFVKREFLRGLFGADGTKPCGKRYNFNGIKLEIRAKKESLE
RTVEFLNDVADLLREFDVDSKITVSPTKEGFIIRLIVTPNDANYLNFLTRVGYAYAKDTYAR
LVGEYIRIKLAYKNIILPGIAEKAIELATVTNSTYAAKVLGVSRDFVVNRLKGTQIGITRDF
MTFEEFMKERVLNGYVIEKVIKKEKLGYLDVYDVTCARDHSFISNGLVSHNC

FIG._3V

NCLTSNSKILTDDGYYIKLEKLKEKLDLHIKIYNTEEGEKSSNILFVSERYADEKIIRIKTE
SGRVLEGSKDHPVLTLNGYVPMGMLKEGDDVIVYPYEGVEYEEPSDEIILDEDDFAEYDKQI
IKYLKDRGLLPLRMDNKNIGIIARLLGFAFGDGSIVKENGDRERLYVAFYGKRETLIKIRED
LEKLGIKASRIYSRKREVEIRNAYGDEYTSLCEDNSIKITSKAFALFMHKLGMPIGKKTEQI
YKIPEWIKKAPKWVKRNFLAGLFGADGSRAVFKNYTPLPINLTMSKSEELKENILEFLNEIK
LLLAEFDIESMIYEIKSLDGRVSYRLAIVGEESIKNFLGRINYEYSGEKKVIGLLAYEYLRR
KDIAKEIRKKCIKRAKELYKKGVTVSEMLKMDEFRNEFISKRLIERAVYENLDEDDVRISTK
FPKFEEFIEKYGVIGGFVIDKIKEIEEISYDSKLYDVGIVSKEHNFIANSIVVHNC

FIG._3W

KCVDGDTLVLTKEFGLIKIKELYEKLDGKGRKIVEGNEEWTELEKPITVYGYKDGKIVEIKA
THVYKGVSSGMVEIRTRTGRKIKVTPIHRLFTGRVTKDGLILKEVMAMHVKPGDRIAVVKKI
DGGEYIKLDSSNVGEIKVPEILNEELAEFLGYLMANGTLKSGIIEIYCDDESLLERVNSLSL
KLFGVGGRIVQKVDGKALVIQSKPLVDVLRRLGVPEDKKVENWKVPRELLLSPSNVVRAFVN
AYIKGKEEVEITLASEEGAYELSYLFAKLGIYVTISKSGEYYKVRVSRRGNLDTIPVEVNGM
PKVLPYEDFRKFAKSIGLEEVAENHLQHIIFDEVIDVRYIPEPQEVYDVTTETHNFVGGNMP
TLLHNT

FIG._3X

*Intein B*
MESG|SPEIEKLSQSDIYWDSIVSITETGVEEVFDLTVPGPHNFVAND|
*Cyclic Insert (With Flag Epitope)*
IIVHN|S|IEQGQGGGMSMDYKDDDDKMRMLEGQAGGLITS|G|CIS
GDSLISLASTGKRVSIKDLLDEKDFEIWAINEQTMKLESKVSRVFCT
*Intein A*
GKKLVYILKTRLGRTIKATANHRFLTIDGWKRLDELSLKEHIALPRK
|LESSSLQL|SIHGYH
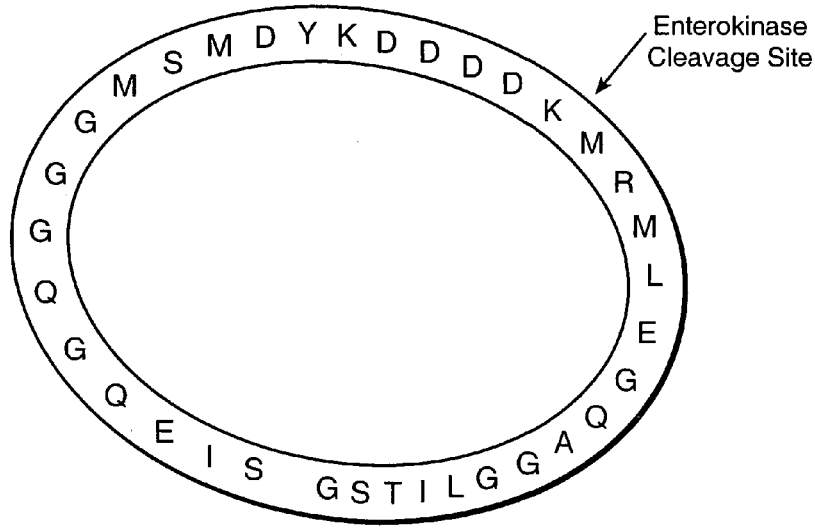
FIG._4A

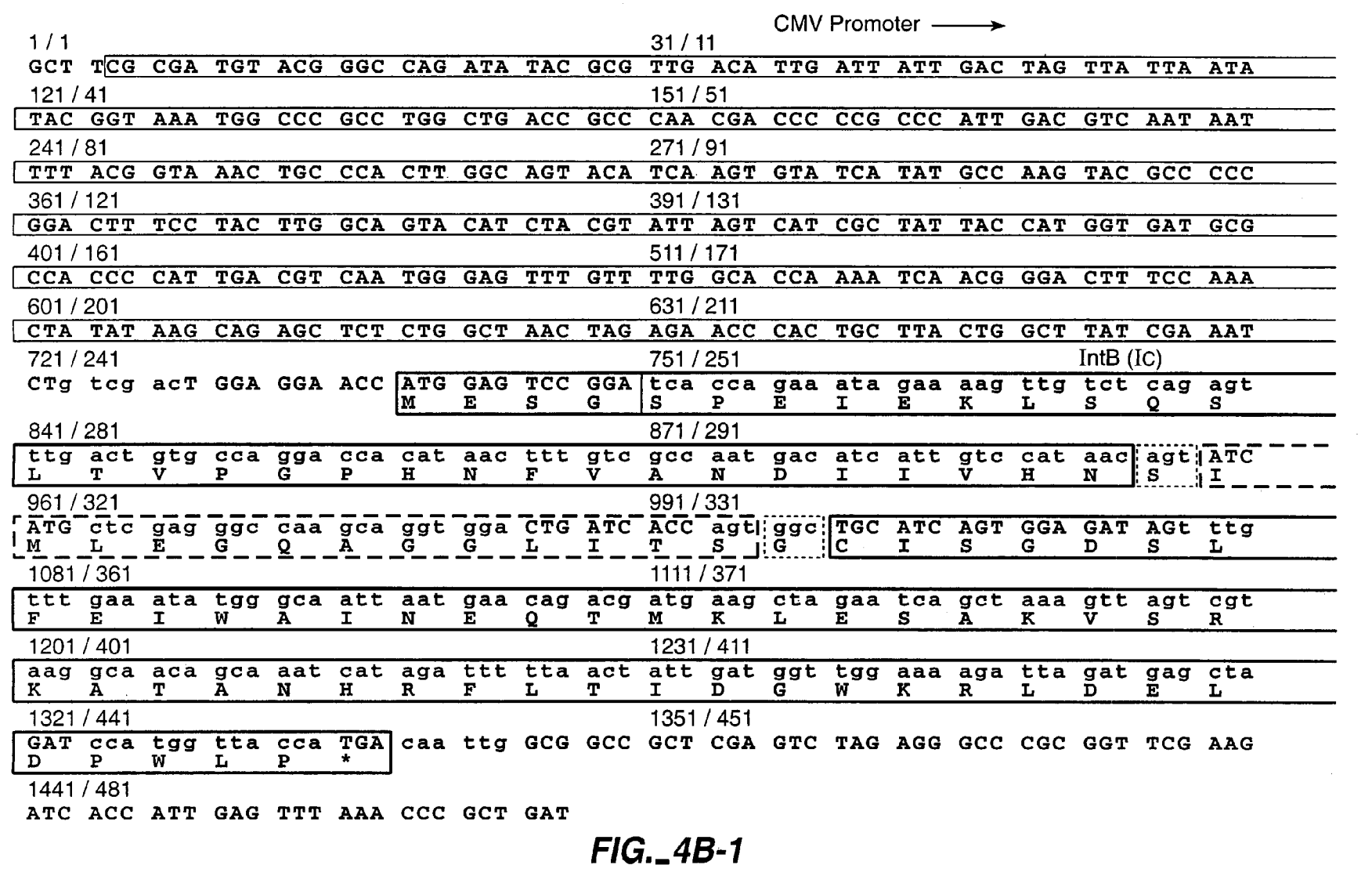

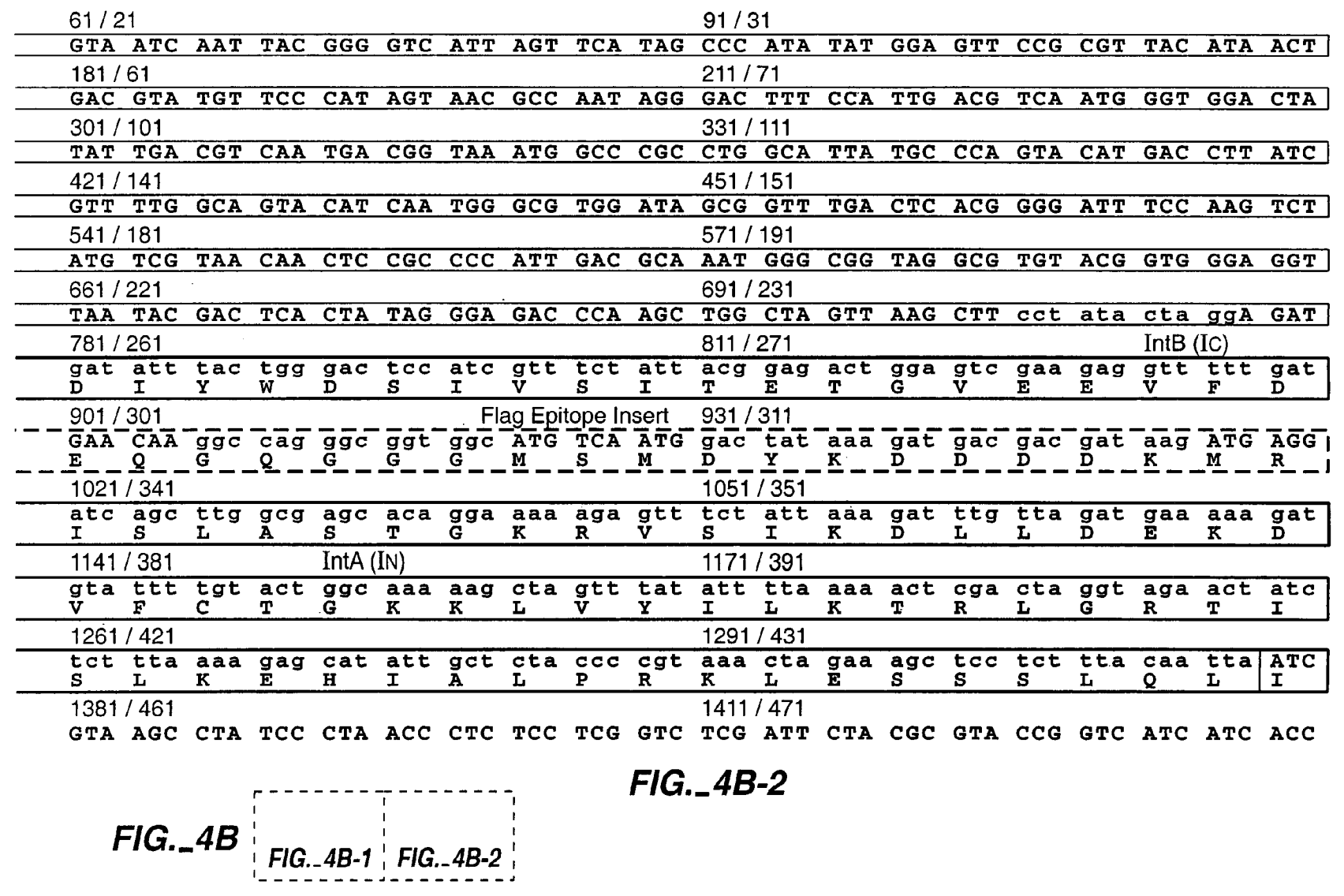

```
ATGGAGTCCGGATCACCAGAAATAGAAAAGTTGTCTCAGAGTGATATTTACTGGGACTCCAT
CGTTTCTATTACGGAGACTGGAGTCGAAGAGGTTTTTGATTTGACTGTGCCAGGGCCCCATA
ACTTTGTGGCCAATGACATCATTGTCCATAACAGTGAGGAGGACCTGGGATCCAGCGTGCAG
CTCGCCGACCACTACCAGCAGAACACCCCCATCGGCGACGGCCCCGTGCTGCTGCCCGACAA
CCACTACCTGAGCACCCAGTCCGCCCTGAGCAAAGACCCCAACGAGAAGCGCGATCACATGG
TCCTGCTGGAGTTCGTGACCGCCGCCGGGATCACTCTCGGCATGGACGAGCTGTACAAGGGG
TCGAACGGGGAATTCTCGCAGGTAGACAAGTCGATGGTGAGCAAGGGCGAGGAGCTGTTCAC
CGGGGTGGTGCCCATCCTGGTCGAGCTGGACGGCGACGTAAACGGCCACAAGTTCAGCGTGT
CCGGCGAGGGCGAGGGCGATGCCACCTACGGCAAGCTGACCCTGAAGTTCATCTGCACCACC
GGCAAGCTGCCCGTGCCCTGGCCCACCCTCGTGACCACCCTGACCTACGGCGTGCAGTGCTT
CAGCCGCTACCCCGACCACATGAAGCAGCACGACTTCTTCAAGTCCGCCATGCCCGAAGGCT
ACGTCCAGGAGCGCACCATCTTCTTCAAGGACGACGGCAACTACAAGACCCGCGCCGAGGTG
AAGTTCGAGGGCGACACCCTGGTGAACCGCATCGAGCTGAAGGGCATCGACTTCAAGGAGGA
CGGCAACATCCTGGGGCACAAGCTGGAGTACAACTACAACAGCCACAACGTCTATATCATGG
CCGACAAGCAGAAGAACGGCATCAAGGTGAACTTCAAGATCCGCCACAACATCGAGGACCTC
GAGCAAAAGCTGATATGCATCTCCGGAaATAGTTTGATCAGCTTGGCGAGCACAGGAAAAAG
AGTTTCTATTAAAGATTTGTTAGATGAAAAGATTTTGAAATATGGGCAATTAATGAACAGA
CGATGAAGCTAGAATCAGCTAAAGTTAGTCGTGTATTTTGTACTGGCAAAAAGCTAGTTTAT
ATTTTAAAAACTCGACTAGGTAGAACTATCAAGGCAACAGCAAATCATAGATTTTTAACTAT
TGATGGTTGGAAAGATTAGATGAGCTATCTTTAAAAGAGCATATTGCTCTACCCCGTAAAC
TAGAAAGCTCCTCTTTACAATTAGGCCTCCGCGGCCAGTACCCCTACGACGTCCCGGACTAC
GCTATCGATTAA
```

FIG._5A

```
MESGSPEIEKLSQSDIYWDSIVSITETGVEEVFDLTVPGPHNFVANDIIVHNSEEDLGSSVQ
LADHYQQNTPIGDGPVLLPDNHYLSTQSALSKDPNEKRDHMVLLEFVTAAGITLGMDELYKG
SNGEFSQVDKSMVSKGEELFTGVVPILVELDGDVNGHKFSVSGEGEGDATYGKLTLKFICTT
GKLPVPWPTLVTTLTYGVQCFSRYPDHMKQHDFFKSAMPEGYVQERTIFFKDDGNYKTRAEV
KFEGDTLVNRIELKGIDFKEDGNILGHKLEYNYNSHNVYIMADKQKNGIKVNFKIRHNIEDL
EQKLICISGNSLISLASTGKRVSIKDLLDEKDFEIWAINEQTMKLESAKVSRVFCTGKKLVY
ILKTRLGRTIKATANHRFLTIDGWKRLDELSLKEHIALPRKLESSSLQLGLRGQYPYDVPDY
AIDZ
```

FIG._5B

```
ATGGAGTCCGGATCACCAGAAATAGAAAAGTTGTCTCAGAGTGATATTTACTGGGACTCCAT
CGTTTCTATTACGGAGACTGGAGTCGAAGAGGTTTTTGATTTGACTGTGCCAGGGCCCCATA
ACTTTGTGGCCAATGACATCATTGTCCATAACAGTGAGGAGGACCTGGGATCCAGCGTGCAG
CTCGCCGACCACTACCAGCAGAACACCCCCATCGGCGACGGCCCCGTGCTGCTGCCCGACAA
CCACTACCTGAGCACCCAGTCCGCCCTGAGCAAAGACCCCAACGAGAAGCGCGATCACATGG
TCCTGCTGGAGTTCGTGACCGCCGCCGGGATCACTCTCGGCATGGACGAGCTGTACAAGGGG
TCGAACGGGGAATTCTCGCAGGTAGACAAGTCGATGGTGAGCAAGGGCGAGGAGCTGTTCAC
CGGGGTGGTGCCCATCCTGGTCGAGCTGGACGGCGACGTAAACGGCCACAAGTTCAGCGTGT
CCGGCGAGGGCGAGGGCGATGCCACCTACGGCAAGCTGACCCTGAAGTTCATCTGCACCACC
GGCAAGCTGCCCGTGCCCTGGCCCACCCTCGTGACCACCCTGACCTACGGCGTGCAGTGCTT
CAGCCGCTACCCCGACCACATGAAGCAGCACGACTTCTTCAAGTCCGCCATGCCCGAAGGCT
ACGTCCAGGAGCGCACCATCTTCTTCAAGGACGACGGCAACTACAAGACCCGCGCCGAGGTG
AAGTTCGAGGGCGACACCCTGGTGAACCGCATCGAGCTGAAGGGCATCGACTTCAAGGAGGA
TGGAGTCCGGATCACCAGAAATAGAAAAGTTGTCTCAGAGTGATATTTACTGGGACTCCATC
GTTTCTATTACGGAGACTGGAGTCGAAGAGGTTTTTGATTTGACTGTGCCAGGGCCCCATAA
CTTTGTGGCCAATGACATCATTGTCCATAACAGTGAGGAGGACCTGGGATCCAGCGTGCAGC
TCGCCGACCACTACCAGCAGAACACCCCCATCGGCGACGGCCCCGTGCTGCTGCCCGACAAC
CACTACCTGAGCACCCAGTCCGCCCTGAGCAAAGACCCCAACGAGAAGCGCGATCACATGGT
CCTGCTGGAGTTCGTGACCGCCGCCGGGATCACTCTCGGCATGGACGAGCTGTACAAGGGGT
CGAACGGGGAATTCTCGCAGGTAGACAAGTCGATGGTGAGCAAGGGCGAGGAGCTGTTCACC
GGGGTGGTGCCCATCCTGGTCGAGCTGGACGGCGACGTAAACGGCCACAAGTTCAGCGTGTC
CGGCGAGGGCGAGGGCGATGCCACCTACGGCAAGCTGACCCTGAAGTTCATCTGCACCACCG
GCAAGCTGCCCGTGCCCTGGCCCACCCTCGTGACCACCCTGACCTACGGCGTGCAGTGCTTC
AGCCGCTACCCCGACCACATGAAGCAGCACGACTTCTTCAAGTCCGCCATGCCCGAAGGCTA
CGTCCAGGAGCGCACCATCTTCTTCAAGGACGACGGCAACTACAAGACCCGCGCCGAGGTGA
AGTTCGAGGGCGACACCCTGGTGAACCGCATCGAGCTGAAGGGCATCGACTTCAAGGAGGAC
GGCAACATCCTGGGGCACAAGCTGGAGTACAACTACAACAGCCACAACGTCTATATCATGGC
CGACAAGCAGAAGAACGGCATCAAGGTGAACTTCAAGATCCGCCACAACATCGAGGACCTCG
AGCAAAAGCTGATATGCATCTCCGGAAATAGTTTGATCAGCTTGGCGAGCACAGGAAAAAGA
GTTTCTATTAAAGATTTGTTAGATGAAAAAGATTTTGAAATATGGGCAATTAATGAACAGAC
GATGAAGCTAGAATCAGCTAAAGTTAGTCGTGTATTTTGTACTGGCAAAAAGCTAGTTTATA
TTTTAAAAACTCGACTAGGTAGAACTATCAAGGCAACAGCAAATCATAaATTTTTAACTATT
GATGGTTGGAAAAGATTAGATGAGCTATCTTTAAAAGAGCATATTGCTCTACCCCGTAAACT
AGAAAGCTCCTCTTTACAATTAGGCCTCCGCGGCCAGTACCCCTACGACGTCCCGGACTACG
CTATCGATTAA
```

*FIG._5C*

```
MESGSPEIEKLSQSDIYWDSIVSITETGVEEVFDLTVPGPHNFVANDIIVHNSEEDLGSSVQ
LADHYQQNTPIGDGPVLLPDNHYLSTQSALSKDPNEKRDHMVLLEFVTAAGITLGMDELYKG
SNGEFSQVDKSMVSKGEELFTGVVPILVELDGDVNGHKFSVSGEGEGDATYGKLTLKFICTT
GKLPVPWPTLVTTLTYGVQCFSRYPDHMKQHDFFKSAMPEGYVQERTIFFKDDGNYKTRAEV
KFEGDTLVNRIELKGIDFKEDGNILGHKLEYNYNSHNVYIMADKQKNGIKVNFKIRHNIEDL
EQKLICISGNSLISLASTGKRVSIKDLLDEKDFEIWAINEQTMKLESAKVSRVFCTGKKLVY
ILKTRLGRTIKATANHKFLTIDGWKRLDELSLKEHIALPRKLESSSLQLGLRGQYPYDVPDY
AIDZ
```

*FIG._5D*

```
ATGGAGTCCGGATCACCAGAAATAGAAAAGTTGTCTCAGAGTGATATTTACTGGGACTCCAT
CGTTTCTATTACGGAGACTGGAGTCGAAGAGGTTTTTGATTTGACTGTGCCAGGGCCCCATA
ACTTTGTGGCCAATGACATCATTGTCCATAACAGTGAGGAGGACCTGGGATCCAGCGTGCAG
CTCGCCGACCACTACCAGCAGAACACCCCCATCGGCGACGGCCCCGTGCTGCTGCCCGACAA
CCACTACCTGAGCACCCAGTCCGCCCTGAGCAAAGACCCCAACGAGAAGCGCGATCACATGG
TCCTGCTGGAGTTCGTGACCGCCGCCGGGATCACTCTCGGCATGGACGAGCTGTACAAGGGG
TCGAACGGGGAATTCTCGCAGGTAGACAAGTCGATGGTGAGCAAGGGCGAGGAGCTGTTCAC
CGGGGTGGTGCCCATCCTGGTCGAGCTGGACGGCGACGTAAACGGCCACAAGTTCAGCGTGT
CCGGCGAGGGCGAGGGCGATGCCACCTACGGCAAGCTGACCCTGAAGTTCATCTGCACCACC
GGCAAGCTGCCCGTGCCCTGGCCCACCCTCGTGACCACCCTGACCTACGGCGTGCAGTGCTT
CAGCCGCTACCCCGACCACATGAAGCAGCACGACTTCTTCAAGTCCGCCATGCCCGAAGGCT
ACGTCCAGGAGCGCACCATCTTCTTCAAGGACGACGGCAACTACAAGACCCGCGCCGAGGTG
AAGTTCGAGGGCGACACCCTGGTGAACCGCATCGAGCTGAAGGGCATCGACTTCAAGGAGGA
CGGCAACATCCTGGGGCACAAGCTGGAGTACAACTACAACAGCCACAACGTCTATATCATGG
CCGACAAGCAGAAGAACGGCATCAAGGTGAACTTCAAGATCCGCCACAACATCGAGGACCTC
GAGCAAAAGCTGATATGCATCTCCGGAaATAGTTTGATCAGCTTGGCGAGCACAGGAAAAAG
AGTTTCTATTAAAGATTTGTTAGATGAAAAAGATTTTGAAATATGGGCAgTTAATGAACAGA
CGATGAAGCTAGAATCAGCTAAAGTTAGTCGTGTATTTGTACTGGCAAAAAGCTAGTTTAT
ATTTTAAAAACTCGACTAGGTAGAACTATCAAGGCAACAGCAAATCATAGATTTTTAACTAT
TGATGGTTGGAAAAGATTAGATGAGCTATCTTTAAAAGAGCATATTGCTCTACCCCGTAAAC
TAGAAAGCTCCTCTTTACAATTAGGCCTCCGCGGCCAGTACCCCTACGACGTCCCGGACTAC
GCTATCGATTAA
```

FIG._5E

```
MESGSPEIEKLSQSDIYWDSIVSITETGVEEVFDLTVPGPHNFVANDIIVHNSEEDLGSSVQ
LADHYQQNTPIGDGPVLLPDNHYLSTQSALSKDPNEKRDHMVLLEFVTAAGITLGMDELYKG
SNGEFSQVDKSMVSKGEELFTGVVPILVELDGDVNGHKFSVSGEGEGDATYGKLTLKFICTT
GKLPVPWPTLVTTLTYGVQCFSRYPDHMKQHDFFKSAMPEGYVQERTIFFKDDGNYKTRAEV
KFEGDTLVNRIELKGIDFKEDGNILGHKLEYNYNSHNVYIMADKQKNGIKVNFKIRHNIEDL
EQKLICISGNSLISLASTGKRVSIKDLLDEKDFEIWAVNEQTMKLESAKVSRVFCTGKKLVY
ILKTRLGRTIKATANHRFLTIDGWKRLDELSLKEHIALPRKLESSSLQLGLRGQYPYDVPDY
AIDZ
```

FIG._5F

```
ATGGAGTCCGGATCACCAGAAATAGAAAAGTTGTCTCAGAGTGATATTTACTGGGACTCCAT
CGTTTCTATTACGGAGACTGGAGTCGAAGAGGTTTTTGATTTGgCcGTGCCAGGGCCCCATA
ACTTTGTGGCCAATGACATCATTGTCCATAACAGTGAGGAGGACCTGGGATCCAGCGTGCAG
CTCGCCGACCACTACCAGCAGAACACCCCCATCGGCGACGGCCCCGTGCTGCTGCCCGACAA
CCACTACCTGAGCACCCAGTCCGCCCTGAGCAAAGACCCCAACGAGAAGCGCGATCACATGG
TCCTGCTGGAGTTCGTGACCGCCGCCGGGATCACTCTCGGCATGGACGAGCTGTACAAGGGG
TCGAACGGGGAATTCTCGCAGGTAGACAAGTCGATGGTGAGCAAGGGCGAGGAGCTGTTCAC
CGGGGTGGTGCCCATCCTGGTCGAGCTGGACGGCGACGTAAACGGCCACAAGTTCAGCGTGT
CCGGCGAGGGCGAGGGCGATGCCACCTACGGCAAGCTGACCCTGAAGTTCATCTGCACCACC
GGCAAGCTGCCCGTGCCCTGGCCCACCCTCGTGACCACCCTGACCTACGGCGTGCAGTGCTT
CAGCCGCTACCCCGACCACATGAAGCAGCACGACTTCTTCAAGTCCGCCATGCCCGAAGGCT
ACGTCCAGGAGCGCACCATCTTCTTCAAGGACGACGGCAACTACAAGACCCGCGCCGAGGTG
AAGTTCGAGGGCGACACCCTGGTGAACCGCATCGAGCTGAAGGGCATCGACTTCAAGGAGGA
CGGCAACATCCTGGGGCACAAGCTGGAGTACAACTACAACAGCCACAACGTCTATATCATGG
CCGACAAGCAGAAGAACGGCATCAAGGTGAACTTCAAGATCCGCCACAACATCGAGGACCTC
GAGCAAAAGCTGATATGCATCTCCGGAAATAGTTTGATCAGCTTGGCGAGCACAGGAAAAAG
AGTTTCTATTAAAGATTTGTTAGATGAAAAAGATTTTGAAATATGGGCAATTAATGAACAGA
CGATGAAGCTAGAATCAGCTAAAGTTAGTCGTGTATTTGTACTGGCAAAAAGCTAGTTTAT
ATTTTAAAAACTCGACTAGGTAGAACTATCAAGGCAACAGCAAATCATAGATTTTTAACTAT
TGATGGTTGGAAAAGATTAGATGAGCTATCTTTAAAAGAGCATATTGCTCTACCCCGTAAAC
TAGAAAGCTCCTCTTTACAATTAGGCCTCCGCGGCCAGTACCCCTACGACGTCCCGGACTAC
GCTATCGATTAA
```

FIG._5G

```
MESGSPEIEKLSQSDIYWDSIVSITETGVEEVFDLAVPGPHNFVANDIIVHNSEEDLGSSVQ
LADHYQQNTPIGDPVLLPDNHYLSTQSALSKDPNEKRDHMVLLEFVTAAGITLGMDELYKG
SNGEFSQVDKSMVSKGEELFTGVVPILVELDGDVNGHKFSVSGEGEGDATYGKLTLKFICTT
GKLPVPWPTLVTTLTYGVQCFSRYPDHMKQHDFFKSAMPEGYVQERTIFFKDDGNYKTRAEV
KFEGDTLVNRIELKGIDFKEDGNILGHKLEYNYNSHNVYIMADKQKNGIKVNFKIRHNIEDL
EQKLICISGNSLISLASTGKRVSIKDLLDEKDFEIWAINEQTMKLESAKVSRVFCTGKKLVY
ILKTRLGRTIKATANHRFLTIDGWKRLDELSLKEHIALPRKLESSSLQLGLRGQYPYDVPDY
AIDZ
```

FIG._5H

```
ATGGAGTCCGGATCACCAGAAATAGAAAAGTTGTCTCAGAGTGATATTTACTGGGACTCCAT
CGTTcCTATTACGGAGACTGGAGTCGAAGAGGTTTTTGATTTGACTGTGCCAGGGCCCCATA
ACTTTGTGGCCAATGACATCATTGTCCATAACAGTGAGGAGGACCTGGGATCCAGCGTGCAG
CTCGCCGACCACTACCAGCAGAACACCCCCATCGGCGACGGCCCCGTGCTGCTGCCCGACAA
CCACTACCTGAGCACCCAGTCCGCCCTGAGCAAAGACCCCAACGAGAAGCGCGATCACATGG
TCCTGCTGGAGTTCGTGACCGCCGCCGGGATCACTCTCGGCATGGACGAGCTGTACAAGGGG
TCGAACGGGGAATTCTCGCAGGTAGACAAGTCGATGGTGAGCAAGGGCGAGGAGCTGTTCAC
CGGGGTGGTGCCCATCCTGGTCGAGCTGGACGGCGACGTAAACGGCCACAAGTTCAGCGTGT
CCGGCGAGGGCGAGGGCGATGCCACCTACGGCAAGCTGACCCTGAAGTTCATCTGCACCACC
GGCAAGCTGCCCGTGCCCTGGCCCACCCTCGTGACCACCCTGACCTACGGCGTGCAGTGCTT
CAGCCGCTACCCCGACCACATGAAGCAGCACGACTTCTTCAAGTCCGCCATGCCCGAAGGCT
ACGTCCAGGAGCGCACCATCTTCTTCAAGGACGACGGCAACTACAAGACCCGCGCCGAGGTG
AAGTTCGAGGGCGACACCCTGGTGAACCGCATCGAGCTGAAGGGCATCGACTTCAAGGAGGA
CGGCAACATCCTGGGGCACAAGCTGGAGTACAACTACAACAGCCACAACGTCTATATCATGG
CCGACAAGCAGAAGAACGGCATCAAGGTGAACTTCAAGATCCGCCACAACATCGAGGACCTC
GAGCAAAAGCTGATATGCATCTCCGGAaATAGTTTGATCAGCTTGGCGAGCACAGGAAAAAG
AGTTTCTATTAAAGATTTGTTAGATGAAAAGATTTTGAAATATGGGCAATTAATGAACAGA
CGATGAAGCTAGAATCAGCTAAAGTTAGTCGTGTATTTGTACTGGCAAAAAGCTAGTTTAT
ATTTTAAAAACTCGACTAGGTAGAACTATCAAGGCAACAGCAAATCATAGATTTTTAACTAT
TGATGGTTGGAAAAGATTAGATGAGCTATCTTTAAAAGAGCATATTGCTCTACCCCGTAAAC
TAGAAAGCTCCTCTTTACAATTAGGCCTCCGCGGCCAGTACCCCTACGACGTCCCGGACTAC
GCTATCGATTAA
```

FIG._5I

```
MESGSPEIEKLSQSDIYWDSIVPITETGVEEVFDLTVPGPHNFVANDIIVHNSEEDLGSSVQ
LADHYQQNTPIGDGPVLLPDNHYLSTQSALSKDPNEKRDHMVLLEFVTAAGITLGMDELYKG
SNGEFSQVDKSMVSKGEELFTGVVPILVELDGDVNGHKFSVSGEGEGDATYGKLTLKFICTT
GKLPVPWPTLVTTLTYGVQCFSRYPDHMKQHDFFKSAMPEGYVQERTIFFKDDGNYKTRAEV
KFEGDTLVNRIELKGIDFKEDGNILGHKLEYNYNSHNVYIMADKQKNGIKVNFKIRHNIEDL
EQKLICISGNSLISLASTGKRVSIKDLLDEKDFEIWAINEQTMKLESAKVSRVFCTGKKLVY
ILKTRLGRTIKATANHRFLTIDGWKRLDELSLKEHIALPRKLESSSLQLGLRGQYPYDVPDY
AIDZ
```

FIG._5J

ATGGAGTCCGGATCACCAGAAATAGAAAAGTTGTCTCAGAGTGATATTTACTGGGACTCCAT
CGTTTCTATTACGGAGACTGGAGTCGAAGAGGTTTTTGATTTGACTGTGCCAGGGCCCCATA
ACTTTGTGGCCAATGACATCATTGTCCATAACAGTGAGGAGGACCTGGGATCCAGCGTGCAG
CTCGCCGACCACTACCAGCAGAACACCCCCATCGGCGACGGCCCCGTGCTGCTGCCCGACAA
CCACTACCTGAGCACCCAGTCCGCCCTGAGCAAAGACCCCAACGAGAAGCGCGATCACATGG
TCCTGCTGGAGTTCGTGACCGCCGCCGGGATCACTCTCGGCATGGACGAGCTGTACAAGGGG
TCGAACGGGGAATTCTCGCAGGTAGACAAGTCGATGGTGAGCAAGGGCGAGGAGCTGTTCAC
CGGGGTGGTGCCCATCCTGGTCGAGCTGGACGGCGACGTAAACGGCCACAAGTTCAGCGTGT
CCGGCGAGGGCGAGGGCGATGCCACCTACGGCAAGCTGACCCTGAAGTTCATCTGCACCACC
GGCAAGCTGCCCGTGCCCTGGCCCACCCTCGTGACCACCCTGACCTACGGCGTGCAGTGCTT
CAGCCGCTACCCCGACCACATGAAGCAGCACGACTTCTTCAAGTCCGCCATGCCCGAAGGCT
ACGTCCAGGAGCGCACCATCTTCTTCAAGGACGACGGCAACTACAAGACCCGCGCCGAGGTG
AAGTTCGAGGGCGACACCCTGGTGAACCGCATCGAGCTGAAGGGCATCGACTTCAAGGAGGA
CGGCAACATCCTGGGGCACAAGCTGGAGTACAACTACAACAGCCACAACGTCTATATCATGG
CCGACAAGCAGAAGAACGGCATCAAGGTGAACTTCAAGATCCGCCACAACATCGAGGACCTC
GAGCAAAAGCTGATATGCATCTCCGGAaATAGTTTGATCAGCTTGGCGAGCACAGGAAAAAG
AGTTTCTATTAAAGATTTGTTAGATGAAAAAGATTTTGAAATATGGGCAATTAATGAACAGA
CGATGAAGCTAGAATCAGCTAAAGTTAGTCGTGTATTTTGTACTGGCAAAAgGCTAGTTTAT
ATTTTAAAAACTCGACTAGGTAGAACTATCAAGGCAACAGCAAATCATAGATTTTTAACTAT
TGATGGTTGGAAAAGATTAGATGAGCTATCTTTAAAAGAGCATATTGCTCTACCCCGTAAAC
TAGAAAGCTCCTCTTTACAATTAGGCCTCCGCGGCCAGTACCCCTACGACGTCCCGGACTAC
GCTATCGATTAA

FIG._5K

MESGSPEIEKLSQSDIYWDSIVSITETGVEEVFDLTVPGPHNFVANDIIVHNSEEDLGSSVQ
LADHYQQNTPIGDGPVLLPDNHYLSTQSALSKDPNEKRDHMVLLEFVTAAGITLGMDELYKG
SNGEFSQVDKSMVSKGEELFTGVVPILVELDGDVNGHKFSVSGEGEGDATYGKLTLKFICTT
GKLPVPWPTLVTTLTYGVQCFSRYPDHMKQHDFFKSAMPEGYVQERTIFFKDDGNYKTRAEV
KFEGDTLVNRIELKGIDFKEDGNILGHKLEYNYNSHNVYIMADKQKNGIKVNFKIRHNIEDL
EQKLICISGNSLISLASTGKRVSIKDLLDEKDFEIWAINEQTMKLESAKVSRVFCTGKRLVY
ILKTRLGRTIKATANHRFLTIDGWKRLDELSLKEHIALPRKLESSSLQLGLRGQYPYDVPDY
AIDZ

FIG._5L

ATGGAGTCCGGATCACCAGAAATAGAAAAGTTGTCTCAGAGTGATATTTACTGGGACTCCAT
CGTTTCTATTACGGAGACTGGAGTCGAAGAGGTTTTTGATTTGACTGTGCCAGGGCCCCATA
ACTTTGTGGCCAATGACATCATTGTCCATAACAGTGAGGAGGACCTGGGATCCAGCGTGCAG
CTCGCCGACCACTACCAGCAGAACACCCCCATCGGCGACGGCCCCGTGCTGCTGCCCGACAA
CCACTACCTGAGCACCCAGTCCGCCCTGAGCAAAGACCCCAACGAGAAGCGCGATCACATGG
TCCTGCTGGAGTTCGTGACCGCCGCCGGGATCACTCTCGGCATGGACGAGCTGTACAAGGGG
TCGAACGGGGAATTCTCGCAGGTAGACAAGTCGATGGTGAGCAAGGGCGAGGAGCTGTTCAC
CGGGGTGGTGCCCATCCTGGTCGAGCTGGACGGCGACGTAAACGGCCACAAGTTCAGCGTGT
CCGGCGAGGGCGAGGGCGATGCCACCTACGGCAAGCTGACCCTGAAGTTCATCTGCACCACC
GGCAAGCTGCCCGTGCCCTGGCCCACCCTCGTGACCACCCTGACCTACGGCGTGCAGTGCTT
CAGCCGCTACCCCGACCACATGAAGCAGCACGACTTCTTCAAGTCCGCCATGCCCGAAGGCT
ACGTCCAGGAGCGCACCATCTTCTTCAAGGACGACGGCAACTACAAGACCCGCGCCGAGGTG
AAGTTCGAGGGCGACACCCTGGTGAACCGCATCGAGCTGAAGGGCATCGACTTCAAGGAGGA
CGGCAACATCCTGGGGCACAAGCTGGAGTACAACTACAACAGCCACAACGTCTATATCATGG
CCGACAAGCAGAAGAACGGCATCAAGGTGAACTTCAAGATCCGCCACAACATCGAGGACCTC
GAGCAAAAGCTGATATGCATCTCCGGAGATAGTTTGATCAGCTTGGCGAGCACAGGAAAAAG
AGTTTCTATTAAAGATTTGTTAGATGAAAAAGATTTTGAAATATGGGCAATTAATGAACAGA
CGATGAAGCTAGAATCAGCTAAAGTTAGTCGTGTATTTTGTACTGGCAAAAAGCTAGTTTAT
ATTTTAAAAACTCGACTAGGTAGAACTATCAAGGCAACAGCAAATCATAaATTTTTAACTAT
TGATGGTTGGAAAAGATTAGATGAGCTATCTTTAAAAGAGCATATTGCTCTACCCCGTAAAC
TAGAAAGCTCCTCTTTACAATTAGGCCTCCGCGGCCAGTACCCCTACGACGTCCCGGACTAC
GCTATCGATTAA

FIG._5M

MESGSPEIEKLSQSDIYWDSIVSITETGVEEVFDLTVPGPHNFVANDIIVHNSEEDLGSSVQ
LADHYQQNTPIGDGPVLLPDNHYLSTQSALSKDPNEKRDHMVLLEFVTAAGITLGMDELYKG
SNGEFSQVDKSMVSKGEELFTGVVPILVELDGDVNGHKFSVSGEGEGDATYGKLTLKFICTT
GKLPVPWPTLVTTLTYGVQCFSRYPDHMKQHDFFKSAMPEGYVQERTIFFKDDGNYKTRAEV
KFEGDTLVNRIELKGIDFKEDGNILGHKLEYNYNSHNVYIMADKQKNGIKVNFKIRHNIEDL
EQKLICISGDSLISLASTGKRVSIKDLLDEKDFEIWAINEQTMKLESAKVSRVFCTGKKLVY
ILKTRLGRTIKATANHKFLTIDGWKRLDELSLKEHIALPRKLESSSLQLGLRGQYPYDVPDY
AIDZ

FIG._5N

```
ATGGAGTCCGGATCACCAGAAATAGAAAAGTTGTCTCAGAGTGATATTTACTGGGACTCCAT
CGTTcCTATTACGGAGACTGGAGTCGAAGAGGTTTTTGATTTGACTGTGCCAGGGCCCCATA
ACTTTGTGGCCAATGACATCATTGTCCATAACAGTGAGGAGGACCTGGGATCCAGCGTGCAG
CTCGCCGACCACTACCAGCAGAACACCCCCATCGGCGACGGCCCCGTGCTGCTGCCCGACAA
CCACTACCTGAGCACCCAGTCCGCCCTGAGCAAAGACCCCAACGAGAAGCGCGATCACATGG
TCCTGCTGGAGTTCGTGACCGCCGCCGGGATCACTCTCGGCATGGACGAGCTGTACAAGGGG
TCGAACGGGGAATTCTCGCAGGTAGACAAGTCGATGGTGAGCAAGGGCGAGGAGCTGTTCAC
CGGGGTGGTGCCCATCCTGGTCGAGCTGGACGGCGACGTAAACGGCCACAAGTTCAGCGTGT
CCGGCGAGGGCGAGGGCGATGCCACCTACGGCAAGCTGACCCTGAAGTTCATCTGCACCACC
GGCAAGCTGCCCGTGCCCTGGCCCACCCTCGTGACCACCCTGACCTACGGCGTGCAGTGCTT
CAGCCGCTACCCCGACCACATGAAGCAGCACGACTTCTTCAAGTCCGCCATGCCCGAAGGCT
ACGTCCAGGAGCGCACCATCTTCTTCAAGGACGACGGCAACTACAAGACCCGCGCCGAGGTG
AAGTTCGAGGGCGACACCCTGGTGAACCGCATCGAGCTGAAGGGCATCGACTTCAAGGAGGA
CGGCAACATCCTGGGGCACAAGCTGGAGTACAACTACAACAGCCACAACGTCTATATCATGG
CCGACAAGCAGAAGAACGGCATCAAGGTGAACTTCAAGATCCGCCACAACATCGAGGACCTC
GAGCAAAAGCTGATATGCATCTCCGGAGATAGTTTGATCAGCTTGGCGAGCACAGGAAAAAG
AGTTTCTATTAAAGATTTGTTAGATGAAAAGATTTTGAAATATGGGCAATTAATGAACAGA
CGATGAAGCTAGAATCAGCTAAAGTTAGTCGTGTATTTGTACTGGCAAAAAGCTAGTTTAT
ATTTTAAAAACTCGACTAGGTAGAACTATCAAGGCAACAGCAAATCATAGATTTTTAACTAT
TGATGGTTGGAAAAGATTAGATGAGCTATCTTTAAAAGAGCATATTGCTCTACCCCGTAAAC
TAGAAAGCTCCTCTTTACAATTAGGCCTCCGCGGCCAGTACCCCTACGACGTCCCGGACTAC
GCTATCGATTAA
```

FIG._5O

```
MESGSPEIEKLSQSDIYWDSIVPITETGVEEVFDLTVPGPHNFVANDIIVHNSEEDLGSSVQ
LADHYQQNTPIGDGPVLLPDNHYLSTQSALSKDPNEKRDHMVLLEFVTAAGITLGMDELYKG
SNGEFSQVDKSMVSKGEELFTGVVPILVELDGDVNGHKFSVSGEGEGDATYGKLTLKFICTT
GKLPVPWPTLVTTLTYGVQCFSRYPDHMKQHDFFKSAMPEGYVQERTIFFKDDGNYKTRAEV
KFEGDTLVNRIELKGIDFKEDGNILGHKLEYNYNSHNVYIMADKQKNGIKVNFKIRHNIEDL
EQKLICISGDSLISLASTGKRVSIKDLLDEKDFEIWAINEQTMKLESAKVSRVFCTGKKLVY
ILKTRLGRTIKATANHRFLTIDGWKRLDELSLKEHIALPRKLESSSLQLGLRGQYPYDVPDY
AIDZ
```

FIG._5P

```
ATGGAGTCCGGATCACCAGAAATAGAAAAGTTGTCTCAGAGTGATATTTACTGGGACTCCAT
CGTTTCTATTACGGAGACTGGAGTCGAAGAGGTTTTTGATTTGACTGTGCCAGGGCCCCATA
ACTTTGTGGCCAATGACATCATTGTCCATAACAGTGAGGAGGACCTGGGATCCAGCGTGCAG
CTCGCCGACCACTACCAGCAGAACACCCCCATCGGCGACGGCCCCGTGCTGCTGCCCGACAA
CCACTACCTGAGCACCCAGTCCGCCCTGAGCAAAGACCCCAACGAGAAGCGCGATCACATGG
TCCTGCTGGAGTTCGTGACCGCCGCCGGGATCACTCTCGGCATGGACGAGCTGTACAAGGGG
TCGAACGGGGAATTCTCGCAGGTAGACAAGTCGATGGTGAGCAAGGGCGAGGAGCTGTTCAC
CGGGGTGGTGCCCATCCTGGTCGAGCTGGACGGCGACGTAAACGGCCACAAGTTCAGCGTGT
CCGGCGAGGGCGAGGGCGATGCCACCTACGGCAAGCTGACCCTGAAGTTCATCTGCACCACC
GGCAAGCTGCCCGTGCCCTGGCCCACCCTCGTGACCACCCTGACCTACGGCGTGCAGTGCTT
CAGCCGCTACCCCGACCACATGAAGCAGCACGACTTCTTCAAGTCCGCCATGCCCGAAGGCT
ACGTCCAGGAGCGCACCATCTTCTTCAAGGACGACGGCAACTACAAGACCCGCGCCGAGGTG
AAGTTCGAGGGCGACACCCTGGTGAACCGCATCGAGCTGAAGGGCATCGACTTCAAGGAGGA
CGGCAACATCCTGGGGCACAAGCTGGAGTACAACTACAACAGCCACAACGTCTATATCATGG
CCGACAAGCAGAAGAACGGCATCAAGGTGAACTTCAAGATCCGCCACAACATCGAGGACCTC
GAGCAAAAGCTGATATGCATCTCCGGAGATAGTTTGATCAGCTTGGCGAGCACAGGAAAAAG
AGTTTCTATTAAAGATTTGTTAGATGAAAAGATTTTGAAATATGGGCAGTTAATGAACAGA
CGATGAAGCTAGAATCAGCTAAAGTTAGTCGTGTATTTTGTACTGGCAAAAAGCTAGTTTAT
ATTTTAAAAACTCGACTAGGTAGAACTATCAAGGCAACAGCAAATCATAGATTTTTAACTAT
TGATGGTTGGAAAAGATTAGATGAGCTATCTTTAAAAGAGCATATTGCTCTACCCCGTAAAC
TAGAAAGCTCCTCTTTACAATTAGGCCTCCGCGGCCAGTACCCCTACGACGTCCCGGACTAC
GCTATCGATTAA
```

FIG._5Q

```
MESGSPEIEKLSQSDIYWDSIVSITETGVEEVFDLTVPGPHNFVANDIIVHNSEEDLGSSVQ
LADHYQQNTPIGDGPVLLPDNHYLSTQSALSKDPNEKRDHMVLLEFVTAAGITLGMDELYKG
SNGEFSQVDKSMVSKGEELFTGVVPILVELDGDVNGHKFSVSGEGEGDATYGKLTLKFICTT
GKLPVPWPTLVTTLTYGVQCFSRYPDHMKQHDFFKSAMPEGYVQERTIFFKDDGNYKTRAEV
KFEGDTLVNRIELKGIDFKEDGNILGHKLEYNYNSHNVYIMADKQKNGIKVNFKIRHNIEDL
EQKLICISGDSLISLASTGKRVSIKDLLDEKDFEIWAVNEQTMKLESAKVSRVFCTGKKLVY
ILKTRLGRTIKATANHRFLTIDGWKRLDELSLKEHIALPRKLESSSLQLGLRGQYPYDVPDY
AIDZ
```

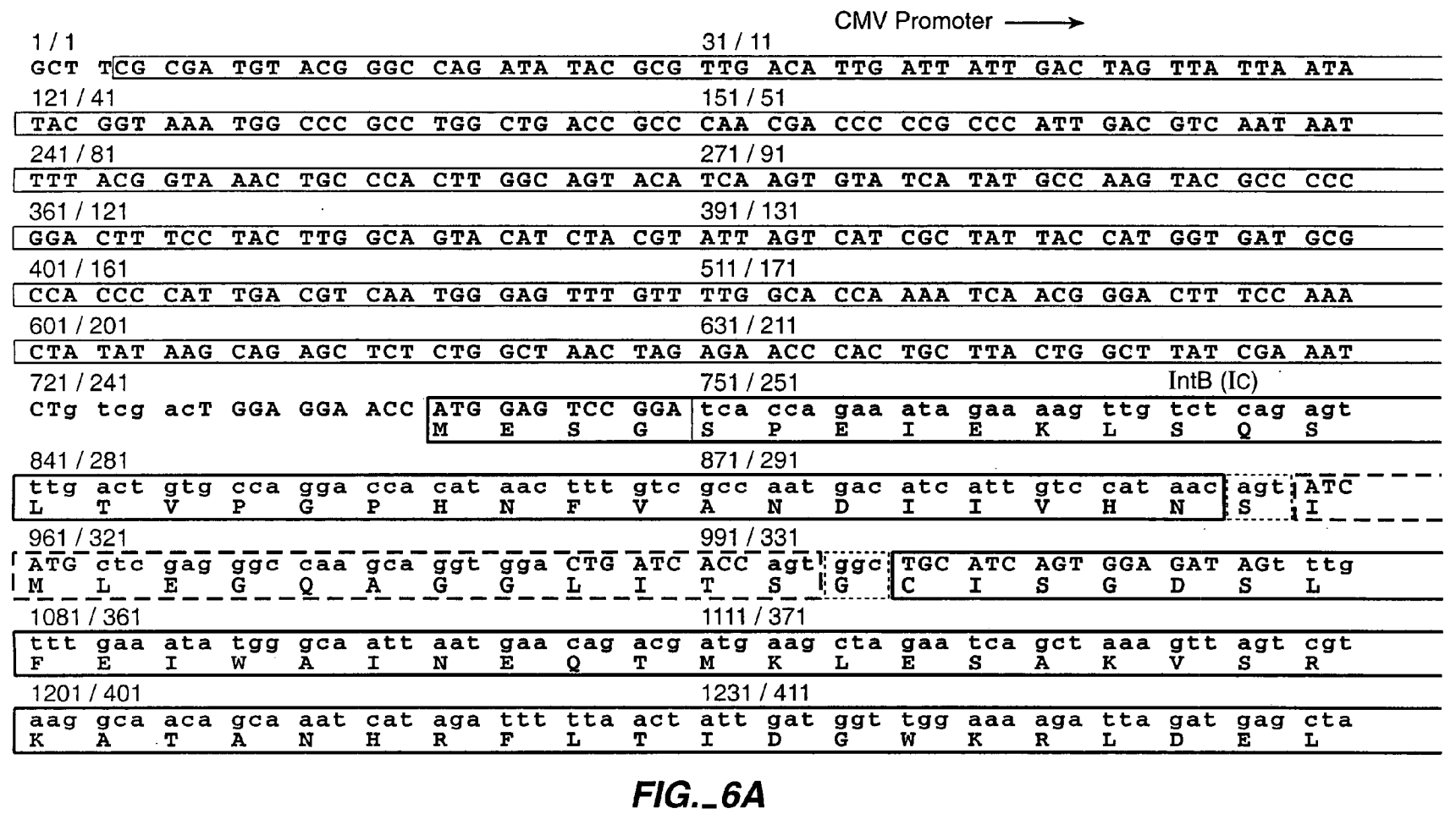

```
 61/21
     GTA ATC AAT TAC GGG GTC ATT AGT TCA TAG CCC ATA TAT GGA GTT CCG CGT TAC ATA ACT
                                                        91/31
181/61
     GAC GTA TGT TCC CAT AGT AAC GCC AAT AGG GAC TTT CCA TTG ACG TCA ATG GGT GGA CTA
                                                       211/71
301/101
     TAT TGA CGT CAA TGA CGG TAA ATG GCC CGC CTG GCA TTA TGC CCA GTA CAT GAC CTT ATC
                                                       331/111
421/141
     GTT TTG GCA GTA CAT CAA TGG GCG TGG ATA GCG GTT TGA CTC ACG GGG ATT TCC AAG TCT
                                                       451/151
541/181
     ATG TCG TAA CAA CTC CGC CCC ATT GAC GCA AAT GGG CGG TAG GCG TGT ACG GTG GGA GGT
                                                       571/191
661/221
     TAA TAC GAC TCA CTA TAG GGA GAC CCA AGC TGG CTA GTT AAG CTT cct ata cta ggA GAT
                                                       691/231                      IntB (IC)
781/261
     gat att tac tgg gac tcc atc gtt tct att acg gag act gga gtc gaa gag ttt gat
      D   I   Y   W   D   S   I   V   S   I   T   E   T   G   V   E   E   F   D
                                                       811/271
901/301                                        Flag Epitope Insert
     GAA CAA ggc cag cag ggt ggc ggt ggc ATG TCA ATG gac tat aaa gat gac gat aag ATG AGG
      E   Q   G   Q   Q   G   G   G   G   M   S   M   D   Y   K   D   D   D   K   M   R
                                                       931/311
         IntA (IN)
1021/341
     atc agc ttg gcg agc aca gga aaa aga gtt tct att aaa gat ttg tta gat gaa aaa gat
      I   S   L   A   S   T   G   K   R   V   S   I   K   D   L   L   D   E   K   D
                                                      1051/351                      1171/391
1141/381
     gta ttt tgt act ggc aaa aag cta gtt tat att tta aaa act cga cta ggt aga act atc
      V   F   C   T   G   K   K   L   V   Y   I   L   K   T   R   L   G   R   T   I
                                                      1171/391
1261/421                                                                            1291/431
     tct tta aaa gag cat att gct cta ccc cgt aaa cta gaa agc tcc tct caa tta ATC
      S   L   K   E   H   I   A   L   P   R   K   L   E   S   S   S   Q   L   I
```

| GAT | ATG | GTG | AGC | AAG | GGC | AAG | GAG | GAG | CTG | TTC | ACC | GGG | GTG | GTG | CCC | ATC | CTG | GTC | GAG | CTG |
|---|---|---|---|---|---|---|---|---|---|---|---|---|---|---|---|---|---|---|---|---|
| D | M | V | S | K | G | K | E | E | L | F | T | G | V | V | P | I | L | V | E | L |

| TAC | GGC | AAG | CTG | ACC | CTG | AAG | TTC | ATC | TGC | ACC | GGC | AAG | CTG | CCC | GTG | CCC | TGG | CCC |
|---|---|---|---|---|---|---|---|---|---|---|---|---|---|---|---|---|---|---|
| Y | G | K | L | T | L | K | F | I | C | T | G | K | L | P | V | P | W | P |

| AAG | CAG | CAC | GAC | TTC | TTC | AAG | TCC | GCC | ATG | CCC | GAA | GGC | TAC | GTC | CAG | GAG | CGC | ACC | ATC | CAC |
|---|---|---|---|---|---|---|---|---|---|---|---|---|---|---|---|---|---|---|---|---|
| K | Q | H | D | F | F | K | S | A | M | P | E | G | Y | V | Q | E | R | T | I | H |

| CTG | GTG | AAC | CGC | ATC | GAG | CTG | AAG | GGC | ATC | GAC | TTC | AAG | GAG | GAC | GGC | AAC | ATC | CTG | GGG |
|---|---|---|---|---|---|---|---|---|---|---|---|---|---|---|---|---|---|---|---|
| L | V | N | R | I | E | L | K | G | I | D | F | K | E | D | G | N | I | L | G |

| AAC | ATC | AAG | GTG | AAC | TTC | AAG | ATC | CGC | CAC | AAC | ATC | GAG | GAC | GGC | AGC | GTG | CAG | CTC |
|---|---|---|---|---|---|---|---|---|---|---|---|---|---|---|---|---|---|---|
| N | I | K | V | N | F | K | I | R | H | N | I | E | D | G | S | V | Q | L |

| CAC | TAC | CTG | AGC | ACC | CAG | TCC | GCC | CTG | AGC | AAA | GAC | CCC | AAC | GAG | AAG | CGC | GAT | CAC | ATG |
|---|---|---|---|---|---|---|---|---|---|---|---|---|---|---|---|---|---|---|---|
| H | Y | L | S | T | Q | S | A | L | S | K | D | P | N | E | K | R | D | H | M |

| TAA |
|---|
| * |

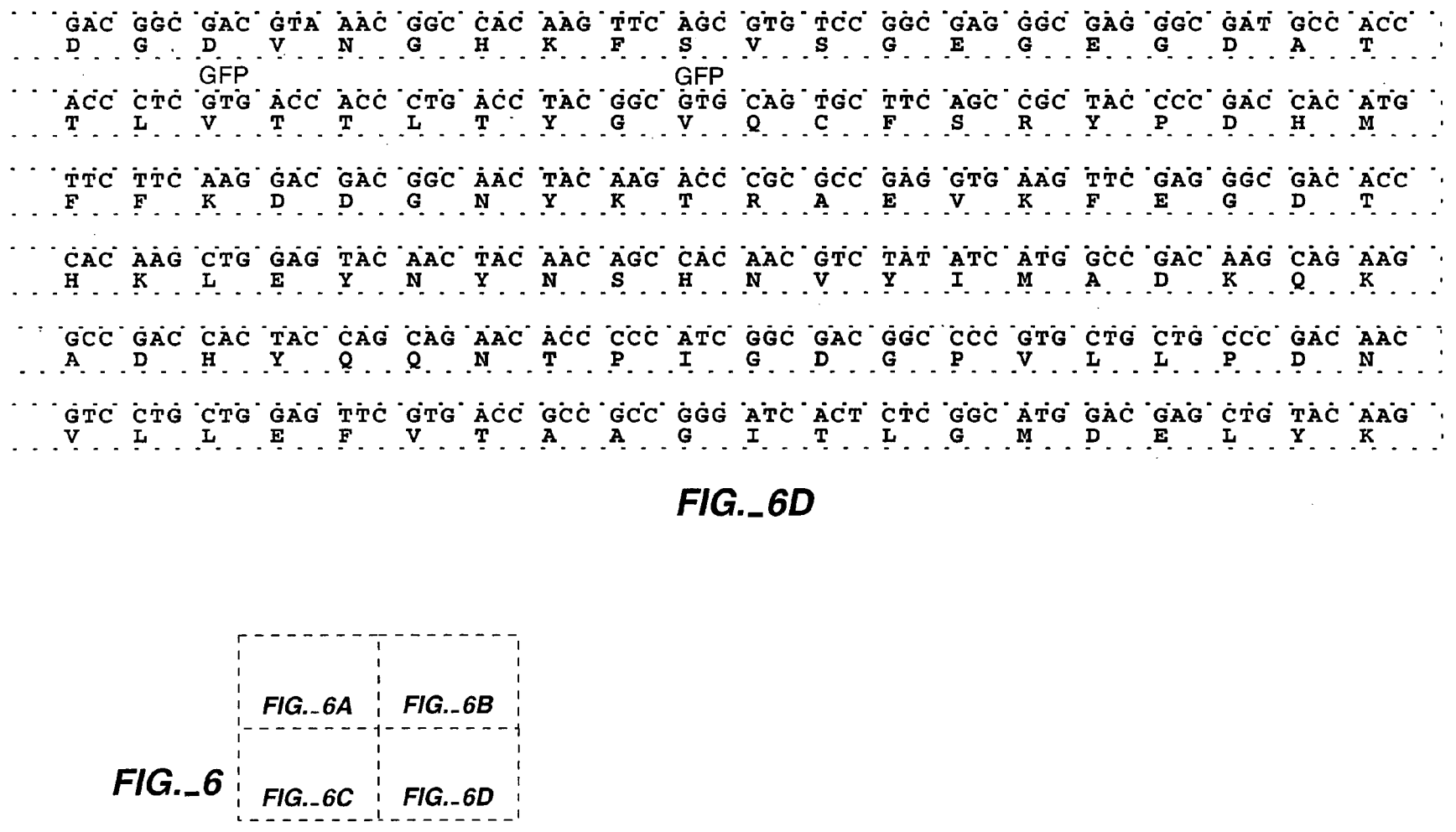

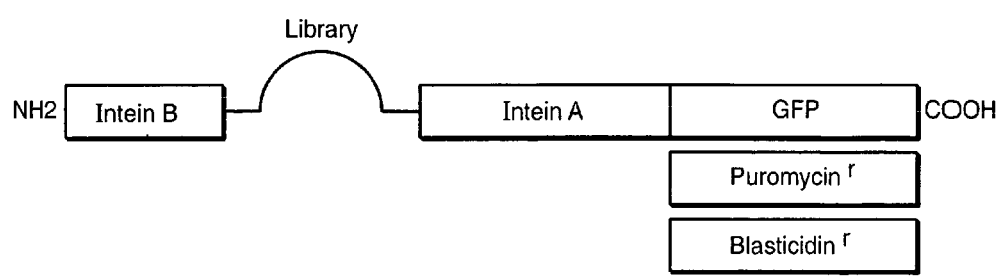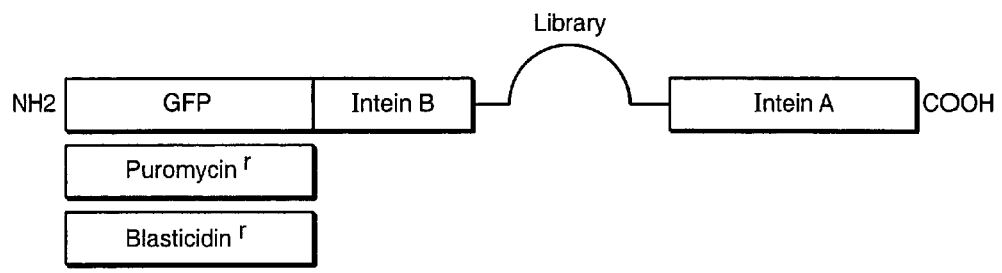
FIG._7

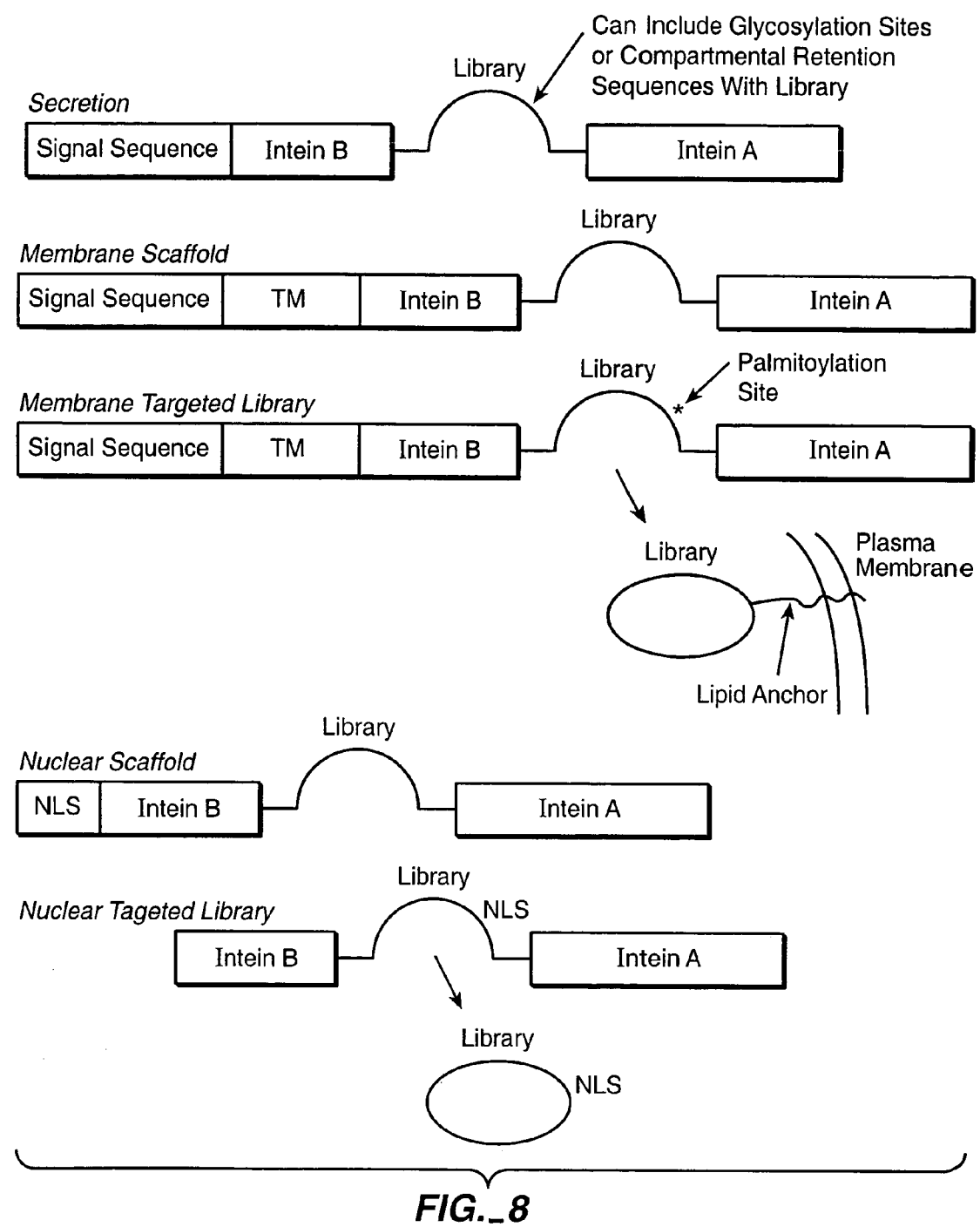
FIG._8

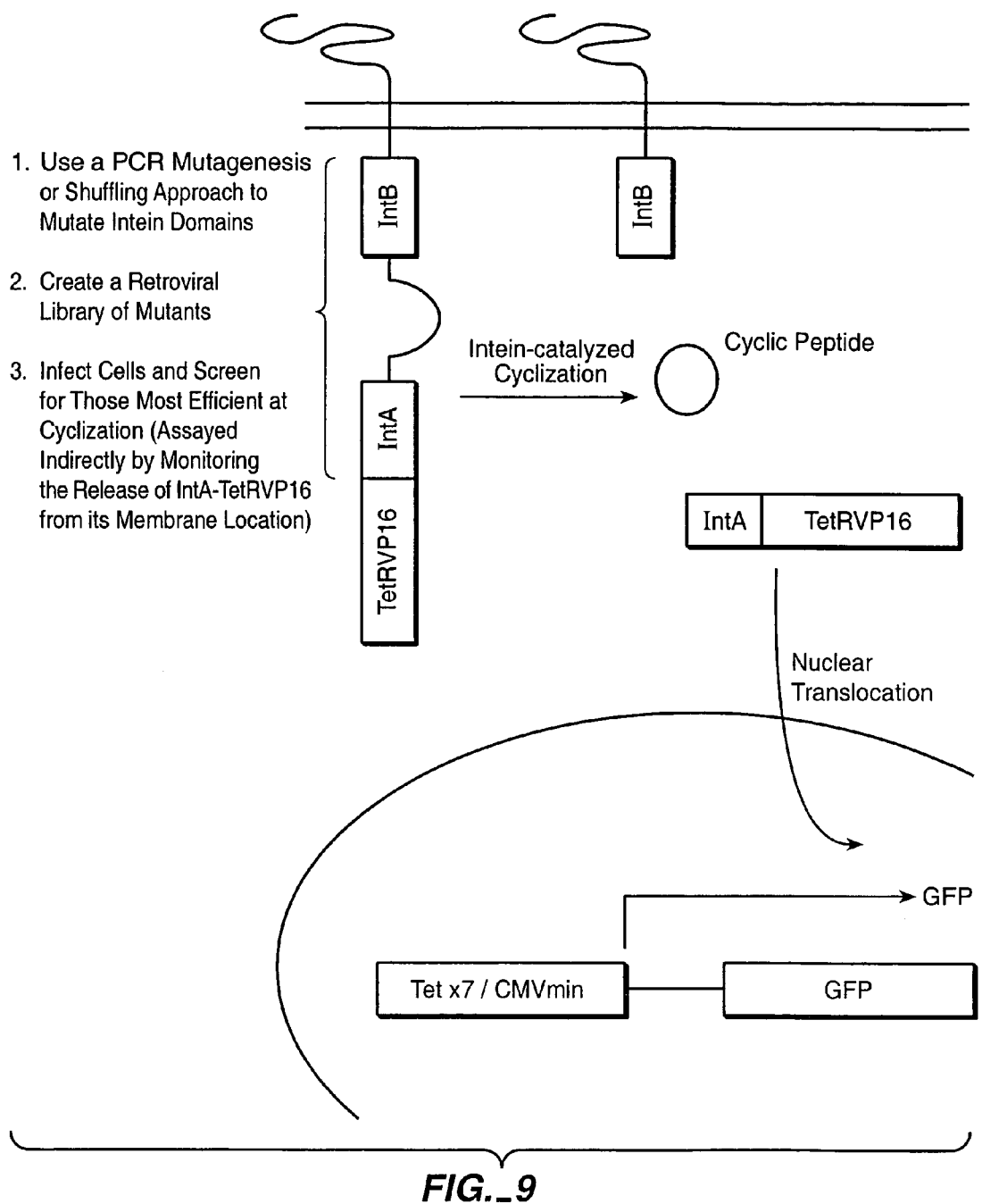
FIG._9

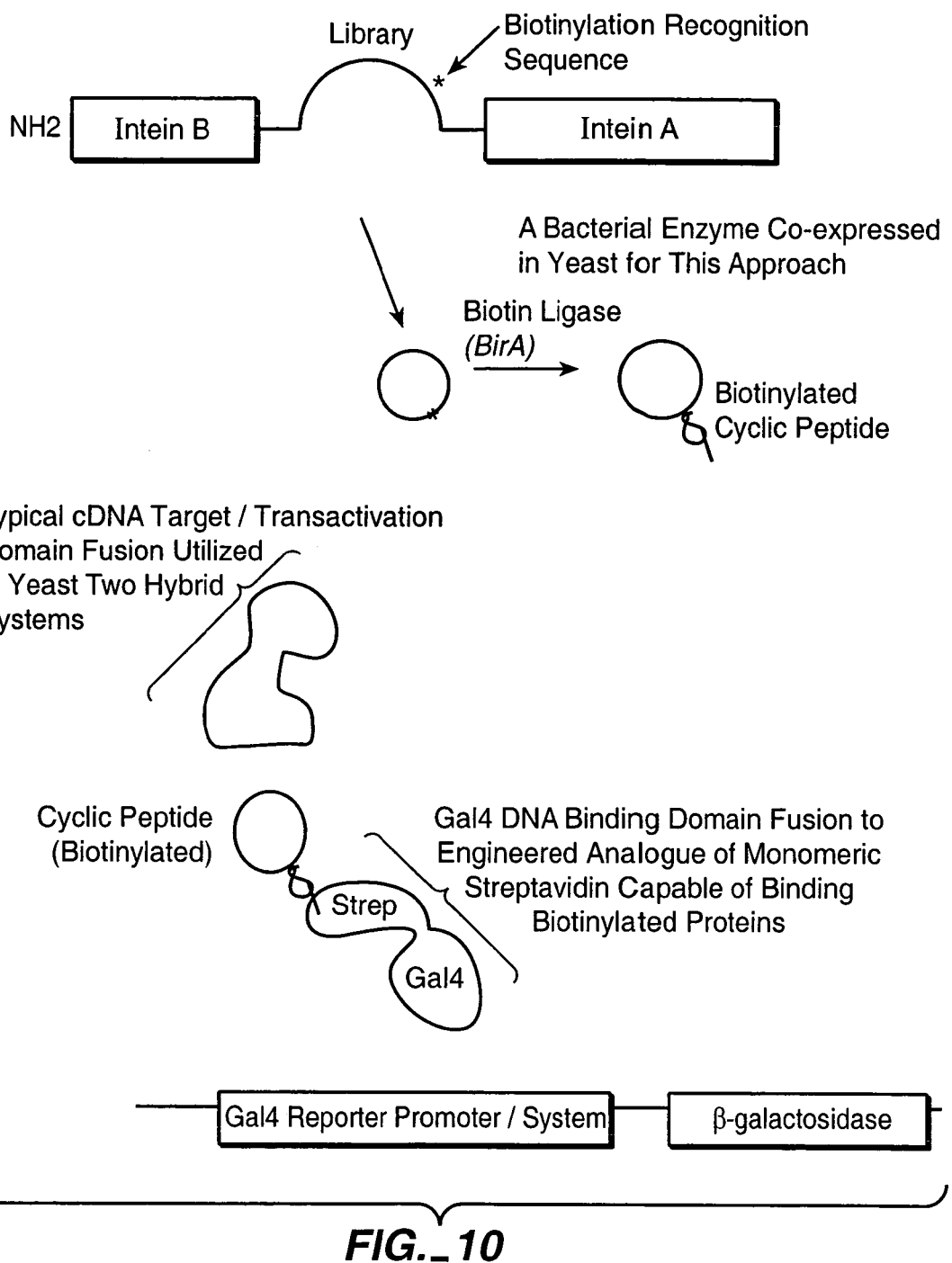
FIG._10

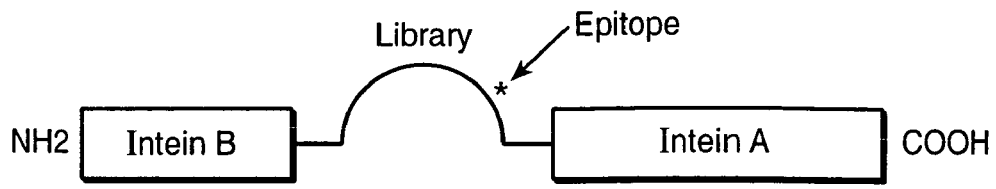
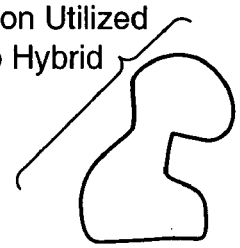
Typical cDNA Target / Transactivation Domain Fusion Utilized in Yeast Two Hybrid Systems
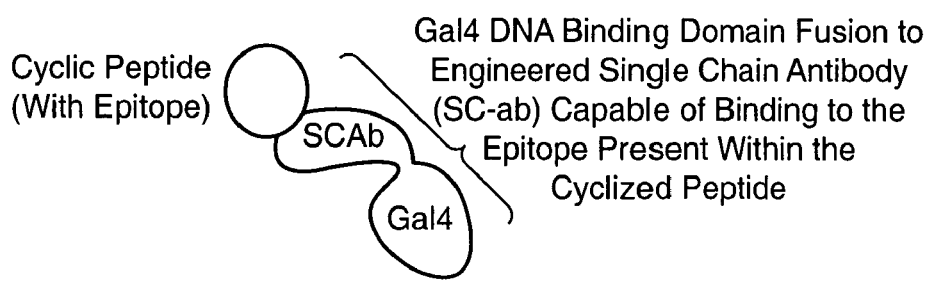
Cyclic Peptide (With Epitope)
Gal4 DNA Binding Domain Fusion to Engineered Single Chain Antibody (SC-ab) Capable of Binding to the Epitope Present Within the Cyclized Peptide
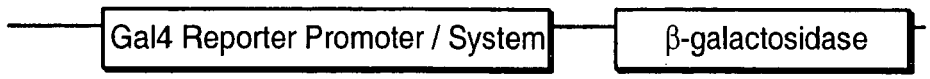
FIG._11

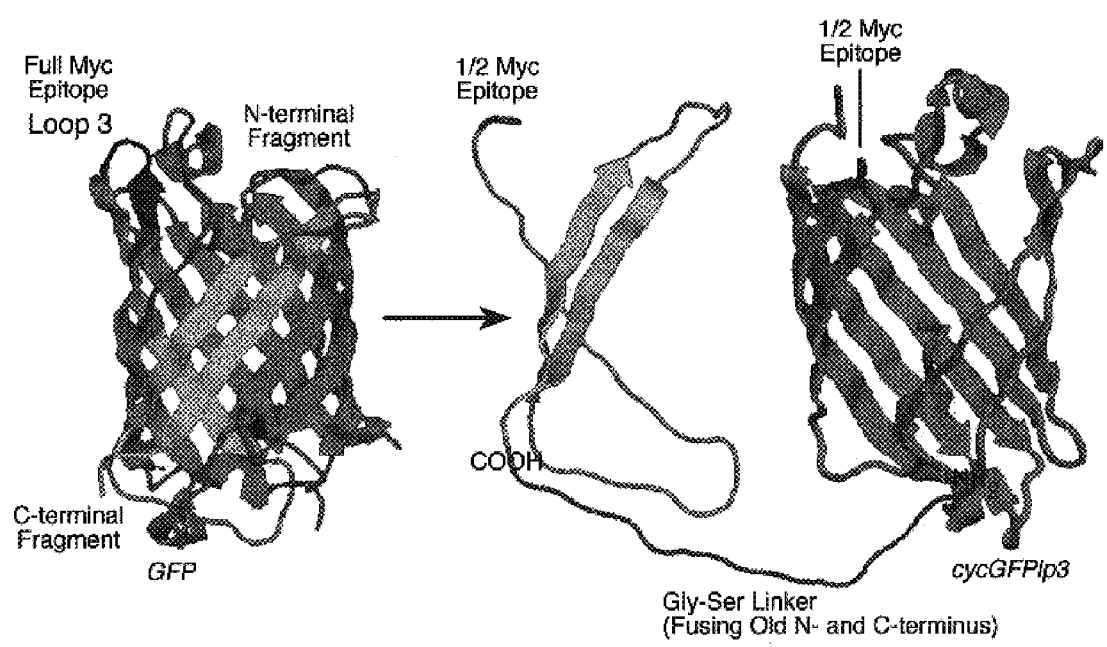
FIG._12A

IntB (Ic)
MESGSPEIEKLSQSDIYWDSIVSITETGVEEVFDLTVPGP myc6-10
HNFVANDIIVHNSEEDLGSSVQLADHYQQNTPIGDGPVLL

PDNHYLSTQSALSKDPNEKRDHMVLLEFVTAAGITLGMDE

Gly-Ser Linker
LYKGSNGEFSQVDKSMVSKGEELFTGVVPILVELDGDVNG

GFP6-1-173
HKFSVSGEGEGDATYGLKTLKFICTTGKLPVPWPTLVTTL

TYGLQCFSRYPDHMKQHDFFKSAMPEGYVQERTIFFKDDG

NYKTRAEVKFEGDTLVNRIELKGIDFKEDGNILGHKLEYN myc1-5
YNSHNVYIMADKQKNGIKVNFKIRHNIEDLEQKLICISGD

SLISLASTGKRVSIKDLLDEKDFEIWAINEQTMKLESAKV

IntA (IN)
SRVFCTGKKLVYILKTRLGRTIKATANHRFLTIDGWKRLD

HA
ELSKLEHIALPRKLESSSLQLGLRGQYPYDVPDYAID

FIG._12B

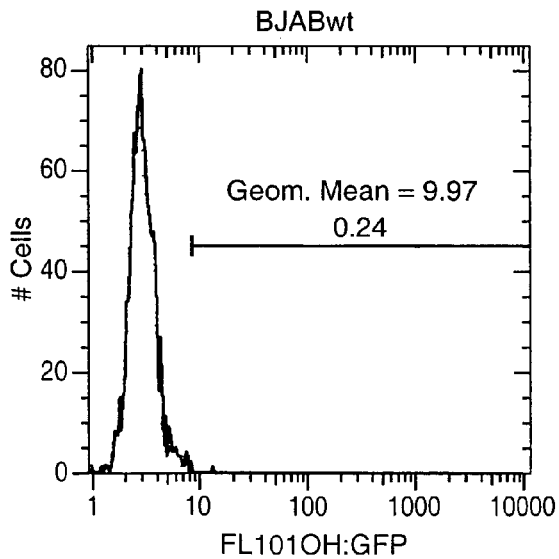

FIG._12D-1

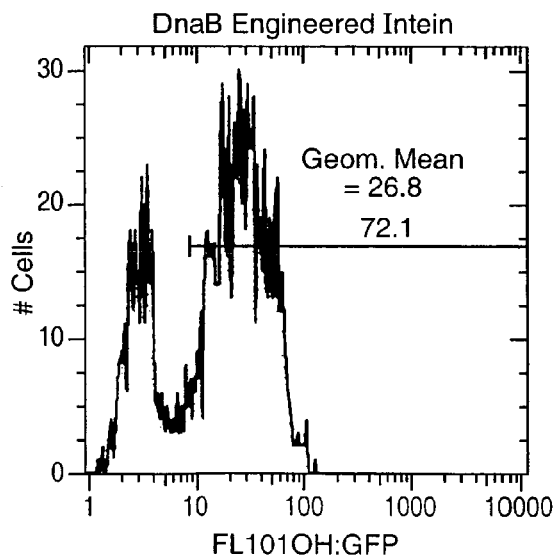

FIG._12D-2

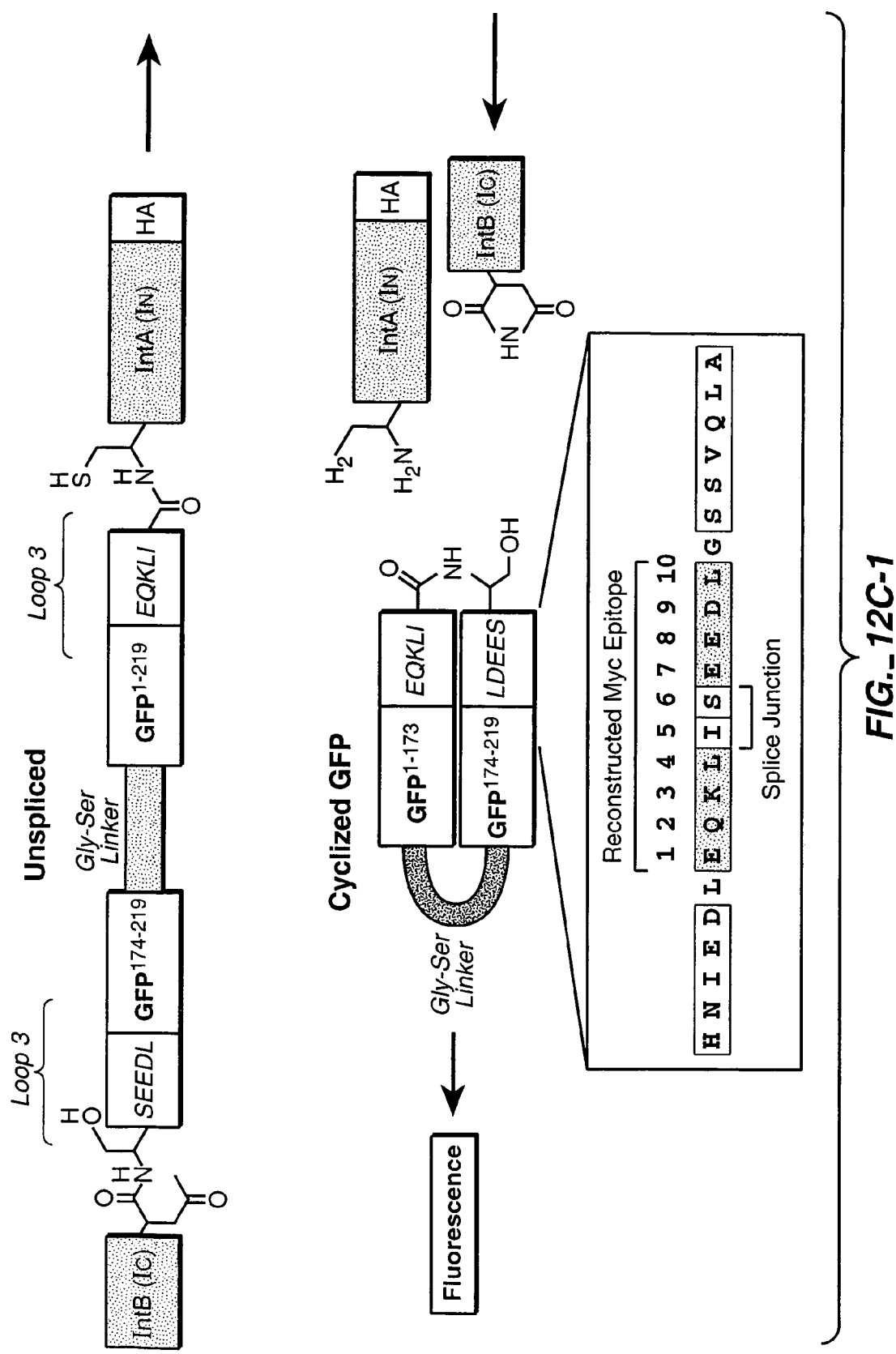
FIG._12C-1

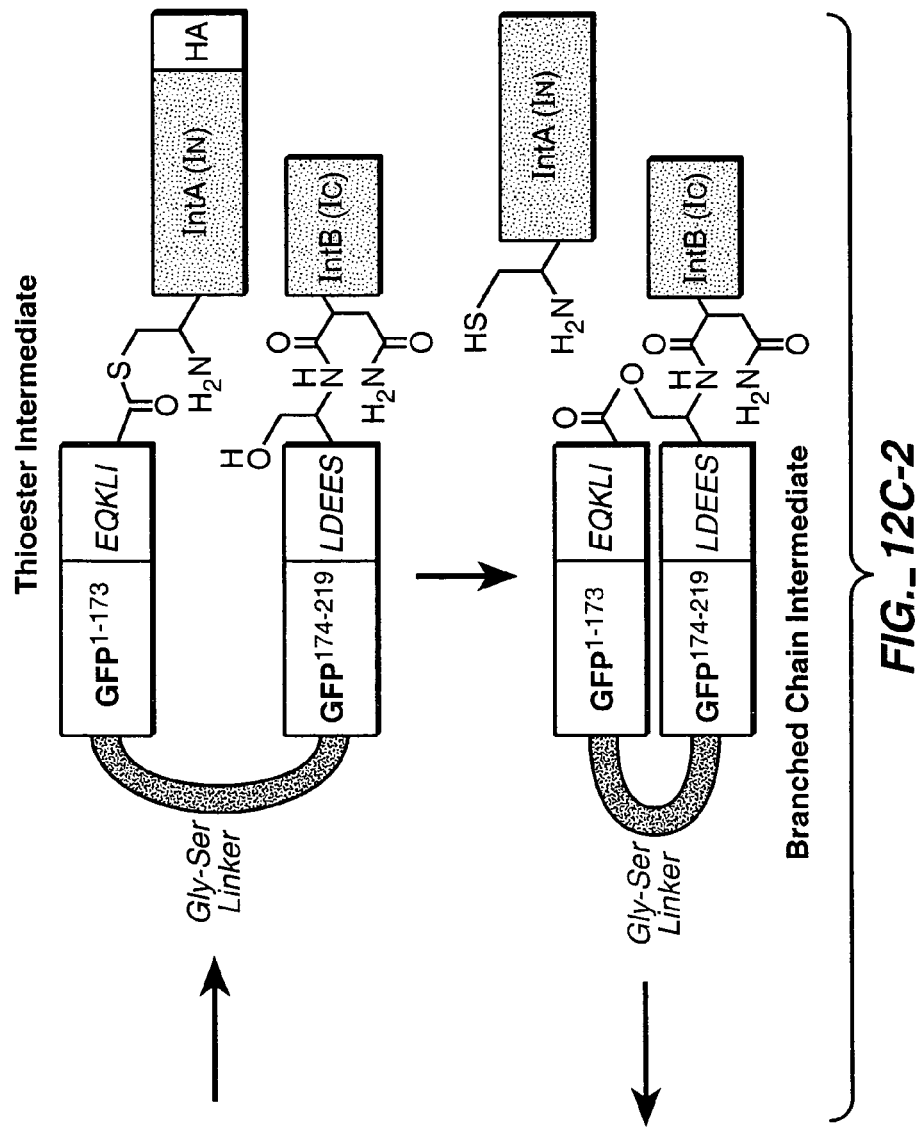
FIG._12C-2

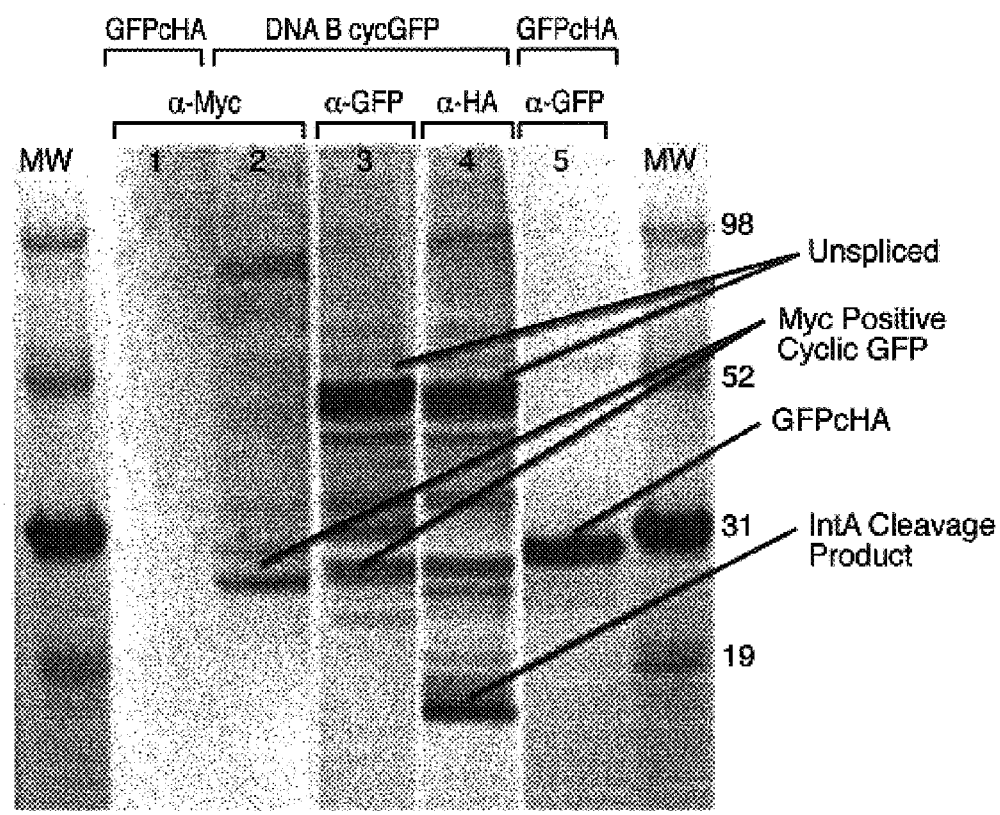
FIG._12E
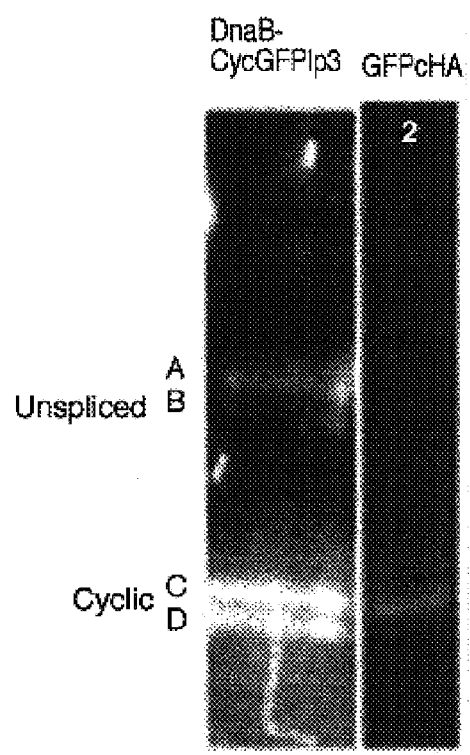
FIG._12F

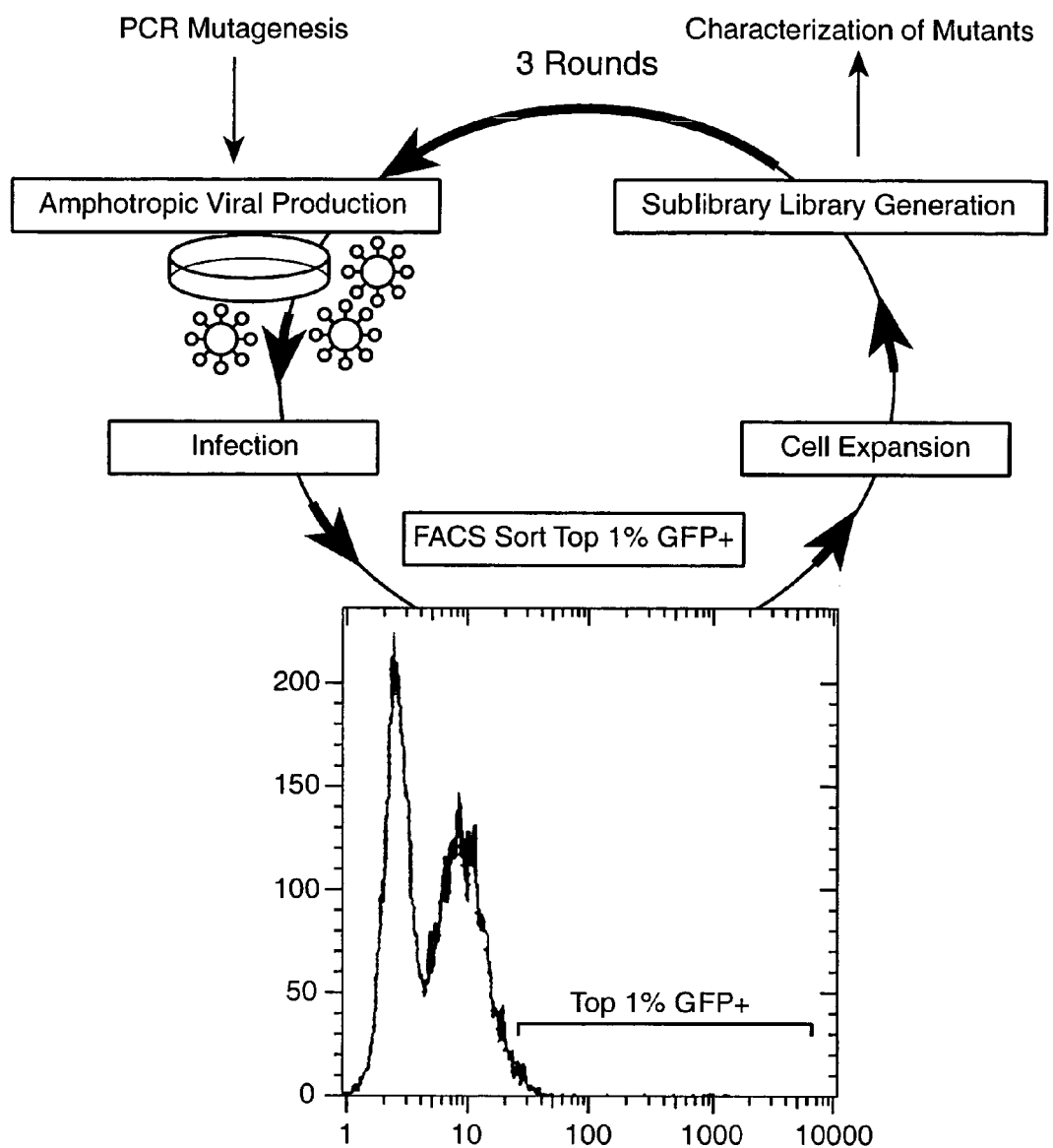
FIG._13A

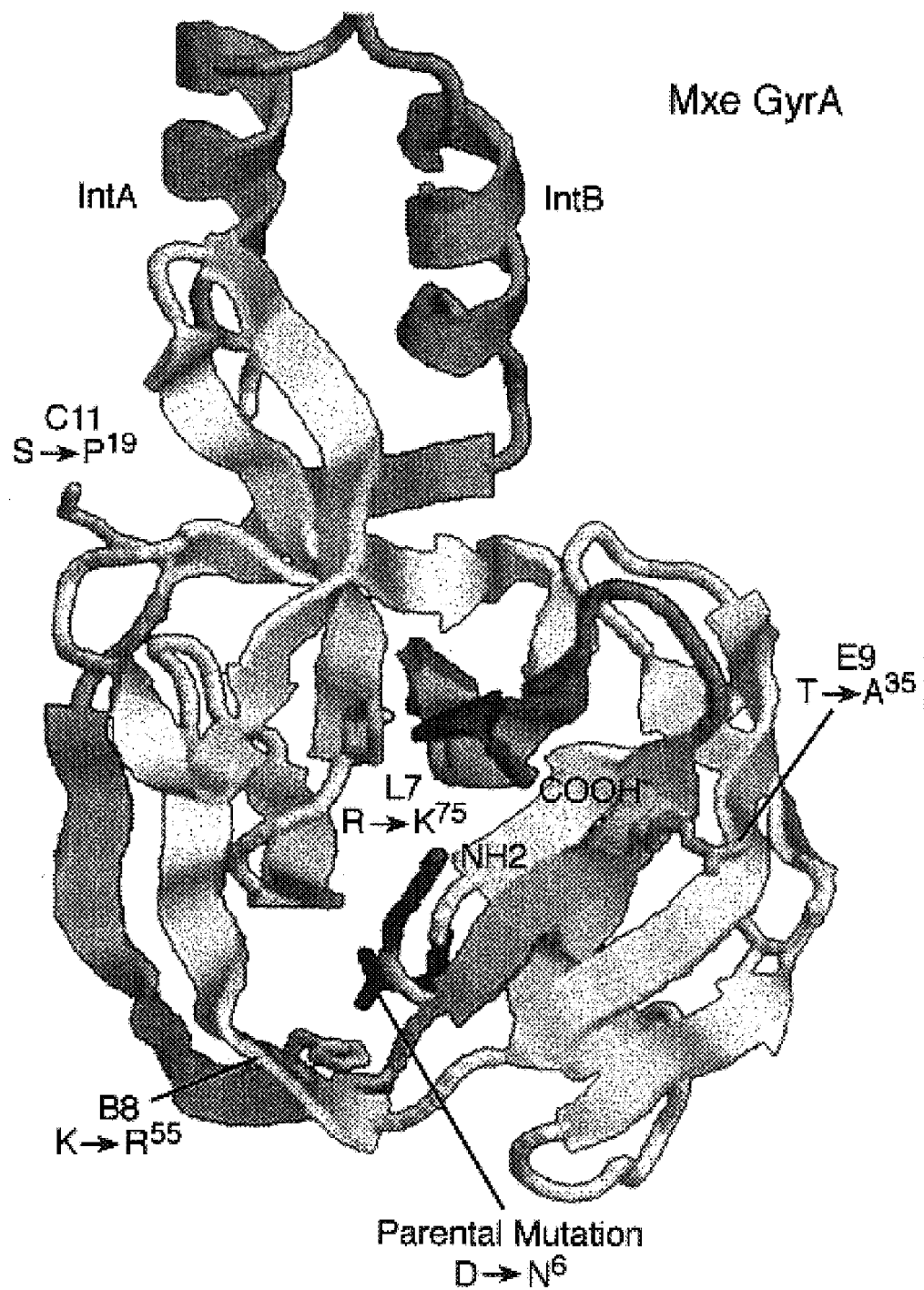
FIG._13B

FIG. 13C

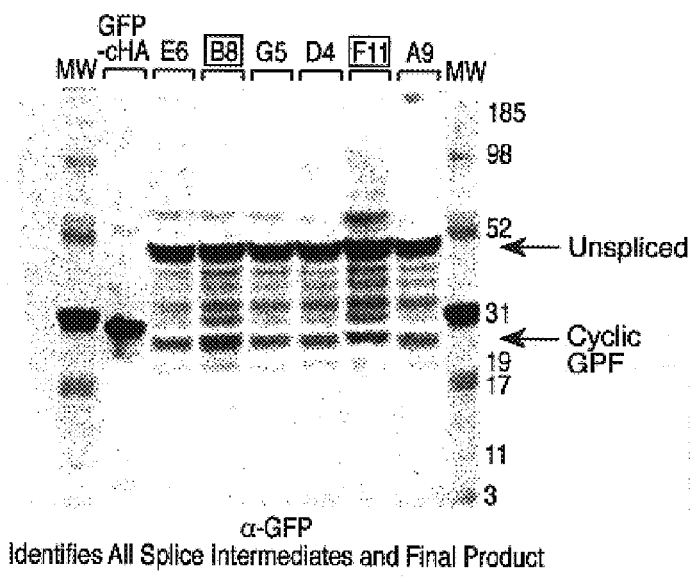
FIG._13D-7
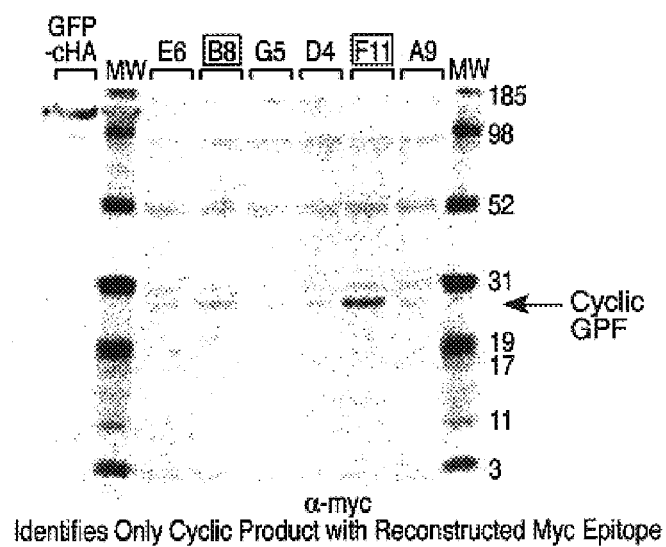
FIG._13D-8
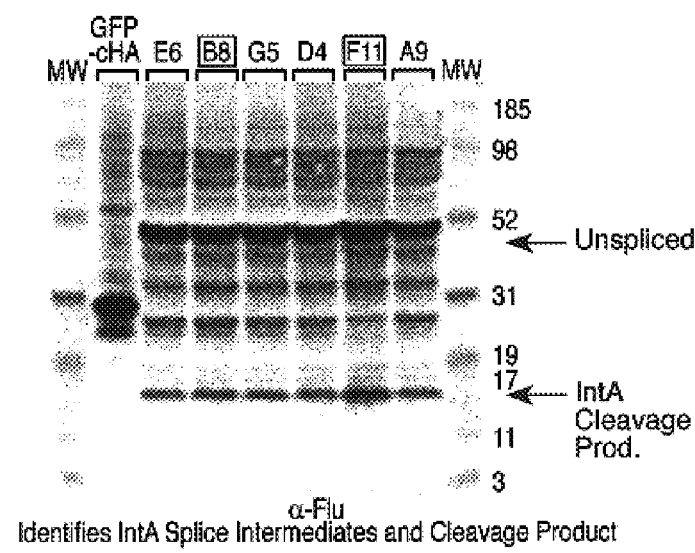
FIG._13D-9

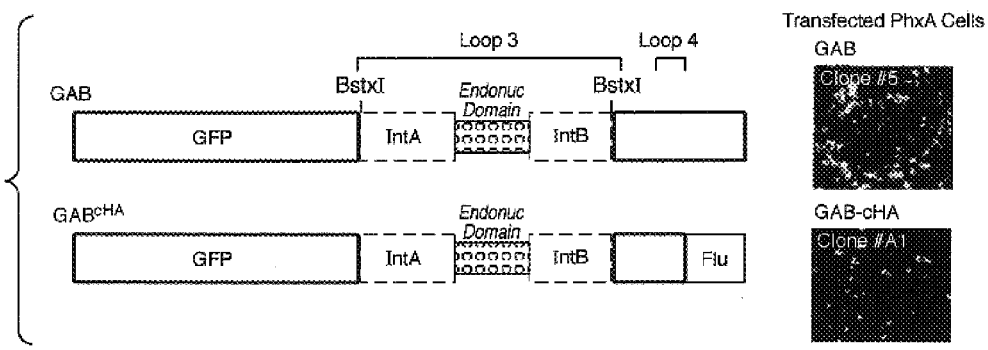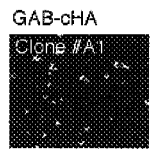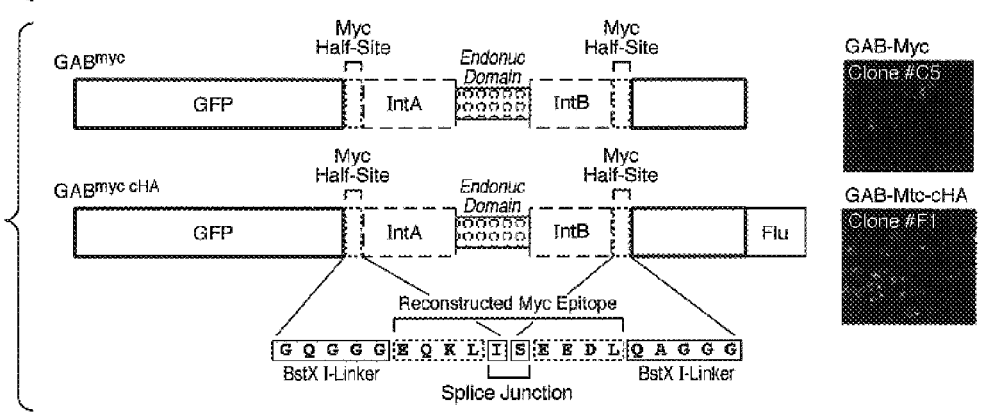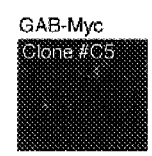
FIG._14A, FIG._14B

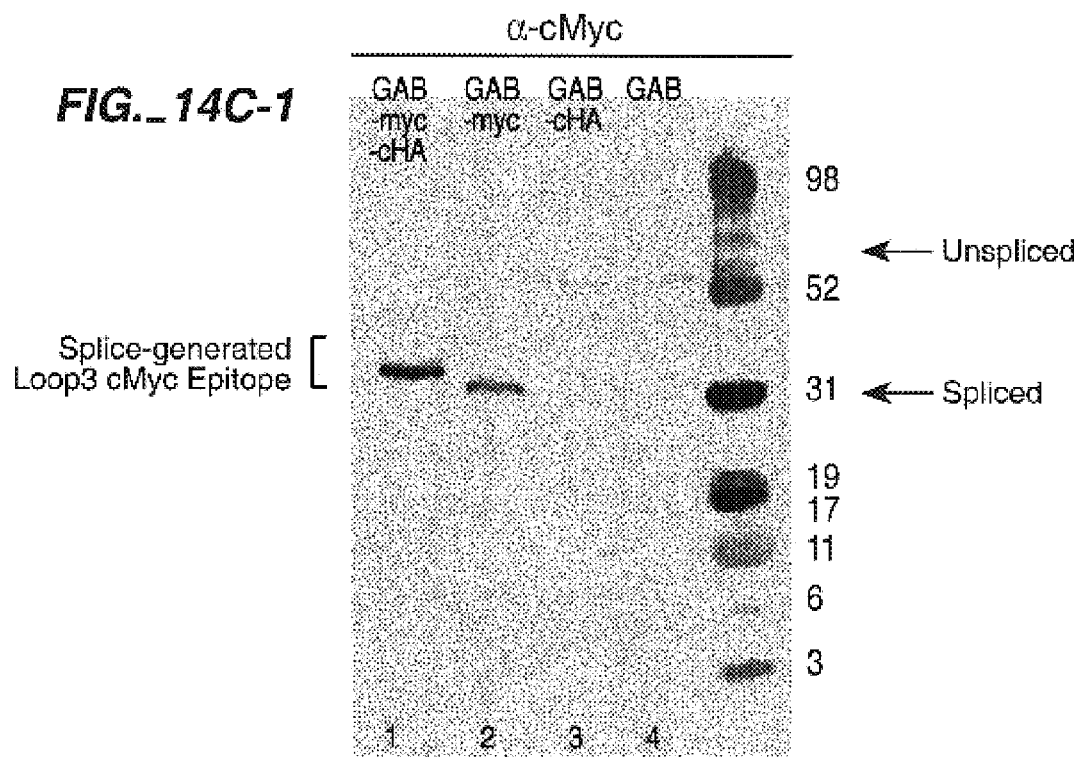
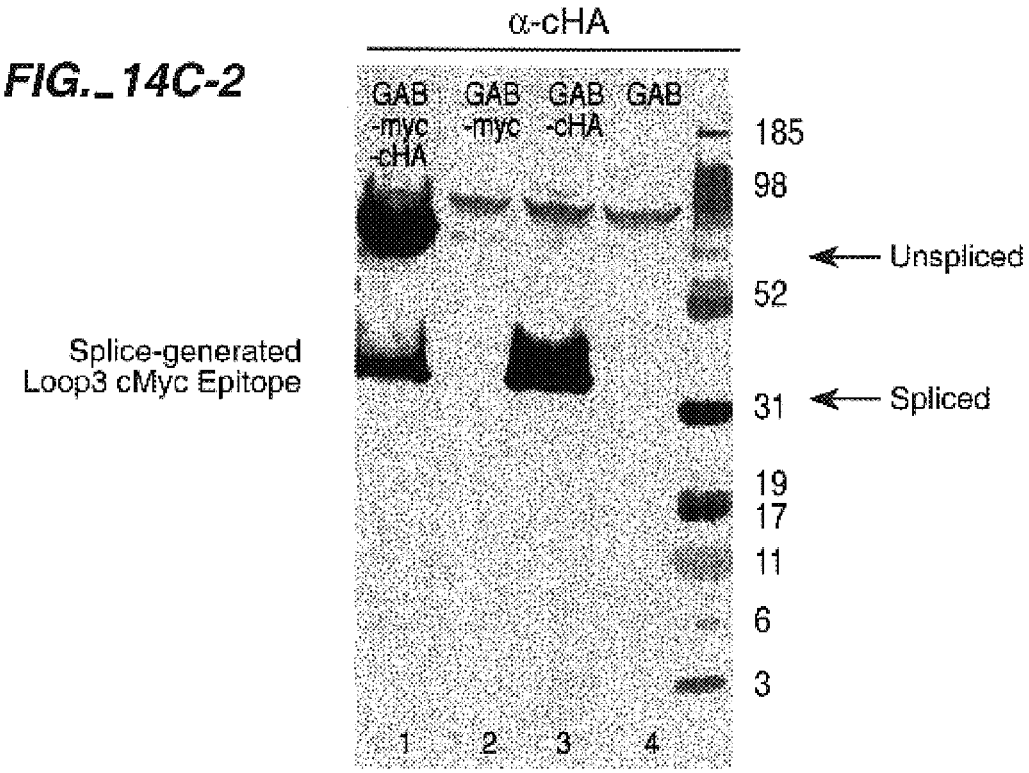

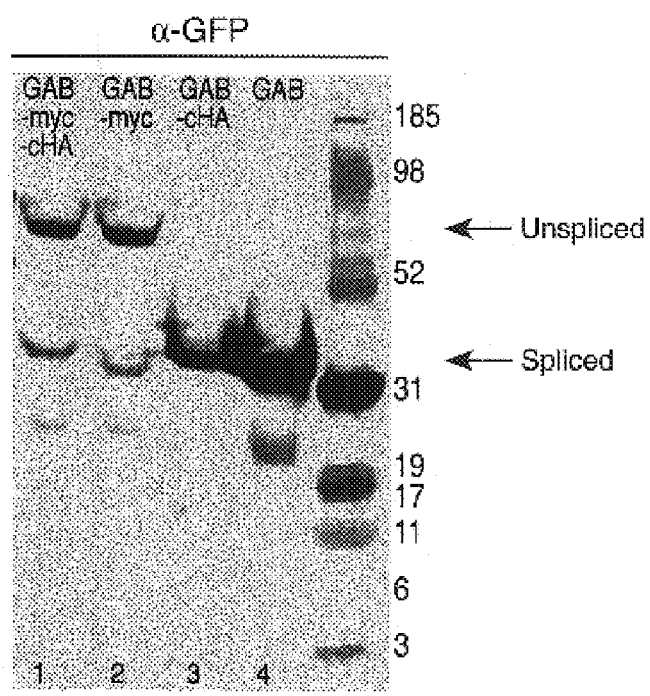
FIG._14C-3

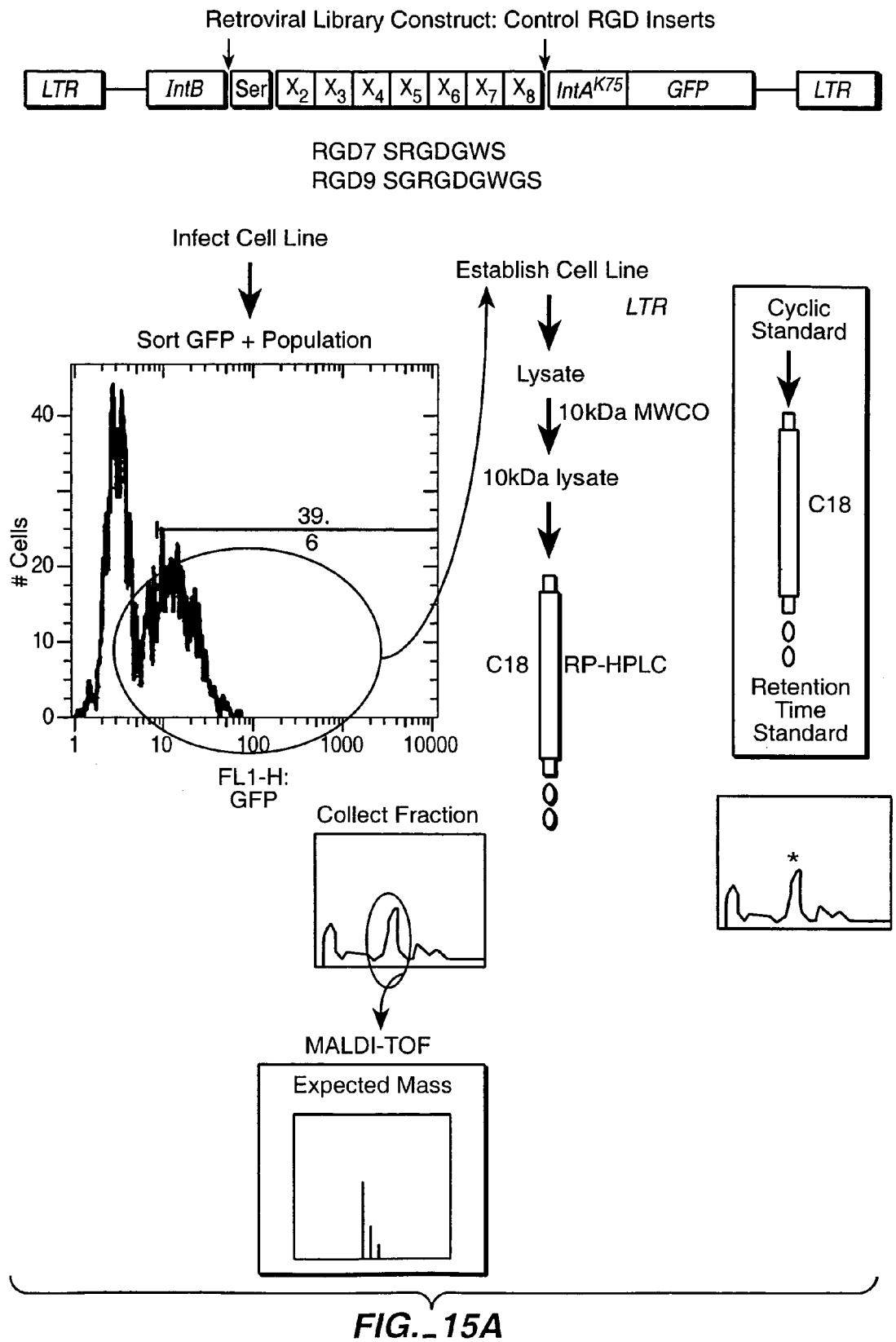
FIG._15A

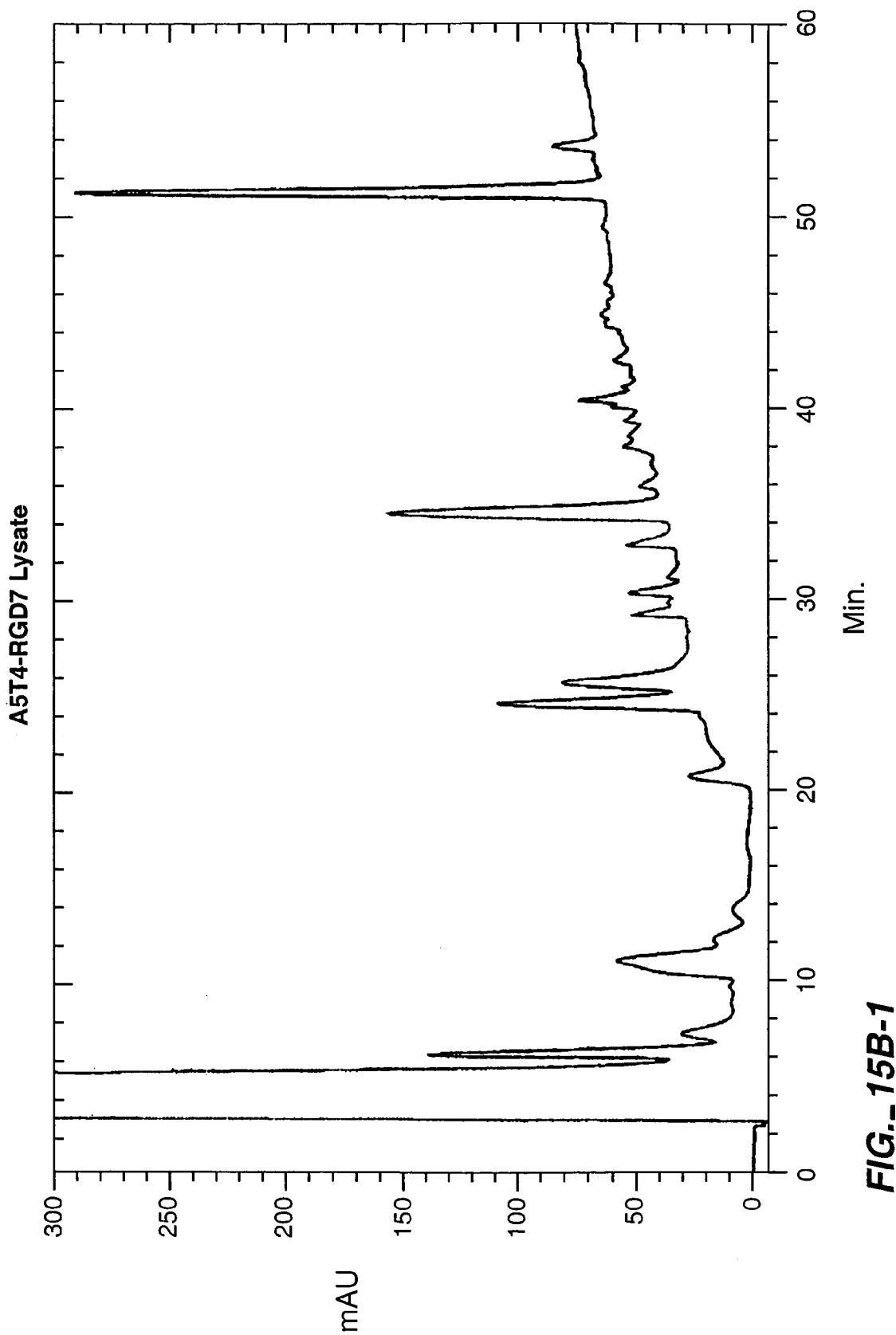
FIG._15B-1

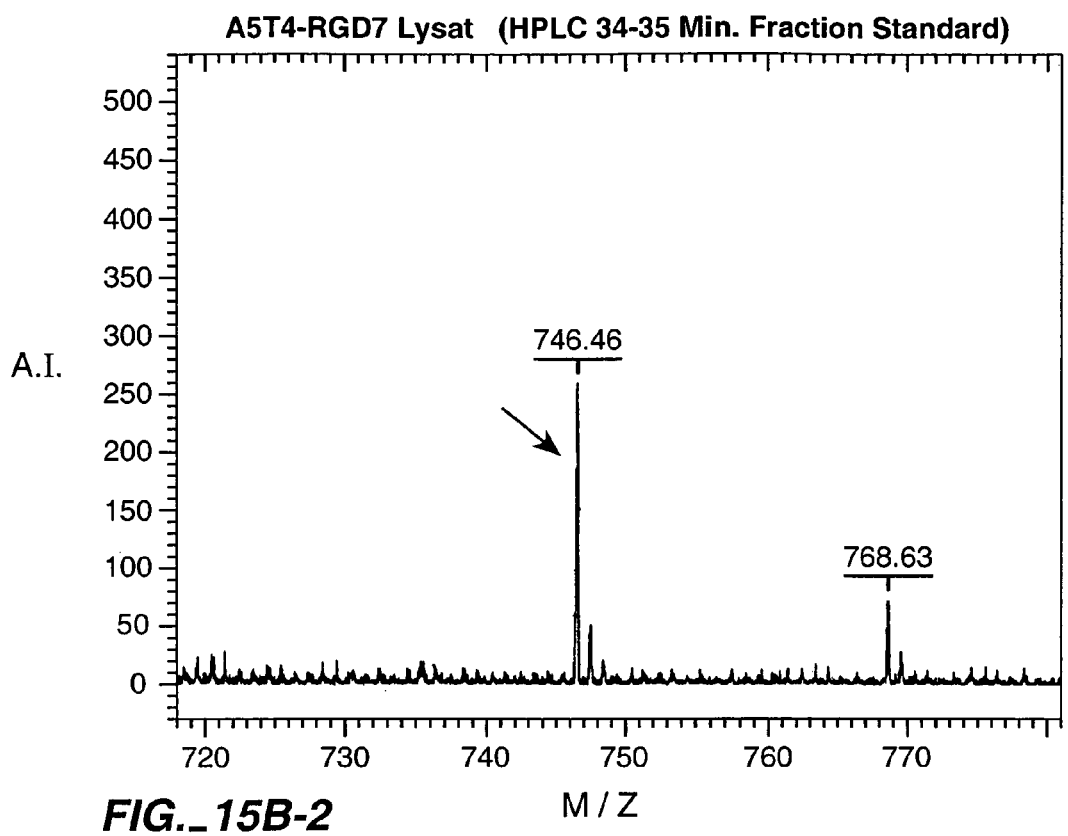
FIG._15B-2
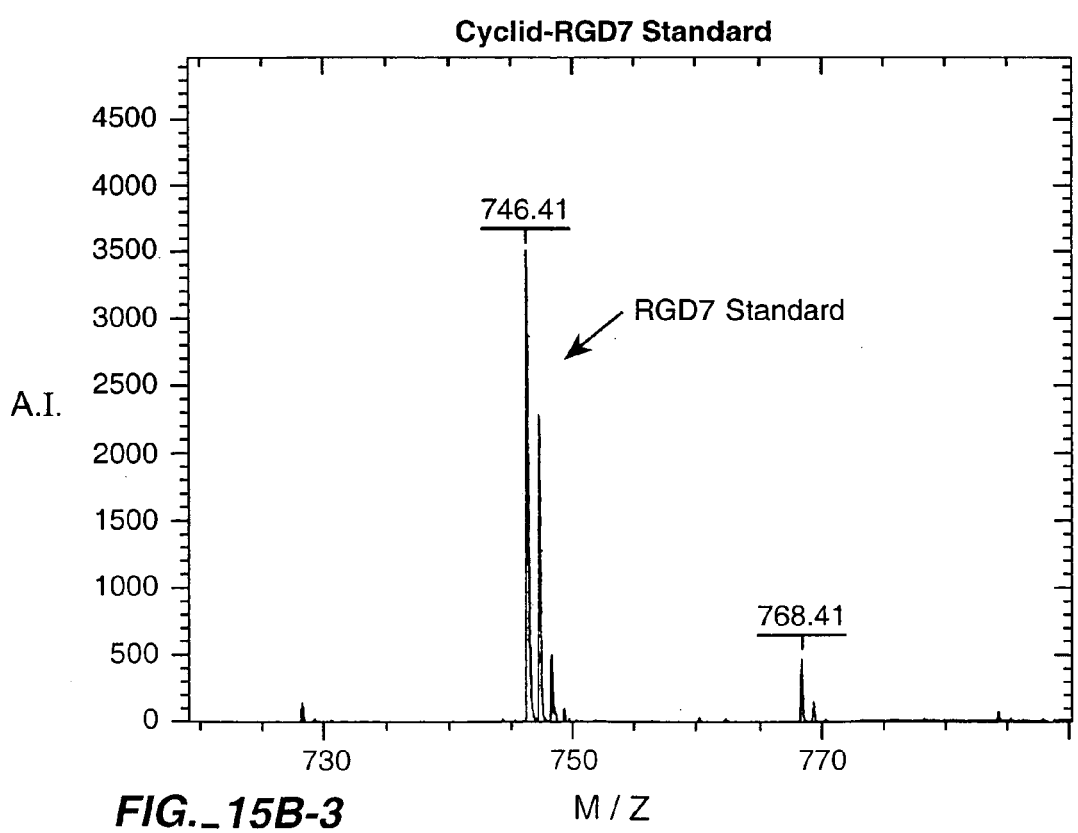
FIG._15B-3

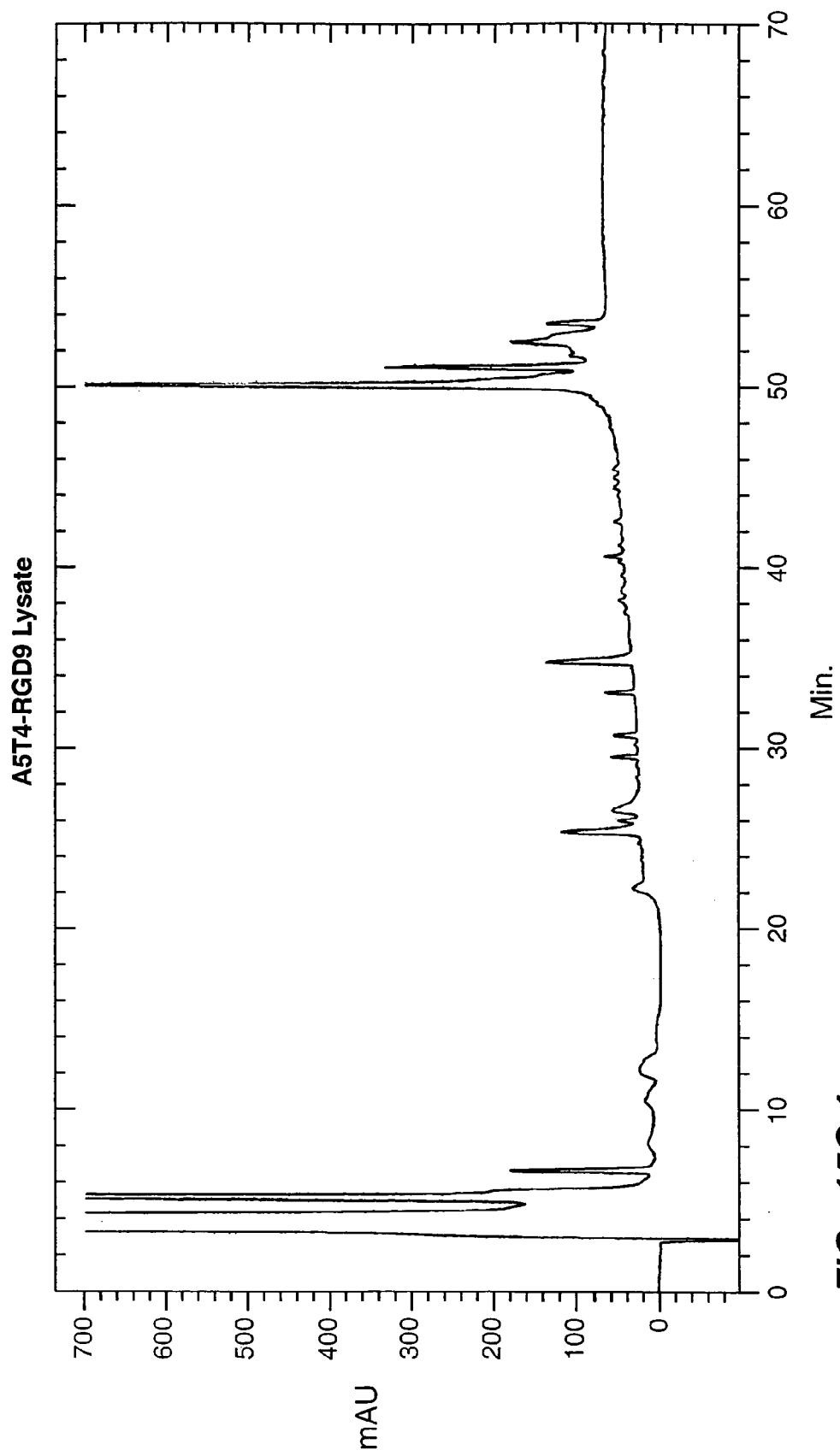
FIG._15C-1

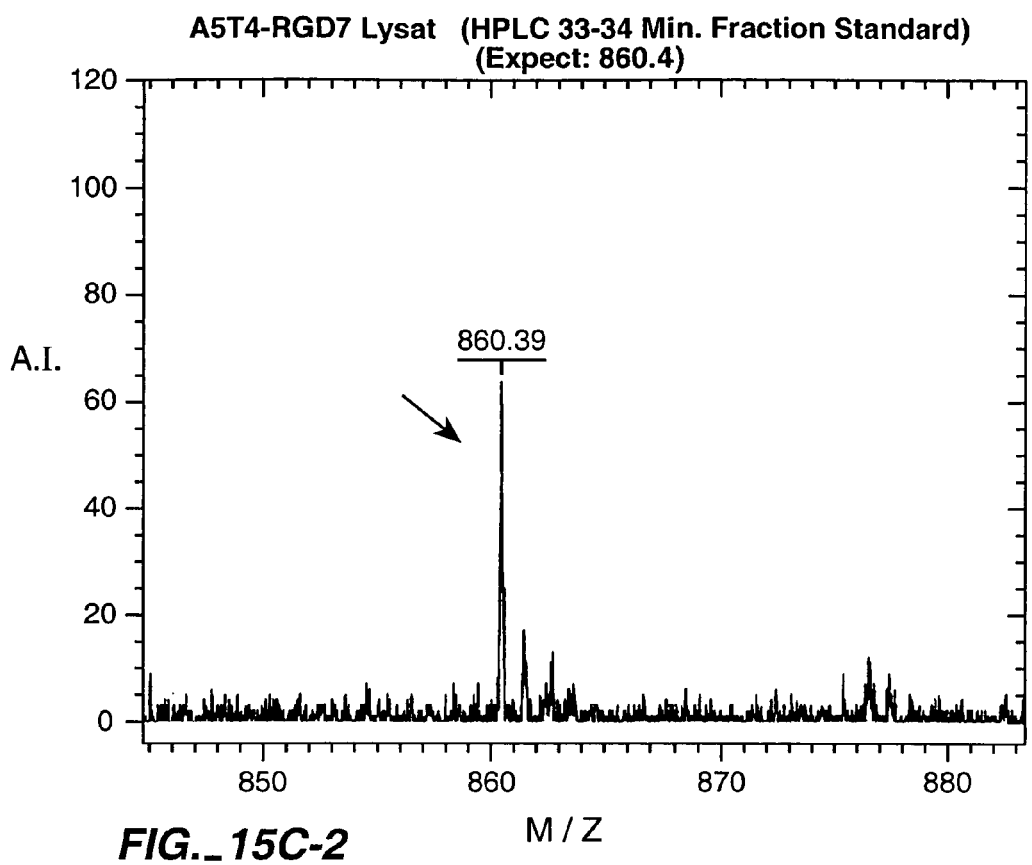
FIG._15C-2
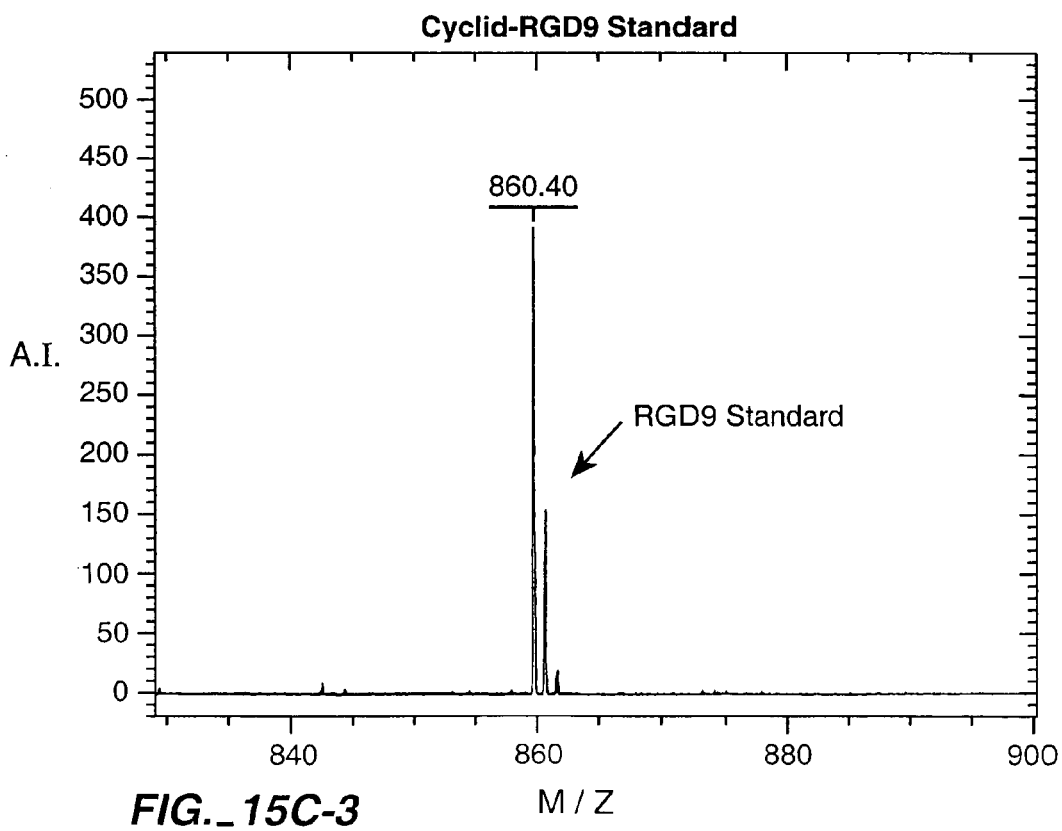
FIG._15C-3

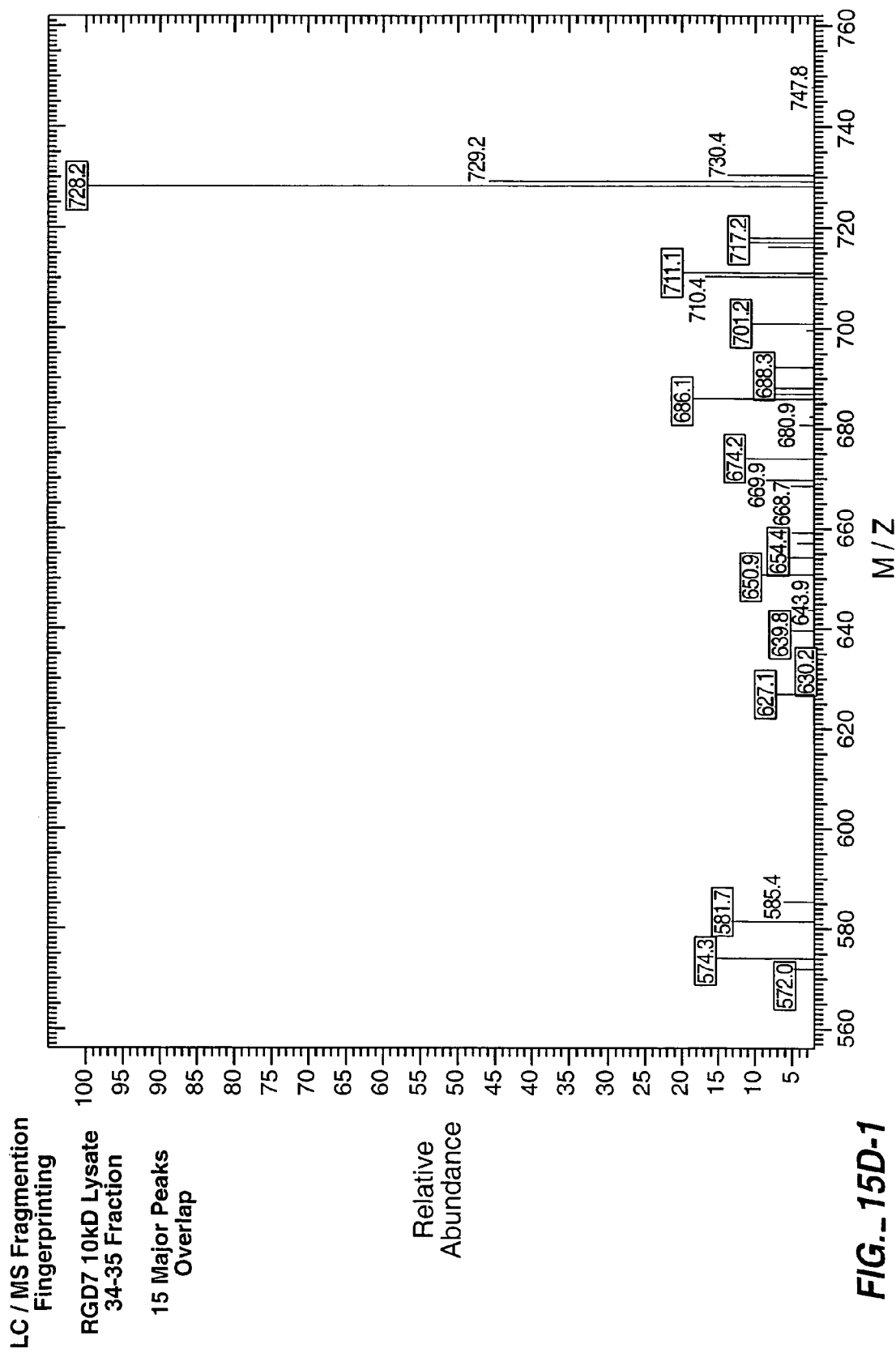

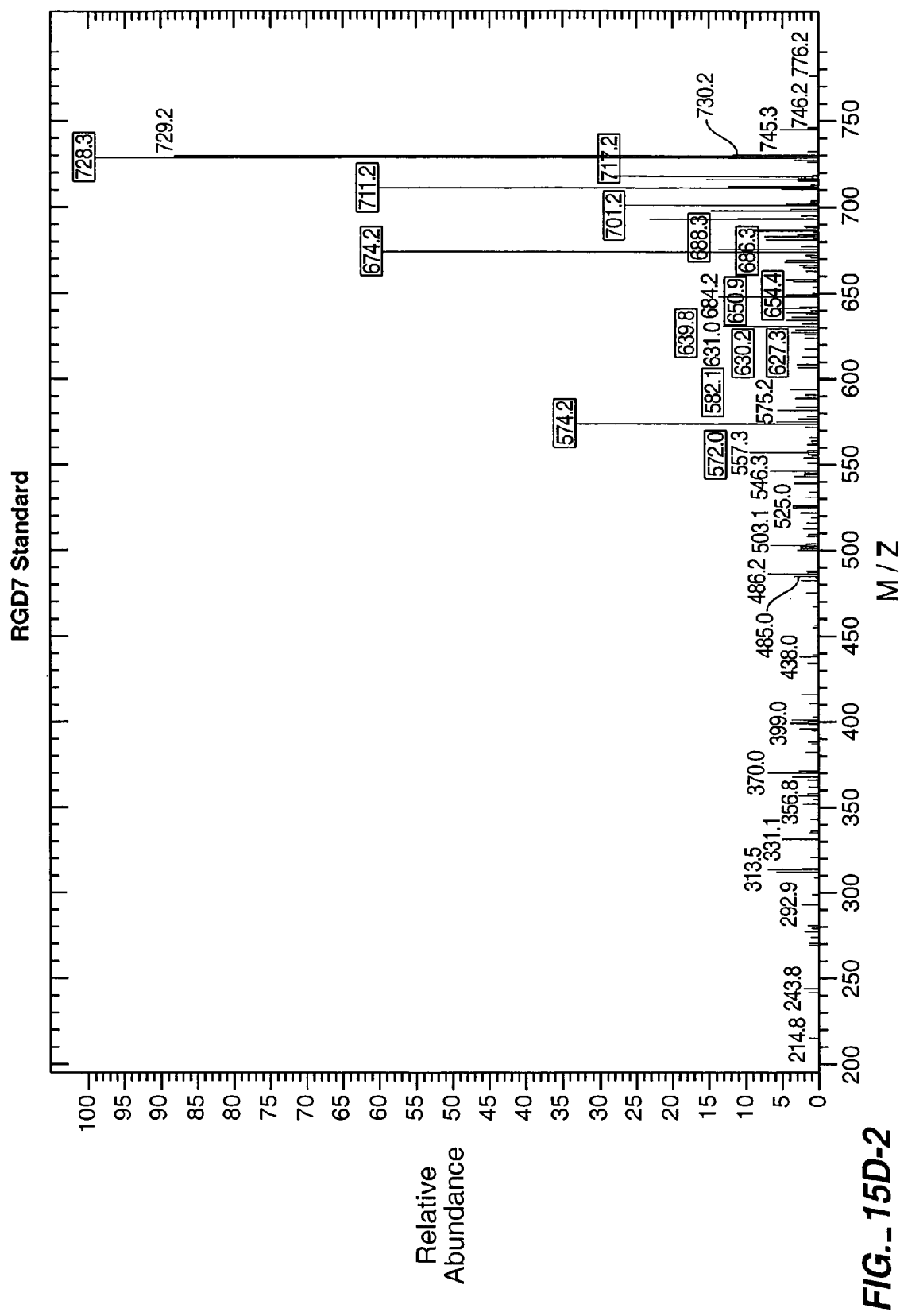

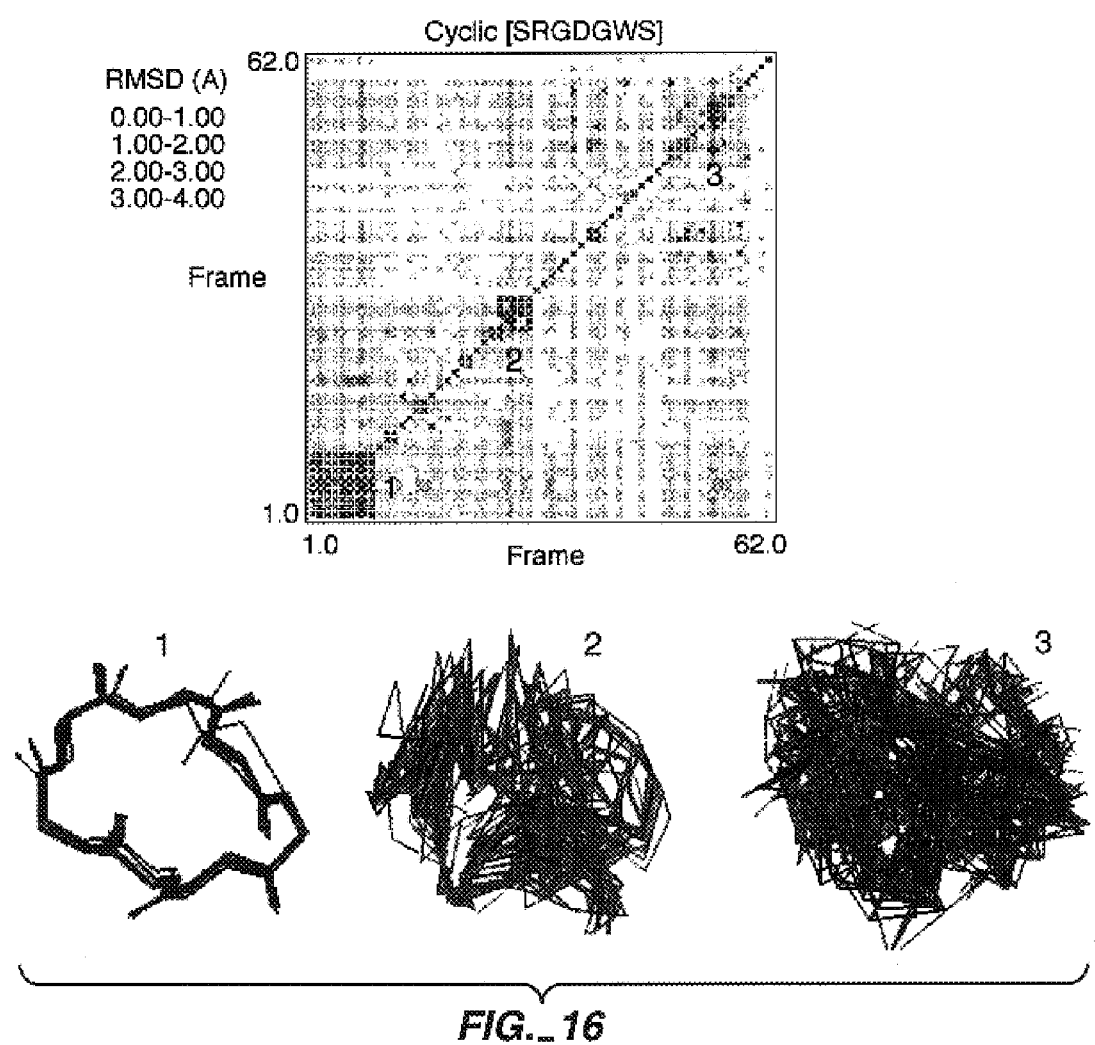
FIG._16

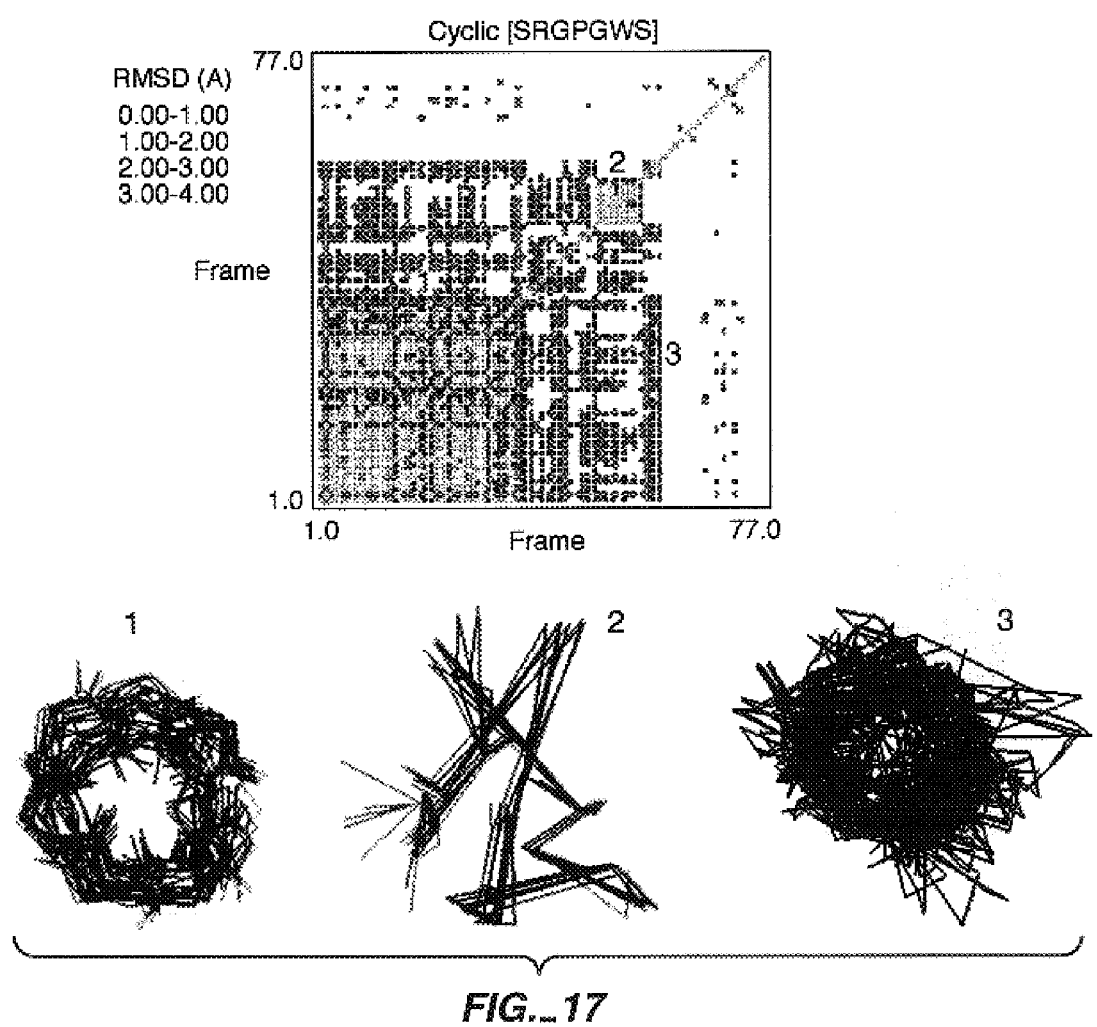
FIG._17

SEQUENCE LISTING

<160> NUMBER OF SEQ ID NOS: 90

<210> SEQ ID NO 1
<211> LENGTH: 431
<212> TYPE: PRT

<213> ORGANISM: Synechocystis PCC6803

<400> SEQUENCE: 1

```
Gly Cys Ile Ser Gly Asp Ser Leu Ile Ser Leu Ala Ser Thr Gly Lys
 1               5                  10                  15
Arg Val Ser Ile Lys Asp Leu Leu Asp Glu Lys Asp Phe Glu Ile Trp
                20                  25                  30
Ala Ile Asn Glu Gln Thr Met Lys Leu Glu Ser Ala Lys Val Ser Arg
            35                  40                  45
Val Phe Cys Thr Gly Lys Lys Leu Val Tyr Ile Leu Lys Thr Arg Leu
        50                  55                  60
Gly Arg Thr Ile Lys Ala Thr Ala Asn His Arg Phe Leu Thr Ile Asp
 65                  70                  75                  80
Gly Trp Lys Arg Leu Asp Glu Leu Ser Leu Lys Glu His Ile Ala Leu
                85                  90                  95
Pro Arg Lys Leu Glu Ser Ser Leu Gln Leu Met Ser Asp Glu Glu
                100                 105                 110
Leu Gly Leu Leu Gly His Leu Ile Gly Asp Gly Cys Thr Leu Pro Arg
            115                 120                 125
His Ala Ile Gln Tyr Thr Ser Asn Lys Ile Glu Leu Ala Glu Lys Val
        130                 135                 140
Val Glu Leu Ala Lys Ala Val Phe Gly Asp Gln Ile Asn Pro Arg Ile
145                 150                 155                 160
Ser Gln Glu Arg Gln Trp Tyr Gln Val Tyr Ile Pro Ala Ser Tyr Arg
                165                 170                 175
Leu Thr His Asn Lys Lys Asn Pro Ile Thr Lys Trp Leu Glu Asn Leu
            180                 185                 190
Asp Val Phe Gly Leu Arg Ser Tyr Glu Lys Phe Val Pro Asn Gln Val
        195                 200                 205
Phe Glu Gln Pro Gln Arg Ala Ile Ala Ile Phe Leu Arg His Leu Trp
    210                 215                 220
Ser Thr Asp Gly Cys Val Lys Leu Ile Val Glu Lys Ser Ser Arg Pro
225                 230                 235                 240
Val Ala Tyr Tyr Ala Thr Ser Ser Glu Lys Leu Ala Lys Asp Val Gln
                245                 250                 255
Ser Leu Leu Leu Lys Leu Gly Ile Asn Ala Arg Leu Ser Lys Ile Ser
            260                 265                 270
Gln Asn Gly Lys Gly Arg Asp Asn Tyr His Val Thr Ile Thr Gly Gln
        275                 280                 285
Ala Asp Leu Gln Ile Phe Val Asp Gln Ile Gly Ala Val Asp Lys Asp
    290                 295                 300
Lys Gln Ala Ser Val Glu Glu Ile Lys Thr His Ile Ala Gln His Gln
305                 310                 315                 320
Ala Asn Thr Asn Arg Asp Val Ile Pro Lys Gln Ile Trp Lys Thr Tyr
                325                 330                 335
Val Leu Pro Gln Ile Gln Ile Lys Gly Ile Thr Thr Arg Asp Leu Gln
            340                 345                 350
Met Arg Leu Gly Asn Ala Tyr Cys Gly Thr Ala Leu Tyr Lys His Asn
        355                 360                 365
Leu Ser Arg Glu Arg Ala Lys Ile Ala Thr Ile Thr Gln Ser Pro
    370                 375                 380
Glu Ile Glu Lys Leu Ser Gln Ser Asp Ile Tyr Trp Asp Ser Ile Val
385                 390                 395                 400
```

```
Ser Ile Thr Glu Thr Gly Val Glu Val Phe Asp Leu Thr Val Pro
                405                 410                 415

Gly Pro His Asn Phe Val Ala Asn Asp Ile Ile Val His Asn Ser
            420                 425                 430

<210> SEQ ID NO 2
<211> LENGTH: 200
<212> TYPE: PRT
<213> ORGANISM: Mycobacterium xenopi

<400> SEQUENCE: 2

Tyr Cys Ile Thr Gly Asp Ala Leu Val Ala Leu Pro Glu Gly Glu Ser
1               5                   10                  15

Val Arg Ile Ala Asp Ile Val Pro Gly Ala Arg Pro Asn Ser Asp Asn
            20                  25                  30

Ala Ile Asp Leu Lys Val Leu Asp Arg His Gly Asn Pro Val Leu Ala
        35                  40                  45

Asp Arg Leu Phe His Ser Gly Glu His Pro Val Tyr Thr Val Arg Thr
    50                  55                  60

Val Glu Gly Leu Arg Val Thr Gly Thr Ala Asn His Pro Leu Leu Cys
65                  70                  75                  80

Leu Val Asp Val Ala Gly Val Pro Thr Leu Leu Trp Lys Leu Ile Asp
                85                  90                  95

Glu Ile Lys Pro Gly Asp Tyr Ala Val Ile Gln Arg Ser Ala Phe Ser
            100                 105                 110

Val Asp Cys Ala Gly Phe Ala Arg Gly Lys Pro Glu Phe Ala Pro Thr
        115                 120                 125

Thr Tyr Thr Val Gly Val Pro Gly Leu Val Arg Phe Leu Glu Ala His
    130                 135                 140

His Arg Asp Pro Asp Ala Gln Ala Ile Ala Asp Glu Leu Thr Asp Gly
145                 150                 155                 160

Arg Phe Tyr Tyr Ala Lys Val Ala Ser Val Thr Asp Ala Gly Val Gln
                165                 170                 175

Pro Val Tyr Ser Leu Arg Val Asp Thr Ala Asp His Ala Phe Ile Thr
            180                 185                 190

Asn Gly Phe Val Ser His Asn Thr
        195                 200

<210> SEQ ID NO 3
<211> LENGTH: 458
<212> TYPE: PRT
<213> ORGANISM: Chlamydomonas eugamentos

<400> SEQUENCE: 3

Glu Cys Leu Thr Ser Asp His Thr Val Leu Thr Thr Arg Gly Trp Ile
1               5                   10                  15

Pro Ile Ala Asp Val Thr Leu Asp Asp Lys Val Ala Val Leu Asp Asn
            20                  25                  30

Asn Thr Gly Glu Met Ser Tyr Gln Asn Pro Gln Lys Val His Lys Tyr
        35                  40                  45

Asp Tyr Glu Gly Pro Met Tyr Glu Val Lys Thr Ala Gly Val Asp Leu
    50                  55                  60

Phe Val Thr Pro Asn His Arg Met Tyr Val Thr Thr Asn Asn Thr
65                  70                  75                  80

Thr Asn Gln Asn Tyr Asn Leu Val Glu Ala Ser Ser Ile Phe Gly Lys
                85                  90                  95
```

-continued

```
Lys Val Arg Tyr Lys Asn Asp Ala Ile Trp Asn Lys Thr Asp Tyr Gln
            100                 105                 110

Phe Ile Leu Pro Glu Thr Ala Thr Leu Thr Gly His Thr Asn Lys Ile
        115                 120                 125

Ser Ser Thr Pro Ala Ile Gln Pro Glu Met Asn Ala Trp Leu Thr Phe
    130                 135                 140

Phe Gly Leu Trp Ile Ala Asn Gly His Thr Thr Lys Ile Ala Glu Lys
145                 150                 155                 160

Thr Ala Glu Asn Asn Gln Gln Lys Gln Arg Tyr Lys Val Ile Leu Thr
                165                 170                 175

Gln Val Lys Glu Asp Val Cys Asp Ile Ile Glu Gln Thr Leu Asn Lys
            180                 185                 190

Leu Gly Phe Asn Phe Ile Arg Ser Gly Lys Asp Tyr Thr Ile Glu Asn
        195                 200                 205

Lys Gln Leu Trp Ser Tyr Leu Asn Pro Phe Asp Asn Gly Ala Leu Asn
    210                 215                 220

Lys Tyr Leu Pro Asp Trp Val Trp Glu Leu Ser Ser Gln Gln Cys Lys
225                 230                 235                 240

Ile Leu Leu Asn Ser Leu Cys Leu Gly Asn Cys Leu Phe Thr Lys Asn
                245                 250                 255

Asp Asp Thr Leu His Tyr Phe Ser Thr Ser Glu Arg Phe Ala Asn Asp
            260                 265                 270

Val Ser Arg Leu Ala Leu His Ala Gly Thr Thr Ser Thr Ile Gln Leu
        275                 280                 285

Glu Ala Ala Pro Ser Asn Leu Tyr Asp Thr Ile Ile Gly Leu Pro Val
    290                 295                 300

Glu Val Asn Thr Thr Leu Trp Arg Val Ile Ile Asn Gln Ser Ser Phe
305                 310                 315                 320

Tyr Ser Tyr Ser Thr Asp Lys Ser Ser Ala Leu Asn Leu Ser Asn Asn
                325                 330                 335

Val Ala Cys Tyr Val Asn Ala Gln Ser Ala Leu Thr Leu Glu Gln Asn
            340                 345                 350

Ser Gln Lys Ile Asn Lys Asn Thr Leu Val Leu Thr Lys Asn Asn Val
        355                 360                 365

Lys Ser Gln Thr Met His Ser Gln Arg Ala Glu Arg Val Asp Thr Ala
    370                 375                 380

Leu Leu Thr Gln Lys Glu Leu Asp Asn Ser Leu Asn His Glu Ile Leu
385                 390                 395                 400

Ile Asn Lys Asn Pro Gly Thr Ser Gln Leu Glu Cys Val Val Asn Pro
                405                 410                 415

Glu Val Asn Asn Thr Ser Thr Asn Asp Arg Phe Val Tyr Tyr Lys Gly
            420                 425                 430

Pro Val Tyr Cys Leu Thr Gly Pro Asn Asn Val Phe Tyr Val Gln Arg
        435                 440                 445

Asn Gly Lys Ala Val Trp Thr Gly Asn Ser
    450                 455

<210> SEQ ID NO 4
<211> LENGTH: 341
<212> TYPE: PRT
<213> ORGANISM: Chilo iridescent virus

<400> SEQUENCE: 4

Leu Cys Val Ala Pro Glu Thr Met Ile Leu Thr Glu Asp Gly Gln Phe
1               5                   10                  15
```

```
Pro Ile Lys Asp Leu Glu Gly Lys Ile Ile Lys Val Trp Asn Gly Asn
            20                  25                  30

Glu Phe Ser Ser Val Thr Val Lys Thr Gly Thr Glu Lys Glu Leu
        35                  40                  45

Leu Glu Val Glu Leu Ser Asn Gly Cys Thr Leu Ser Cys Thr Pro Glu
    50                  55                  60

His Lys Phe Ile Ile Val Lys Ser Tyr Thr Glu Ala Lys Lys Gln Lys
65                  70                  75                  80

Thr Asp Asp Asn Ala Ile Ala Asn Ala Glu Arg Val Asp Ala Gln Asp
                85                  90                  95

Leu Lys Pro Arg Met Lys Leu Ile Lys Phe Asp Leu Pro Thr Leu Phe
            100                 105                 110

Gly Asn Ser Glu His Asp Ile Lys Tyr Pro Tyr Thr His Gly Phe Phe
                115                 120                 125

Cys Gly Asp Gly Thr Tyr Thr Lys Tyr Gly Lys Pro Gln Leu Ser Leu
130                 135                 140

Tyr Gly Asp Lys Lys Glu Leu Leu Thr Tyr Leu Asp Val Arg Thr Met
145                 150                 155                 160

Thr Gly Leu Glu Asp Ala Ser Gly Arg Leu Asn Thr Trp Leu Pro Leu
                165                 170                 175

Asp Leu Ala Pro Lys Phe Asp Val Pro Ile Asn Ser Ser Leu Glu Cys
            180                 185                 190

Arg Met Glu Trp Leu Ala Gly Tyr Leu Asp Ala Asp Gly Cys Val Phe
        195                 200                 205

Arg Asn Gly Thr Asn Glu Ser Ile Gln Val Ser Cys Ile His Leu Asp
210                 215                 220

Phe Leu Lys Arg Ile Gln Leu Leu Ile Gly Met Gly Val Thr Ser
225                 230                 235                 240

Lys Ile Thr Lys Leu His Asp Glu Lys Ile Thr Thr Met Pro Asp Gly
            245                 250                 255

Lys Gly Gly Gln Lys Pro Tyr Ser Cys Lys Pro Ile Trp Arg Leu Phe
        260                 265                 270

Ile Ser Ser Ser Gly Leu Tyr His Leu Ser Glu Gln Gly Phe Glu Thr
    275                 280                 285

Arg Arg Leu Lys Trp Glu Pro Arg Gln Pro Gln Arg Asn Ala Glu Arg
290                 295                 300

Phe Val Glu Val Leu Lys Val Asn Lys Thr Gly Arg Val Asp Asp Thr
305                 310                 315                 320

Tyr Cys Phe Thr Glu Pro Ile Asn His Ala Gly Val Phe Asn Gly Ile
                325                 330                 335

Leu Thr Gly Gln Cys
            340

<210> SEQ ID NO 5
<211> LENGTH: 473
<212> TYPE: PRT
<213> ORGANISM: Candida tropicalis

<400> SEQUENCE: 5

Gly Cys Phe Thr Lys Gly Thr Gln Val Met Met Ala Asp Gly Ala Asp
1               5                   10                  15

Lys Ser Ile Glu Ser Ile Glu Val Gly Asp Lys Val Met Gly Lys Asp
            20                  25                  30

Gly Met Pro Arg Glu Val Val Gly Leu Pro Arg Gly Tyr Asp Asp Met
```

-continued

```
             35                   40                   45
Tyr Lys Val Arg Gln Leu Ser Ser Thr Arg Arg Asn Ala Lys Ser Glu
 50                   55                   60
Gly Leu Met Asp Phe Thr Val Ser Ala Asp His Lys Leu Ile Leu Lys
 65                   70                   75                   80
Thr Lys Gln Asp Val Lys Ile Ala Thr Arg Lys Ile Gly Gly Asn Thr
                 85                   90                   95
Tyr Thr Gly Val Thr Phe Tyr Val Leu Glu Lys Thr Lys Thr Gly Ile
                100                  105                  110
Glu Leu Val Lys Ala Lys Thr Lys Val Phe Gly His His Ile His Gly
                115                  120                  125
Gln Asn Gly Ala Glu Glu Lys Ala Ala Thr Phe Ala Ala Gly Ile Asp
                130                  135                  140
Ser Lys Glu Tyr Ile Asp Trp Ile Ile Glu Ala Arg Asp Tyr Val Gln
145                  150                  155                  160
Val Asp Glu Ile Val Lys Thr Ser Thr Thr Gln Met Ile Asn Pro Val
                165                  170                  175
His Phe Glu Ser Gly Lys Leu Gly Asn Trp Leu His Glu His Lys Gln
                180                  185                  190
Asn Lys Ser Leu Ala Pro Gln Leu Gly Tyr Leu Leu Gly Thr Trp Ala
                195                  200                  205
Gly Ile Gly Asn Val Lys Ser Ser Ala Phe Thr Met Asn Ser Lys Asp
                210                  215                  220
Asp Val Lys Leu Ala Thr Arg Ile Met Asn Tyr Ser Ser Lys Leu Gly
225                  230                  235                  240
Met Thr Cys Ser Ser Thr Glu Ser Gly Glu Leu Asn Val Ala Glu Asn
                245                  250                  255
Glu Glu Glu Phe Phe Asn Asn Leu Gly Ala Glu Lys Asp Glu Ala Gly
                260                  265                  270
Asp Phe Thr Phe Asp Glu Phe Thr Asp Ala Met Asp Glu Leu Thr Ile
                275                  280                  285
Asn Val His Gly Ala Ala Ala Ser Lys Lys Asn Asn Leu Leu Trp Asn
                290                  295                  300
Ala Leu Lys Ser Leu Gly Phe Arg Ala Lys Ser Thr Asp Ile Val Lys
305                  310                  315                  320
Ser Ile Pro Gln His Ile Ala Val Asp Asp Ile Val Val Arg Glu Ser
                325                  330                  335
Leu Ile Ala Gly Leu Val Asp Ala Ala Gly Asn Val Glu Thr Lys Ser
                340                  345                  350
Asn Gly Ser Ile Glu Ala Val Val Arg Thr Ser Phe Arg His Val Ala
                355                  360                  365
Arg Gly Leu Val Lys Ile Ala His Ser Leu Gly Ile Glu Ser Ser Ile
370                  375                  380
Asn Ile Lys Asp Thr His Ile Asp Ala Ala Gly Val Arg Gln Glu Phe
385                  390                  395                  400
Ala Cys Ile Val Asn Leu Thr Gly Ala Pro Leu Ala Gly Val Leu Ser
                405                  410                  415
Lys Cys Ala Leu Ala Arg Asn Gln Thr Pro Val Val Lys Phe Thr Arg
                420                  425                  430
Asp Pro Val Leu Phe Asn Phe Asp Leu Ile Lys Ser Ala Lys Glu Asn
                435                  440                  445
Tyr Tyr Gly Ile Thr Leu Ala Glu Glu Thr Asp His Gln Phe Leu Leu
450                  455                  460
```

-continued

Ser Asn Met Ala Leu Val His Asn Cys
465                 470

<210> SEQ ID NO 6
<211> LENGTH: 162
<212> TYPE: PRT
<213> ORGANISM: Guillardia theta

<400> SEQUENCE: 6

Gly Cys Leu Ser Tyr Ala Thr Asn Gln Pro Tyr Phe Leu Lys Ser Asp
1               5                   10                  15

Asn Val Asn Phe Ser Lys Leu Thr Ser Leu Lys Val Ser Asn His Tyr
                20                  25                  30

Ile Leu Ser Ala Thr Leu Glu Leu Leu Ile Pro Phe Gln Tyr Asn Arg
            35                  40                  45

Ile Tyr Pro Ile Val Ser Leu Ile Lys Arg Glu Leu Gln Thr Gly Tyr
        50                  55                  60

Lys Val Val Tyr Glu Leu Asp Phe Tyr Ile Ser Val Ile Val Ser Thr
65                  70                  75                  80

Val Glu His Tyr Val Leu Thr Leu Asn Gly Trp Lys Arg Ile Leu Glu
                85                  90                  95

Leu Thr Val Asp Asp Leu Val Ala Thr Leu Asp Ile Gln Tyr Leu Ile
            100                 105                 110

Tyr Asn Asn Thr Glu Val Asp Leu Phe Ser Ser Asn Val Ile Phe Ser
        115                 120                 125

Ser Val Ile Asn Leu Ile Cys Met Asn Arg Ile Asn Val Tyr Asp Phe
130                 135                 140

Trp Ile Pro Lys Thr Asn Asn Phe Phe Val Asn Ala Leu Leu Val His
145                 150                 155                 160

Asn Ser

<210> SEQ ID NO 7
<211> LENGTH: 152
<212> TYPE: PRT
<213> ORGANISM: Porphyra purpurea

<400> SEQUENCE: 7

Gly Cys Ile Ser Lys Phe Ser His Ile Met Trp Ser His Val Ser Lys
1               5                   10                  15

Pro Leu Phe Asn Phe Ser Ile Lys Lys Ser His Met Asn Phe Asn
                20                  25                  30

Lys Asn Ile Tyr Gln Leu Leu Asp Gln Gly Glu Ala Phe Ile Ser Arg
            35                  40                  45

Gln Asp Lys Lys Thr Thr Tyr Lys Ile Arg Thr Asn Ser Glu Lys Tyr
        50                  55                  60

Leu Glu Leu Thr Ser Asn His Lys Ile Leu Thr Leu Arg Gly Trp Gln
65                  70                  75                  80

Arg Cys Asp Gln Leu Leu Cys Asn Asp Met Ile Thr Thr Gln Ile Gly
                85                  90                  95

Phe Glu Leu Ser Arg Lys Lys Lys Tyr Leu Leu Asn Cys Ile Pro Phe
            100                 105                 110

Ser Leu Cys Asn Phe Glu Thr Leu Ala Asn Ile Asn Ile Ser Asn Phe
        115                 120                 125

Gln Asn Val Phe Asp Phe Ala Ala Asn Pro Ile Pro Asn Phe Ile Ala
130                 135                 140

-continued

Asn Asn Ile Ile Val His Asn Ser
145                 150

<210> SEQ ID NO 8
<211> LENGTH: 456
<212> TYPE: PRT
<213> ORGANISM: Saccharomyces cerevisiae

<400> SEQUENCE: 8

Gly Cys Phe Ala Lys Gly Thr Asn Val Leu Met Ala Asp Gly Ser Ile
1               5                   10                  15

Glu Cys Ile Glu Asn Ile Glu Val Gly Asn Lys Val Met Gly Lys Asp
            20                  25                  30

Gly Arg Pro Arg Glu Val Ile Lys Leu Pro Arg Gly Arg Glu Thr Met
        35                  40                  45

Tyr Ser Val Val Gln Lys Ser Gln His Arg Ala His Lys Ser Asp Ser
    50                  55                  60

Ser Arg Glu Val Pro Glu Leu Leu Lys Phe Thr Cys Asn Ala Thr His
65                  70                  75                  80

Glu Leu Val Val Arg Thr Pro Arg Ser Val Arg Arg Leu Ser Arg Thr
                85                  90                  95

Ile Lys Gly Val Glu Tyr Phe Glu Val Ile Thr Phe Glu Met Gly Gln
            100                 105                 110

Lys Lys Ala Pro Asp Gly Arg Ile Val Glu Leu Val Lys Glu Val Ser
        115                 120                 125

Lys Ser Tyr Pro Ile Ser Glu Gly Pro Glu Arg Ala Asn Glu Leu Val
    130                 135                 140

Glu Ser Tyr Arg Lys Ala Ser Asn Lys Ala Tyr Phe Glu Trp Thr Ile
145                 150                 155                 160

Glu Ala Arg Asp Leu Ser Leu Gly Ser His Val Arg Lys Ala Thr
                165                 170                 175

Tyr Gln Thr Tyr Ala Pro Ile Leu Tyr Glu Asn Asp His Phe Phe Asp
            180                 185                 190

Tyr Met Gln Lys Ser Lys Phe His Leu Thr Ile Glu Gly Pro Lys Val
        195                 200                 205

Leu Ala Tyr Leu Leu Gly Leu Trp Ile Gly Asp Gly Leu Ser Asp Arg
    210                 215                 220

Ala Thr Phe Ser Val Asp Ser Arg Asp Thr Ser Leu Met Glu Arg Val
225                 230                 235                 240

Thr Glu Tyr Ala Glu Lys Leu Asn Leu Cys Ala Glu Tyr Lys Asp Arg
                245                 250                 255

Lys Glu Pro Gln Val Ala Lys Thr Val Asn Leu Tyr Ser Lys Val Val
            260                 265                 270

Arg Gly Asn Gly Ile Arg Asn Asn Leu Asn Thr Glu Asn Pro Leu Trp
        275                 280                 285

Asp Ala Ile Val Gly Leu Gly Phe Leu Lys Asp Gly Val Lys Asn Ile
    290                 295                 300

Pro Ser Phe Leu Ser Thr Asp Asn Ile Gly Thr Arg Glu Thr Phe Leu
305                 310                 315                 320

Ala Gly Leu Ile Asp Ser Asp Gly Tyr Val Thr Asp Glu His Gly Ile
                325                 330                 335

Lys Ala Thr Ile Lys Thr Ile His Thr Ser Val Arg Asp Gly Leu Val
            340                 345                 350

Ser Leu Ala Arg Ser Leu Gly Leu Val Val Ser Val Asn Ala Glu Pro
        355                 360                 365

```
Ala Lys Val Asp Met Asn Gly Thr Lys His Lys Ile Ser Tyr Ala Ile
    370                 375                 380

Tyr Met Ser Gly Gly Asp Val Leu Leu Asn Val Leu Ser Lys Cys Ala
385                 390                 395                 400

Gly Ser Lys Lys Phe Arg Pro Ala Pro Ala Ala Phe Ala Arg Glu
            405                 410                 415

Cys Arg Gly Phe Tyr Phe Glu Leu Gln Glu Leu Lys Glu Asp Asp Tyr
            420                 425                 430

Tyr Gly Ile Thr Leu Ser Asp Asp Ser Asp His Gln Phe Leu Leu Ala
            435                 440                 445

Asn Gln Val Val Val His Asn Cys
    450                 455

<210> SEQ ID NO 9
<211> LENGTH: 366
<212> TYPE: PRT
<213> ORGANISM: Mycobacterium flavescens

<400> SEQUENCE: 9

Gly Cys Phe Ala Tyr Gly Thr Arg Gly Ala Leu Ala Asp Gly Thr Thr
1               5                   10                  15

Glu Lys Ile Gly Lys Ile Val Asn Gln Lys Met Asp Val Glu Val Met
            20                  25                  30

Ser Tyr Asp Pro Asp Thr Asp Gln Val Val Pro Arg Lys Val Val Asn
        35                  40                  45

Trp Phe Asn Asn Gly Pro Ala Glu Gln Phe Leu Gln Phe Thr Val Glu
    50                  55                  60

Lys Ser Gly Gly Asn Gly Lys Ser Gln Phe Ala Ala Thr Pro Asn His
65                  70                  75                  80

Leu Ile Arg Thr Pro Ala Gly Trp Thr Glu Ala Gly Asp Leu Val Ala
                85                  90                  95

Gly Asp Arg Val Met Ala Ala Glu Pro His Arg Leu Ser Asp Gln Gln
            100                 105                 110

Phe Gln Val Val Leu Gly Ser Leu Met Gly Asp Gly Asn Leu Ser Pro
        115                 120                 125

Asn Arg Arg Asp Arg Asn Gly Val Arg Phe Arg Met Gly His Gly Ala
130                 135                 140

Lys Gln Val Asp Tyr Leu Gln Trp Lys Thr Ala Leu Leu Gly Asn Ile
145                 150                 155                 160

Lys His Ser Thr His Val Asn Asp Lys Gly Ala Thr Phe Val Asp Phe
                165                 170                 175

Thr Pro Leu Pro Glu Leu Ala Glu Leu Gln Arg Ala Val Tyr Leu Gly
            180                 185                 190

Asp Gly Lys Lys Phe Leu Ser Glu Glu Asn Phe Lys Ala Leu Thr Pro
        195                 200                 205

Leu Ala Leu Val Phe Trp Tyr Met Asp Asp Gly Pro Phe Thr Val Arg
    210                 215                 220

Ser Lys Gly Leu Gln Glu Arg Thr Ala Gly Ser Gly Arg Ile Glu
225                 230                 235                 240

Ile Cys Val Glu Ala Met Ser Glu Gly Asn Arg Ile Arg Leu Arg Asp
                245                 250                 255

Tyr Leu Arg Asp Thr His Gly Leu Asp Val Arg Leu Arg Leu Ser Gly
            260                 265                 270

Ala Ala Gly Lys Ser Val Leu Val Phe Ser Thr Ala Ser Ser Ala Lys
```

```
                275                 280                 285
Phe Gln Glu Leu Val Ala Pro Tyr Ile Thr Pro Ser Met Glu Tyr Lys
        290                 295                 300

Leu Leu Pro Arg Phe Arg Gly Gln Gly Ala Val Thr Pro Gln Phe Val
305                 310                 315                 320

Glu Pro Thr Gln Arg Leu Val Pro Ala Arg Val Leu Asp Val His Val
                325                 330                 335

Lys Pro His Thr Arg Ser Met Asn Arg Phe Asp Ile Glu Val Glu Gly
            340                 345                 350

Asn His Asn Tyr Phe Val Asp Gly Val Met Val His Asn Ser
            355                 360                 365

<210> SEQ ID NO 10
<211> LENGTH: 124
<212> TYPE: PRT
<213> ORGANISM: Synechocystis PCC6803

<400> SEQUENCE: 10

Tyr Cys Leu Ser Phe Gly Thr Glu Ile Leu Thr Val Glu Tyr Gly Pro
1               5                   10                  15

Leu Pro Ile Gly Lys Ile Val Ser Glu Ile Asn Cys Ser Val Tyr
            20                  25                  30

Ser Val Asp Pro Glu Gly Arg Val Tyr Thr Gln Ala Ile Ala Gln Trp
        35                  40                  45

His Asp Arg Gly Glu Gln Glu Val Leu Glu Tyr Glu Leu Glu Asp Gly
    50                  55                  60

Ser Val Ile Arg Ala Thr Ser Asp His Arg Phe Leu Thr Thr Asp Tyr
65                  70                  75                  80

Gln Leu Leu Ala Ile Glu Glu Ile Phe Ala Arg Gln Leu Asp Leu Leu
                85                  90                  95

Thr Leu Glu Asn Ile Lys Gln Thr Glu Glu Ala Leu Asp Asn His Arg
            100                 105                 110

Leu Pro Phe Pro Leu Leu Asp Ala Gly Thr Ile Lys
        115                 120

<210> SEQ ID NO 11
<211> LENGTH: 147
<212> TYPE: PRT
<213> ORGANISM: Mycobacterium leprae

<400> SEQUENCE: 11

Lys Ala Leu Ala Leu Asp Thr Pro Leu Pro Thr Pro Thr Gly Trp Thr
1               5                   10                  15

Ala Met Gly Asp Val Ala Val Gly Asp Glu Leu Leu Ala Val Asp Glu
            20                  25                  30

Ala Pro Thr Arg Val Val Ala Thr Glu Val Met Leu Gly Arg Pro
        35                  40                  45

Cys Tyr Glu Ile Glu Phe Ser Asp Gly Thr Val Ile Ala Asp Ala
    50                  55                  60

Gln His Gln Trp Pro Thr Ser Tyr Gly Ile Arg Thr Ser Ala Gln Leu
65                  70                  75                  80

Arg Cys Gly Leu Asp Ile Ile Ala Ala Gly Ser Thr Pro Arg His
                85                  90                  95

Ala Gly Arg Leu Thr Thr Ala Ala Phe Met Ala Pro Val Leu Cys Ile
            100                 105                 110

Asp Ser Val Arg Arg Val Arg Ser Val Pro Val Arg Cys Val Glu Val
```

```
            115                 120                 125
Asp Asn Ala Ala His Leu Tyr Leu Ala Gly Arg Gly Met Val Pro Thr
    130                 135                 140

His Asn Ser
145

<210> SEQ ID NO 12
<211> LENGTH: 170
<212> TYPE: PRT
<213> ORGANISM: Methanococcus jannaschii

<400> SEQUENCE: 12

Gly Ala Leu Ala Tyr Asp Glu Pro Ile Tyr Leu Ser Asp Gly Asn Ile
1               5                  10                  15

Ile Asn Ile Gly Glu Phe Val Asp Lys Phe Lys Lys Tyr Lys Asn
            20                  25                  30

Ser Ile Lys Lys Glu Asp Asn Gly Phe Gly Trp Ile Asp Ile Gly Asn
        35                  40                  45

Glu Asn Ile Tyr Ile Lys Ser Phe Asn Lys Leu Ser Leu Ile Ile Glu
50                  55                  60

Asp Lys Arg Ile Leu Arg Val Trp Arg Lys Lys Tyr Ser Gly Lys Leu
65                  70                  75                  80

Ile Lys Ile Thr Thr Lys Asn Arg Arg Glu Ile Thr Leu Thr His Asp
                85                  90                  95

His Pro Val Tyr Ile Ser Lys Thr Gly Glu Val Leu Glu Ile Asn Ala
            100                 105                 110

Glu Met Val Lys Val Gly Asp Tyr Ile Tyr Ile Pro Lys Asn Asn Thr
        115                 120                 125

Ile Asn Leu Asp Glu Val Ile Lys Val Glu Thr Val Asp Tyr Asn Gly
    130                 135                 140

His Ile Tyr Asp Leu Thr Val Glu Asp Asn His Thr Tyr Ile Ala Gly
145                 150                 155                 160

Lys Asn Glu Gly Phe Ala Val Ser Asn Cys
                165                 170

<210> SEQ ID NO 13
<211> LENGTH: 524
<212> TYPE: PRT
<213> ORGANISM: Pyrococcus furiosus

<400> SEQUENCE: 13

Gly Ala Leu Tyr Asp Phe Ser Val Ile Gln Leu Ser Asn Gly Arg Phe
1               5                  10                  15

Val Leu Ile Gly Asp Leu Val Glu Glu Leu Phe Lys Lys Tyr Ala Glu
            20                  25                  30

Lys Ile Lys Thr Tyr Lys Asp Leu Glu Tyr Ile Glu Leu Asn Glu Glu
        35                  40                  45

Asp Arg Phe Glu Val Val Ser Val Ser Pro Asp Leu Lys Ala Asn Lys
50                  55                  60

His Val Val Ser Arg Val Trp Arg Arg Lys Val Arg Glu Gly Glu Lys
65                  70                  75                  80

Leu Ile Arg Ile Lys Thr Arg Thr Gly Asn Glu Ile Ile Leu Thr Arg
                85                  90                  95

Asn His Pro Leu Phe Ala Phe Ser Asn Gly Asp Val Val Arg Lys Glu
            100                 105                 110

Ala Glu Lys Leu Lys Val Gly Asp Arg Val Ala Val Met Met Arg Pro
```

```
            115                 120                 125
Pro Ser Pro Gln Thr Lys Ala Val Val Asp Pro Ala Ile Tyr Val
    130                 135                 140
Lys Ile Ser Asp Tyr Tyr Leu Val Pro Asn Gly Lys Gly Met Ile Lys
145                 150                 155                 160
Val Pro Asn Asp Gly Ile Pro Pro Glu Lys Ala Gln Tyr Leu Leu Ser
                165                 170                 175
Val Asn Ser Tyr Pro Val Lys Leu Val Arg Glu Val Asp Glu Lys Leu
            180                 185                 190
Ser Tyr Leu Ala Gly Val Ile Leu Gly Asp Gly Tyr Ile Ser Ser Asn
        195                 200                 205
Gly Tyr Tyr Ile Ser Ala Thr Phe Asp Asp Glu Ala Tyr Met Asp Ala
    210                 215                 220
Phe Val Ser Val Val Ser Asp Phe Ile Pro Asn Tyr Val Pro Ser Ile
225                 230                 235                 240
Arg Lys Asn Gly Asp Tyr Thr Ile Val Thr Val Gly Ser Lys Ile Phe
                245                 250                 255
Ala Glu Met Leu Ser Arg Ile Phe Gly Ile Pro Arg Gly Arg Lys Ser
            260                 265                 270
Met Trp Asp Ile Pro Asp Val Val Leu Ser Asn Asp Asp Leu Met Arg
        275                 280                 285
Tyr Phe Ile Ala Gly Leu Phe Asp Ala Asp Gly Tyr Val Asp Glu Asn
    290                 295                 300
Gly Pro Ser Ile Val Leu Val Thr Lys Ser Glu Thr Val Ala Arg Lys
305                 310                 315                 320
Ile Trp Tyr Val Leu Gln Arg Leu Gly Ile Ile Ser Thr Val Ser Arg
                325                 330                 335
Val Lys Ser Arg Gly Phe Lys Glu Gly Glu Leu Phe Arg Val Ile Ile
            340                 345                 350
Ser Gly Val Glu Asp Leu Ala Lys Phe Ala Lys Phe Ile Pro Leu Arg
        355                 360                 365
His Ser Arg Lys Arg Ala Lys Leu Met Glu Ile Leu Arg Thr Lys Lys
    370                 375                 380
Pro Tyr Arg Gly Arg Arg Thr Tyr Arg Val Pro Ile Ser Ser Asp Met
385                 390                 395                 400
Ile Ala Pro Leu Arg Gln Met Leu Gly Leu Thr Val Ala Glu Leu Ser
                405                 410                 415
Lys Leu Ala Ser Tyr Tyr Ala Gly Glu Lys Val Ser Glu Ser Leu Ile
            420                 425                 430
Arg His Ile Glu Lys Gly Arg Val Lys Glu Ile Arg Arg Ser Thr Leu
        435                 440                 445
Lys Gly Ile Ala Leu Ala Leu Gln Gln Ile Ala Lys Asp Val Gly Asn
    450                 455                 460
Glu Glu Ala Trp Val Arg Ala Lys Arg Leu Gln Leu Ile Ala Glu Gly
465                 470                 475                 480
Asp Val Tyr Trp Asp Glu Val Val Ser Val Glu Glu Val Asp Pro Lys
                485                 490                 495
Glu Leu Gly Ile Glu Tyr Val Tyr Asp Leu Thr Val Glu Asp Asp His
            500                 505                 510
Asn Tyr Val Ala Asn Gly Ile Leu Val Ser Asn Cys
        515                 520

<210> SEQ ID NO 14
```

<211> LENGTH: 136
<212> TYPE: PRT
<213> ORGANISM: Methanobacterium thermoautotrophicum (delta H strain)

<400> SEQUENCE: 14

```
Pro Cys Val Ser Gly Asp Thr Ile Val Met Thr Ser Gly Gly Pro Arg
1               5                   10                  15

Thr Val Ala Glu Leu Glu Gly Lys Pro Phe Thr Ala Leu Ile Arg Gly
            20                  25                  30

Ser Gly Tyr Pro Cys Pro Ser Gly Phe Phe Arg Thr Cys Glu Arg Asp
        35                  40                  45

Val Tyr Asp Leu Arg Thr Arg Glu Gly His Cys Leu Arg Leu Thr His
    50                  55                  60

Asp His Arg Val Leu Val Met Asp Gly Gly Leu Glu Trp Arg Ala Ala
65                  70                  75                  80

Gly Glu Leu Glu Arg Gly Asp Arg Leu Val Met Asp Asp Ala Ala Gly
                85                  90                  95

Glu Phe Pro Ala Leu Ala Thr Phe Arg Gly Leu Arg Gly Ala Gly Arg
            100                 105                 110

Gln Asp Val Tyr Asp Ala Thr Val Tyr Gly Ala Ser Ala Phe Thr Ala
        115                 120                 125

Asn Gly Phe Ile Val His Asn Cys
    130                 135
```

<210> SEQ ID NO 15
<211> LENGTH: 456
<212> TYPE: PRT
<213> ORGANISM: Pyrococuss furiosus

<400> SEQUENCE: 15

```
Gly Cys Ile Asp Gly Lys Ala Lys Ile Ile Phe Glu Asn Glu Gly Glu
1               5                   10                  15

Glu His Leu Thr Thr Met Glu Glu Met Tyr Glu Arg Tyr Lys His Leu
            20                  25                  30

Gly Glu Phe Tyr Asp Glu Glu Tyr Asn Arg Trp Gly Ile Asp Val Ser
        35                  40                  45

Asn Val Pro Ile Tyr Val Lys Ser Phe Asp Pro Glu Ser Lys Arg Val
    50                  55                  60

Val Lys Gly Lys Val Asn Val Ile Trp Lys Tyr Glu Leu Gly Lys Asp
65                  70                  75                  80

Val Thr Lys Tyr Glu Ile Ile Thr Asn Lys Gly Thr Lys Ile Leu Thr
                85                  90                  95

Ser Pro Trp His Pro Phe Phe Val Leu Thr Pro Asp Phe Lys Ile Val
            100                 105                 110

Glu Lys Arg Ala Asp Glu Leu Lys Glu Gly Asp Ile Leu Ile Gly Gly
        115                 120                 125

Met Pro Asp Gly Glu Asp Tyr Lys Phe Ile Phe Asp Tyr Trp Leu Ala
    130                 135                 140

Gly Phe Ile Ala Gly Asp Gly Cys Phe Asp Lys Tyr His Ser His Val
145                 150                 155                 160

Lys Gly His Glu Tyr Ile Tyr Asp Arg Leu Arg Ile Tyr Asp Tyr Arg
                165                 170                 175

Ile Glu Thr Phe Glu Ile Ile Asn Asp Tyr Leu Glu Lys Thr Phe Gly
            180                 185                 190

Arg Lys Tyr Ser Ile Gln Lys Asp Arg Asn Ile Tyr Tyr Ile Asp Ile
        195                 200                 205
```

-continued

Lys Ala Arg Asn Ile Thr Ser His Tyr Leu Lys Leu Leu Glu Gly Ile
            210                 215                 220

Asp Asn Gly Ile Pro Pro Gln Ile Leu Lys Glu Gly Lys Asn Ala Val
225                 230                 235                 240

Leu Ser Phe Ile Ala Gly Leu Phe Asp Ala Glu Gly His Val Ser Asn
            245                 250                 255

Lys Pro Gly Ile Glu Leu Gly Met Val Asn Lys Arg Leu Ile Glu Asp
            260                 265                 270

Val Thr His Tyr Leu Asn Ala Leu Gly Ile Lys Ala Arg Ile Arg Glu
            275                 280                 285

Lys Leu Arg Lys Asp Gly Ile Asp Tyr Val Leu His Val Glu Glu Tyr
    290                 295                 300

Ser Ser Leu Leu Arg Phe Tyr Glu Leu Ile Gly Lys Asn Leu Gln Asn
305                 310                 315                 320

Glu Glu Lys Arg Glu Lys Leu Gly Lys Val Leu Ser Asn His Lys Gly
                325                 330                 335

Gly Asn Phe Gly Leu Pro Leu Asn Phe Asn Ala Phe Lys Glu Trp Ala
            340                 345                 350

Ser Glu Tyr Gly Val Glu Phe Lys Thr Asn Gly Ser Gln Thr Ile Ala
            355                 360                 365

Ile Ile Asn Asp Glu Arg Ile Ser Leu Gly Gln Trp His Thr Arg Asn
    370                 375                 380

Arg Val Ser Lys Ala Val Leu Val Lys Met Leu Arg Lys Leu Tyr Glu
385                 390                 395                 400

Ala Thr Lys Asp Glu Glu Val Lys Arg Met Leu His Leu Ile Glu Gly
                405                 410                 415

Leu Glu Val Val Arg His Ile Thr Thr Thr Asn Glu Pro Arg Thr Phe
            420                 425                 430

Tyr Asp Leu Thr Val Glu Asn Tyr Gln Asn Tyr Leu Ala Gly Glu Asn
            435                 440                 445

Gly Met Ile Phe Val His Asn Thr
    450                 455

<210> SEQ ID NO 16
<211> LENGTH: 539
<212> TYPE: PRT
<213> ORGANISM: Pyrocucuss sp. GB-D

<400> SEQUENCE: 16

Asn Ser Ile Leu Pro Glu Glu Trp Val Pro Leu Ile Lys Asn Gly Lys
1               5                   10                  15

Val Lys Ile Phe Arg Ile Gly Asp Phe Val Asp Gly Leu Met Lys Ala
            20                  25                  30

Asn Gln Gly Lys Val Lys Lys Thr Gly Asp Thr Glu Val Leu Glu Val
        35                  40                  45

Ala Gly Ile His Ala Phe Ser Phe Asp Arg Lys Ser Lys Lys Ala Arg
    50                  55                  60

Val Met Ala Val Lys Ala Val Ile Arg His Tyr Ser Gly Asn Val
65                  70                  75                  80

Tyr Arg Ile Val Leu Asn Ser Gly Arg Lys Ile Thr Ile Thr Glu Gly
            85                  90                  95

His Ser Leu Phe Val Tyr Arg Asn Gly Asp Leu Val Glu Ala Thr Gly
        100                 105                 110

Glu Asp Val Lys Ile Gly Asp Leu Leu Ala Val Pro Arg Ser Val Asn

-continued

```
            115                 120                 125
Leu Pro Glu Lys Arg Glu Arg Leu Asn Ile Val Glu Leu Leu Asn
    130                 135                 140
Leu Ser Pro Glu Glu Thr Glu Asp Ile Ile Leu Thr Ile Pro Val Lys
145                 150                 155                 160
Gly Arg Lys Asn Phe Phe Lys Gly Met Leu Arg Thr Leu Arg Trp Ile
                165                 170                 175
Phe Gly Glu Glu Lys Arg Val Arg Thr Ala Ser Arg Tyr Leu Arg His
                180                 185                 190
Leu Glu Asn Leu Gly Tyr Ile Arg Leu Arg Lys Ile Gly Tyr Asp Ile
                195                 200                 205
Ile Asp Lys Glu Gly Leu Glu Lys Tyr Arg Thr Leu Tyr Glu Lys Leu
210                 215                 220
Val Asp Val Val Arg Tyr Asn Gly Asn Lys Arg Glu Tyr Leu Val Glu
225                 230                 235                 240
Phe Asn Ala Val Arg Asp Val Ile Ser Leu Met Pro Glu Glu Leu
                245                 250                 255
Lys Glu Trp Arg Ile Gly Thr Arg Asn Gly Phe Arg Met Gly Thr Phe
                260                 265                 270
Val Asp Ile Asp Glu Asp Phe Ala Lys Leu Leu Gly Tyr Tyr Val Ser
                275                 280                 285
Glu Gly Ser Ala Arg Lys Trp Lys Asn Gln Thr Gly Gly Trp Ser Tyr
                290                 295                 300
Thr Val Arg Leu Tyr Asn Glu Asn Asp Glu Val Leu Asp Asp Met Glu
305                 310                 315                 320
His Leu Ala Lys Lys Phe Phe Gly Lys Val Arg Gly Lys Asn Tyr
                325                 330                 335
Val Glu Ile Pro Lys Lys Met Ala Tyr Ile Ile Phe Glu Ser Leu Cys
                340                 345                 350
Gly Thr Leu Ala Glu Asn Lys Arg Val Pro Glu Val Ile Phe Thr Ser
                355                 360                 365
Ser Lys Gly Val Arg Trp Ala Phe Leu Glu Gly Tyr Phe Ile Gly Asp
    370                 375                 380
Gly Asp Val His Pro Ser Lys Arg Val Arg Leu Ser Thr Lys Ser Glu
385                 390                 395                 400
Leu Leu Val Asn Gly Leu Val Leu Leu Asn Ser Leu Gly Val Ser
                405                 410                 415
Ala Ile Lys Leu Gly Tyr Asp Ser Gly Val Tyr Arg Val Tyr Val Asn
                420                 425                 430
Glu Glu Leu Lys Phe Thr Glu Tyr Arg Lys Lys Asn Val Tyr His
                435                 440                 445
Ser His Ile Val Pro Lys Asp Ile Leu Lys Glu Thr Phe Gly Lys Val
    450                 455                 460
Phe Gln Lys Asn Ile Ser Tyr Lys Lys Phe Arg Glu Leu Val Glu Asn
465                 470                 475                 480
Gly Lys Leu Asp Arg Glu Lys Ala Lys Arg Ile Glu Trp Leu Leu Asn
                485                 490                 495
Gly Asp Ile Val Leu Asp Arg Val Val Glu Ile Lys Arg Glu Tyr Tyr
                500                 505                 510
Asp Gly Tyr Val Tyr Asp Leu Ser Val Asp Glu Asp Glu Asn Phe Leu
                515                 520                 525
Ala Gly Phe Gly Phe Leu Tyr Ala His Asn Ser
    530                 535
```

<210> SEQ ID NO 17
<211> LENGTH: 391
<212> TYPE: PRT
<213> ORGANISM: Thermococcus hydrothermalis

<400> SEQUENCE: 17

```
Asp Ser Val Thr Gly Glu Thr Glu Ile Ile Ile Lys Arg Asn Gly Lys
 1               5                  10                  15

Val Glu Phe Val Ala Ile Glu Glu Leu Phe Gln Arg Val Asp Tyr Arg
             20                  25                  30

Ile Gly Glu Lys Glu Tyr Cys Val Leu Glu Gly Val Glu Ala Leu Thr
         35                  40                  45

Leu Asp Asn Arg Gly Arg Leu Val Trp Lys Ser Val Pro Tyr Val Met
     50                  55                  60

Arg His Arg Thr Asn Lys Arg Ile Tyr Arg Val Trp Phe Thr Asn Ser
 65                  70                  75                  80

Trp Tyr Leu Asp Val Thr Glu Asp His Ser Leu Ile Gly Tyr Met Asn
                 85                  90                  95

Thr Ser Lys Val Lys Pro Gly Lys Pro Leu Lys Glu Arg Leu Val Glu
            100                 105                 110

Val Lys Pro Gly Glu Leu Gly Glu Ser Val Lys Ser Leu Ile Thr Pro
        115                 120                 125

Asn Arg Ala Ile Ala His Gly Ile Arg Val Asn Pro Ile Ala Val Lys
    130                 135                 140

Leu Trp Glu Leu Ile Gly Leu Leu Val Gly Asp Gly Asn Trp Gly Gly
145                 150                 155                 160

Gln Ser Asn Trp Ala Lys Tyr Asn Val Gly Leu Ser Leu Gly Leu Asp
                165                 170                 175

Lys Glu Glu Ile Glu Glu Lys Ile Leu Lys Pro Leu Lys Asn Thr Gly
            180                 185                 190

Ile Ile Ser Asn Tyr Tyr Asp Lys Ser Lys Lys Gly Asp Val Ser Ile
        195                 200                 205

Leu Ser Lys Trp Leu Ala Arg Phe Met Val Arg Tyr Phe Lys Asp Glu
    210                 215                 220

Ser Gly Ser Lys Arg Ile Pro Glu Phe Met Phe Asn Leu Pro Arg Glu
225                 230                 235                 240

Tyr Ile Glu Ala Phe Leu Arg Gly Leu Phe Ser Ala Asp Gly Thr Val
                245                 250                 255

Ser Leu Arg Lys Gly Val Pro Glu Val Arg Leu Thr Ser Val Asn Pro
            260                 265                 270

Glu Leu Ser Ser Ser Val Arg Lys Leu Leu Trp Leu Val Gly Val Ser
        275                 280                 285

Asn Ser Met Phe Val Glu Thr Asn Pro Asn Arg Tyr Leu Gly Lys Glu
    290                 295                 300

Ser Gly Thr His Ser Val His Val Arg Ile Lys Asp Lys His Arg Phe
305                 310                 315                 320

Ala Glu Arg Ile Gly Phe Leu Leu Asp Arg Lys Ala Thr Lys Leu Ser
                325                 330                 335

Glu Asn Leu Gly Gly His Thr Ser Lys Lys Arg Ala Tyr Lys Tyr Asp
            340                 345                 350

Phe Asp Leu Val Tyr Pro Lys Lys Val Glu Glu Ile Ala Tyr Asp Gly
        355                 360                 365

Tyr Val Tyr Asp Ile Glu Val Glu Gly Thr His Arg Phe Phe Ala Asn
```

```
       370                 375                 380
Gly Ile Leu Val His Asn Thr
385                 390

<210> SEQ ID NO 18
<211> LENGTH: 389
<212> TYPE: PRT
<213> ORGANISM: Pyrococcus furiosus

<400> SEQUENCE: 18

Lys Cys Leu Leu Pro Glu Glu Lys Val Leu Pro Glu Ile Gly Leu
 1               5                  10                  15

Val Thr Leu Arg Glu Leu Phe Glu Leu Ala Asn Glu Val Val Lys
                20                  25                  30

Asp Glu Glu Lys Glu Val Arg Lys Leu Gly Lys Met Leu Thr Gly Val
                35                  40                  45

Asp Glu Arg Gly Asn Val Lys Leu Leu Asn Ala Leu Tyr Val Trp Arg
 50                  55                  60

Val Ala His Lys Gly Glu Met Ile Arg Val Lys Val Asn Gly Trp Tyr
65                   70                  75                  80

Ser Val Thr Val Thr Pro Glu His Pro Phe Leu Thr Asn Arg Gly Trp
                85                  90                  95

Val Lys Ala Gly Glu Leu Lys Glu Gly Asp Tyr Ile Ala Ile Pro Arg
                100                 105                 110

Arg Val Tyr Gly Asn Glu Asp Leu Met Lys Phe Ser Lys Ile Ala Lys
                115                 120                 125

Glu Leu Gly Ile Lys Gly Asp Glu Lys Glu Phe Tyr Leu Ala Gly Ala
                130                 135                 140

Ser Leu Asp Ile Pro Ile Lys Val Leu Phe Leu Ala Pro Ser Lys Leu
145                 150                 155                 160

Val Ser Ala Phe Leu Arg Gly Tyr Phe Asp Ala Lys Gly Val Val Arg
                165                 170                 175

Glu Asn Tyr Ile Glu Val Pro Leu Phe Glu Asp Leu Pro Leu Leu Leu
                180                 185                 190

Leu Arg Phe Gly Ile Val Ser Arg Ile Glu Lys Ser Thr Leu Lys Ile
                195                 200                 205

Ser Gly Lys Arg Asn Leu Glu Leu Phe Arg Lys His Val Gly Phe Thr
                210                 215                 220

Asp Ser Glu Lys Ala Lys Ala Leu Asp Glu Leu Ile Ser Lys Ala Lys
225                 230                 235                 240

Glu Ser Glu Arg Tyr Pro Ile Leu Glu Glu Leu Arg Arg Leu Gly Leu
                245                 250                 255

Leu Phe Gly Phe Thr Arg Asn Glu Leu Arg Ile Glu Glu Asn Pro Thr
                260                 265                 270

Tyr Glu Val Leu Met Glu Ile Leu Glu Arg Ile Glu Arg Gly Ser Pro
                275                 280                 285

Asn Leu Ala Glu Lys Ile Ala Val Leu Glu Gly Arg Ile Lys Glu Glu
                290                 295                 300

Asn Tyr Leu Arg Ile Leu Glu Glu Gly Leu Ile Glu Asn Gly Lys
305                 310                 315                 320

Leu Thr Glu Leu Gly Lys Glu Leu Leu Glu Val Trp Arg Asn Arg Glu
                325                 330                 335

Phe Asp Ser Lys Asp Val Asp Tyr Val Arg Asn Ile Val Glu Asn Leu
                340                 345                 350
```

```
Val Phe Leu Pro Val Glu Lys Val Glu Arg Ile Glu Tyr Glu Gly Tyr
            355                 360                 365

Val Tyr Asp Val Thr Thr Glu Thr His Asn Phe Val Ala Asn Gly Ile
    370                 375                 380

Leu Val His Asn Thr
385

<210> SEQ ID NO 19
<211> LENGTH: 476
<212> TYPE: PRT
<213> ORGANISM: Pyrococcus horikoshii OT3

<400> SEQUENCE: 19

Gln Cys Phe Ser Gly Glu Glu Val Ile Ile Val Glu Lys Gly Lys Asp
1               5                   10                  15

Arg Lys Val Val Lys Leu Arg Glu Phe Val Glu Asp Ala Leu Lys Glu
            20                  25                  30

Pro Ser Gly Glu Gly Met Asp Gly Asp Ile Lys Val Thr Tyr Lys Asp
        35                  40                  45

Leu Arg Gly Glu Asp Val Arg Ile Leu Thr Lys Asp Gly Phe Val Lys
    50                  55                  60

Leu Leu Tyr Val Asn Lys Arg Glu Gly Lys Gln Lys Leu Arg Lys Ile
65                  70                  75                  80

Val Asn Leu Asp Lys Asp Tyr Trp Leu Ala Val Thr Pro Asp His Lys
                85                  90                  95

Val Phe Thr Ser Glu Gly Leu Lys Glu Ala Gly Glu Ile Thr Glu Lys
            100                 105                 110

Asp Glu Ile Ile Arg Val Pro Leu Val Ile Leu Asp Gly Pro Lys Ile
        115                 120                 125

Ala Ser Thr Tyr Gly Glu Asp Gly Lys Phe Asp Asp Tyr Ile Arg Trp
    130                 135                 140

Lys Lys Tyr Tyr Glu Lys Thr Gly Asn Gly Tyr Lys Arg Ala Ala Lys
145                 150                 155                 160

Glu Leu Asn Ile Lys Glu Ser Thr Leu Arg Trp Trp Thr Gln Gly Ala
                165                 170                 175

Lys Pro Asn Ser Leu Lys Met Ile Glu Glu Leu Glu Lys Leu Asn Leu
            180                 185                 190

Leu Pro Leu Thr Ser Glu Asp Ser Arg Leu Glu Lys Val Ala Ile Ile
        195                 200                 205

Leu Gly Ala Leu Phe Ser Asp Gly Asn Ile Asp Arg Asn Phe Asn Thr
    210                 215                 220

Leu Ser Phe Ile Ser Ser Glu Arg Lys Ala Ile Glu Arg Phe Val Glu
225                 230                 235                 240

Thr Leu Lys Glu Leu Phe Gly Glu Phe Asn Tyr Glu Ile Arg Asp Asn
                245                 250                 255

His Glu Ser Leu Gly Lys Ser Ile Leu Phe Arg Thr Trp Asp Arg Arg
            260                 265                 270

Ile Ile Arg Phe Phe Val Ala Leu Gly Ala Pro Val Gly Asn Lys Thr
        275                 280                 285

Lys Val Lys Leu Glu Leu Pro Trp Trp Ile Lys Leu Lys Pro Ser Leu
    290                 295                 300

Phe Leu Ala Phe Met Asp Gly Leu Tyr Ser Gly Asp Gly Ser Val Pro
305                 310                 315                 320

Arg Phe Ala Arg Tyr Glu Glu Gly Ile Lys Phe Asn Gly Thr Phe Glu
                325                 330                 335
```

```
Ile Ala Gln Leu Thr Asp Asp Val Glu Lys Lys Leu Pro Phe Phe Glu
            340                 345                 350

Glu Ile Ala Trp Tyr Leu Ser Phe Phe Gly Ile Lys Ala Lys Val Arg
            355                 360                 365

Val Asp Lys Thr Gly Asp Lys Tyr Lys Val Arg Leu Ile Phe Ser Gln
            370                 375                 380

Ser Ile Asp Asn Val Leu Asn Phe Leu Glu Phe Ile Pro Ile Ser Leu
385                 390                 395                 400

Ser Pro Ala Lys Arg Glu Lys Phe Leu Arg Glu Val Glu Ser Tyr Leu
            405                 410                 415

Ala Ala Val Pro Glu Ser Ser Leu Ala Gly Arg Ile Glu Glu Leu Arg
            420                 425                 430

Glu His Phe Asn Arg Ile Lys Lys Gly Glu Arg Arg Ser Phe Ile Glu
            435                 440                 445

Thr Trp Glu Val Val Asn Val Thr Tyr Asn Val Thr Thr Glu Thr Gly
            450                 455                 460

Asn Leu Leu Ala Asn Gly Leu Phe Val Lys Asn Ser
465                 470                 475

<210> SEQ ID NO 20
<211> LENGTH: 496
<212> TYPE: PRT
<213> ORGANISM: Methanococcus jannaschii

<400> SEQUENCE: 20

Leu Cys Leu Thr Pro Asp Thr Tyr Val Val Leu Gly Asp Gly Arg Ile
1               5                  10                  15

Glu Thr Ile Glu Asp Ile Val Asn Ala Lys Glu Arg Asn Val Leu Ser
            20                  25                  30

Leu Asp Leu Asp Asn Leu Ser Ile Lys Ile Asp Thr Ala Ile Lys Phe
            35                  40                  45

Trp Lys Leu Arg Tyr Asn Gly Asn Leu Ser Lys Ile Thr Leu Ser Asn
            50                  55                  60

Asn Tyr Glu Leu Lys Ala Thr Pro Asp His Cys Leu Leu Val Leu Arg
65                  70                  75                  80

Asp Asn Gln Leu Lys Trp Ile Pro Ala Lys Asp Ile Lys Glu Asn Asp
            85                  90                  95

Tyr Ile Ala Met Pro Phe Asn Tyr Lys Val Glu Arg Lys Pro Ile Ser
            100                 105                 110

Leu Leu Asn Leu Leu Lys Tyr Leu Asp Ile Thr Asp Val Leu Ile Glu
            115                 120                 125

Phe Asp Glu Asn Ser Thr Ile Phe Glu Lys Ile Ala Glu Tyr Ile Arg
            130                 135                 140

Asn Asn Ile Lys Thr Ser Thr Lys Tyr Lys Tyr Leu Arg Asn Arg Arg
145                 150                 155                 160

Val Pro Leu Lys Tyr Leu Ile Glu Trp Asn Phe Asp Leu Asp Glu Ile
            165                 170                 175

Glu Lys Glu Ala Lys Tyr Ile Tyr Lys Ser Val Ala Gly Thr Lys Lys
            180                 185                 190

Ile Pro Leu Phe Lys Leu Asp Glu Arg Phe Trp Tyr Phe Ala Gly Leu
            195                 200                 205

Val Leu Gly Asp Gly Ser Ile Gln Asp Ser Lys Ile Arg Ile Ala Gln
            210                 215                 220

Thr Pro Leu Lys Asp Val Lys Ser Ile Leu Asp Glu Thr Phe Pro Phe
```

```
                225                 230                 235                 240
Leu His Asn Trp Ile Ser Gly Asn Gln Val Ile Ile Ser Asn Pro Ile
                245                 250                 255

Ile Ala Glu Ile Leu Glu Lys Leu Gly Met Arg Asn Gly Lys Leu Asn
                260                 265                 270

Gly Ile Ile Phe Ser Leu Pro Glu Ser Tyr Ile Asn Ala Leu Ile Ala
                275                 280                 285

Gly Tyr Phe Asp Thr Asp Gly Cys Phe Ser Leu Leu Tyr Asp Lys Lys
                290                 295                 300

Ala Lys Lys His Asn Leu Arg Met Val Leu Thr Ser Lys Arg Arg Asp
305                 310                 315                 320

Val Leu Glu Lys Ile Gly Ile Tyr Leu Asn Ser Ile Gly Ile Leu Asn
                325                 330                 335

Thr Leu His Lys Ser Arg Glu Val Tyr Ser Leu Ile Ile Ser Asn Lys
                340                 345                 350

Ser Leu Glu Thr Phe Lys Glu Lys Ile Ala Lys Tyr Leu Lys Ile Arg
                355                 360                 365

Lys Glu Ala Phe Ile Asn Gly Tyr Lys Thr Tyr Lys Lys Glu His Glu
                370                 375                 380

Glu Arg Phe Glu Cys Asp Leu Leu Pro Val Lys Glu Val Phe Lys Lys
385                 390                 395                 400

Leu Thr Phe Glu Lys Gly Arg Lys Glu Ile Leu Lys Asp Ser Lys Ile
                405                 410                 415

His Ile Glu Asn Trp Tyr Lys Glu Lys Thr Asn Asn Ile Pro Arg Glu
                420                 425                 430

Lys Leu Lys Thr Val Leu Arg Tyr Ala Asn Asn Ser Glu His Lys Glu
                435                 440                 445

Phe Leu Glu Lys Ile Val Asn Gly Asp Ile Ser Phe Val Arg Val Lys
                450                 455                 460

Lys Val Glu Asn Ile Pro Tyr Asp Gly Tyr Val Tyr Asp Leu Ser Ile
465                 470                 475                 480

Lys His Asn Gln Asn Phe Ile Ser Asn Gly Val Ile Ser His Asn Cys
                485                 490                 495

<210> SEQ ID NO 21
<211> LENGTH: 527
<212> TYPE: PRT
<213> ORGANISM: Pyrococcus horikoshii OT3

<400> SEQUENCE: 21

Lys Cys Leu Thr Gly Asp Thr Lys Val Ile Ala Asn Gly Gln Leu Phe
1               5                   10                  15

Glu Leu Arg Glu Leu Val Glu Lys Ile Ser Gly Gly Lys Phe Gly Pro
                20                  25                  30

Thr Pro Val Lys Gly Leu Lys Val Ile Gly Ile Asp Glu Asp Gly Lys
                35                  40                  45

Leu Arg Glu Phe Glu Val Gln Tyr Val Tyr Lys Asp Lys Thr Glu Arg
                50                  55                  60

Leu Ile Arg Ile Arg Thr Arg Leu Gly Arg Glu Leu Lys Val Thr Pro
65                  70                  75                  80

Tyr His Pro Leu Leu Val Asn Arg Arg Asn Gly Glu Ile Lys Trp Val
                85                  90                  95

Lys Ala Glu Glu Leu Lys Pro Gly Asp Lys Leu Ala Val Pro Arg Phe
                100                 105                 110
```

-continued

```
Leu Pro Ile Val Thr Gly Glu Asp Pro Leu Ala Glu Trp Leu Gly Tyr
        115                 120                 125

Phe Leu Gly Gly Tyr Ala Asp Ser Lys Glu Asn Leu Ile Met Phe
    130                 135                 140

Thr Asn Glu Asp Pro Leu Leu Arg Gln Arg Phe Met Glu Leu Thr Glu
145                 150                 155                 160

Lys Leu Phe Ser Asp Ala Arg Ile Arg Glu Ile Thr His Glu Asn Gly
                165                 170                 175

Thr Ser Lys Val Tyr Val Asn Ser Lys Ala Leu Lys Leu Val Asn
                180                 185                 190

Ser Leu Gly Asn Ala His Ile Pro Lys Glu Cys Trp Arg Gly Ile Arg
        195                 200                 205

Ser Phe Leu Arg Ala Tyr Phe Asp Cys Asn Gly Val Lys Gly Asn
    210                 215                 220

Ala Ile Val Leu Ala Thr Ala Ser Lys Glu Met Ser Gln Glu Ile Ala
225                 230                 235                 240

Tyr Ala Leu Ala Gly Phe Gly Ile Ile Ser Arg Ile Gln Glu Tyr Arg
                245                 250                 255

Val Ile Ile Ser Gly Ser Asp Asn Val Lys Lys Phe Leu Asn Glu Ile
        260                 265                 270

Gly Phe Ile Asn Arg Asn Lys Leu Glu Lys Ala Leu Lys Leu Val Lys
    275                 280                 285

Lys Asp Asp Pro Gly His Asp Gly Leu Glu Ile Asn Tyr Glu Leu Ile
290                 295                 300

Ser Tyr Val Lys Asp Arg Leu Arg Leu Ser Phe Asn Asp Lys Arg
305                 310                 315                 320

Ser Trp Ser Tyr Arg Glu Ala Lys Glu Ile Ser Trp Glu Leu Met Lys
                325                 330                 335

Glu Ile Tyr Tyr Arg Leu Asp Glu Leu Glu Lys Leu Lys Glu Ser Leu
        340                 345                 350

Ser Arg Gly Ile Leu Ile Asp Trp Asn Glu Val Ala Lys Arg Ile Glu
    355                 360                 365

Glu Val Ala Glu Glu Thr Gly Ile Arg Ala Asp Glu Leu Leu Glu Tyr
370                 375                 380

Ile Glu Gly Lys Arg Lys Leu Ser Phe Lys Asp Tyr Ile Lys Ile Ala
385                 390                 395                 400

Lys Val Leu Gly Ile Asp Val Glu His Thr Ile Glu Ala Met Arg Val
                405                 410                 415

Phe Ala Arg Lys Tyr Ser Ser Tyr Ala Glu Ile Gly Arg Arg Leu Gly
        420                 425                 430

Thr Trp Asn Ser Ser Val Lys Thr Ile Leu Glu Ser Asn Ala Val Asn
    435                 440                 445

Val Glu Ile Leu Glu Arg Ile Arg Lys Ile Glu Leu Glu Leu Ile Glu
450                 455                 460

Glu Ile Leu Ser Asp Glu Lys Leu Lys Glu Gly Ile Ala Tyr Leu Ile
465                 470                 475                 480

Phe Leu Ser Gln Asn Glu Leu Tyr Trp Asp Ile Thr Lys Val Glu
                485                 490                 495

Glu Leu Arg Gly Glu Phe Ile Ile Tyr Asp Leu His Val Pro Gly Tyr
        500                 505                 510

His Asn Phe Ile Ala Gly Asn Met Pro Thr Val Val His Asn Thr
    515                 520                 525
```

<210> SEQ ID NO 22
<211> LENGTH: 610
<212> TYPE: PRT
<213> ORGANISM: Pyrococcus abyssi

<400> SEQUENCE: 22

```
Ser Cys Val Thr Gly Asp Thr Lys Val Tyr Thr Pro Asp Glu Arg Glu
 1               5                  10                  15

Val Lys Ile Arg Asp Phe Met Asn Tyr Phe Glu Asn Gly Leu Ile Lys
             20                  25                  30

Glu Val Ser Asn Arg Ile Gly Arg Asp Thr Val Ile Ala Ala Val Ser
         35                  40                  45

Phe Asn Ser Arg Ile Val Gly His Pro Val Tyr Arg Leu Thr Leu Glu
     50                  55                  60

Ser Gly Arg Ile Ile Glu Ala Thr Gly Asp His Met Phe Leu Thr Pro
 65                  70                  75                  80

Glu Gly Trp Lys Gln Thr Tyr Asp Ile Lys Glu Gly Ser Glu Val Leu
                 85                  90                  95

Val Lys Pro Thr Leu Glu Gly Thr Pro Tyr Glu Pro Asp Pro Arg Val
            100                 105                 110

Ile Ile Asp Ile Lys Glu Phe Tyr Asn Phe Leu Glu Lys Ile Glu Arg
        115                 120                 125

Glu His Asn Leu Lys Pro Leu Lys Glu Ala Lys Thr Phe Arg Glu Leu
    130                 135                 140

Ile Thr Lys Asp Lys Glu Lys Ile Leu Arg Arg Ala Leu Glu Leu Arg
145                 150                 155                 160

Ala Glu Ile Glu Asn Gly Leu Thr Lys Arg Glu Ala Glu Ile Leu Glu
                165                 170                 175

Leu Ile Ser Ala Asp Thr Trp Ile Pro Arg Ala Glu Leu Glu Lys Lys
            180                 185                 190

Ala Arg Ile Ser Arg Thr Arg Leu Asn Gln Ile Leu Gln Arg Leu Glu
        195                 200                 205

Lys Lys Gly Tyr Ile Glu Arg Arg Ile Glu Gly Arg Lys Gln Phe Val
    210                 215                 220

Arg Lys Ile Arg Asn Gly Lys Ile Leu Arg Asn Ala Met Asp Ile Lys
225                 230                 235                 240

Arg Ile Leu Glu Glu Glu Phe Gly Ile Lys Ile Ser Tyr Thr Thr Val
                245                 250                 255

Lys Lys Leu Leu Ser Gly Asn Val Asp Gly Met Ala Tyr Arg Ile Leu
            260                 265                 270

Lys Glu Val Lys Glu Lys Trp Leu Val Arg Tyr Asp Asp Glu Lys Ala
        275                 280                 285

Gly Ile Leu Ala Arg Val Val Gly Phe Ile Leu Gly Asp Gly His Leu
    290                 295                 300

Ala Arg Asn Gly Arg Ile Trp Phe Asn Ser Ser Lys Glu Glu Leu Glu
305                 310                 315                 320

Met Leu Ala Asn Asp Leu Arg Lys Leu Gly Leu Lys Pro Ser Glu Ile
                325                 330                 335

Ile Glu Arg Asp Ser Ser Glu Ile Gln Gly Arg Lys Val Lys Gly
            340                 345                 350

Arg Ile Tyr Met Leu Tyr Val Asp Asn Ala Ala Phe His Ala Leu Leu
        355                 360                 365

Arg Phe Trp Lys Val Glu Val Gly Asn Lys Thr Lys Lys Gly Tyr Thr
    370                 375                 380
```

```
Val Pro Glu Trp Ile Lys Lys Gly Asn Leu Phe Val Lys Arg Glu Phe
385                 390                 395                 400

Leu Arg Gly Leu Phe Gly Ala Asp Gly Thr Lys Pro Cys Gly Lys Arg
            405                 410                 415

Tyr Asn Phe Asn Gly Ile Lys Leu Glu Ile Arg Ala Lys Lys Glu Ser
        420                 425                 430

Leu Glu Arg Thr Val Glu Phe Leu Asn Asp Val Ala Asp Leu Leu Arg
    435                 440                 445

Glu Phe Asp Val Asp Ser Lys Ile Thr Val Ser Pro Thr Lys Glu Gly
450                 455                 460

Phe Ile Ile Arg Leu Ile Val Thr Pro Asn Asp Ala Asn Tyr Leu Asn
465                 470                 475                 480

Phe Leu Thr Arg Val Gly Tyr Ala Tyr Ala Lys Asp Thr Tyr Ala Arg
            485                 490                 495

Leu Val Gly Glu Tyr Ile Arg Ile Lys Leu Ala Tyr Lys Asn Ile Ile
            500                 505                 510

Leu Pro Gly Ile Ala Glu Lys Ala Ile Glu Leu Ala Thr Val Thr Asn
            515                 520                 525

Ser Thr Tyr Ala Ala Lys Val Leu Gly Val Ser Arg Asp Phe Val Val
    530                 535                 540

Asn Arg Leu Lys Gly Thr Gln Ile Gly Ile Thr Arg Asp Phe Met Thr
545                 550                 555                 560

Phe Glu Glu Phe Met Lys Glu Arg Val Leu Asn Gly Tyr Val Ile Glu
                565                 570                 575

Lys Val Ile Lys Lys Glu Lys Leu Gly Tyr Leu Asp Val Tyr Asp Val
            580                 585                 590

Thr Cys Ala Arg Asp His Ser Phe Ile Ser Asn Gly Leu Val Ser His
            595                 600                 605

Asn Cys
    610

<210> SEQ ID NO 23
<211> LENGTH: 490
<212> TYPE: PRT
<213> ORGANISM: Methanococcus jannaschii

<400> SEQUENCE: 23

Asn Cys Leu Thr Ser Asn Ser Lys Ile Leu Thr Asp Asp Gly Tyr Tyr
1               5                   10                  15

Ile Lys Leu Glu Lys Leu Lys Glu Lys Leu Asp Leu His Ile Lys Ile
            20                  25                  30

Tyr Asn Thr Glu Glu Gly Glu Lys Ser Ser Asn Ile Leu Phe Val Ser
        35                  40                  45

Glu Arg Tyr Ala Asp Glu Lys Ile Ile Arg Ile Lys Thr Glu Ser Gly
    50                  55                  60

Arg Val Leu Glu Gly Ser Lys Asp His Pro Val Leu Thr Leu Asn Gly
65                  70                  75                  80

Tyr Val Pro Met Gly Met Leu Lys Glu Gly Asp Asp Val Ile Val Tyr
                85                  90                  95

Pro Tyr Glu Gly Val Glu Tyr Glu Pro Ser Asp Glu Ile Ile Leu
            100                 105                 110

Asp Glu Asp Asp Phe Ala Glu Tyr Asp Lys Gln Ile Ile Lys Tyr Leu
        115                 120                 125

Lys Asp Arg Gly Leu Leu Pro Leu Arg Met Asp Asn Lys Asn Ile Gly
    130                 135                 140
```

```
Ile Ile Ala Arg Leu Leu Gly Phe Ala Phe Gly Asp Gly Ser Ile Val
145                 150                 155                 160

Lys Glu Asn Gly Asp Arg Glu Arg Leu Tyr Val Ala Phe Tyr Gly Lys
                165                 170                 175

Arg Glu Thr Leu Ile Lys Ile Arg Glu Asp Leu Glu Lys Leu Gly Ile
            180                 185                 190

Lys Ala Ser Arg Ile Tyr Ser Arg Lys Arg Glu Val Glu Ile Arg Asn
        195                 200                 205

Ala Tyr Gly Asp Glu Tyr Thr Ser Leu Cys Glu Asp Asn Ser Ile Lys
    210                 215                 220

Ile Thr Ser Lys Ala Phe Ala Leu Phe Met His Lys Leu Gly Met Pro
225                 230                 235                 240

Ile Gly Lys Lys Thr Glu Gln Ile Tyr Lys Ile Pro Glu Trp Ile Lys
                245                 250                 255

Lys Ala Pro Lys Trp Val Lys Arg Asn Phe Leu Ala Gly Leu Phe Gly
            260                 265                 270

Ala Asp Gly Ser Arg Ala Val Phe Lys Asn Tyr Thr Pro Leu Pro Ile
        275                 280                 285

Asn Leu Thr Met Ser Lys Ser Glu Glu Leu Lys Glu Asn Ile Leu Glu
290                 295                 300

Phe Leu Asn Glu Ile Lys Leu Leu Ala Glu Phe Asp Ile Glu Ser
305                 310                 315                 320

Met Ile Tyr Glu Ile Lys Ser Leu Asp Gly Arg Val Ser Tyr Arg Leu
                325                 330                 335

Ala Ile Val Gly Glu Glu Ser Ile Lys Asn Phe Leu Gly Arg Ile Asn
            340                 345                 350

Tyr Glu Tyr Ser Gly Glu Lys Lys Val Ile Gly Leu Leu Ala Tyr Glu
        355                 360                 365

Tyr Leu Arg Arg Lys Asp Ile Ala Lys Glu Ile Arg Lys Lys Cys Ile
370                 375                 380

Lys Arg Ala Lys Glu Leu Tyr Lys Lys Gly Val Thr Val Ser Glu Met
385                 390                 395                 400

Leu Lys Met Asp Glu Phe Arg Asn Glu Phe Ile Ser Lys Arg Leu Ile
                405                 410                 415

Glu Arg Ala Val Tyr Glu Asn Leu Asp Glu Asp Val Arg Ile Ser
            420                 425                 430

Thr Lys Phe Pro Lys Phe Glu Glu Phe Ile Glu Lys Tyr Gly Val Ile
        435                 440                 445

Gly Gly Phe Val Ile Asp Lys Ile Lys Glu Ile Glu Glu Ile Ser Tyr
450                 455                 460

Asp Ser Lys Leu Tyr Asp Val Gly Ile Val Ser Lys Glu His Asn Phe
465                 470                 475                 480

Ile Ala Asn Ser Ile Val Val His Asn Cys
                485                 490

<210> SEQ ID NO 24
<211> LENGTH: 378
<212> TYPE: PRT
<213> ORGANISM: Pyrococcus horikoshii OT3

<400> SEQUENCE: 24

Lys Cys Val Asp Gly Asp Thr Leu Val Leu Thr Lys Glu Phe Gly Leu
1               5                   10                  15

Ile Lys Ile Lys Glu Leu Tyr Glu Lys Leu Asp Gly Lys Gly Arg Lys
```

```
                20                  25                  30
Ile Val Glu Gly Asn Glu Glu Trp Thr Glu Leu Glu Lys Pro Ile Thr
             35                  40                  45

Val Tyr Gly Tyr Lys Asp Gly Lys Ile Val Glu Ile Lys Ala Thr His
 50                  55                  60

Val Tyr Lys Gly Val Ser Ser Gly Met Val Glu Ile Arg Thr Arg Thr
 65                  70                  75                  80

Gly Arg Lys Ile Lys Val Thr Pro Ile His Arg Leu Phe Thr Gly Arg
                 85                  90                  95

Val Thr Lys Asp Gly Leu Ile Leu Lys Glu Val Met Ala Met His Val
                100                 105                 110

Lys Pro Gly Asp Arg Ile Ala Val Val Lys Lys Ile Asp Gly Gly Glu
            115                 120                 125

Tyr Ile Lys Leu Asp Ser Ser Asn Val Gly Glu Ile Lys Val Pro Glu
        130                 135                 140

Ile Leu Asn Glu Glu Leu Ala Glu Phe Leu Gly Tyr Leu Met Ala Asn
145                 150                 155                 160

Gly Thr Leu Lys Ser Gly Ile Ile Glu Ile Tyr Cys Asp Asp Glu Ser
                165                 170                 175

Leu Leu Glu Arg Val Asn Ser Leu Ser Leu Lys Leu Phe Gly Val Gly
            180                 185                 190

Gly Arg Ile Val Gln Lys Val Asp Gly Lys Ala Leu Val Ile Gln Ser
        195                 200                 205

Lys Pro Leu Val Asp Val Leu Arg Arg Leu Gly Val Pro Glu Asp Lys
210                 215                 220

Lys Val Glu Asn Trp Lys Val Pro Arg Glu Leu Leu Leu Ser Pro Ser
225                 230                 235                 240

Asn Val Val Arg Ala Phe Val Asn Ala Tyr Ile Lys Gly Lys Glu Glu
                245                 250                 255

Val Glu Ile Thr Leu Ala Ser Glu Glu Gly Ala Tyr Glu Leu Ser Tyr
            260                 265                 270

Leu Phe Ala Lys Leu Gly Ile Tyr Val Thr Ile Ser Lys Ser Gly Glu
        275                 280                 285

Tyr Tyr Lys Val Arg Val Ser Arg Arg Gly Asn Leu Asp Thr Ile Pro
    290                 295                 300

Val Glu Val Asn Gly Met Pro Lys Val Leu Pro Tyr Glu Asp Phe Arg
305                 310                 315                 320

Lys Phe Ala Lys Ser Ile Gly Leu Glu Glu Val Ala Glu Asn His Leu
                325                 330                 335

Gln His Ile Ile Phe Asp Glu Val Ile Asp Val Arg Tyr Ile Pro Glu
            340                 345                 350

Pro Gln Glu Val Tyr Asp Val Thr Thr Glu Thr His Asn Phe Val Gly
        355                 360                 365

Gly Asn Met Pro Thr Leu Leu His Asn Thr
    370                 375

<210> SEQ ID NO 25
<211> LENGTH: 198
<212> TYPE: PRT
<213> ORGANISM: Artificial sequence
<220> FEATURE:
<223> OTHER INFORMATION: modified wild-type Ssp DnaB Intien

<400> SEQUENCE: 25

Met Glu Ser Gly Ser Pro Glu Ile Glu Lys Leu Ser Gln Ser Asp Ile
```

```
                1               5                    10                   15
          Tyr Trp Asp Ser Ile Val Ser Ile Thr Glu Thr Gly Val Glu Val
                        20                  25                  30

Phe Asp Leu Thr Val Pro Gly Pro His Asn Phe Val Ala Asn Asp Ile
                        35                  40                  45

Ile Val His Asn Ser Ile Glu Gln Gly Gln Gly Gly Met Ser Met
                        50                  55                  60

Asp Tyr Lys Asp Asp Asp Lys Met Arg Met Leu Glu Gly Gln Ala
          65                  70                  75                  80

Gly Gly Leu Ile Thr Ser Gly Cys Ile Ser Asp Ser Leu Ile Ser
                        85                  90                  95

Leu Ala Ser Thr Gly Lys Arg Val Ser Ile Lys Asp Leu Leu Asp Glu
                        100                 105                 110

Lys Asp Phe Glu Ile Trp Ala Ile Asn Glu Gln Thr Met Lys Leu Glu
                        115                 120                 125

Ser Lys Val Ser Arg Val Phe Cys Thr Gly Lys Lys Leu Val Tyr Ile
                        130                 135                 140

Leu Lys Thr Arg Leu Gly Arg Thr Ile Lys Ala Thr Ala Asn His Arg
          145                 150                 155                 160

Phe Leu Thr Ile Asp Gly Trp Lys Arg Leu Asp Glu Leu Ser Leu Lys
                        165                 170                 175

Glu His Ile Ala Leu Pro Arg Lys Leu Glu Ser Ser Leu Gln Leu
                        180                 185                 190

Ser Ile His Gly Tyr His
                        195

<210> SEQ ID NO 26
<211> LENGTH: 35
<212> TYPE: PRT
<213> ORGANISM: Artificial sequence
<220> FEATURE:
<223> OTHER INFORMATION: FLAG epitope

<400> SEQUENCE: 26

Ser Ile Glu Gln Gly Gln Gly Gly Gly Met Ser Met Asp Tyr Lys Asp
1               5                   10                  15

Asp Asp Asp Lys Met Arg Met Leu Glu Gly Gln Ala Gly Gly Leu Ile
                20                  25                  30

Thr Ser Gly
        35

<210> SEQ ID NO 27
<211> LENGTH: 1467
<212> TYPE: DNA
<213> ORGANISM: Synechocystis PCC6803
<220> FEATURE:
<221> NAME/KEY: CDS
<222> LOCATION: (739)..(1338)
<223> OTHER INFORMATION:

<400> SEQUENCE: 27
gcttcgcgat gtacgggcca gatatacgcg ttgacattga ttattgacta gttattaata     60
gtaatcaatt acgggtcat tagttcatag cccatatatg gagttccgcg ttacataact     120
tacggtaaat ggcccgcctg gctgaccgcc caacgacccc cgcccattga cgtcaataat     180
gacgtatgtt cccatagtaa cgccaatagg gactttccat tgacgtcaat ggtggacta    240 tttacggtaa actgcccact tggcagtaca tcaagtgtat catatgccaa gtacgccccc    300
```

```
tattgacgtc aatgacggta aatggcccgc ctggcattat gcccagtaca tgaccttatc        360
ggactttcct acttggcagt acatctacgt attagtcatc gctattacca tggtgatgcg        420
gttttggcag tacatcaatg ggcgtggata gcggtttgac tcacggggat ttccaagtct        480
ccaccccatt gacgtcaatg ggagtttgtt ttggcaccaa aatcaacggg actttccaaa        540
atgtcgtaac aactccgccc cattgacgca aatgggcggt aggcgtgtac ggtgggaggt        600
ctatataagc agagctctct ggctaactag agaacccact gcttactggc ttatcgaaat        660
taatacgact cactataggg agacccaagc tggctagtta agcttcctat actaggagat        720
ctgtcgactg gaggaacc atg gag tcc gga tca cca gaa ata gaa aag ttg        771
                    Met Glu Ser Gly Ser Pro Glu Ile Glu Lys Leu
                     1               5                  10 tct cag agt gat att tac tgg gac tcc atc gtt tct att acg gag act          819
Ser Gln Ser Asp Ile Tyr Trp Asp Ser Ile Val Ser Ile Thr Glu Thr
            15                  20                  25 gga gtc gaa gag gtt ttt gat ttg act gtg cca gga cca cat aac ttt          867
Gly Val Glu Glu Val Phe Asp Leu Thr Val Pro Gly Pro His Asn Phe
        30                  35                  40 gtc gcc aat gac atc att gtc cat aac agt atc gaa caa ggc cag ggc          915
Val Ala Asn Asp Ile Ile Val His Asn Ser Ile Glu Gln Gly Gln Gly
    45                  50                  55 ggt ggc atg tca atg gac tat aaa gat gac gac gat aag atg agg atg          963
Gly Gly Met Ser Met Asp Tyr Lys Asp Asp Asp Asp Lys Met Arg Met
60                  65                  70                  75 ctc gag ggc caa gca ggt gga ctg atc acc agt ggc tgc atc agt gga         1011
Leu Glu Gly Gln Ala Gly Gly Leu Ile Thr Ser Gly Cys Ile Ser Gly
                80                  85                  90 gat agt ttg atc agc ttg gcg agc aca gga aaa aga gtt tct att aaa         1059
Asp Ser Leu Ile Ser Leu Ala Ser Thr Gly Lys Arg Val Ser Ile Lys
            95                 100                 105 gat ttg tta gat gaa aaa gat ttt gaa ata tgg gca att aat gaa cag         1107
Asp Leu Leu Asp Glu Lys Asp Phe Glu Ile Trp Ala Ile Asn Glu Gln
        110                 115                 120 acg atg aag cta gaa tca gct aaa gtt agt cgt gta ttt tgt act ggc         1155
Thr Met Lys Leu Glu Ser Ala Lys Val Ser Arg Val Phe Cys Thr Gly
    125                 130                 135 aaa aag cta gtt tat att tta aaa act cga cta ggt aga act atc aag         1203
Lys Lys Leu Val Tyr Ile Leu Lys Thr Arg Leu Gly Arg Thr Ile Lys
140                 145                 150                 155 gca aca gca aat cat aga ttt tta act att gat ggt tgg aaa aga tta         1251
Ala Thr Ala Asn His Arg Phe Leu Thr Ile Asp Gly Trp Lys Arg Leu
                160                 165                 170 gat gag cta tct tta aaa gag cat att gct cta ccc cgt aaa cta gaa         1299
Asp Glu Leu Ser Leu Lys Glu His Ile Ala Leu Pro Arg Lys Leu Glu
            175                 180                 185 agc tcc tct tta caa tta atc gat cca tgg tta cca tga caattggcgg         1348
Ser Ser Ser Leu Gln Leu Ile Asp Pro Trp Leu Pro
        190                 195 ccgctcgagt ctagagggcc cgcggttcga aggtaagcct atccctaacc ctctcctcgg       1408
tctcgattct acgcgtaccg gtcatcatca ccatcaccat tgagtttaaa cccgctgat        1467

<210> SEQ ID NO 28
<211> LENGTH: 199
<212> TYPE: PRT
<213> ORGANISM: Synechocystis PCC6803

<400> SEQUENCE: 28

Met Glu Ser Gly Ser Pro Glu Ile Glu Lys Leu Ser Gln Ser Asp Ile
```

```
                1               5                   10                  15
Tyr Trp Asp Ser Ile Val Ser Ile Thr Glu Thr Gly Val Glu Val
                    20                  25                  30

Phe Asp Leu Thr Val Pro Gly Pro His Asn Phe Val Ala Asn Asp Ile
            35                  40                  45

Ile Val His Asn Ser Ile Glu Gln Gly Gln Gly Gly Met Ser Met
    50                  55                  60

Asp Tyr Lys Asp Asp Asp Lys Met Arg Met Leu Glu Gly Gln Ala
65                  70                  75                  80

Gly Gly Leu Ile Thr Ser Gly Cys Ile Ser Gly Asp Ser Leu Ile Ser
                85                  90                  95

Leu Ala Ser Thr Gly Lys Arg Val Ser Ile Lys Asp Leu Leu Asp Glu
            100                 105                 110

Lys Asp Phe Glu Ile Trp Ala Ile Asn Glu Gln Thr Met Lys Leu Glu
            115                 120                 125

Ser Ala Lys Val Ser Arg Val Phe Cys Thr Gly Lys Lys Leu Val Tyr
    130                 135                 140

Ile Leu Lys Thr Arg Leu Gly Arg Thr Ile Lys Ala Thr Ala Asn His
145                 150                 155                 160

Arg Phe Leu Thr Ile Asp Gly Trp Lys Arg Leu Asp Glu Leu Ser Leu
                165                 170                 175

Lys Glu His Ile Ala Leu Pro Arg Lys Leu Glu Ser Ser Leu Gln
            180                 185                 190

Leu Ile Asp Pro Trp Leu Pro
            195
```

<210> SEQ ID NO 29
<211> LENGTH: 1314
<212> TYPE: DNA
<213> ORGANISM: Synechocystis PCC6803

<400> SEQUENCE: 29

```
atggagtccg gatcaccaga aatagaaaag ttgtctcaga gtgatatttta ctgggactcc      60
atcgtttcta ttacggagac tggagtcgaa gaggtttttg atttgactgt gccagggccc     120
cataactttg tggccaatga catcattgtc cataacagtg aggaggacct gggatccagc     180
gtgcagctcg ccgaccacta ccagcagaac ccccatcg gcgacggccc cgtgctgctg       240
cccgacaacc actacctgag cacccagtcc gccctgagca agacccccaa cgagaagcgc     300
gatcacatgg tcctgctgga gttcgtgacc gccgcggga tcactctcgg catggacgag      360
ctgtacaagg gtcgaacgg ggaattctcg caggtagaca agtcgatggt gagcaagggc      420
gaggagctgt tcaccgggt ggtgcccatc ctggtcgagc tggacggcga cgtaaacggc      480
cacaagttca gcgtgtccgg cgagggcgag ggcgatgcca cctacggcaa gctgaccctg     540
aagttcatct gcaccaccgg caagctgccc gtgcctggc ccaccctcgt gaccaccctg      600
acctacggcg tgcagtgctt cagccgctac cccgaccaca tgaagcagca cgacttcttc     660
aagtccgcca tgcccgaagg ctacgtccag gagcgcacca tcttcttcaa ggacgacggc     720
aactacaaga cccgcgccga ggtgaagttc gagggcgaca ccctggtgaa ccgcatcgag     780
ctgaagggca tcgacttcaa ggaggacggc aacatcctgg gcacaagct ggagtacaac      840
tacaacagcc acaacgtcta tatcatggcc gacaagcaga agaacggcat caaggtgaac     900
ttcaagatcc gccacaacat cgaggacctc gagcaaaagc tgtatatgcat ctccggaaat   960
agtttgatca gcttggcgag cacaggaaaa agagtttcta ttaaagattt gttagatgaa    1020
```

-continued

```
aaagattttg aaatatgggc aattaatgaa cagacgatga agctagaatc agctaaagtt    1080
agtcgtgtat tttgtactgg caaaaagcta gtttatattt taaaaactcg actaggtaga    1140
actatcaagg caacagcaaa tcatagattt ttaactattg atggttggaa aagattagat    1200
gagctatctt taaaagagca tattgctcta ccccgtaaac tagaaagctc ctctttacaa    1260
ttaggcctcc gcggccagta cccctacgac gtcccggact acgctatcga ttaa          1314
```

<210> SEQ ID NO 30
<211> LENGTH: 438
<212> TYPE: PRT
<213> ORGANISM: Synechocystis PCC6803

<400> SEQUENCE: 30

```
Met Glu Ser Gly Ser Pro Glu Ile Glu Lys Leu Ser Gln Ser Asp Ile
1               5                   10                  15

Tyr Trp Asp Ser Ile Val Ser Ile Thr Glu Thr Gly Val Glu Glu Val
            20                  25                  30

Phe Asp Leu Thr Val Pro Gly Pro His Asn Phe Val Ala Asn Asp Ile
        35                  40                  45

Ile Val His Asn Ser Glu Glu Asp Leu Gly Ser Ser Val Gln Leu Ala
    50                  55                  60

Asp His Tyr Gln Gln Asn Thr Pro Ile Gly Asp Gly Pro Val Leu Leu
65                  70                  75                  80

Pro Asp Asn His Tyr Leu Ser Thr Gln Ser Ala Leu Ser Lys Asp Pro
                85                  90                  95

Asn Glu Lys Arg Asp His Met Val Leu Leu Glu Phe Val Thr Ala Ala
            100                 105                 110

Gly Ile Thr Leu Gly Met Asp Glu Leu Tyr Lys Gly Ser Asn Gly Glu
        115                 120                 125

Phe Ser Gln Val Asp Lys Ser Met Val Ser Lys Gly Glu Glu Leu Phe
    130                 135                 140

Thr Gly Val Val Pro Ile Leu Val Glu Leu Asp Gly Asp Val Asn Gly
145                 150                 155                 160

His Lys Phe Ser Val Ser Gly Glu Gly Glu Gly Asp Ala Thr Tyr Gly
                165                 170                 175

Lys Leu Thr Leu Lys Phe Ile Cys Thr Thr Gly Lys Leu Pro Val Pro
            180                 185                 190

Trp Pro Thr Leu Val Thr Thr Leu Thr Tyr Gly Val Gln Cys Phe Ser
        195                 200                 205

Arg Tyr Pro Asp His Met Lys Gln His Asp Phe Phe Lys Ser Ala Met
    210                 215                 220

Pro Glu Gly Tyr Val Gln Glu Arg Thr Ile Phe Phe Lys Asp Asp Gly
225                 230                 235                 240

Asn Tyr Lys Thr Arg Ala Glu Val Lys Phe Glu Gly Asp Thr Leu Val
                245                 250                 255

Asn Arg Ile Glu Leu Lys Gly Ile Asp Phe Lys Glu Asp Gly Asn Ile
            260                 265                 270

Leu Gly His Lys Leu Glu Tyr Asn Tyr Asn Ser His Asn Val Tyr Ile
        275                 280                 285

Met Ala Asp Lys Gln Lys Asn Gly Ile Lys Val Asn Phe Lys Ile Arg
    290                 295                 300

His Asn Ile Glu Asp Leu Glu Gln Lys Leu Ile Cys Ile Ser Gly Asn
305                 310                 315                 320
```

```
Ser Leu Ile Ser Leu Ala Ser Thr Gly Lys Arg Val Ser Ile Lys Asp
            325                 330                 335

Leu Leu Asp Glu Lys Asp Phe Glu Ile Trp Ala Ile Asn Glu Gln Thr
        340                 345                 350

Met Lys Leu Glu Ser Ala Lys Val Ser Arg Val Phe Cys Thr Gly Lys
            355                 360                 365

Lys Leu Val Tyr Ile Leu Lys Thr Arg Leu Gly Arg Thr Ile Lys Ala
        370                 375                 380

Thr Ala Asn His Arg Phe Leu Thr Ile Asp Gly Trp Lys Arg Leu Asp
385                 390                 395                 400

Glu Leu Ser Leu Lys Glu His Ile Ala Leu Pro Arg Lys Leu Glu Ser
            405                 410                 415

Ser Ser Leu Gln Leu Gly Leu Arg Gly Gln Tyr Pro Tyr Asp Val Pro
            420                 425                 430

Asp Tyr Ala Ile Asp Glx
        435
```

<210> SEQ ID NO 31
<211> LENGTH: 1314
<212> TYPE: DNA
<213> ORGANISM: Synechocystis PCC6803

<400> SEQUENCE: 31

```
atggagtccg atcaccaga aatagaaaag ttgtctcaga gtgatattta ctgggactcc      60
atcgtttcta ttacggagac tggagtcgaa gaggttttg atttgactgt gccagggccc     120
cataactttg tggccaatga catcattgtc cataacagtg aggaggacct gggatccagc    180
gtgcagctcg ccgaccacta ccagcagaac accccatcg cgacggccc cgtgctgctg      240
cccgacaacc actacctgag cacccagtcc gccctgagca agaccccaa cgagaagcgc     300
gatcacatgg tcctgctgga gttcgtgacc gccgccggga tcactctcgg catggacgag    360
ctgtacaagg ggtcgaacgg ggaattctcg caggtagaca agtcgatggt gagcaagggc    420
gaggagctgt tcaccggggt ggtgcccatc ctggtcgagc tggacggcga cgtaaacggc    480
cacaagttca gcgtgtccgg cgagggcgag ggcgatgcca cctacggcaa gctgaccctg    540
aagttcatct gcaccaccgg caagctgccc gtgccctggc ccaccctcgt gaccaccctg    600
acctacggcg tgcagtgctt cagccgctac cccgaccaca tgaagcagca cgacttcttc    660
aagtccgcca tgcccgaagg ctacgtccag gagcgcacca tcttcttcaa ggacgacggc    720
aactacaaga cccgcgccga ggtgaagttc gagggcgaca ccctggtgaa ccgcatcgag    780
ctgaagggca tcgacttcaa ggaggacggc aacatcctgg ggcacaagct ggagtacaac    840
tacaacagcc acaacgtcta tatcatggcc gacaagcaga gaacggcat caaggtgaac    900
ttcaagatcc gccacaacat cgaggacctc gagcaaaagc tgatatgcat ctccggaaat    960
agtttgatca gcttggcgag cacaggaaaa agagtttcta ttaaagattt gttagatgaa  1020
aaagattttg aaatatgggc aattaatgaa cagacgatga gctagaatc agctaaagtt  1080
agtcgtgtat tttgtactgg caaaaagcta gtttatattt taaaaactcg actaggtaga  1140
actatcaagg caacagcaaa tcataaattt ttaactattg atggttggaa aagattagat  1200
gagctatctt taaagagca tattgctcta ccccgtaaac tagaaagctc ctctttacaa  1260
ttaggcctcc gcggccagta ccctacgac gtcccggact acgctatcga ttaa           1314
```

<210> SEQ ID NO 32
<211> LENGTH: 438

```
<212> TYPE: PRT
<213> ORGANISM: Synechocystis PCC6803

<400> SEQUENCE: 32

Met Glu Ser Gly Ser Pro Glu Ile Glu Lys Leu Ser Gln Ser Asp Ile
1               5                   10                  15

Tyr Trp Asp Ser Ile Val Ser Ile Thr Glu Thr Gly Val Glu Glu Val
            20                  25                  30

Phe Asp Leu Thr Val Pro Gly Pro His Asn Phe Val Ala Asn Asp Ile
        35                  40                  45

Ile Val His Asn Ser Glu Glu Asp Leu Gly Ser Ser Val Gln Leu Ala
    50                  55                  60

Asp His Tyr Gln Gln Asn Thr Pro Ile Gly Asp Gly Pro Val Leu Leu
65                  70                  75                  80

Pro Asp Asn His Tyr Leu Ser Thr Gln Ser Ala Leu Ser Lys Asp Pro
                85                  90                  95

Asn Glu Lys Arg Asp His Met Val Leu Leu Glu Phe Val Thr Ala Ala
            100                 105                 110

Gly Ile Thr Leu Gly Met Asp Glu Leu Tyr Lys Gly Ser Asn Gly Glu
        115                 120                 125

Phe Ser Gln Val Asp Lys Ser Met Val Ser Lys Gly Glu Glu Leu Phe
    130                 135                 140

Thr Gly Val Val Pro Ile Leu Val Glu Leu Asp Gly Asp Val Asn Gly
145                 150                 155                 160

His Lys Phe Ser Val Ser Gly Glu Gly Glu Gly Asp Ala Thr Tyr Gly
                165                 170                 175

Lys Leu Thr Leu Lys Phe Ile Cys Thr Thr Gly Lys Leu Pro Val Pro
            180                 185                 190

Trp Pro Thr Leu Val Thr Thr Leu Thr Tyr Gly Val Gln Cys Phe Ser
        195                 200                 205

Arg Tyr Pro Asp His Met Lys Gln His Asp Phe Phe Lys Ser Ala Met
    210                 215                 220

Pro Glu Gly Tyr Val Gln Glu Arg Thr Ile Phe Phe Lys Asp Asp Gly
225                 230                 235                 240

Asn Tyr Lys Thr Arg Ala Glu Val Lys Phe Glu Gly Asp Thr Leu Val
                245                 250                 255

Asn Arg Ile Glu Leu Lys Gly Ile Asp Phe Lys Glu Asp Gly Asn Ile
            260                 265                 270

Leu Gly His Lys Leu Glu Tyr Asn Tyr Asn Ser His Asn Val Tyr Ile
        275                 280                 285

Met Ala Asp Lys Gln Lys Asn Gly Ile Lys Val Asn Phe Lys Ile Arg
    290                 295                 300

His Asn Ile Glu Asp Leu Glu Gln Lys Leu Ile Cys Ile Ser Gly Asn
305                 310                 315                 320

Ser Leu Ile Ser Leu Ala Ser Thr Gly Lys Arg Val Ser Ile Lys Asp
                325                 330                 335

Leu Leu Asp Glu Lys Asp Phe Glu Ile Trp Ala Ile Asn Glu Gln Thr
            340                 345                 350

Met Lys Leu Glu Ser Ala Lys Val Ser Arg Val Phe Cys Thr Gly Lys
        355                 360                 365

Lys Leu Val Tyr Ile Leu Lys Thr Arg Leu Gly Arg Thr Ile Lys Ala
    370                 375                 380

Thr Ala Asn His Lys Phe Leu Thr Ile Asp Gly Trp Lys Arg Leu Asp
385                 390                 395                 400
```

```
Glu Leu Ser Leu Lys Glu His Ile Ala Leu Pro Arg Lys Leu Glu Ser
                405                 410                 415
Ser Ser Leu Gln Leu Gly Leu Arg Gly Gln Tyr Pro Tyr Asp Val Pro
            420                 425                 430
Asp Tyr Ala Ile Asp Glx
        435
```

<210> SEQ ID NO 33
<211> LENGTH: 1314
<212> TYPE: DNA
<213> ORGANISM: Synechocystis PCC6803

<400> SEQUENCE: 33

| | | | | | |
|---|---|---|---|---|---|
| atggagtccg | gatcaccaga | aatagaaaag | ttgtctcaga | gtgatattta | ctgggactcc | 60 |
| atcgtttcta | ttacggagac | tggagtcgaa | gaggtttttg | atttgactgt | gccagggccc | 120 |
| cataactttg | tggccaatga | catcattgtc | cataacagtg | aggaggacct | gggatccagc | 180 |
| gtgcagctcg | ccgaccacta | ccagcagaac | ccccatcg | gcgacggccc | cgtgctgctg | 240 |
| cccgacaacc | actacctgag | cacccagtcc | gccctgagca | agacccccaa | cgagaagcgc | 300 |
| gatcacatgg | tcctgctgga | gttcgtgacc | gccgccggga | tcactctcgg | catggacgag | 360 |
| ctgtacaagg | gtcgaacgg | ggaattctcg | caggtagaca | gtcgatggt | gagcaagggc | 420 |
| gaggagctgt | tcaccggggt | ggtgcccatc | ctggtcgagc | tggacggcga | cgtaaacggc | 480 |
| cacaagttca | gcgtgtccgg | cgagggcgag | ggcgatgcca | cctacggcaa | gctgaccctg | 540 |
| aagttcatct | gcaccaccgg | caagctgccc | gtgccctggc | ccaccctcgt | gaccaccctg | 600 |
| acctacggcg | tgcagtgctt | cagccgctac | cccgaccaca | tgaagcagca | cgacttcttc | 660 |
| aagtccgcca | tgcccgaagg | ctacgtccag | gagcgcacca | tcttcttcaa | ggacgacggc | 720 |
| aactacaaga | cccgcgccga | ggtgaagttc | gagggcgaca | ccctggtgaa | ccgcatcgag | 780 |
| ctgaagggca | tcgacttcaa | ggaggacggc | aacatcctgg | ggcacaagct | ggagtacaac | 840 |
| tacaacagcc | acaacgtcta | tatcatggcc | gacaagcaga | agaacggcat | caaggtgaac | 900 |
| ttcaagatcc | gccacaacat | cgaggacctc | gagcaaaagc | tgatatgcat | ctccggaaat | 960 |
| agtttgatca | gcttggcgag | cacaggaaaa | gagtttcta | ttaaagattt | gttagatgaa | 1020 |
| aaagattttg | aaatatgggc | agttaatgaa | cagacgatga | agctagaatc | agctaaagtt | 1080 |
| agtcgtgtat | tttgtactgg | caaaaagcta | gtttatattt | taaaaactcg | actaggtaga | 1140 |
| actatcaagg | caacagcaaa | tcatagattt | ttaactattg | atggttggaa | aagattagat | 1200 |
| gagctatctt | taaaagagca | tattgctcta | ccccgtaaac | tagaaagctc | ctctttacaa | 1260 |
| ttaggcctcc | gcggccagta | cccctacgac | gtcccggact | acgctatcga | ttaa | 1314 |

<210> SEQ ID NO 34
<211> LENGTH: 438
<212> TYPE: PRT
<213> ORGANISM: Synechocystis PCC6803

<400> SEQUENCE: 34

```
Met Glu Ser Gly Ser Pro Glu Ile Glu Lys Leu Ser Gln Ser Asp Ile
1               5                   10                  15
Tyr Trp Asp Ser Ile Val Ser Ile Thr Glu Thr Gly Val Glu Glu Val
            20                  25                  30
Phe Asp Leu Thr Val Pro Gly Pro His Asn Phe Val Ala Asn Asp Ile
        35                  40                  45
```

```
Ile Val His Asn Ser Glu Glu Asp Leu Gly Ser Ser Val Gln Leu Ala
 50                  55                  60

Asp His Tyr Gln Gln Asn Thr Pro Ile Gly Asp Gly Pro Val Leu Leu
 65                  70                  75                  80

Pro Asp Asn His Tyr Leu Ser Thr Gln Ser Ala Leu Ser Lys Asp Pro
                 85                  90                  95

Asn Glu Lys Arg Asp His Met Val Leu Glu Phe Val Thr Ala Ala
            100                 105                 110

Gly Ile Thr Leu Gly Met Asp Glu Leu Tyr Lys Gly Ser Asn Gly Glu
            115                 120                 125

Phe Ser Gln Val Asp Lys Ser Met Val Ser Lys Gly Glu Glu Leu Phe
130                 135                 140

Thr Gly Val Val Pro Ile Leu Val Glu Leu Asp Gly Asp Val Asn Gly
145                 150                 155                 160

His Lys Phe Ser Val Ser Gly Glu Gly Glu Gly Asp Ala Thr Tyr Gly
                165                 170                 175

Lys Leu Thr Leu Lys Phe Ile Cys Thr Thr Gly Lys Leu Pro Val Pro
            180                 185                 190

Trp Pro Thr Leu Val Thr Thr Leu Thr Tyr Gly Val Gln Cys Phe Ser
            195                 200                 205

Arg Tyr Pro Asp His Met Lys Gln His Asp Phe Phe Lys Ser Ala Met
210                 215                 220

Pro Glu Gly Tyr Val Gln Glu Arg Thr Ile Phe Phe Lys Asp Asp Gly
225                 230                 235                 240

Asn Tyr Lys Thr Arg Ala Glu Val Lys Phe Glu Gly Asp Thr Leu Val
                245                 250                 255

Asn Arg Ile Glu Leu Lys Gly Ile Asp Phe Lys Glu Asp Gly Asn Ile
            260                 265                 270

Leu Gly His Lys Leu Glu Tyr Asn Tyr Asn Ser His Asn Val Tyr Ile
            275                 280                 285

Met Ala Asp Lys Gln Lys Asn Gly Ile Lys Val Asn Phe Lys Ile Arg
290                 295                 300

His Asn Ile Glu Asp Leu Glu Gln Lys Leu Ile Cys Ile Ser Gly Asn
305                 310                 315                 320

Ser Leu Ile Ser Leu Ala Ser Thr Gly Lys Arg Val Ser Ile Lys Asp
                325                 330                 335

Leu Leu Asp Glu Lys Asp Phe Glu Ile Trp Ala Val Asn Glu Gln Thr
            340                 345                 350

Met Lys Leu Glu Ser Ala Lys Val Ser Arg Val Phe Cys Thr Gly Lys
            355                 360                 365

Lys Leu Val Tyr Ile Leu Lys Thr Arg Leu Gly Arg Thr Ile Lys Ala
370                 375                 380

Thr Ala Asn His Arg Phe Leu Thr Ile Asp Gly Trp Lys Arg Leu Asp
385                 390                 395                 400

Glu Leu Ser Leu Lys Glu His Ile Ala Leu Pro Arg Lys Leu Glu Ser
                405                 410                 415

Ser Ser Leu Gln Leu Gly Leu Arg Gly Gln Tyr Pro Tyr Asp Val Pro
            420                 425                 430

Asp Tyr Ala Ile Asp Glx
            435

<210> SEQ ID NO 35
<211> LENGTH: 1314
<212> TYPE: DNA
```

<213> ORGANISM: Synechocystis PCC6803

<400> SEQUENCE: 35

```
atggagtccg gatcaccaga aatagaaaag ttgtctcaga gtgatattta ctgggactcc      60
atcgtttcta ttacggagac tggagtcgaa gaggttttg atttggccgt gccagggccc     120
cataactttg tggccaatga catcattgtc cataacagtg aggaggacct gggatccagc    180
gtgcagctcg ccgaccacta ccagcagaac accccatcg gcgacggccc cgtgctgctg    240
cccgacaacc actacctgag cacccagtcc gccctgagca agacccccaa cgagaagcgc    300
gatcacatgg tcctgctgga gttcgtgacc gccgccggga tcactctcgg catggacgag    360
ctgtacaagg ggtcgaacgg ggaattctcg caggtagaca gtcgatggt gagcaagggc     420
gaggagctgt tcaccggggt ggtgcccatc ctggtcgagc tggacggcga cgtaaacggc    480
cacaagttca gcgtgtccgg cgagggcgag ggcgatgcca cctacggcaa gctgaccctg    540
aagttcatct gcaccaccgg caagctgccc gtgccctggc ccaccctcgt gaccaccctg    600
acctacggcg tgcagtgctt cagccgctac cccgaccaca tgaagcagca cgacttcttc    660
aagtccgcca tgcccgaagg ctacgtccag gagcgcacca tcttcttcaa ggacgacggc    720
aactacaaga cccgcgccga ggtgaagttc gagggcgaca ccctggtgaa ccgcatcgag    780
ctgaagggca tcgacttcaa ggaggacggc aacatcctgg ggcacaagct ggagtacaac    840
tacaacagcc acaacgtcta tatcatggcc gacaagcaga agaacggcat caaggtgaac    900
ttcaagatcc gccacaacat cgaggacctc gagcaaaagc tgatatgcat ctccggaaat    960
agtttgatca gcttggcgag cacaggaaaa agagtttcta ttaaagattt gttagatgaa   1020
aaagattttg aaatatgggc aattaatgaa cagacgatga agctagaatc agctaaagtt   1080
agtcgtgtat tttgtactgg caaaaagcta gtttatattt taaaaactcg actaggtaga   1140
actatcaagg caacagcaaa tcatagattt ttaactattg atggttgaa aagattagat    1200
gagctatctt taaaagagca tattgctcta ccccgtaaac tagaaagctc ctctttacaa   1260
ttaggcctcc gcggccagta cccctacgac gtcccggact acgctatcga ttaa          1314
```

<210> SEQ ID NO 36
<211> LENGTH: 438
<212> TYPE: PRT
<213> ORGANISM: Synechocystis PCC6803

<400> SEQUENCE: 36

```
Met Glu Ser Gly Ser Pro Glu Ile Glu Lys Leu Ser Gln Ser Asp Ile
  1               5                  10                  15

Tyr Trp Asp Ser Ile Val Ser Ile Thr Glu Thr Gly Val Glu Glu Val
             20                  25                  30

Phe Asp Leu Ala Val Pro Gly Pro His Asn Phe Val Ala Asn Asp Ile
         35                  40                  45

Ile Val His Asn Ser Glu Glu Asp Leu Gly Ser Ser Val Gln Leu Ala
     50                  55                  60

Asp His Tyr Gln Gln Asn Thr Pro Ile Gly Asp Gly Pro Val Leu Leu
 65                  70                  75                  80

Pro Asp Asn His Tyr Leu Ser Thr Gln Ser Ala Leu Ser Lys Asp Pro
                 85                  90                  95

Asn Glu Lys Arg Asp His Met Val Leu Leu Glu Phe Val Thr Ala Ala
            100                 105                 110

Gly Ile Thr Leu Gly Met Asp Glu Leu Tyr Lys Gly Ser Asn Gly Glu
        115                 120                 125
```

-continued

```
Phe Ser Gln Val Asp Lys Ser Met Val Ser Lys Gly Glu Glu Leu Phe
    130                 135                 140

Thr Gly Val Val Pro Ile Leu Val Glu Leu Asp Gly Asp Val Asn Gly
145                 150                 155                 160

His Lys Phe Ser Val Ser Gly Glu Gly Glu Gly Asp Ala Thr Tyr Gly
                165                 170                 175

Lys Leu Thr Leu Lys Phe Ile Cys Thr Thr Gly Lys Leu Pro Val Pro
            180                 185                 190

Trp Pro Thr Leu Val Thr Thr Leu Thr Tyr Gly Val Gln Cys Phe Ser
        195                 200                 205

Arg Tyr Pro Asp His Met Lys Gln His Asp Phe Phe Lys Ser Ala Met
210                 215                 220

Pro Glu Gly Tyr Val Gln Glu Arg Thr Ile Phe Phe Lys Asp Asp Gly
225                 230                 235                 240

Asn Tyr Lys Thr Arg Ala Glu Val Lys Phe Glu Gly Asp Thr Leu Val
                245                 250                 255

Asn Arg Ile Glu Leu Lys Gly Ile Asp Phe Lys Glu Asp Gly Asn Ile
            260                 265                 270

Leu Gly His Lys Leu Glu Tyr Asn Tyr Asn Ser His Asn Val Tyr Ile
        275                 280                 285

Met Ala Asp Lys Gln Lys Asn Gly Ile Lys Val Asn Phe Lys Ile Arg
290                 295                 300

His Asn Ile Glu Asp Leu Glu Gln Lys Leu Ile Cys Ile Ser Gly Asn
305                 310                 315                 320

Ser Leu Ile Ser Leu Ala Ser Thr Gly Lys Arg Val Ser Ile Lys Asp
                325                 330                 335

Leu Leu Asp Glu Lys Asp Phe Glu Ile Trp Ala Ile Asn Glu Gln Thr
            340                 345                 350

Met Lys Leu Glu Ser Ala Lys Val Ser Arg Val Phe Cys Thr Gly Lys
        355                 360                 365

Lys Leu Val Tyr Ile Leu Lys Thr Arg Leu Gly Arg Thr Ile Lys Ala
370                 375                 380

Thr Ala Asn His Arg Phe Leu Thr Ile Asp Gly Trp Lys Arg Leu Asp
385                 390                 395                 400

Glu Leu Ser Leu Lys Glu His Ile Ala Leu Pro Arg Lys Leu Glu Ser
                405                 410                 415

Ser Ser Leu Gln Leu Gly Leu Arg Gly Gln Tyr Pro Tyr Asp Val Pro
            420                 425                 430

Asp Tyr Ala Ile Asp Glx
        435
```

<210> SEQ ID NO 37
<211> LENGTH: 1314
<212> TYPE: DNA
<213> ORGANISM: Synechocystis PCC6803

<400> SEQUENCE: 37

| | | |
|---|---|---|
| atggagtccg gatcaccaga aatagaaaag ttgtctcaga gtgatattta ctgggactcc | 60 |
| atcgttccta ttacggagac tggagtcgaa gaggtttttg atttgactgt gccagggccc | 120 |
| cataactttg tggccaatga catcattgtc cataacagtg aggaggacct gggatccagc | 180 |
| gtgcagctcg ccgaccacta ccagcagaac ccccatcg gcgacggccc cgtgctgctg | 240 |
| cccgacaacc actacctgag cacccagtcc gccctgagca agaccccaa cgagaagcgc | 300 |

-continued

```
gatcacatgg tcctgctgga gttcgtgacc gccgccggga tcactctcgg catggacgag    360
ctgtacaagg ggtcgaacgg ggaattctcg caggtagaca agtcgatggt gagcaagggc    420
gaggagctgt tcaccggggt ggtgcccatc ctggtcgagc tggacggcga cgtaaacggc    480
cacaagttca gcgtgtccgg cgagggcgag ggcgatgcca cctacggcaa gctgaccctg    540
aagttcatct gcaccaccgg caagctgccc gtgccctggc ccaccctcgt gaccaccctg    600
acctacggcg tgcagtgctt cagccgctac cccgaccaca tgaagcagca cgacttcttc    660
aagtccgcca tgcccgaagg ctacgtccag gagcgcacca tcttcttcaa ggacgacggc    720
aactacaaga cccgcgccga ggtgaagttc gagggcgaca ccctggtgaa ccgcatcgag    780
ctgaagggca tcgacttcaa ggaggacggc aacatcctgg ggcacaagct ggagtacaac    840
tacaacagcc acaacgtcta tatcatggcc gacaagcaga agaacggcat caaggtgaac    900
ttcaagatcc gccacaacat cgaggacctc gagcaaaagc tgatatgcat ctccggaaat    960
agtttgatca gcttggcgag cacaggaaaa agagtttcta ttaaagattt gttagatgaa    1020
aaagattttg aaatatgggc aattaatgaa cagacgatga agctagaatc agctaaagtt    1080
agtcgtgtat tttgtactgg caaaaagcta gtttatattt taaaaactcg actaggtaga    1140
actatcaagg caacagcaaa tcatagattt ttaactattg atggttggaa aagattagat    1200
gagctatctt taaagagca tattgctcta ccccgtaaac tagaaagctc ctctttacaa    1260
ttaggcctcc gcggccagta cccctacgac gtcccggact acgctatcga ttaa          1314
```

<210> SEQ ID NO 38
<211> LENGTH: 438
<212> TYPE: PRT
<213> ORGANISM: Synechocystis PCC6803

<400> SEQUENCE: 38

```
Met Glu Ser Gly Ser Pro Glu Ile Glu Lys Leu Ser Gln Ser Asp Ile
1               5                   10                  15

Tyr Trp Asp Ser Ile Val Pro Ile Thr Glu Thr Gly Val Glu Glu Val
                20                  25                  30

Phe Asp Leu Thr Val Pro Gly Pro His Asn Phe Val Ala Asn Asp Ile
            35                  40                  45

Ile Val His Asn Ser Glu Glu Asp Leu Gly Ser Ser Val Gln Leu Ala
        50                  55                  60

Asp His Tyr Gln Gln Asn Thr Pro Ile Gly Asp Gly Pro Val Leu Leu
65                  70                  75                  80

Pro Asp Asn His Tyr Leu Ser Thr Gln Ser Ala Leu Ser Lys Asp Pro
                85                  90                  95

Asn Glu Lys Arg Asp His Met Val Leu Leu Glu Phe Val Thr Ala Ala
                100                 105                 110

Gly Ile Thr Leu Gly Met Asp Glu Leu Tyr Lys Gly Ser Asn Gly Glu
            115                 120                 125

Phe Ser Gln Val Asp Lys Ser Met Val Ser Lys Gly Glu Glu Leu Phe
        130                 135                 140

Thr Gly Val Val Pro Ile Leu Val Glu Leu Asp Gly Asp Val Asn Gly
145                 150                 155                 160

His Lys Phe Ser Val Ser Gly Glu Gly Glu Gly Asp Ala Thr Tyr Gly
                165                 170                 175

Lys Leu Thr Leu Lys Phe Ile Cys Thr Thr Gly Lys Leu Pro Val Pro
            180                 185                 190

Trp Pro Thr Leu Val Thr Thr Leu Thr Tyr Gly Val Gln Cys Phe Ser
```

```
                195                 200                 205
Arg Tyr Pro Asp His Met Lys Gln His Asp Phe Phe Lys Ser Ala Met
    210                 215                 220

Pro Glu Gly Tyr Val Gln Glu Arg Thr Ile Phe Phe Lys Asp Asp Gly
225                 230                 235                 240

Asn Tyr Lys Thr Arg Ala Glu Val Lys Phe Glu Gly Asp Thr Leu Val
                245                 250                 255

Asn Arg Ile Glu Leu Lys Gly Ile Asp Phe Lys Glu Asp Gly Asn Ile
            260                 265                 270

Leu Gly His Lys Leu Glu Tyr Asn Tyr Asn Ser His Asn Val Tyr Ile
        275                 280                 285

Met Ala Asp Lys Gln Lys Asn Gly Ile Lys Val Asn Phe Lys Ile Arg
    290                 295                 300

His Asn Ile Glu Asp Leu Glu Gln Lys Leu Ile Cys Ile Ser Gly Asn
305                 310                 315                 320

Ser Leu Ile Ser Leu Ala Ser Thr Gly Lys Arg Val Ser Ile Lys Asp
                325                 330                 335

Leu Leu Asp Glu Lys Asp Phe Glu Ile Trp Ala Ile Asn Glu Gln Thr
            340                 345                 350

Met Lys Leu Glu Ser Ala Lys Val Ser Arg Val Phe Cys Thr Gly Lys
        355                 360                 365

Lys Leu Val Tyr Ile Leu Lys Thr Arg Leu Gly Arg Thr Ile Lys Ala
    370                 375                 380

Thr Ala Asn His Arg Phe Leu Thr Ile Asp Gly Trp Lys Arg Leu Asp
385                 390                 395                 400

Glu Leu Ser Leu Lys Glu His Ile Ala Leu Pro Arg Lys Leu Glu Ser
                405                 410                 415

Ser Ser Leu Gln Leu Gly Leu Arg Gly Gln Tyr Pro Tyr Asp Val Pro
            420                 425                 430

Asp Tyr Ala Ile Asp Glx
        435

<210> SEQ ID NO 39
<211> LENGTH: 1314
<212> TYPE: DNA
<213> ORGANISM: Synechocystis PCC6803

<400> SEQUENCE: 39
atggagtccg gatcaccaga aatagaaaag ttgtctcaga gtgatattta ctgggactcc    60
atcgtttcta ttacggagac tggagtcgaa gaggtttttg atttgactgt gccagggccc   120
cataactttg tggccaatga catcattgtc cataacagtg aggaggacct gggatccagc   180
gtgcagctcg ccgaccacta ccagcagaac accccatcg gcgacggccc cgtgctgctg    240
cccgacaacc actacctgag cacccagtcc gccctgagca agacccccaa cgagaagcgc   300
gatcacatgg tcctgctgga gttcgtgacc gccgccggga tcactctcgg catggacgag   360
ctgtacaagg ggtcgaacgg ggaattctcg caggtagaca agtcgatggt gagcaagggc   420
gaggagctgt tcaccggggt ggtgcccatc ctggtcgagc tggacggcga cgtaaacggc   480
cacaagttca gcgtgtccgg cgagggcgag ggcgatgcca cctacggcaa gctgaccctg   540
aagttcatct gcaccaccgg caagctgccc gtgcctggc ccaccctcgt gaccaccctg   600
acctacggcg tgcagtgctt cagccgctac cccgaccaca tgaagcagca cgacttcttc   660
aagtccgcca tgcccgaagg ctacgtccag gagcgcacca tcttcttcaa ggacgacggc   720
```

```
aactacaaga cccgcgccga ggtgaagttc gagggcgaca ccctggtgaa ccgcatcgag    780
ctgaagggca tcgacttcaa ggaggacggc aacatcctgg ggcacaagct ggagtacaac    840
tacaacagcc acaacgtcta tatcatggcc gacaagcaga agaacggcat caaggtgaac    900
ttcaagatcc gccacaacat cgaggacctc gagcaaaagc tgatatgcat ctccggaaat    960
agtttgatca gcttggcgag cacaggaaaa agagtttcta ttaaagattt gttagatgaa   1020
aaagattttg aaatatgggc aattaatgaa cagacgatga agctagaatc agctaaagtt   1080
agtcgtgtat tttgtactgg caaaaggcta gtttatattt taaaaactcg actaggtaga   1140
actatcaagg caacagcaaa tcatagattt ttaactattg atggttggaa agattagat    1200 gagctatctt taaaagagca tattgctcta ccccgtaaac tagaaagctc ctctttacaa   1260
ttaggcctcc gcggccagta cccctacgac gtcccggact acgctatcga ttaa         1314
```

<210> SEQ ID NO 40
<211> LENGTH: 438
<212> TYPE: PRT
<213> ORGANISM: Synechocystis PCC6803

<400> SEQUENCE: 40

```
Met Glu Ser Gly Ser Pro Glu Ile Glu Lys Leu Ser Gln Ser Asp Ile
1               5                   10                  15

Tyr Trp Asp Ser Ile Val Ser Ile Thr Glu Thr Gly Val Glu Val
            20                  25                  30

Phe Asp Leu Thr Val Pro Gly Pro His Asn Phe Val Ala Asn Asp Ile
            35                  40                  45

Ile Val His Asn Ser Glu Glu Asp Leu Gly Ser Ser Val Gln Leu Ala
    50                  55                  60

Asp His Tyr Gln Gln Asn Thr Pro Ile Gly Asp Gly Pro Val Leu Leu
65                  70                  75                  80

Pro Asp Asn His Tyr Leu Ser Thr Gln Ser Ala Leu Ser Lys Asp Pro
                85                  90                  95

Asn Glu Lys Arg Asp His Met Val Leu Leu Glu Phe Val Thr Ala Ala
            100                 105                 110

Gly Ile Thr Leu Gly Met Asp Glu Leu Tyr Lys Gly Ser Asn Gly Glu
        115                 120                 125

Phe Ser Gln Val Asp Lys Ser Met Val Ser Lys Gly Glu Glu Leu Phe
    130                 135                 140

Thr Gly Val Val Pro Ile Leu Val Glu Leu Asp Gly Asp Val Asn Gly
145                 150                 155                 160

His Lys Phe Ser Val Ser Gly Glu Gly Glu Gly Asp Ala Thr Tyr Gly
                165                 170                 175

Lys Leu Thr Leu Lys Phe Ile Cys Thr Thr Gly Lys Leu Pro Val Pro
            180                 185                 190

Trp Pro Thr Leu Val Thr Thr Leu Thr Tyr Gly Val Gln Cys Phe Ser
        195                 200                 205

Arg Tyr Pro Asp His Met Lys Gln His Asp Phe Phe Lys Ser Ala Met
    210                 215                 220

Pro Glu Gly Tyr Val Gln Glu Arg Thr Ile Phe Phe Lys Asp Asp Gly
225                 230                 235                 240

Asn Tyr Lys Thr Arg Ala Glu Val Lys Phe Glu Gly Asp Thr Leu Val
                245                 250                 255

Asn Arg Ile Glu Leu Lys Gly Ile Asp Phe Lys Glu Asp Gly Asn Ile
            260                 265                 270
```

```
Leu Gly His Lys Leu Glu Tyr Asn Tyr Asn Ser His Asn Val Tyr Ile
        275                 280                 285
Met Ala Asp Lys Gln Lys Asn Gly Ile Lys Val Asn Phe Lys Ile Arg
        290                 295                 300
His Asn Ile Glu Asp Leu Glu Gln Lys Leu Ile Cys Ile Ser Gly Asn
305                 310                 315                 320
Ser Leu Ile Ser Leu Ala Ser Thr Gly Lys Arg Val Ser Ile Lys Asp
                325                 330                 335
Leu Leu Asp Glu Lys Asp Phe Glu Ile Trp Ala Ile Asn Glu Gln Thr
            340                 345                 350
Met Lys Leu Glu Ser Ala Lys Val Ser Arg Val Phe Cys Thr Gly Lys
        355                 360                 365
Arg Leu Val Tyr Ile Leu Lys Thr Arg Leu Gly Arg Thr Ile Lys Ala
    370                 375                 380
Thr Ala Asn His Arg Phe Leu Thr Ile Asp Gly Trp Lys Arg Leu Asp
385                 390                 395                 400
Glu Leu Ser Leu Lys Glu His Ile Ala Leu Pro Arg Lys Leu Glu Ser
                405                 410                 415
Ser Ser Leu Gln Leu Gly Leu Arg Gly Gln Tyr Pro Tyr Asp Val Pro
            420                 425                 430
Asp Tyr Ala Ile Asp Glx
        435
```

<210> SEQ ID NO 41
<211> LENGTH: 1314
<212> TYPE: DNA
<213> ORGANISM: Synechocystis PCC6803

<400> SEQUENCE: 41

```
atggagtccg gatcaccaga aatagaaaag ttgtctcaga gtgatattta ctgggactcc        60
atcgtttcta ttacggagac tggagtcgaa gaggtttttg atttgactgt gccagggccc       120
cataactttg tggccaatga catcattgtc cataacagtg aggaggacct gggatccagc       180
gtgcagctcg ccgaccacta ccagcagaac ccccccatcg cgacggcccc cgtgctgctg       240
cccgacaacc actacctgag cacccagtcc gccctgagca agaccccaa cgagaagcgc        300
gatcacatgg tcctgctgga gttcgtgacc gcgccggga tcactctcgg catgacgag         360
ctgtacaagg ggtcgaacgg ggaattctcg caggtagaca agtcgatggt gagcaagggc       420
gaggagctgt tcaccggggt ggtgcccatc ctggtcgagc tggacggcga cgtaaacggc       480
cacaagttca gcgtgtccgg cgagggcgag ggcgatgcca cctacggcaa gctgaccctg       540
aagttcatct gcaccaccgg caagctgccc gtgccctggc ccaccctcgt gaccaccctg       600
acctacggcg tgcagtgctt cagccgctac cccgaccaca tgaagcagca cgacttcttc       660
aagtccgcca tgcccgaagg ctacgtccag gagcgcacca tcttcttcaa ggacgacggc       720
aactacaaga cccgcgccga ggtgaagttc gagggcgaca ccctggtgaa ccgcatcgag       780
ctgaagggca tcgacttcaa ggaggacggc aacatcctgg ggcacaagct ggagtacaac       840
tacaacagcc acaacgtcta tatcatggcc gacaagcaga agaacggcat caaggtgaac       900
ttcaagatcc gccacaacat cgaggacctc gagcaaaagc tgatatgcat ctccggagat       960
agtttgatca gcttggcgag cacaggaaaa agagtttcta ttaaagattt gttagatgaa      1020
aaagattttg aaatatgggc aattaatgaa cagacgatga agctagaatc agctaaagtt      1080
agtcgtgtat tttgtactgg caaaaagcta gtttatattt taaaaactcg actaggtaga      1140
```

```
actatcaagg caacagcaaa tcataaattt ttaactattg atggttggaa aagattagat    1200
gagctatctt taaaagagca tattgctcta ccccgtaaac tagaaagctc ctctttacaa    1260
ttaggcctcc gcggccagta cccctacgac gtcccggact acgctatcga ttaa          1314
```

<210> SEQ ID NO 42
<211> LENGTH: 438
<212> TYPE: PRT
<213> ORGANISM: Synechocystis PCC6803

<400> SEQUENCE: 42

```
Met Glu Ser Gly Ser Pro Glu Ile Glu Lys Leu Ser Gln Ser Asp Ile
1               5                   10                  15

Tyr Trp Asp Ser Ile Val Ser Ile Thr Glu Thr Gly Val Glu Glu Val
            20                  25                  30

Phe Asp Leu Thr Val Pro Gly Pro His Asn Phe Val Ala Asn Asp Ile
        35                  40                  45

Ile Val His Asn Ser Glu Glu Asp Leu Gly Ser Val Gln Leu Ala
    50                  55                  60

Asp His Tyr Gln Gln Asn Thr Pro Ile Gly Asp Gly Pro Val Leu Leu
65                  70                  75                  80

Pro Asp Asn His Tyr Leu Ser Thr Gln Ser Ala Leu Ser Lys Asp Pro
                85                  90                  95

Asn Glu Lys Arg Asp His Met Val Leu Leu Glu Phe Val Thr Ala Ala
            100                 105                 110

Gly Ile Thr Leu Gly Met Asp Glu Leu Tyr Lys Gly Ser Asn Gly Glu
        115                 120                 125

Phe Ser Gln Val Asp Lys Ser Met Val Ser Lys Gly Glu Glu Leu Phe
    130                 135                 140

Thr Gly Val Val Pro Ile Leu Val Glu Leu Asp Gly Asp Val Asn Gly
145                 150                 155                 160

His Lys Phe Ser Val Ser Gly Glu Gly Glu Gly Asp Ala Thr Tyr Gly
                165                 170                 175

Lys Leu Thr Leu Lys Phe Ile Cys Thr Thr Gly Lys Leu Pro Val Pro
            180                 185                 190

Trp Pro Thr Leu Val Thr Thr Leu Thr Tyr Gly Val Gln Cys Phe Ser
        195                 200                 205

Arg Tyr Pro Asp His Met Lys Gln His Asp Phe Phe Lys Ser Ala Met
    210                 215                 220

Pro Glu Gly Tyr Val Gln Glu Arg Thr Ile Phe Phe Lys Asp Asp Gly
225                 230                 235                 240

Asn Tyr Lys Thr Arg Ala Glu Val Lys Phe Glu Gly Asp Thr Leu Val
                245                 250                 255

Asn Arg Ile Glu Leu Lys Gly Ile Asp Phe Lys Glu Asp Gly Asn Ile
            260                 265                 270

Leu Gly His Lys Leu Glu Tyr Asn Tyr Asn Ser His Asn Val Tyr Ile
        275                 280                 285

Met Ala Asp Lys Gln Lys Asn Gly Ile Lys Val Asn Phe Lys Ile Arg
    290                 295                 300

His Asn Ile Glu Asp Leu Glu Gln Lys Leu Ile Cys Ile Ser Gly Asp
305                 310                 315                 320

Ser Leu Ile Ser Leu Ala Ser Thr Gly Lys Arg Val Ser Ile Lys Asp
                325                 330                 335

Leu Leu Asp Glu Lys Asp Phe Glu Ile Trp Ala Ile Asn Glu Gln Thr
            340                 345                 350
```

Met Lys Leu Glu Ser Ala Lys Val Ser Arg Val Phe Cys Thr Gly Lys
                355                 360                 365

Lys Leu Val Tyr Ile Leu Lys Thr Arg Leu Gly Arg Thr Ile Lys Ala
            370                 375                 380

Thr Ala Asn His Lys Phe Leu Thr Ile Asp Gly Trp Lys Arg Leu Asp
385                 390                 395                 400

Glu Leu Ser Leu Lys Glu His Ile Ala Leu Pro Arg Lys Leu Glu Ser
                405                 410                 415

Ser Ser Leu Gln Leu Gly Leu Arg Gly Gln Tyr Pro Tyr Asp Val Pro
            420                 425                 430

Asp Tyr Ala Ile Asp Glx
        435

<210> SEQ ID NO 43
<211> LENGTH: 1314
<212> TYPE: DNA
<213> ORGANISM: Synechocystis PCC6803

<400> SEQUENCE: 43
atggagtccg gatcaccaga aatagaaaag ttgtctcaga gtgatattta ctgggactcc      60
atcgttccta ttacggagac tggagtcgaa gaggttttg atttgactgt gccagggccc      120
cataactttg tggccaatga catcattgtc cataacagtg aggaggacct gggatccagc      180
gtgcagctcg ccgaccacta ccagcagaac acccccatcg cgacggccc cgtgctgctg      240
cccgacaacc actacctgag cacccagtcc gccctgagca agacccccaa cgagaagcgc      300
gatcacatgg tcctgctgga gttcgtgacc gccgccggga tcactctcgg catggacgag      360
ctgtacaagg ggtcgaacgg ggaattctcg caggtagaca agtcgatggt gagcaagggc      420
gaggagctgt tcaccggggt ggtgcccatc ctggtcgagc tggacggcga cgtaaacggc      480
cacaagttca gcgtgtccgg cgagggcgag ggcgatgcca cctacggcaa gctgaccctg      540
aagttcatct gcaccaccgg caagctgccc gtgccctggc ccaccctcgt gaccaccctg      600
acctacggcg tgcagtgctt cagccgctac cccgaccaca tgaagcagca cgacttcttc      660
aagtccgcca tgcccgaagg ctacgtccag gagcgcacca tcttcttcaa ggacgacggc      720
aactacaaga cccgcgccga ggtgaagttc gagggcgaca ccctggtgaa ccgcatcgag      780
ctgaagggca tcgacttcaa ggaggacggc aacatcctgg gcacaagct ggagtacaac      840
tacaacagcc acaacgtcta tatcatggcc gacaagcaga gaacggcat caaggtgaac      900
ttcaagatcc gccacaacat cgaggacctc gagcaaaagc tgatatgcat ctccggagat      960
agtttgatca gcttggcgag cacaggaaaa agagtttcta ttaaagattt gttagatgaa    1020
aaagattttg aaatatgggc aattaatgaa cagacgatga agctagaatc agctaaagtt    1080
agtcgtgtat tttgtactgg caaaaagcta gtttatattt taaaaactcg actaggtaga    1140
actatcaagg caacagcaaa tcatagattt ttaactattg atggttggaa aagattagat    1200
gagctatctt taaagagca tattgctcta ccccgtaaac tagaaagctc ctctttacaa    1260
ttaggcctcc gcggccagta cccctacgac gtcccggact acgctatcga ttaa         1314

<210> SEQ ID NO 44
<211> LENGTH: 438
<212> TYPE: PRT
<213> ORGANISM: Synechocystis PCC6803

<400> SEQUENCE: 44

```
Met Glu Ser Gly Ser Pro Glu Ile Glu Lys Leu Ser Gln Ser Asp Ile
1               5                   10                  15

Tyr Trp Asp Ser Ile Val Pro Ile Thr Glu Thr Gly Val Glu Glu Val
            20                  25                  30

Phe Asp Leu Thr Val Pro Gly Pro His Asn Phe Val Ala Asn Asp Ile
            35              40                  45

Ile Val His Asn Ser Glu Glu Asp Leu Gly Ser Ser Val Gln Leu Ala
50                      55                  60

Asp His Tyr Gln Gln Asn Thr Pro Ile Gly Asp Gly Pro Val Leu Leu
65                  70              75                      80

Pro Asp Asn His Tyr Leu Ser Thr Gln Ser Ala Leu Ser Lys Asp Pro
                85                  90                  95

Asn Glu Lys Arg Asp His Met Val Leu Leu Glu Phe Val Thr Ala Ala
            100             105                 110

Gly Ile Thr Leu Gly Met Asp Glu Leu Tyr Lys Gly Ser Asn Gly Glu
            115             120                 125

Phe Ser Gln Val Asp Lys Ser Met Val Ser Lys Gly Glu Glu Leu Phe
    130             135                 140

Thr Gly Val Val Pro Ile Leu Val Glu Leu Asp Gly Asp Val Asn Gly
145                 150                 155                 160

His Lys Phe Ser Val Ser Gly Glu Gly Glu Gly Asp Ala Thr Tyr Gly
                165                 170                 175

Lys Leu Thr Leu Lys Phe Ile Cys Thr Thr Gly Lys Leu Pro Val Pro
            180                 185                 190

Trp Pro Thr Leu Val Thr Thr Leu Thr Tyr Gly Val Gln Cys Phe Ser
        195                 200                 205

Arg Tyr Pro Asp His Met Lys Gln His Asp Phe Phe Lys Ser Ala Met
    210                 215                 220

Pro Glu Gly Tyr Val Gln Glu Arg Thr Ile Phe Phe Lys Asp Asp Gly
225                 230                 235                 240

Asn Tyr Lys Thr Arg Ala Glu Val Lys Phe Glu Gly Asp Thr Leu Val
            245                 250                 255

Asn Arg Ile Glu Leu Lys Gly Ile Asp Phe Lys Glu Asp Gly Asn Ile
            260                 265                 270

Leu Gly His Lys Leu Glu Tyr Asn Tyr Asn Ser His Asn Val Tyr Ile
        275                 280                 285

Met Ala Asp Lys Gln Lys Asn Gly Ile Lys Val Asn Phe Lys Ile Arg
    290                 295                 300

His Asn Ile Glu Asp Leu Glu Gln Lys Leu Ile Cys Ile Ser Gly Asp
305                 310                 315                 320

Ser Leu Ile Ser Leu Ala Ser Thr Gly Lys Arg Val Ser Ile Lys Asp
            325                 330                 335

Leu Leu Asp Glu Lys Asp Phe Glu Ile Trp Ala Ile Asn Glu Gln Thr
        340                 345                 350

Met Lys Leu Glu Ser Ala Lys Val Ser Arg Val Phe Cys Thr Gly Lys
    355                 360                 365

Lys Leu Val Tyr Ile Leu Lys Thr Arg Leu Gly Arg Thr Ile Lys Ala
    370                 375                 380

Thr Ala Asn His Arg Phe Leu Thr Ile Asp Gly Trp Lys Arg Leu Asp
385                 390                 395                 400

Glu Leu Ser Leu Lys Glu His Ile Ala Leu Pro Arg Lys Leu Glu Ser
            405                 410                 415

Ser Ser Leu Gln Leu Gly Leu Arg Gly Gln Tyr Pro Tyr Asp Val Pro
```

```
                420               425               430
Asp Tyr Ala Ile Asp Glx
        435

<210> SEQ ID NO 45
<211> LENGTH: 1314
<212> TYPE: DNA
<213> ORGANISM: Synechocystis PCC6803

<400> SEQUENCE: 45
atggagtccg gatcaccaga aatagaaaag ttgtctcaga gtgatattta ctgggactcc      60
atcgtttcta ttacggagac tggagtcgaa gaggttttg atttgactgt gccagggccc     120
cataactttg tggccaatga catcattgtc cataacagtg aggaggacct gggatccagc     180
gtgcagctcg ccgaccacta ccagcagaac accccatcg gcgacggccc cgtgctgctg     240
cccgacaacc actacctgag cacccagtcc gccctgagca agacccccaa cgagaagcgc     300
gatcacatgg tcctgctgga gttcgtgacc gccgccggga tcactctcgg catggacgag     360
ctgtacaagg ggtcgaacgg ggaattctcg caggtagaca gtcgatggt gagcaagggc      420 gaggagctgt tcaccggggt ggtgcccatc ctggtcgagc tggacggcga cgtaaacggc     480
cacaagttca gcgtgtccgg cgagggcgag ggcgatgcca cctacggcaa gctgaccctg     540
aagttcatct gcaccaccgg caagctgccc gtgcctggc ccaccctcgt gaccaccctg      600
acctacggcg tgcagtgctt cagccgctac cccgaccaca tgaagcagca cgacttcttc     660
aagtccgcca tgcccgaagg ctacgtccag gagcgcacca tcttcttcaa ggacgacggc     720
aactacaaga cccgcgccga ggtgaagttc gagggcgaca ccctggtgaa ccgcatcgag     780
ctgaagggca tcgacttcaa ggaggacggc aacatcctgg ggcacaagct ggagtacaac      840
tacaacagcc acaacgtcta tatcatggcc gacaagcaga gaacggcat caaggtgaac      900 ttcaagatcc gccacaacat cgaggacctc gagcaaaagc tgatatgcat ctccggagat     960
agtttgatca gcttggcgag cacaggaaaa agagtttcta ttaaagattt gttagatgaa    1020 aaagatttg aaatatgggc agttaatgaa cagacgatga agctagaatc agctaaagtt     1080
agtcgtgtat tttgtactgg caaaaagcta gtttatattt taaaaactcg actaggtaga    1140
actatcaagg caacagcaaa tcatagattt ttaactattg atggttggaa agattagat    1200 gagctatctt taaaagagca tattgctcta ccccgtaaac tagaaagctc ctctttacaa    1260
ttaggcctcc gcggccagta cccctacgac gtcccggact acgctatcga ttaa          1314

<210> SEQ ID NO 46
<211> LENGTH: 438
<212> TYPE: PRT
<213> ORGANISM: Synechocystis PCC6803

<400> SEQUENCE: 46

Met Glu Ser Gly Ser Pro Glu Ile Glu Lys Leu Ser Gln Ser Asp Ile
1               5                   10                  15

Tyr Trp Asp Ser Ile Val Ser Ile Thr Glu Thr Gly Val Glu Glu Val
            20                  25                  30

Phe Asp Leu Thr Val Pro Gly Pro His Asn Phe Val Ala Asn Asp Ile
        35                  40                  45

Ile Val His Asn Ser Glu Glu Asp Leu Gly Ser Ser Val Gln Leu Ala
    50                  55                  60

Asp His Tyr Gln Gln Asn Thr Pro Ile Gly Asp Gly Pro Val Leu Leu
65                  70                  75                  80
```

```
Pro Asp Asn His Tyr Leu Ser Thr Gln Ser Ala Leu Ser Lys Asp Pro
                85                  90                  95

Asn Glu Lys Arg Asp His Met Val Leu Glu Phe Val Thr Ala Ala
            100                 105                 110

Gly Ile Thr Leu Gly Met Asp Glu Leu Tyr Lys Gly Ser Asn Gly Glu
        115                 120                 125

Phe Ser Gln Val Asp Lys Ser Met Val Ser Lys Gly Glu Leu Phe
    130                 135                 140

Thr Gly Val Val Pro Ile Leu Val Glu Leu Asp Gly Asp Val Asn Gly
145                 150                 155                 160

His Lys Phe Ser Val Ser Gly Glu Gly Glu Gly Asp Ala Thr Tyr Gly
                165                 170                 175

Lys Leu Thr Leu Lys Phe Ile Cys Thr Thr Gly Lys Leu Pro Val Pro
                180                 185                 190

Trp Pro Thr Leu Val Thr Thr Leu Thr Tyr Gly Val Gln Cys Phe Ser
            195                 200                 205

Arg Tyr Pro Asp His Met Lys Gln His Asp Phe Phe Lys Ser Ala Met
    210                 215                 220

Pro Glu Gly Tyr Val Gln Glu Arg Thr Ile Phe Phe Lys Asp Asp Gly
225                 230                 235                 240

Asn Tyr Lys Thr Arg Ala Glu Val Lys Phe Glu Gly Asp Thr Leu Val
                245                 250                 255

Asn Arg Ile Glu Leu Lys Gly Ile Asp Phe Lys Glu Asp Gly Asn Ile
            260                 265                 270

Leu Gly His Lys Leu Glu Tyr Asn Tyr Asn Ser His Asn Val Tyr Ile
        275                 280                 285

Met Ala Asp Lys Gln Lys Asn Gly Ile Lys Val Asn Phe Lys Ile Arg
    290                 295                 300

His Asn Ile Glu Asp Leu Glu Gln Lys Leu Ile Cys Ile Ser Gly Asp
305                 310                 315                 320

Ser Leu Ile Ser Leu Ala Ser Thr Gly Lys Arg Val Ser Ile Lys Asp
                325                 330                 335

Leu Leu Asp Glu Lys Asp Phe Glu Ile Trp Ala Val Asn Glu Gln Thr
            340                 345                 350

Met Lys Leu Glu Ser Ala Lys Val Ser Arg Val Phe Cys Thr Gly Lys
        355                 360                 365

Lys Leu Val Tyr Ile Leu Lys Thr Arg Leu Gly Arg Thr Ile Lys Ala
    370                 375                 380

Thr Ala Asn His Arg Phe Leu Thr Ile Asp Gly Trp Lys Arg Leu Asp
385                 390                 395                 400

Glu Leu Ser Leu Lys Glu His Ile Ala Leu Pro Arg Lys Leu Glu Ser
                405                 410                 415

Ser Ser Leu Gln Leu Gly Leu Arg Gly Gln Tyr Pro Tyr Asp Val Pro
            420                 425                 430

Asp Tyr Ala Ile Asp Glx
        435

<210> SEQ ID NO 47
<211> LENGTH: 2043
<212> TYPE: DNA
<213> ORGANISM: Synechocystis PCC6803
<220> FEATURE:
<221> NAME/KEY: CDS
<222> LOCATION: (739)..(2043)
<223> OTHER INFORMATION:
```

<400> SEQUENCE: 47

```
gcttcgcgat gtacgggcca gatatacgcg ttgacattga ttattgacta gttattaata      60
gtaatcaatt acgggtcat tagttcatag cccatatatg gagttccgcg ttacataact     120
tacggtaaat ggcccgcctg gctgaccgcc caacgacccc cgcccattga cgtcaataat    180
gacgtatgtt cccatagtaa cgccaatagg gactttccat tgacgtcaat gggtggacta    240
tttacggtaa actgcccact tggcagtaca tcaagtgtat catatgccaa gtacgccccc    300
tattgacgtc aatgacggta aatggcccgc ctggcattat gcccagtaca tgaccttatc    360
ggactttcct acttggcagt acatctacgt attagtcatc gctattacca tggtgatgcg    420
gttttggcag tacatcaatg ggcgtggata gcggtttgac tcacgggat ttccaagtct    480
ccacccccatt gacgtcaatg ggagtttgtt ttggcaccaa aatcaacggg actttccaaa    540
atgtcgtaac aactccgccc cattgacgca aatgggcggt aggcgtgtac ggtgggaggt    600
ctatataagc agagctctct ggctaactag agaacccact gcttactggc ttatcgaaat    660
taatacgact cactataggg agacccaagc tggctagtta agcttcctag actaggagat    720
ctgtcgactg gaggaacc atg gag tcc gga tca cca gaa ata gaa aag ttg      771
              Met Glu Ser Gly Ser Pro Glu Ile Glu Lys Leu
                1               5                  10
tct cag agt gat att tac tgg gac tcc atc gtt tct att acg gag act      819
Ser Gln Ser Asp Ile Tyr Trp Asp Ser Ile Val Ser Ile Thr Glu Thr
            15                  20                  25
gga gtc gaa gag gtt ttt gat ttg act gtg cca gga cca cat aac ttt      867
Gly Val Glu Glu Val Phe Asp Leu Thr Val Pro Gly Pro His Asn Phe
        30                  35                  40
gtc gcc aat gac atc att gtc cat aac agt atc gaa caa ggc cag ggc      915
Val Ala Asn Asp Ile Ile Val His Asn Ser Ile Glu Gln Gly Gln Gly
    45                  50                  55
ggt ggc atg tca atg gac tat aaa gat gac gac gat aag atg agg atg      963
Gly Gly Met Ser Met Asp Tyr Lys Asp Asp Asp Asp Lys Met Arg Met
60                  65                  70                  75
ctc gag ggc caa gca ggt gga ctg atc acc agt ggc tgc atc agt gga     1011
Leu Glu Gly Gln Ala Gly Gly Leu Ile Thr Ser Gly Cys Ile Ser Gly
                80                  85                  90
gat agt ttg atc agc ttg gcg agc aca gga aaa aga gtt tct att aaa     1059
Asp Ser Leu Ile Ser Leu Ala Ser Thr Gly Lys Arg Val Ser Ile Lys
            95                 100                 105
gat ttg tta gat gaa aaa gat ttt gaa ata tgg gca att aat gaa cag     1107
Asp Leu Leu Asp Glu Lys Asp Phe Glu Ile Trp Ala Ile Asn Glu Gln
        110                 115                 120
acg atg aag cta gaa tca gct aaa gtt agt cgt gta ttt tgt act ggc     1155
Thr Met Lys Leu Glu Ser Ala Lys Val Ser Arg Val Phe Cys Thr Gly
    125                 130                 135
aaa aag cta gtt tat att tta aaa act cga cta ggt aga act atc aag     1203
Lys Lys Leu Val Tyr Ile Leu Lys Thr Arg Leu Gly Arg Thr Ile Lys
140                 145                 150                 155
gca aca gca aat cat aga ttt tta act att gat ggt tgg aaa aga tta     1251
Ala Thr Ala Asn His Arg Phe Leu Thr Ile Asp Gly Trp Lys Arg Leu
                160                 165                 170
gat gag cta tct tta aaa gag cat att gct cta ccc gta aaa cta gaa     1299
Asp Glu Leu Ser Leu Lys Glu His Ile Ala Leu Pro Arg Lys Leu Glu
            175                 180                 185
agc tcc tct tta caa tta atc gat atg gtg agc aag ggc gag gag ctg     1347
Ser Ser Ser Leu Gln Leu Ile Asp Met Val Ser Lys Gly Glu Glu Leu
        190                 195                 200
```

```
ttc acc ggg gtg gtg ccc atc ctg gtc gag ctg gac ggc gac gta aac    1395
Phe Thr Gly Val Val Pro Ile Leu Val Glu Leu Asp Gly Asp Val Asn
205             210                 215 ggc cac aag ttc agc gtg tcc ggc gag ggc gag ggc gat gcc acc tac    1443
Gly His Lys Phe Ser Val Ser Gly Glu Gly Glu Gly Asp Ala Thr Tyr
220             225                 230                 235 ggc aag ctg acc ctg aag ttc atc tgc acc acc ggc aag ctg ccc gtg    1491
Gly Lys Leu Thr Leu Lys Phe Ile Cys Thr Thr Gly Lys Leu Pro Val
        240                 245                 250 ccc tgg ccc acc ctc gtg acc acc ctg acc tac ggc gtg cag tgc ttc    1539
Pro Trp Pro Thr Leu Val Thr Thr Leu Thr Tyr Gly Val Gln Cys Phe
            255                 260                 265 agc cgc tac ccc gac cac atg aag cag cac gac ttc ttc aag tcc gcc    1587
Ser Arg Tyr Pro Asp His Met Lys Gln His Asp Phe Phe Lys Ser Ala
                270                 275                 280 atg ccc gaa ggc tac gtc cag gag cgc acc atc ttc ttc aag gac gac    1635
Met Pro Glu Gly Tyr Val Gln Glu Arg Thr Ile Phe Phe Lys Asp Asp
285             290                 295 ggc aac tac aag acc cgc gcc gag gtg aag ttc gag ggc gac acc ctg    1683
Gly Asn Tyr Lys Thr Arg Ala Glu Val Lys Phe Glu Gly Asp Thr Leu
300             305                 310                 315 gtg aac cgc atc gag ctg aag ggc atc gac ttc aag gag gac ggc aac    1731
Val Asn Arg Ile Glu Leu Lys Gly Ile Asp Phe Lys Glu Asp Gly Asn
        320                 325                 330 atc ctg ggg cac aag ctg gag tac aac tac aac agc cac aac gtc tat    1779
Ile Leu Gly His Lys Leu Glu Tyr Asn Tyr Asn Ser His Asn Val Tyr
            335                 340                 345 atc atg gcc gac aag cag aag aac ggc atc aag gtg aac ttc aag atc    1827
Ile Met Ala Asp Lys Gln Lys Asn Gly Ile Lys Val Asn Phe Lys Ile
                350                 355                 360 cgc cac aac atc gag gac ggc agc gtg cag ctc gcc gac cac tac cag    1875
Arg His Asn Ile Glu Asp Gly Ser Val Gln Leu Ala Asp His Tyr Gln
365             370                 375 cag aac acc ccc atc ggc gac ggc ccc gtg ctg ctg ccc gac aac cac    1923
Gln Asn Thr Pro Ile Gly Asp Gly Pro Val Leu Leu Pro Asp Asn His
380             385                 390                 395 tac ctg agc acc cag tcc gcc ctg agc aaa gac ccc aac gag aag cgc    1971
Tyr Leu Ser Thr Gln Ser Ala Leu Ser Lys Asp Pro Asn Glu Lys Arg
        400                 405                 410 gat cac atg gtc ctg ctg gag ttc gtg acc gcc gcc ggg atc act ctc    2019
Asp His Met Val Leu Leu Glu Phe Val Thr Ala Ala Gly Ile Thr Leu
            415                 420                 425 ggc atg gac gag ctg tac aag taa                                    2043
Gly Met Asp Glu Leu Tyr Lys
        430
```

<210> SEQ ID NO 48
<211> LENGTH: 434
<212> TYPE: PRT
<213> ORGANISM: Synechocystis PCC6803

<400> SEQUENCE: 48

```
Met Glu Ser Gly Ser Pro Glu Ile Glu Lys Leu Ser Gln Ser Asp Ile
1               5                   10                  15

Tyr Trp Asp Ser Ile Val Ser Ile Thr Glu Thr Gly Val Glu Glu Val
            20                  25                  30

Phe Asp Leu Thr Val Pro Gly Pro His Asn Phe Val Ala Asn Asp Ile
        35                  40                  45

Ile Val His Asn Ser Ile Glu Gln Gly Gln Gly Gly Gly Met Ser Met
    50                  55                  60
```

```
Asp Tyr Lys Asp Asp Asp Lys Met Arg Met Leu Glu Gly Gln Ala
 65                  70                  75                  80

Gly Gly Leu Ile Thr Ser Gly Cys Ile Ser Gly Asp Ser Leu Ile Ser
             85                  90                  95

Leu Ala Ser Thr Gly Lys Arg Val Ser Ile Lys Asp Leu Leu Asp Glu
            100                 105                 110

Lys Asp Phe Glu Ile Trp Ala Ile Asn Glu Gln Thr Met Lys Leu Glu
            115                 120                 125

Ser Ala Lys Val Ser Arg Val Phe Cys Thr Lys Lys Leu Val Tyr
    130                 135                 140

Ile Leu Lys Thr Arg Leu Gly Arg Thr Ile Lys Ala Thr Ala Asn His
145                 150                 155                 160

Arg Phe Leu Thr Ile Asp Gly Trp Lys Arg Leu Asp Glu Leu Ser Leu
                165                 170                 175

Lys Glu His Ile Ala Leu Pro Arg Lys Leu Glu Ser Ser Leu Gln
            180                 185                 190

Leu Ile Asp Met Val Ser Lys Gly Glu Glu Leu Phe Thr Gly Val Val
            195                 200                 205

Pro Ile Leu Val Glu Leu Asp Gly Asp Val Asn Gly His Lys Phe Ser
210                 215                 220

Val Ser Gly Glu Gly Glu Gly Asp Ala Thr Tyr Gly Lys Leu Thr Leu
225                 230                 235                 240

Lys Phe Ile Cys Thr Thr Gly Lys Leu Pro Val Pro Trp Pro Thr Leu
                245                 250                 255

Val Thr Thr Leu Thr Tyr Gly Val Gln Cys Phe Ser Arg Tyr Pro Asp
                260                 265                 270

His Met Lys Gln His Asp Phe Phe Lys Ser Ala Met Pro Glu Gly Tyr
            275                 280                 285

Val Gln Glu Arg Thr Ile Phe Phe Lys Asp Asp Gly Asn Tyr Lys Thr
    290                 295                 300

Arg Ala Glu Val Lys Phe Glu Gly Asp Thr Leu Val Asn Arg Ile Glu
305                 310                 315                 320

Leu Lys Gly Ile Asp Phe Lys Glu Asp Gly Asn Ile Leu Gly His Lys
                325                 330                 335

Leu Glu Tyr Asn Tyr Asn Ser His Asn Val Tyr Ile Met Ala Asp Lys
            340                 345                 350

Gln Lys Asn Gly Ile Lys Val Asn Phe Lys Ile Arg His Asn Ile Glu
    355                 360                 365

Asp Gly Ser Val Gln Leu Ala Asp His Tyr Gln Gln Asn Thr Pro Ile
370                 375                 380

Gly Asp Gly Pro Val Leu Leu Pro Asp Asn His Tyr Leu Ser Thr Gln
385                 390                 395                 400

Ser Ala Leu Ser Lys Asp Pro Asn Glu Lys Arg Asp His Met Val Leu
                405                 410                 415

Leu Glu Phe Val Thr Ala Ala Gly Ile Thr Leu Gly Met Asp Glu Leu
            420                 425                 430

Tyr Lys

<210> SEQ ID NO 49
<211> LENGTH: 437
<212> TYPE: PRT
<213> ORGANISM: Artificial sequence
<220> FEATURE:
<223> OTHER INFORMATION: DnaB intein cyclization scaffold with GFP
```

<400> SEQUENCE: 49

```
Met Glu Ser Gly Ser Pro Glu Ile Glu Lys Leu Ser Gln Ser Asp Ile
1               5                   10                  15

Tyr Trp Asp Ser Ile Val Ser Ile Thr Glu Thr Gly Val Glu Val
            20                  25                  30

Phe Asp Leu Thr Val Pro Gly Pro His Asn Phe Val Ala Asn Asp Ile
        35                  40                  45

Ile Val His Asn Ser Glu Glu Asp Leu Gly Ser Ser Val Gln Leu Ala
    50                  55                  60

Asp His Tyr Gln Gln Asn Thr Pro Ile Gly Asp Gly Pro Val Leu Leu
65                  70                  75                  80

Pro Asp Asn His Tyr Leu Ser Thr Gln Ser Ala Leu Ser Lys Asp Pro
                85                  90                  95

Asn Glu Lys Arg Asp His Met Val Leu Leu Glu Phe Val Thr Ala Ala
            100                 105                 110

Gly Ile Thr Leu Gly Met Asp Glu Leu Tyr Lys Gly Ser Asn Gly Glu
        115                 120                 125

Phe Ser Gln Val Asp Lys Ser Met Val Ser Lys Gly Glu Glu Leu Phe
    130                 135                 140

Thr Gly Val Val Pro Ile Leu Val Glu Leu Asp Gly Asp Val Asn Gly
145                 150                 155                 160

His Lys Phe Ser Val Ser Gly Glu Gly Glu Gly Asp Ala Thr Tyr Gly
                165                 170                 175

Leu Lys Thr Leu Lys Phe Ile Cys Thr Thr Gly Lys Leu Pro Val Pro
            180                 185                 190

Trp Pro Thr Leu Val Thr Thr Leu Thr Tyr Gly Leu Gln Cys Phe Ser
        195                 200                 205

Arg Tyr Pro Asp His Met Lys Gln His Asp Phe Phe Lys Ser Ala Met
    210                 215                 220

Pro Glu Gly Tyr Val Gln Glu Arg Thr Ile Phe Phe Lys Asp Asp Gly
225                 230                 235                 240

Asn Tyr Lys Thr Arg Ala Glu Val Lys Phe Glu Gly Asp Thr Leu Val
                245                 250                 255

Asn Arg Ile Glu Leu Lys Gly Ile Asp Phe Lys Glu Asp Gly Asn Ile
            260                 265                 270

Leu Gly His Lys Leu Glu Tyr Asn Tyr Asn Ser His Asn Val Tyr Ile
        275                 280                 285

Met Ala Asp Lys Gln Lys Asn Gly Ile Lys Val Asn Phe Lys Ile Arg
    290                 295                 300

His Asn Ile Glu Asp Leu Glu Gln Lys Leu Ile Cys Ile Ser Gly Asp
305                 310                 315                 320

Ser Leu Ile Ser Leu Ala Ser Thr Gly Lys Arg Val Ser Ile Lys Asp
                325                 330                 335

Leu Leu Asp Glu Lys Asp Phe Glu Ile Trp Ala Ile Asn Glu Gln Thr
            340                 345                 350

Met Lys Leu Glu Ser Ala Lys Val Ser Arg Val Phe Cys Thr Gly Lys
        355                 360                 365

Lys Leu Val Tyr Ile Leu Lys Thr Arg Leu Gly Arg Thr Ile Lys Ala
    370                 375                 380

Thr Ala Asn His Arg Phe Leu Thr Ile Asp Gly Trp Lys Arg Leu Asp
385                 390                 395                 400

Glu Leu Ser Lys Leu Glu His Ile Ala Leu Pro Arg Lys Leu Glu Ser
```

```
                    405                 410                 415
Ser Ser Leu Gln Leu Gly Leu Arg Gly Gln Tyr Pro Tyr Asp Val Pro
        420                 425                 430

Asp Tyr Ala Ile Asp
        435

<210> SEQ ID NO 50
<211> LENGTH: 5
<212> TYPE: PRT
<213> ORGANISM: Unknown
<220> FEATURE:
<223> OTHER INFORMATION: fragment of myc epitope

<400> SEQUENCE: 50

Ser Glu Glu Asp Leu
1               5

<210> SEQ ID NO 51
<211> LENGTH: 5
<212> TYPE: PRT
<213> ORGANISM: Unknown
<220> FEATURE:
<223> OTHER INFORMATION: fragment of myc epitope

<400> SEQUENCE: 51

Glu Gln Lys Leu Ile
1               5

<210> SEQ ID NO 52
<211> LENGTH: 23
<212> TYPE: PRT
<213> ORGANISM: Artificial sequence
<220> FEATURE:
<223> OTHER INFORMATION: fragment from cyclized GFP and reconstructed
      myc epitope

<400> SEQUENCE: 52

His Asn Ile Glu Asp Leu Glu Gln Lys Leu Ile Ser Glu Glu Asp Leu
1               5                   10                  15

Gly Ser Ser Val Gln Leu Ala
            20

<210> SEQ ID NO 53
<211> LENGTH: 5
<212> TYPE: PRT
<213> ORGANISM: Unknown
<220> FEATURE:
<223> OTHER INFORMATION: fragment of myc epitope

<400> SEQUENCE: 53

Leu Asp Glu Glu Ser
1               5

<210> SEQ ID NO 54
<211> LENGTH: 155
<212> TYPE: PRT
<213> ORGANISM: Synechocystis PCC6803

<400> SEQUENCE: 54

Cys Ile Ser Gly Asp Ser Leu Ile Ser Leu Ala Ser Thr Gly Lys Arg
1               5                   10                  15

Val Ser Ile Lys Asp Leu Leu Asp Glu Lys Asp Phe Glu Ile Trp Ala
            20                  25                  30

Ile Asn Glu Gln Thr Met Lys Leu Glu Ser Ala Lys Val Ser Arg Val
```

```
                    35                  40                  45
Phe Cys Thr Gly Lys Lys Leu Val Tyr Ile Leu Lys Thr Arg Leu Gly
 50                  55                  60

Arg Thr Ile Lys Ala Thr Ala Asn His Arg Phe Leu Thr Ile Asp Gly
 65                  70                  75                  80

Trp Lys Arg Leu Asp Glu Leu Ser Leu Lys Glu His Ile Ala Leu Pro
                 85                  90                  95

Arg Lys Leu Glu Ser Ser Ser Leu Gln Leu Ser Pro Glu Ile Glu Lys
                100                 105                 110

Leu Ser Gln Ser Asp Ile Tyr Trp Asp Ser Ile Val Ser Ile Thr Glu
                115                 120                 125

Thr Gly Val Glu Glu Val Phe Asp Leu Thr Val Pro Gly Pro His Asn
130                 135                 140

Phe Val Ala Asn Asp Ile Ile Val His Asn Ser
145                 150                 155

<210> SEQ ID NO 55
<211> LENGTH: 199
<212> TYPE: PRT
<213> ORGANISM: Mycobacterium xenopi

<400> SEQUENCE: 55

Cys Ile Thr Gly Asp Ala Leu Val Ala Leu Pro Glu Gly Glu Ser Val
 1               5                  10                  15

Arg Ile Ala Asp Ile Val Pro Gly Ala Arg Pro Asn Ser Asp Asn Ala
                 20                  25                  30

Ile Asp Leu Lys Val Leu Asp Arg His Gly Asn Pro Val Leu Ala Asp
                 35                  40                  45

Arg Leu Phe His Ser Gly Glu His Pro Val Tyr Thr Val Arg Thr Val
 50                  55                  60

Glu Gly Leu Arg Val Thr Gly Thr Ala Asn His Pro Leu Leu Cys Leu
 65                  70                  75                  80

Val Asp Val Ala Gly Val Pro Thr Leu Leu Trp Lys Leu Ile Asp Glu
                 85                  90                  95

Ile Lys Pro Gly Asp Tyr Ala Val Ile Gln Arg Ser Ala Phe Ser Val
                100                 105                 110

Asp Cys Ala Gly Phe Ala Arg Gly Lys Pro Glu Phe Ala Pro Thr Thr
                115                 120                 125

Tyr Thr Val Gly Val Pro Gly Leu Val Arg Phe Leu Glu Ala His His
130                 135                 140

Arg Asp Pro Asp Ala Gln Ala Ile Ala Asp Glu Leu Thr Asp Gly Arg
145                 150                 155                 160

Phe Tyr Tyr Ala Pro Val Ala Ser Val Thr Asp Ala Gly Val Gln Pro
                165                 170                 175

Val Tyr Ser Leu Arg Val Asp Thr Ala Asp His Ala Phe Ile Thr Asn
                180                 185                 190

Gly Phe Val Ser His Asn Thr
                195

<210> SEQ ID NO 56
<211> LENGTH: 20
<212> TYPE: PRT
<213> ORGANISM: Artificial sequence
<220> FEATURE:
<223> OTHER INFORMATION: reconstructed myc epitopope with BstX I-Linker

<400> SEQUENCE: 56
```

```
Gly Gln Gly Gly Gly Glu Gln Lys Leu Ile Ser Glu Glu Asp Leu Gln
1               5                   10                  15

Ala Gly Gly Gly
            20

<210> SEQ ID NO 57
<211> LENGTH: 7
<212> TYPE: PRT
<213> ORGANISM: Unknown
<220> FEATURE:
<223> OTHER INFORMATION: cyclic peptide

<400> SEQUENCE: 57

Ser Arg Gly Asp Gly Trp Ser
1               5

<210> SEQ ID NO 58
<211> LENGTH: 9
<212> TYPE: PRT
<213> ORGANISM: Unknown
<220> FEATURE:
<223> OTHER INFORMATION: cyclic peptide

<400> SEQUENCE: 58

Ser Gly Arg Gly Asp Gly Trp Gly Ser
1               5

<210> SEQ ID NO 59
<211> LENGTH: 7
<212> TYPE: PRT
<213> ORGANISM: Unknown
<220> FEATURE:
<223> OTHER INFORMATION: cyclic peptide

<400> SEQUENCE: 59

Ser Arg Gly Pro Gly Trp Ser
1               5

<210> SEQ ID NO 60
<211> LENGTH: 7
<212> TYPE: PRT
<213> ORGANISM: Simian virus 40

<400> SEQUENCE: 60

Pro Lys Lys Lys Arg Lys Val
1               5

<210> SEQ ID NO 61
<211> LENGTH: 6
<212> TYPE: PRT
<213> ORGANISM: Homo sapiens

<400> SEQUENCE: 61

Ala Arg Arg Arg Arg Pro
1               5

<210> SEQ ID NO 62
<211> LENGTH: 10
<212> TYPE: PRT
<213> ORGANISM: Mus musculus

<400> SEQUENCE: 62

Glu Glu Val Gln Arg Lys Arg Gln Lys Leu
1               5                   10
```

<210> SEQ ID NO 63
<211> LENGTH: 9
<212> TYPE: PRT
<213> ORGANISM: Mus musculus

<400> SEQUENCE: 63

Glu Glu Lys Arg Lys Arg Thr Tyr Glu
1               5

<210> SEQ ID NO 64
<211> LENGTH: 20
<212> TYPE: PRT
<213> ORGANISM: Xenopus laevis

<400> SEQUENCE: 64

Ala Val Lys Arg Pro Ala Ala Thr Lys Lys Ala Gly Gln Ala Lys Lys
1               5                   10                  15

Lys Lys Leu Asp
            20

<210> SEQ ID NO 65
<211> LENGTH: 31
<212> TYPE: PRT
<213> ORGANISM: Mus musculus

<400> SEQUENCE: 65

Met Ala Ser Pro Leu Thr Arg Phe Leu Ser Leu Asn Leu Leu Leu Leu
1               5                   10                  15

Gly Glu Ser Ile Leu Gly Ser Gly Glu Ala Lys Pro Gln Ala Pro
            20                  25                  30

<210> SEQ ID NO 66
<211> LENGTH: 21
<212> TYPE: PRT
<213> ORGANISM: Homo sapiens

<400> SEQUENCE: 66

Met Ser Ser Phe Gly Tyr Arg Thr Leu Thr Val Ala Leu Phe Thr Leu
1               5                   10                  15

Ile Cys Cys Pro Gly
            20

<210> SEQ ID NO 67
<211> LENGTH: 51
<212> TYPE: PRT
<213> ORGANISM: Mus musculus

<400> SEQUENCE: 67

Pro Gln Arg Pro Glu Asp Cys Arg Pro Arg Gly Ser Val Lys Gly Thr
1               5                   10                  15

Gly Leu Asp Phe Ala Cys Asp Ile Tyr Ile Trp Ala Pro Leu Ala Gly
            20                  25                  30

Ile Cys Val Ala Leu Leu Leu Ser Leu Ile Ile Thr Leu Ile Cys Tyr
                35                  40                  45

His Ser Arg
    50

<210> SEQ ID NO 68
<211> LENGTH: 33
<212> TYPE: PRT
<213> ORGANISM: Homo sapiens

```
<400> SEQUENCE: 68

Met Val Ile Ile Val Thr Val Val Ser Val Leu Leu Ser Leu Phe Val
1               5                   10                  15

Thr Ser Val Leu Leu Cys Phe Ile Phe Gly Gln His Leu Arg Gln Gln
            20                  25                  30

Arg

<210> SEQ ID NO 69
<211> LENGTH: 37
<212> TYPE: PRT
<213> ORGANISM: Rattus sp.

<400> SEQUENCE: 69

Pro Asn Lys Gly Ser Gly Thr Thr Ser Gly Thr Thr Arg Leu Leu Ser
1               5                   10                  15

Gly His Thr Cys Phe Thr Leu Thr Gly Leu Leu Gly Thr Leu Val Thr
            20                  25                  30

Met Gly Leu Leu Thr
            35

<210> SEQ ID NO 70
<211> LENGTH: 14
<212> TYPE: PRT
<213> ORGANISM: Homo sapiens

<400> SEQUENCE: 70

Met Gly Ser Ser Lys Ser Lys Pro Lys Asp Pro Ser Gln Arg
1               5                   10

<210> SEQ ID NO 71
<211> LENGTH: 26
<212> TYPE: PRT
<213> ORGANISM: Homo sapiens

<400> SEQUENCE: 71

Leu Leu Gln Arg Leu Phe Ser Arg Gln Asp Cys Cys Gly Asn Cys Ser
1               5                   10                  15

Asp Ser Glu Glu Glu Leu Pro Thr Arg Leu
            20                  25

<210> SEQ ID NO 72
<211> LENGTH: 20
<212> TYPE: PRT
<213> ORGANISM: Rattus norvegicus

<400> SEQUENCE: 72

Lys Gln Phe Arg Asn Cys Met Leu Thr Ser Leu Cys Cys Gly Lys Asn
1               5                   10                  15

Pro Leu Gly Asp
            20

<210> SEQ ID NO 73
<211> LENGTH: 19
<212> TYPE: PRT
<213> ORGANISM: Homo sapiens

<400> SEQUENCE: 73

Leu Asn Pro Pro Asp Glu Ser Gly Pro Gly Cys Met Ser Cys Lys Cys
1               5                   10                  15

Val Leu Ser
```

```
<210> SEQ ID NO 74
<211> LENGTH: 5
<212> TYPE: PRT
<213> ORGANISM: Artificial sequence
<220> FEATURE:
<223> OTHER INFORMATION: lysosomal degradation sequence

<400> SEQUENCE: 74

Lys Phe Glu Arg Gln
1               5

<210> SEQ ID NO 75
<211> LENGTH: 36
<212> TYPE: PRT
<213> ORGANISM: Cricetulus griseus

<400> SEQUENCE: 75

Met Leu Ile Pro Ile Ala Gly Phe Phe Ala Leu Ala Gly Leu Val Leu
1               5                   10                  15

Ile Val Leu Ile Ala Tyr Leu Ile Gly Arg Lys Arg Ser His Ala Gly
            20                  25                  30

Tyr Gln Thr Ile
        35

<210> SEQ ID NO 76
<211> LENGTH: 35
<212> TYPE: PRT
<213> ORGANISM: Homo sapiens

<400> SEQUENCE: 76

Leu Val Pro Ile Ala Val Gly Ala Ala Leu Ala Gly Val Leu Ile Leu
1               5                   10                  15

Val Leu Leu Ala Tyr Phe Ile Gly Leu Lys His His His Ala Gly Tyr
            20                  25                  30

Glu Gln Phe
        35

<210> SEQ ID NO 77
<211> LENGTH: 27
<212> TYPE: PRT
<213> ORGANISM: Yeast

<400> SEQUENCE: 77

Met Leu Arg Thr Ser Ser Leu Phe Thr Arg Arg Val Gln Pro Ser Leu
1               5                   10                  15

Phe Ser Arg Asn Ile Leu Arg Leu Gln Ser Thr
            20                  25

<210> SEQ ID NO 78
<211> LENGTH: 25
<212> TYPE: PRT
<213> ORGANISM: Yeast

<400> SEQUENCE: 78

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 79
<211> LENGTH: 64
<212> TYPE: PRT
```

<213> ORGANISM: Yeast

<400> SEQUENCE: 79

Met Phe Ser Met Leu Ser Lys Arg Trp Ala Gln Arg Thr Leu Ser Lys
1               5                   10                  15

Ser Phe Tyr Ser Thr Ala Thr Gly Ala Ala Lys Ser Gly Lys Leu
            20                  25                  30

Thr Gln Lys Leu Val Thr Ala Gly Val Ala Ala Ala Gly Ile Thr Ala
            35                  40                  45

Ser Thr Leu Leu Tyr Ala Asp Ser Leu Thr Ala Glu Ala Met Thr Ala
        50                  55                  60

<210> SEQ ID NO 80
<211> LENGTH: 41
<212> TYPE: PRT
<213> ORGANISM: Yeast

<400> SEQUENCE: 80

Met Lys Ser Phe Ile Thr Arg Asn Lys Thr Ala Ile Leu Ala Thr Val
1               5                   10                  15

Ala Ala Thr Gly Thr Ala Ile Gly Ala Tyr Tyr Tyr Asn Gln Leu
            20                  25                  30

Gln Gln Gln Gln Gln Arg Gly Lys Lys
            35                  40

<210> SEQ ID NO 81
<211> LENGTH: 4
<212> TYPE: PRT
<213> ORGANISM: Homo sapiens

<400> SEQUENCE: 81

Lys Asp Glu Leu
1

<210> SEQ ID NO 82
<211> LENGTH: 15
<212> TYPE: PRT
<213> ORGANISM: unidentified adenovirus

<400> SEQUENCE: 82

Leu Tyr Leu Ser Arg Arg Ser Phe Ile Asp Glu Lys Lys Met Pro
1               5                   10                  15

<210> SEQ ID NO 83
<211> LENGTH: 19
<212> TYPE: PRT
<213> ORGANISM: Homo sapiens

<400> SEQUENCE: 83

Leu Asn Pro Pro Asp Glu Ser Gly Pro Gly Cys Met Ser Cys Lys Cys
1               5                   10                  15

Val Leu Ser

<210> SEQ ID NO 84
<211> LENGTH: 15
<212> TYPE: PRT
<213> ORGANISM: Homo sapiens

<400> SEQUENCE: 84

Leu Thr Glu Pro Thr Gln Pro Thr Arg Asn Gln Cys Cys Ser Asn
1               5                   10                  15

-continued

```
<210> SEQ ID NO 85
<211> LENGTH: 9
<212> TYPE: PRT
<213> ORGANISM: Unknown
<220> FEATURE:
<223> OTHER INFORMATION: cyclin B1 destruction sequence

<400> SEQUENCE: 85

Arg Thr Ala Leu Gly Asp Ile Gly Asn
1               5

<210> SEQ ID NO 86
<211> LENGTH: 20
<212> TYPE: PRT
<213> ORGANISM: Unknown
<220> FEATURE:
<223> OTHER INFORMATION: signal sequence from Interleukin-2

<400> SEQUENCE: 86

Met Tyr Arg Met Gln Leu Leu Ser Cys Ile Ala Leu Ser Leu Ala Leu
1               5                   10                  15

Val Thr Asn Ser
            20

<210> SEQ ID NO 87
<211> LENGTH: 29
<212> TYPE: PRT
<213> ORGANISM: Homo sapiens

<400> SEQUENCE: 87

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr
            20                  25

<210> SEQ ID NO 88
<211> LENGTH: 27
<212> TYPE: PRT
<213> ORGANISM: Homo sapiens

<400> SEQUENCE: 88

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn
            20                  25

<210> SEQ ID NO 89
<211> LENGTH: 18
<212> TYPE: PRT
<213> ORGANISM: Influenza virus

<400> SEQUENCE: 89

Met Lys Ala Lys Leu Leu Val Leu Leu Tyr Ala Phe Val Ala Gly Asp
1               5                   10                  15

Gln Ile

<210> SEQ ID NO 90
<211> LENGTH: 24
<212> TYPE: PRT
<213> ORGANISM: Unknown
<220> FEATURE:
<223> OTHER INFORMATION: signal sequence from Interleukin-4

<400> SEQUENCE: 90
```

```
Met Gly Leu Thr Ser Gln Leu Leu Pro Pro Leu Phe Phe Leu Leu Ala
1               5                   10                  15

Cys Ala Gly Asn Phe Val His Gly
                20
```

IN VIVO PRODUCTION OF CYCLIC PEPTIDES

This application claims the benefit of U.S. Ser. No. 60/187,130, filed Mar. 6, 2000.

FIELD OF THE INVENTION

The present invention relates to methods and compositions for generating intracellular cyclic peptide and protein libraries.

BACKGROUND OF THE INVENTION

Combinatorial libraries of synthetic and natural products are important sources of molecular information for the development of pharmacologic agents. Linear peptide libraries, containing known and random peptide sequences, are particularly good sources of new and novel compounds for drug development because of the diversity of structures which can be generated. Drawbacks to linear peptide libraries are: (1) linear peptides are generally flexible molecules with entropic limitations on achieving productive biologically active conformations; (2) linear peptides are susceptible to proteolytic enzymes; and, (3) linear peptides are inherently unstable. For this reason, approaches utilizing conformational and topographical constraints to restrict the number of conformational states a peptide molecule may assume have been sought. See, for example, Hruby, (1982) Life Sci., 31:189; Hruby, et al., (1990) Biochem. J. 268: 249.249 (1990).

Head-to-tail (backbone) peptide cyclization has been used to rigidify structure and improve in vivo stability of small bioactive peptides (see Camarero and Muir, (1999) J. Am. Chem. Soc., 121:5597–5598). An important consequence of peptide cyclization is retention of biological activity and/or the identification of new classes of pharmacological agents. Cyclic peptides have been reported that inhibit T-cell adhesion (Jois, et al. (1999) J. Pept. Res., 53:18–29), PDGF action (Brennand, et al. (1997) FEBS Lett., 413:70–74), and function as new classes of drugs (Kimura et al., (1997) J. Antibiot., 50:373–378; Eriksson, et al., (1989) Exp. Cell Res., 185:86–100).

Strategies for the preparation of circular polypeptides from linear precursors have been described. For example, a chemical cross-linking approach was used to prepare a backbone cyclized version of bovine pancreatic trypsin inhibitor (Goldenburg and Creighton (1983) J. Mol. Biol., 165:407–413). Other approaches include chemical (Camarero, et al., (1998) Angew. Chem. Int. Ed., 37:347–349; Tam and Lu (1998) Prot. Sci., 7:1583–1592; Camarero and Muir (1997) Chem. Commun., 1997:1369–1370; and Zhang and Tam (1997) J. Am. Chem. Soc. 119:2363–2370) and enzymatic (Jackson et al., (1995) J. Am. Chem. Soc., 117: 819–820) intramolecular ligation methods which allow linear synthetic peptides to be efficiently cyclized under aqueous conditions. However, the requirement for synthetic peptide precursors has limited these chemical/enzymatic cyclization approaches to systems that are both ex vivo and limited to relatively small peptides.

One solution to this problem has been to generate circular recombinant peptides and proteins using a native chemical ligation approach. This approach utilizes inteins (internal proteins) to catalyze head-to-tail peptide and protein ligation in vivo (see, for example, Evans, et al. (1999) J. Biol. Chem. 274:18359–18363; Iwai and Plückthun (1999) FEBS Lett. 459:166–172; Wood, et al. (1999) Nature Biotechnology 17:889–892; Camarero and Muir (1999) J. Am. Chem. Soc., 121:5597–5598; and Scott, et al. (1999) Proc. Natl. Acad. Sci. USA, 96:13638–13643).

Inteins are self-splicing proteins that occur as in-frame insertions in specific host proteins. In a self-splicing reaction, inteins excise themselves from a precursor protein, while the flanking regions, the exteins, become joined to restore host gene function. Inteins can also catalyze a trans-ligation self-splicing reaction. Approaches making use of the trans ligation reaction include splitting the intein into two parts and reassembling the two parts in vitro, each fused to a different extein (Southworth, et al., (1998) EMBO J. 17:918–926). A somewhat different approach uses an intein domain, and the reaction is then triggered with a thiolate nucleophile, such as DTT (Xu, et al., (1998) Protein Sci., 7:2256–2264).

The ability to construct intein fusions to proteins of interest has found several applications. For example, inteins can be used in conjunction with an affinity group to purify a desired protein (Wood, et al. (1999) Nature Biotechnology, 17:889–892). Circular recombinant fusion proteins have been created by cloning into a commercially available intein expression system (Camarero and Muir, (1999) J. Am. Chem. Soc., 121:5597–5598; Iwai and Plückthun (1999) FEBS Lett. 459:166–172; and Evans, et al. (1999) J. Biol. Chem. 274:18359–18363). In another approach, a mechanism for in vivo split intein-mediated circular ligation of peptides and proteins via permutation of the order of elements in the fusion protein precursor has been used to express cyclic products in bacteria (Scott, et al., (1999) Proc. Natl. Acad. Sci. USA, 96:13638–13643).

Cyclic peptide libraries have been generated in phage (Koivunen, et al., (1995) Biotechnology 13:265–70) and by using the backbone cyclic proteinomimetic approach (Friedler, et al., (1998) Biochemistry, 37:5616–22). Methods for modifying inteins for the purpose of creating cyclic peptides and/or proteins have been recently described (Benkovic, et al., WO 00/36093). It is an object of this invention to utilize intein function, derived from wild-type or mutant intein structures, to generate cyclic peptide libraries in vivo. The utilization of mutant intein structures for this purpose are of particular focus since these have been optimized for function in the specific context of an intein scaffold engineered to result in peptide/protein cyclization. Methods are described for generating, identifying, and utilizing mutants with altered splicing/cyclization activity for use with cyclic peptide/protein libraries. Intein-generated cyclic libraries are described for the identification of cyclic peptides/proteins capable of altering a given cellular phenotype. Accordingly, it is an object of the invention to provide compositions and methods useful in the generation of random fusion polypeptide libraries in vivo.

BRIEF DESCRIPTION OF THE DRAWINGS

FIG. 1A depicts head to tail protein cyclization by reconfigured/engineered intein.

FIG. 1B depicts the mechanism of cyclization by reconfigured/engineered intein.

FIG. 2A depicts intein catalyzed ligation by the Mxe GyrA intein. In the indicated configuration, intein catalyzed ligation joins the extein residues located at the junction points with each of the two intein motifs.

FIG. 2B depicts the outcome of a motif reorganization resulting in the production of a cyclic peptide. Motif reorganziation involves providing intein B with its own translational start codon and placing intein B amino-terminal to intein A.

FIG. 3A (SEQ ID NO:1) depicts the amino acid sequence of intein Ssp DnaB from *Synechocystis* sp. strain PCC6803.

FIG. 3B (SEQ ID NO:2) depicts the amino acid sequence of intein Mxe GyrA from *Mycobacterium xenopi*.

FIG. 3C (SEQ ID NO:3) depicts the amino acid sequence of intein Ceu ClpP from *Chlamydomonas eugametos*.

FIG. 3D (SEQ ID NO:4) depicts the amino acid sequence of intein CIV RIR1 from *Chilo* iridescent virus.

FIG. 3E (SEQ ID NO:5) depicts the amino acid sequence of intein Ctr VMA from *Candida tropicalis*.

FIG. 3F (SEQ ID NO:6) depicts the amino acid sequence of intein Gth DnaB from *Guillardia theta*.

FIG. 3G (SEQ ID NO:7) depicts the amino acid sequence of intein Ppu DnaB from *Porphyra purpurea*.

FIG. 3H (SEQ ID NO:8) depicts the amino acid sequence of intein Sce VMA from *Saccharomyces cerevisiae*.

FIG. 3I (SEQ ID NO:9) depicts the amino acid sequence of intein Mfl RecA from *Mycobacterium flavescens*.

FIG. 3J (SEQ ID NO:10) depicts the amino acid sequence of intein Ssp DnaE from *Synechocystis* sp. strain PCC6803.

FIG. 3K (SEQ ID NO:11) depicts the amino acid sequence of intein Mle DnaB from *Mycobacterium leprae*.

FIG. 3L (SEQ ID NO:12) depicts the amino acid sequence of intein Mja KlbA from *Methanococcus jannaschii*.

FIG. 3M (SEQ ID NO:13) depicts the amino acid sequence of intein Pfu KlbA from *Pyrococcus furiosus*.

FIG. 3N (SEQ ID NO:14) depicts the amino acid sequence of intein Mth RIR1 from *Methanobacterium thermoautotrophicum* (delta H strain).

FIG. 3O (SEQ ID NO:15) depicts the amino acid sequence of intein Pfu RIR1-1 from *Pyrococcus furiosus*.

FIG. 3P (SEQ ID NO:16) depicts the amino acid sequence of intein Psp-GBD Pol from *Pyrococcus* sp. GB-D.

FIG. 3Q (SEQ ID NO:17) depicts the amino acid sequence of intein Thy Pol-2 from *Thermococcus hydrothermalis*.

FIG. 3R (SEQ ID NO:18) depicts the amino acid sequence of intein Pfu IF2 from *Pyrococcus furiosus*.

FIG. 3S (SEQ ID NO:19) depicts the amino acid sequence of intein Pho Lon from *Pyrococcus horikoshii* OT3.

FIG. 3T (SEQ ID NO:20) depicts the amino acid sequence of intein Mja r-Gyr from *Methanococcus jannaschii*.

FIG. 3U (SEQ ID NO:21) depicts the amino acid sequence of intein Pho RFC from *Pyrococcus horikoshii* OT3.

FIG. 3V (SEQ ID NO:22) depicts the amino acid sequence of intein Pab RFC-2 from *Pyrococcus abyssi*.

FIG. 3W (SEQ ID NO:23) depicts the amino acid sequence of intein Mja RtcB (Mja Hyp-2) from *Methanococcus jannaschii*.

FIG. 3X (SEQ ID NO:24) depicts the amino acid sequence of intein Pho VMA from *Pyrococcus horikoshii* OT3.

FIG. 4A (SEQ ID NO:25 & 26) depicts the amino acid sequence of a modified wild-type Ssp DnaB Intein configured to generate a cyclic peptide containing a FLAG epitope. The DNA sequence is given in FIGS. 4B-1 and 4B-2 (SEQ ID NOS:27 &28).

FIGS. 5A and B (SEQ ID NOS:29 & 30) depict the nucleotide and amino acid sequence of the intein Ssp DnaB J3 template used to generate intein mutants L7-J3, E6-J3, E9-J3, C11-J3 and B8-J3, with improved splicing efficiency. The J3 template carries a mutation which results in an amino acid change D to N at position 320. Thus, all mutants based on the J3 template are double mutants.

FIGS. 5C and D (SEQ ID NOS:31 & 32) depict the nucleotide and amino acid sequence of intein mutant L7-J3. L7 has two mutations which result in amino acid changes: 1) D to N at position 320 and 2) R to K at position 389.

FIGS. 5E and F (SEQ ID NOS:33 & 34) depict the nucleotide and amino acid sequence of intein mutant E6-J3. E6 has two mutations which result in amino acid changes: 1) D to N at position 320 and 2) I to V at position 34.

FIGS. 5G and H (SEQ ID NOS:35 & 36) depict the nucleotide and amino acid sequence of intein mutant E9-J3. E9 has two mutations which result in amino acid changes: 1) D to N at position 320 and 2) T to A at position 36.

FIGS. 5I and J (SEQ ID NOS:37 & 38) depict the nucleotide and amino acid sequence of intein mutant C11-J3. C11 has two mutations which result in amino acid changes: 1) D to N at position 320 and 2) S to P at position 23.

FIGS. 5K and L (SEQ ID NOS:39 & 40) depict the nucleotide and amino acid sequence of intein mutant B8-J3. B8 has two mutations which result in amino acid changes: 1) D to N at position 320 and 2) K to R at position 369.

FIGS. 5M and N (SEQ ID NOS:41 & 42) depict the nucleotide and amino acid sequence of intein mutant L7-wt, which was generated from an Ssp DnaB wild-type (wt) template. Mutants generated from the wt template carry a single mutation which effects splicing efficiency. L7-wt carries a single mutation which results in the amino acid change R to K at position 389.

FIGS. 5O and P (SEQ ID NOS:43 & 44) depict the nucleotide and amino acid sequence of intein mutant C11-wt. C11-wt has a single mutation which result in the amino acid change S to P at position 23.

FIGS. 5Q and R (SEQ ID NOS:45 & 46) depict the nucleotide and amino acid sequence of intein mutant E6-wt. E6-wt has a single mutation which result in the amino acid change I to V at position 34.

FIGS. 6A–6D (SEQ ID NOS:47 & 48) depict the DNA sequence for a N-terminally fused GFP version of the Ssp DnaB intein.

FIG. 7 depicts reporter proteins which can be used for the selection and/or detection of intein-based libraries.

FIG. 8 depicts localization sequences which can be used to target cyclic peptide libraries.

FIG. 9 depicts a random mutagenesis approach used in the optimization of intein cyclization function.

FIG. 10 depicts a biotinylation approach for use in a yeast two hybrid system.

FIG. 11 depicts a single chain antibody approach for use in a yeast two hybrid system.

FIG. 12 depicts the fluorescent reporter system used to quantify intein cyclization. FIG. 12A depicts GFP split at the loop 3 junction and reversal of the translation order of the N- and C-terminal fragments. The termini are fused using a glycine-serine linker. The GFP is positioned within the Ssp DnaB intein cyclization scaffold. Cyclized product reconstitutes both structure and fluorescence of GFP. In addition, splicing one-half of the myc epitope onto either side of the loop 3 junction allows for reconstruction of the myc epitope upon cyclization.

FIG. 12B (SEQ ID NO:49) provides the amino acid sequence of DNAB intein cyclization scaffold with GFP.

FIG. 12C (SEQ ID NOS:50–53) depicts the mechanism of intein catalyzed cyclization of inverted loop 3 of GFP.

FIG. 12D shows the results from a FACS analysis of the cyclization efficiency of wild-type Ssp DnaB intein in mammalian cells.

FIG. 12E shows the results from a Western analysis of a Ssp DnaB catalyzed cyclization in mammalian cells.

FIG. 12F shows the results from a native gel and the signals from GFP fluorescence. The majority of the fluorescence arises from the formation of cyclized GFP product, bands C and D.

Figure 13C:
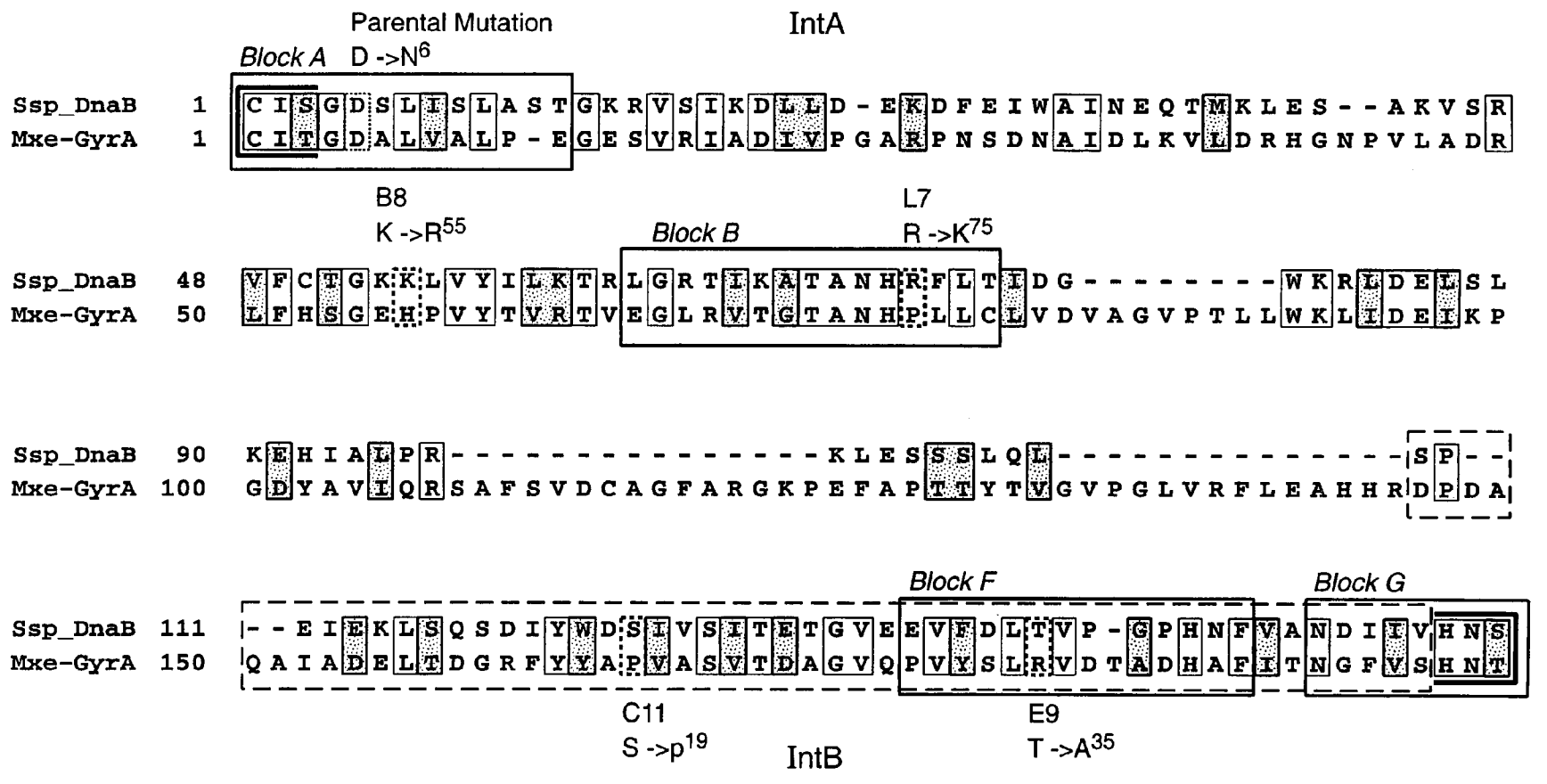

FIG. 13 illustrates a functional screen for isolating randomly-generated mutants with altered cyclization activity. FIG. 13A depicts a functional screen for intein mutants with altered cyclization activity. FIG. 13B depicts mutations modeled on the Mxe GyrA intein structure. FIG. 13C (SEQ ID NOS:54 & 55) depicts the sequence alignment of Mxe GyrA SEQ ID NOS:55 and Ssp DnaB inteins SEQ ID NOS:54. Mutants are identified in shaded color.

FIG. 14 depicts intein-mediated excision/ligation in mammalian cells. FIG. 14 A depicts constructs in which Ssp DnaB intein is inserted into loop 3 of GFP (i.e., GAB) or GFP with a C-terminal myc epitope. FIG. 14B depicts constructs similar to those shown in 14A, except that the myc epitope (SEQ ID NO:56) half-sites are positioned onto the extreme ends of each splice junction. FIG. 14C depicts Western blot analysis of lysates from transfected *Phoenix* cells. Lanes 3 and 4 demonstrate efficient splicing with only slight amounts of unspliced product detected.

FIGS. 15A–D depict a method for detecting cyclic peptides in mammalian cells. FIG. 15A (SEQ ID NOS:57 & 58) depicts an overview of the method in which cyclic peptides are detected in mammalian cells expressing a GFP fused intein scaffold with cyclic peptide inserts. FIGS. 15 B and C depict the MS analysis of mammalian cell lysates expressing the cyclic peptide products from RGD7 (15B) and RGD9 (15C). FIG. 15D depicts an example of LC/MS fragmentation fingerprinting of the cyclic peptide product of an intein construct.

FIG. 16 depicts the low energy conformers associated with cyclic peptide SRGDGWS (SEQ ID NO:57).

FIG. 17 depicts the low energy conformers associated with cyclic peptide SRGPGWS (SEQ ID NO:59).

DETAILED DESCRIPTION OF THE INVENTION

Peptide libraries are an important source of new and novel drugs. However, a number of hurdles must be overcome in order to express and subsequently screen functional peptides and proteins in cells. Foremost amongst these hurdles is the need to retain biological activity of the peptides in a cellular environment. To overcome this problem, the present invention is directed to fusions of intein motifs and random peptides such that circular peptides are formed which retain biological activity.

Figures 1, 13D:
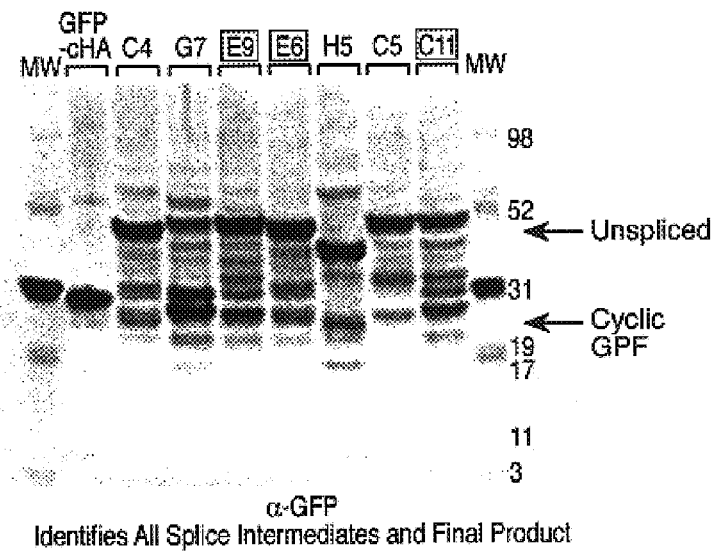
FIG. 13D shows the results from a western analysis of isolated mutants. DnaB mutants E9-J3, E6-J3, C11-J3, L7-J3, and B8-J3 have cyclization efficiencies greater than the J3 starting intein template.

Thus, generally, the present invention provides methods for generating libraries of cyclic peptides using inteins. Inteins are self-splicing proteins that occur as in-frame insertions in specific host proteins. In a self-splicing reaction, inteins excise themselves from a precursor protein, while the flanking regions, the exteins, become joined via a new peptide bond to form a linear protein. By changing the N to C terminal orientation of the intein segments, the ends of the extein join, forming a cyclized extein. FIG. 1 illustrates intein catalyzed joining of extein residues located at the junction points with each of the two intein motifs.

Because intein function is not strongly influenced by the nature of the extein polypeptide sequences located between them, standard recombinant methods can be used to insert random libraries into this position. Placement of these intein libraries into any number of delivery systems allows for the subsequent expression of unique cyclic peptides within individual cells. Such cells can then be screened to identify peptides of interest.

Accordingly, the present invention provides fusion polypeptides comprising intein motifs and peptides.

By "fusion polypeptide" or "fusion peptide" or grammatical equivalents herein is meant a protein composed of a plurality of protein components, that while typically unjoined in their native state, are joined by their respective amino and carboxyl termini through a peptide linkage to form a single continuous polypeptide. "Protein" in this context includes proteins, polypeptides and peptides. Plurality in this context means at least two, and preferred embodiments generally utilize two components. It will be appreciated that the protein components can be joined directly or joined through a peptide linker/spacer as outlined below. In addition, as outlined below, additional components such as fusion partners including targeting sequences, etc. may be used.

The present invention provides fusion proteins of intein motifs and random peptides. By "inteins", or "intein motifs", or "intein domains", or grammatical equivalents herein is meant a protein sequence which, during protein splicing, is excised from a protein precursor. Also included within in the definition of intein motifs are DNA sequences encoding inteins and mini-inteins.

Many inteins, are bifunctional proteins mediating both protein splicing and DNA cleavage. Such elements consist of a protein splicing domain interrupted by an endonuclease domain. Because endonuclease activity is not required for protein splicing, mini-inteins with accurate splicing activity can be generated by deletion of this central domain (Wood, et al., (1999) *Nature Biotechnology,* 17:889–892), hereby incorporated by reference.

Protein splicing involves four nucleophilic displacements by three conserved splice junction residues. These residues, located near the intein/extein junctions, include the initial cysteine, serine, or threonine of the intein, which intiates splicing with an acyl shift. The conserved cysteine, serine, or threonine of the extein, which ligates the exteins through nucleophilic attack, and the conserved C-terminal histidine and asparagine of the intein, which releases the intein from the ligated exteins through succinimide formation. See Wood, et al., (1999) supra.

Inteins also catalyze a trans-ligation reaction. The ability of intein function to be reconstituted in trans by spatially separated intein domains suggests that reorganization of the self-splicing motifs can be used to produce peptides with a circular topology.

Figures 2, 13D:
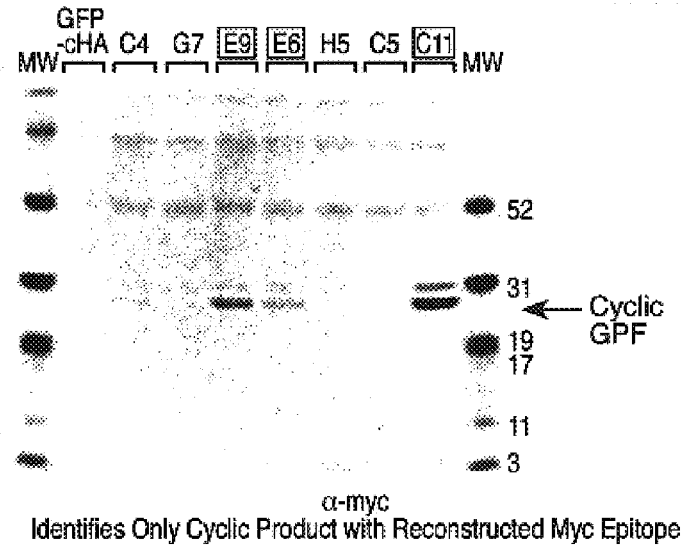
Figures 3, 13D:
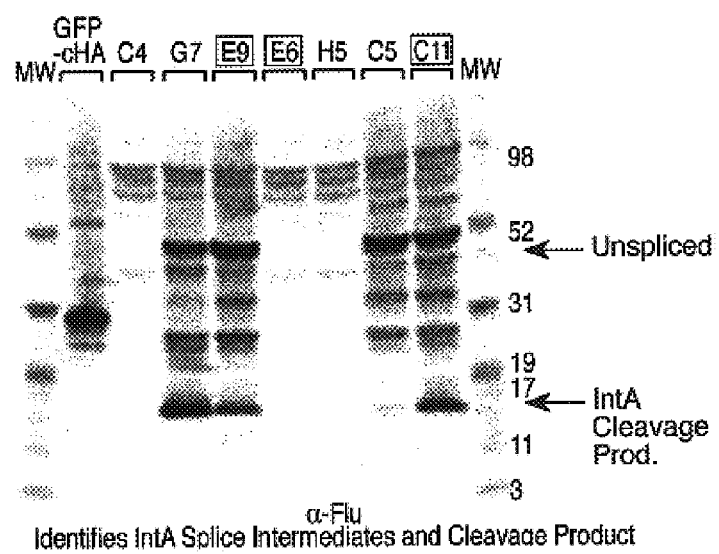

In a preferred embodiment, the translational order in which the N- and C-terminal intein motifs are normally synthesized within a polypetide chain is reversed. Generally, a reversal in the translational order in which the N- and C-terminal intein motifs are synthesized should not fundamentally change the enzymatic function of the intein. However, the location of the intervening peptide's amino and carboxy termini are altered in such a way that the product of the intein ligation reaction is no longer linear, but rather is cyclized. FIG. 2 illustrates the outcome of a motif reorganization in which intein B has been given its own translational start codon and placed amino-terminal to intein A. To effectively express unique peptides in cells, fusion polypeptides comprising a C-terminal motif, a peptide and a N-terminal motif are selected or designed for the production of random libraries of cyclic peptides in vivo.

In a preferred embodiment, the fusion polypeptide is designed with the primary sequence from the N-terminus comprising IA-target-IB. IA is defined herein as the C-terminal intein motif, IB is defined herein as the N-terminal intein motif and target is defined herein as a peptide. DNA sequences encoding the inteins may be obtained from a prokaryotic DNA sequence, such as a bacterial DNA sequence, or a eukaryotic DNA sequence, such as a yeast DNA sequence. The Intein Registry includes a list of all experimental and theoretical inteins discovered to date and submitted to the registry at world wide web neb.com/inteins/int_reg.html.

In a preferred embodiment, fusion polypeptides are designed using intein motifs selected from organisms belonging to the Eucarya and Eubacteria, with the intein Ssp DnaB (GenBank accession number Q55418) being particularly preferred. The GenBank accession numbers for other intein proteins and nucleic acids include, but are not limited to: Ceu ClpP (GenBank acession number P42379); CIV RIR1 (T03053); Ctr VMA (GenBank accession number A46080); Gth DnaB (GenBank accession number O78411); Ppu DnaB (GenBank accession number P51333); Sce VMA (GenBank accession number PXBYVA); Mf1 RecA (GenBank accession number not given); Mxe GyrA (GenBank accession number P72065); Ssp DnaE (GenBank accession number S76958 & S75328); and Mle DnaB (GenBank accession number CAA17948.1)

In other embodiments, inteins with alternative splicing mechanisms are preferred (see Southworth, et al., (2000) EMBO J., 19:5019–26). The GenBank accession numbers for inteins with alternative splicing mechanisms include, but are not limited to: Mja KlbA (GenBank accession number Q58191); and, Pfu KlbA (PF_949263 in UMBI).

In yet other embodiments, inteins from thermophilic organisms are used. Random mutagenesis or directed evolution (i.e. PCR shuffling, etc.) of inteins from these organisms could lead to the isolation of temperature sensitive mutants. Thus, inteins from thermophiles (i.e., Archaea) which find use in the invention are: Mth RIR1 (GenBank accession number G69186); Pfu RIR1-1 (AAB36947.1); Psp-GBD Pol (GenBank accession number AAA67132.1); Thy Pol-2 (GenBank accession number CAC18555.1); Pfu IF2 (PF_1088001 in UMBI); Pho Lon Baa29538.1); Mja r-Gyr (GenBank accession number G64488); Pho RFC (GenBank accession number F71231); Pab RFC-2 (GenBank accession number C75198); Mja RtcB (also referred to as Mja Hyp-2; GenBank accession number Q58095); and, Pho VMA (NT01PH1971 in Tigr).

Figures 4, 13D:
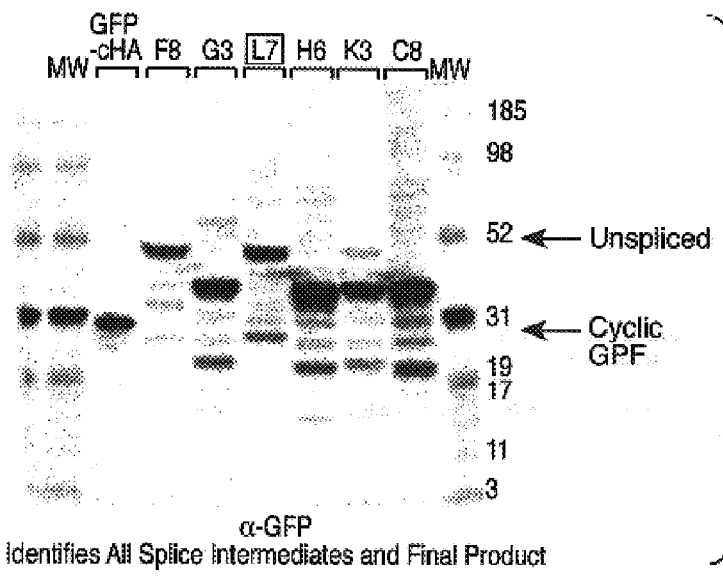

Preferred fusion polypeptides of the invention increase the efficiency of the cyclization reaction by selecting or designing intein motifs with altered cyclization activity when expressed in vivo. In a preferred embodiment, the fusion polypeptides of the invention employ the DNA sequence encoding the Synechocystis ssp. strain PCC6803 DnaB intein. A particularly preferred fusion polypeptide structure is illustrated in FIGS. 4A and 4B (SEQ ID NOS: 25–28).

Figures 5, 13D:
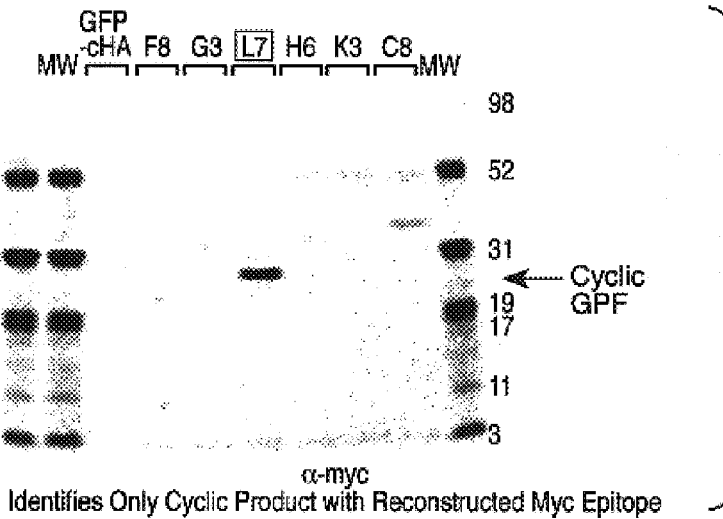

In a preferred embodiment, fusion polypeptides are designed using mutant intein sequences with altered cyclization activity as described below. Preferred mutant intein sequences include, but are not limited to, those shown in FIG. 5 (SEQ ID NOS:29–46).

In a preferred embodiment, the fusion polypeptides of the invention comprise peptides. That is, the fusion polypeptides of the invention are translation products of nucleic acids. In this embodiment, nucleic acids are introduced into cells, and the cells express the nucleic acids to form peptides. Generally, peptides ranging from about 4 amino acids in length to about 100 amino acids may be used, with peptides ranging from about 5 to about 50 being preferred, with from about 5 to about 30 being particularly preferred and from about 6 to about 20 being especially preferred.

In a preferred embodiment, the fusion polypeptides of the invention comprise random peptides. By "random peptides" herein is meant that each peptide consists of essentially random amino acids. Since generally these random peptides (or nucleic acids, discussed below) are chemically synthesized, they may incorporate any amino acid at any position. The synthetic process can be designed to generate randomized proteins to allow the formation of all or most of the possible combinations over the length of the sequence, thus forming a library of randomized peptides.

In a preferred embodiment, the fusion polypeptides of the invention comprise peptides derived from a cDNA library.

The fusion polypeptide preferably includes additional components, including, but not limited to, reporter proteins and fusion partners.

In a preferred embodiment, the fusion polypeptides of the invention comprise a reporter protein. By "reporter protein" or grammatical equivalents herein is meant a protein that by its presence in or on a cell or when secreted in the media allow the cell to be distinguished from a cell that does not contain the reporter protein. As described herein, the cell usually comprises a reporter gene that encodes the reporter protein.

Reporter genes fall into several classes, as outlined above, including, but not limited to, detection genes, indirectly detectable genes, and survival genes. See FIG. 6.

In a preferred embodiment, the reporter protein is a detectable protein. A "detectable protein" or "detection protein" (encoded by a detectable or detection gene) is a protein that can be used as a direct label; that is, the protein is detectable (and preferably, a cell comprising the detectable protein is detectable) without further manipulations or constructs. As outlined herein, preferred embodiments of screening utilize cell sorting (for example via FACS) to detect reporter (and thus peptide library) expression. Thus, in this embodiment, the protein product of the reporter gene itself can serve to distinguish cells that are expressing the detectable gene. In this embodiment, suitable detectable genes include those encoding autofluorescent proteins.

Detectable enzyme products resulting from the intein cyclization reaction may also be used to detect cells that are expressing the detectable product. Examples of enzymes which can be used include luciferase, $\beta$-galactosidase, $\beta$-lactamase, puromycin resistance protein, etc.

As is known in the art, there are a variety of autofluorescent proteins known; these generally are based on the green fluorescent protein (GFP) from Aequorea and variants thereof; including, but not limited to, GFP, (Chalfie, et al., "Green Fluorescent Protein as a Marker for Gene Expression," Science 263(5148):802–805 (1994)); enhanced GFP (EGFP; Clontech—Genbank Accession Number U55762)), blue fluorescent protein (BFP; Quantum Biotechnologies, Inc. 1801 de Maisonneuve Blvd. West, 8th Floor, Montreal (Quebec) Canada H3H 1J9; Stauber, R. H. Biotechniques 24(3):462–471 (1998); Heim, R. and Tsien, R. Y. Curr. Biol. 6:178–182 (1996)), enhanced yellow fluorescent protein (EYFP; Clontech Laboratories, Inc., 1020 East Meadow Circle, Palo Alto, Calif. 94303) and red fluorescent protein. In addition, there are recent reports of autofluorescent proteins from *Renilla* and *Ptilosarcus* species. See WO 92/15673; WO 95/07463; WO 98/14605; WO 98/26277; WO 99/49019; U.S. Pat. No. 5,292,658; U.S. Pat. No. 5,418,155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925,558; all of which are expressly incorporated herein by reference.

Preferred fluorescent molecules include but are not limited to green fluorescent protein (GFP; from *Aquorea* and *Renilla* species), blue fluorescent protein (BFP), yellow fluorescent protein (YFP), and red fluorescent protein (RFP).

In a preferred embodiment, the reporter protein is *Aequorea* green fluorescent protein or one of its variants; see Cody et al., Biochemistry 32:1212–1218 (1993); and Inouye and Tsuji, FEBS Lett. 341:277–280 (1994), both of which are expressly incorporated by reference herein. However, as is understood by those in the art, fluorescent proteins from other species may be used.

Accordingly, the present invention provides fusions of green fluorescent protein (GFP) and random peptides. By "green fluorescent protein" or "GFP" herein is meant a protein with at least 30% sequence identity to GFP and exhibits fluorescence at 490 to 600 nm. The wild-type GFP is 238 amino acids in length, contains a modified tripeptide fluorophore buried inside a relatively rigid β-can structure which protects the fluorophore from the solvent, and thus solvent quenching. See Prasher et al., Gene 111(2):229–233 (1992); Cody et al., Biochem. 32(5):1212–1218 (1993); Ormo et al, Science 273:1392–1395 (1996); and Yang et al., Nat. Biotech. 14:1246–1251 (1996), all of which are hereby incorporated by reference in their entirety). Included within the definition of GFP are derivatives of GFP, including amino acid substitutions, insertions and deletions. See for example WO 98/06737 and U.S. Pat. No. 5,777,079, both of which are hereby incorporated by reference in their entirety. Accordingly, the GFP proteins utilized in the present invention may be shorter or longer than the wild type sequence. Thus, in a preferred embodiment, included within the definition of GFP proteins are portions or fragments of the wild type sequence. For example, GFP deletion mutants can be made. At the N-terminus, it is known that only the first amino acid of the protein may be deleted without loss of fluorescence. At the C-terminus, up to 7 residues can be deleted without loss of fluorescence; see Phillips et al., Current Opin. Structural Biol. 7:821 (1997)).

For fusions involving fluorescent proteins other than GFP, proteins with at least 24% sequence homology to YFP, RFP, BFP are included with the scope of the present invention.

In a preferred embodiment, intein A is fused to the N-terminus of GFP. The fusion can be direct, i.e. with no additional residues between the C-terminus of intein A and the N-terminus of GFP, or indirect; that is, intervening amino acids are inserted between the N-terminus of GFP and the C-terminus of intein A. See FIG. 7.

In a preferred embodiment, intein B is fused to the C-terminus of GFP. As above for N-terminal fusions, the fusion can be direct or indirect.

In a preferred embodiment, the reporter protein is an indirectly detectable protein. As for the reporter proteins, cells that contain the indirectly detectable protein can be distinguished from those that do not; however, this is as a result of a secondary event. For example, a preferred embodiment utilizes "enzymatically detectable" reporters that comprise enzymes, such as luciferase, β-galactosidase, and β-lactamase, which will act on chromogenic, and particularly fluorogenic, substrates, to generate fluorescence. Alternatively, the indirectly detectable protein may require a recombinant construct in a cell that may be activated by the reporter; for example, transcription factors or inducers that will bind to a promoter linked to an autofluorescent protein such that transcription of the autofluorescent protein occurs.

In a preferred embodiment, the indirectly detectable protein is a DNA-binding protein which can bind to a DNA binding site and activate transcription of an operably linked reporter gene. The reporter gene can be any of the detectable genes, such as green fluorescent protein, or any of the survival genes, outlined herein. The DNA binding site(s) to which the DNA binding protein is binding is (are) placed proximal to a basal promoter that contains sequences required for recognition by the basic transcription machinery (e.g., RNA polymerase II). The promoter controls expression of a reporter gene. Following introduction of this chimeric reporter construct into an appropriate cell, an increase of the reporter gene product provides an indication that the DNA binding protein bound to its DNA binding site and activated transcription. Preferably, in the absence of the DNA binding protein, no reporter gene product is made. Alternatively, a low basal level of reporter gene product may be tolerated in the case when a strong increase in reporter gene product is observed upon the addition of the DNA binding protein, or the DNA binding protein encoding gene. It is well known in the art to generate vectors comprising DNA binding site(s) for a DNA binding protein to be analyzed, promoter sequences and reporter genes.

In a preferred embodiment, the DNA-binding protein is a cell type specific DNA binding protein which can bind to a nucleic acid binding site within a promoter region to which endogenous proteins do not bind at all or bind very weakly. These cell type specific DNA-binding proteins comprise transcriptional activators, such as Oct-2 [Mueller et al., Nature 336(6199):544–51 (1988)] which e.g., is expressed in lymphoid cells and not in fibroblast cells. Expression of this DNA binding protein in HeLa cells, which usually do not express this protein, is sufficient for a strong transcriptional activation of B-cell specific promoters, comprising a DNA binding site for Oct-2 (Mueller et al., supra).

In a preferred embodiment, the indirectly detectable protein is a DNA-binding/transcription activator fusion protein which can bind to a DNA binding site and activate transcription of an operably linked reporter gene. Briefly, transcription can be activated through the use of two functional domains of a transcription activator protein; a domain or sequence of amino acids that recognizes and binds to a nucleic acid sequence, i.e. a nucleic acid binding domain, and a domain or sequence of amino acids that will activate transcription when brought into proximity to the target sequence. Thus the transcriptional activation domain is thought to function by contacting other proteins required in transcription, essentially bringing in the machinery of transcription. It must be localized at the target gene by the nucleic acid binding domain, which putatively functions by positioning the transcriptional activation domain at the transcriptional complex of the target gene.

The DNA binding domain and the transcriptional activator domain can be either from the same transcriptional activator protein, or can be from different proteins (see McKnight et al., Proc. Natl. Acad. Sci. USA 89:7061 (1987); Ghosh et al., J. Mol. Biol. 234(3):610–619 (1993); and Curran et al., 55:395 (1988)). A variety of transcriptional activator proteins comprising an activation domain and a DNA binding domain are known in the art.

In a preferred embodiment the DNA-binding/transcription activator fusion protein is a tetracycline repressor protein (TetR)-VP16 fusion protein. This bipartite fusion protein consists of a DNA binding domain (TetR) and a transcription activation domain (VP16). TetR binds with high specificity to the tetracycline operator sequence, (tetO). The VP16 domain is capable of activating gene expression of a gene of interest, provided that it is recruited to a functional promoter. Employing a tetracycline repressor protein (TetR)-VP16 fusion protein, a suitable eukaryotic expression system which can be tightly controlled by the addition or omission of tetracycline or doxycycline has been described (Gossen and Bujard, Proc. Natl. Acad. Sci. U.S.A. 89:5547–5551; Gossen et al., Science 268:1766–1769 (1995)].

It is an object of the instant application to fuse intein amino acid sequences to DNA-binding/transcription activator proteins and/or to DNA-binding/transcription activator fusion proteins. N-terminal and C-terminal fusions are all contemplated. The site of fusion may be determined based on the structure of DNA-binding/transcription activator fusion protein, which are determined [e.g., TetR; see Orth et al., J. Mol. Biol. 285(2):455–61 (1999); Orth et al., J. Mol. Biol. 279(2):439–47 (1998); Hinrichs et al., Science 264 (5157):418–20 (1994); and Kisker et al., J. Mol. Biol. 247(2):260–80 (1995)].

In a preferred embodiment, the reporter protein is a survival protein. By "survival protein", "selection protein" or grammatical equivalents herein is meant a protein without which the cell cannot survive, such as drug resistance genes. As described herein, the cell usually does not naturally contain an active form of the survival protein which is used as a scaffold protein. As further described herein, the cell usually comprises a survival gene that encodes the survival protein.

The expression of a survival protein is usually not quantified in terms of protein activity, but rather recognized by conferring a characteristic phenotype onto a cell which comprises the respective survival gene or selection gene. Such survival genes may provide resistance to a selection agent (i.e., an antibiotic) to preferentially select only those cells which contain and express the respective survival gene. The variety of survival genes is quite broad and continues to grow (for review see Kriegler, Gene Transfer and Expression: A Laboratory Manual, W.H. Freeman and Company, New York, 1990). Typically, the DNA containing the resistance-conferring phenotype is transfected into a cell and subsequently the cell is treated with media containing the concentration of drug appropriate for the selective survival and expansion of the transfected and now drug-resistant cells.

Selection agents such as ampicillin, kanamycin and tetracycline have been widely used for selection procedures in prokaryotes [e.g., see Waxman and Strominger, Annu. Rev. Biochem. 52:825–69 (1983); Davies and Smith, Annu. Rev. Microbiol. 32:469–518 (1978); and Franklin, Biochem J., 105(1):371–8 (1967)]. Suitable selection agents for the selection of eukaryotic cells include, but are not limited to, blasticidin [Izumi et al., Exp. Cell Res., 197(2):229–33 (1991); Kimura et al., Biochim. Biophys. Acta 1219(3): 653–9 (1994); Kimura et al., Mol. Gen. Genet. 242(2):121–9 (1994)], histidinol D [Hartman and Mulligan; Proc. Natl. Acad. Sci. U.S.A., 85(21):8047–51 (1988)], hygromycin [Gritz and Davies, Gene 25(2–3):179–88 (1983); Sorensen et al., Gene 112(2):257–60 (1992)], neomycin [Davies and Jimenez, Am. J. Trop. Med. Hyg., 29(5 Suppl):1089–92 (1980); Southern and Berg, J. Mol. Appl. Genet., 1(4): 327–41 (19820], puromycin [de la Luna et al., Gene 62(1): 121–6 (1988)] and bleomycin/phleomycin/zeocin antibiotics [Mulsant et al., Somat Cell. Mol. Genet. 14(3):243–52 (1988).

Survival genes encoding enzymes mediating such a drug-resistant phenotype and protocols for their use are known in the art (see Kriegler, supra). Suitable survival genes include, but are not limited to thymidine kinase [TK; Wigler et al., Cell 11:233 (1977)], adenine phosphoribosyltransferase [APRT; Lowry et al., Cell 22:817 (1980); Murray et al., Gene 31:233 (1984); Stambrook et al., Som. Cell. Mol. Genet. 4:359 (1982)], hypoxanthine-guanine phosphoribosyltransferase [HGPRT; Jolly et al., Proc. Natl. Acad. Sci. U.S.A. 80:477 (1983)], dihydrofolate reductase [DHFR; Subramani et al., Mol. Cell. Biol. 1:854 (1985); Kaufman and Sharp, J. Mol. Biol. 159:601 (1982); Simonsen and Levinson, Proc. Natl. Acad. Sci. U.S.A. 80:2495 (1983)] aspartate transcarbamylase [Ruiz and Wahl, Mol. Cell. Biol. 6:3050 (1986)], ornithine decarboxylase [Chiang and McConlogue, Mol. Cell. Biol. 8:764 (1988)], aminoglycoside phosphotransferase [Southern and Berg, Mol. Appl. Gen. 1:327 (1982); Davies and Jiminez, supra], hygromycin-B-phosphotransferase [Gritz and Davies, supra; Sugden et al., Mol. Cell. Biol. 5:410 (1985); Palmer et al., Proc. Natl. Acad. Sci. U.S.A. 84:1055 (1987)], xanthine-guanine phosphoribosyltransferase [Mulligan and Berg, Proc. Natl. Acad. Sci. U.S.A. 78:2072 (1981)], tryptophan synthetase [Hartman and Mulligan, Proc. Natl. Acad. Sci. U.S.A. 85:8047 (1988)], histidinol dehydrogenase (Hartman and Mulligan, supra), multiple drug resistance biochemical marker [Kane et al., Mol. Cell. Biol. 8:3316 (1988); Choi et al., Cell 53:519 (1988)], blasticidin S deaminase [Izumi et al., Exp. Cell. Res. 197(2):229–33 (1991)], bleomycin hydrolase [Mulsant et al., supra], and puromycin-N-acetyl-transferase [Lacalle et al., Gene 79(2):375–80 (1989)], In another preferred embodiment, the survival protein is blasticidin S deaminase, which is encoded by the bsr gene [Izumi et al., Exp. Cell. Res. 197(2):229–33 (1991)]. When transferred into almost any cell, this dominant selectable gene confers resistance to media comprising the antibiotic blasticidin S. Blasticidin S deaminase encoding genes have been cloned. They are used widely as a selectable marker on various vectors and the nucleotide sequences are available (e.g., see GenBank accession numbers D83710, U75992, and U75991).

It is an object of the instant application to fuse intein motif sequences to blasticidin S deaminase. N-terminal and C-terminal fusions are all contemplated. The site of fusion may be determined based on the structure of *Aspergillus terreus* blasticidin S deaminase, which has been determined [Nakasako et al., Acta Crystallogr. D. Biol. Crystallogr. 55(Pt2): 547–8 (1999)]. Also, internal fusions can be done; see PCT US99/23715, hereby incorporated by reference.

In another preferred embodiment, the survival protein is puromycin-N-acetyl-transferase, which is encoded by the pac gene [Lacalle et al., Gene 79(2):375–80 (1989)]. When transferred into almost any cell, this dominant selectable gene confers resistance to media comprising puromycin. A puromycin-N-acetyltransferase encoding gene has been cloned. It is used widely as a selectable marker on various vectors and the nucleotide sequences are available (e.g., see GenBank accession numbers Z75185 and M25346).

It is an object of the instant application to fuse intein motif sequences puromycin-N-acetyl-transferase. N-terminal and C-terminal, dual N- and C-terminal and one or more internal fusions are all contemplated.

In a preferred embodiment, in addition to the intein motifs and peptides, the fusion polypeptides of the present invention preferably include additional components, including, but not limited to, fusion partners.

By "fusion partner" herein is meant a sequence that is associated with the fusion polypeptide that confers upon all members of the library in that class a common function or ability. Fusion partners can be heterologous (i.e. not native to the host cell), or synthetic (not native to any cell). Suitable fusion partners include, but are not limited to: a) targeting sequences, defined below, which allow the localization of the peptide into a subcellular or extracellular compartment; b) rescue sequences as defined below, which allow the purification or isolation of either the peptides or the nucleic acids encoding them; or c), any combination of a) and b).

In a preferred embodiment, the fusion partner is a targeting sequence. As will be appreciated by those in the art, the localization of proteins within a cell is a simple method for increasing effective concentration and determining function. For example, RAF1 when localized to the mitochondrial membrane can inhibit the anti-apoptotic effect of BCL-2. Similarly, membrane bound Sos induces Ras mediated signaling in T-lymphocytes. These mechanisms are thought to rely on the principle of limiting the search space for ligands, that is to say, the localization of a protein to the plasma membrane limits the search for its ligand to that limited dimensional space near the membrane as opposed to the three dimensional space of the cytoplasm. Alternatively, the concentration of a protein can also be simply increased by nature of the localization. Shuttling the proteins into the nucleus confines them to a smaller space thereby increasing concentration. Finally, the ligand or target may simply be localized to a specific compartment, and inhibitors must be localized appropriately.

Thus, suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signalling selective degradation, of itself or co-bound proteins; and signal sequences capable of constitutively localizing the peptides to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion. See FIG. 8.

In a preferred embodiment, the targeting sequence is a nuclear localization signal (NLS). NLSes are generally short, positively charged (basic) domains that serve to direct the entire protein in which they occur to the cell's nucleus. Numerous NLS amino acid sequences have been reported including single basic NLSes such as that of the SV40 (monkey virus) large T Antigen (Pro Lys Lys Lys Arg Lys Val (SEQ ID NO:60)), Kalderon (1984), et al., Cell, 39:499–509; the human retinoic acid receptor-β nuclear localization signal (ARRRRP (SEQ ID NO:61)); NFκB p50 (EEVQRKRQKL (SEQ ID NO:62); Ghosh et al., Cell 62:1019 (1990); NFκB p65 (EEKRKRTYE (SEQ ID NO:63); Nolan et al., Cell 64:961 (1991); and others (see for example Boulikas, J. Cell. Biochem. 55(1):32–58 (1994), hereby incorporated by reference) and double basic NLSes exemplified by that of the *Xenopus* (African clawed toad) protein, nucleoplasmin (Ala Val Lys Arg Pro Ala Ala Thr Lys Lys Ala Gly Gln Ala Lys Lys Lys Lys Leu Asp (SEQ ID NO:64)), Dingwall, et al., Cell, 30:449–458, 1982 and Dingwall, et al., J. Cell Biol., 107:641–849; 1988). Numerous localization studies have demonstrated that NLSes incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990.

In a preferred embodiment, the targeting sequence is a membrane anchoring signal sequence. This is particularly useful since many parasites and pathogens bind to the membrane, in addition to the fact that many intracellular events originate at the plasma membrane. Thus, membrane-bound peptide libraries are useful for both the identification of important elements in these processes as well as for the discovery of effective inhibitors. The invention provides methods for presenting the randomized expression product extracelluarly or in the cytoplasmic space. For extracellular presentation, a membrane anchoring region is provided at the carboxyl terminus of the peptide presentation structure. The randomized expression product region is expressed on the cell surface and presented to the extracellular space, such that it can bind to other surface molecules (affecting their function) or molecules present in the extracellular medium. The binding of such molecules could confer function on the cells expressing a peptide that binds the molecule. The cytoplasmic region could be neutral or could contain a domain that, when the extracellular randomized expression product region is bound, confers a function on the cells (activation of a kinase, phosphatase, binding of other cellular components to effect function). Similarly, the randomized expression product-containing region could be contained within a cytoplasmic region, and the transmembrane region and extracellular region remain constant or have a defined function.

Membrane-anchoring sequences are well known in the art and are based on the genetic geometry of mammalian transmembrane molecules. Peptides are inserted into the membrane based on a signal sequence (designated herein as ssTM) and require a hydrophobic transmembrane domain (herein TM). The transmembrane proteins are inserted into the membrane such that the regions encoded 5' of the transmembrane domain are extracellular and the sequences 3' become intracellular. Of course, if these transmembrane domains are placed 5' of the variable region, they will serve to anchor it as an intracellular domain, which may be desirable in some embodiments. ssTMs and TMs are known for a wide variety of membrane bound proteins, and these sequences may be used accordingly, either as pairs from a particular protein or with each component being taken from a different protein, or alternatively, the sequences may be synthetic, and derived entirely from consensus as artificial delivery domains.

As will be appreciated by those in the art, membrane-anchoring sequences, including both ssTM and TM, are known for a wide variety of proteins and any of these may be used. Particularly preferred membrane-anchoring sequences include, but are not limited to, those derived from CD8, ICAM-2, IL-8R, CD4 and LFA-1.

Useful sequences include sequences from: 1) class I integral membrane proteins such as IL-2 receptor β-chain (residues 1–26 are the signal sequence, 241–265 are the transmembrane residues; see Hatakeyama et al., Science 244:551 (1989) and von Heijne et al, Eur. J. Biochem.

174:671 (1988)) and insulin receptor β-chain (residues 1–27 are the signal, 957–959 are the transmembrane domain and 960–1382 are the cytoplasmic domain; see Hatakeyama, supra, and Ebina et al., Cell 40:747 (1985)); 2) class II integral membrane proteins such as neutral endopeptidase (residues 29–51 are the transmembrane domain, 2–28 are the cytoplasmic domain; see Malfroy et al., Biochem. Biophys. Res. Commun. 144:59 (1987)); 3) type III proteins such as human cytochrome P450 NF25 (Hatakeyama, supra); and 4) type IV proteins such as human P-glycoprotein (Hatakeyama, supra). Particularly preferred are CD8 and ICAM-2. For example, the signal sequences from CD8 and ICAM-2 lie at the extreme 5' end of the transcript. These consist of the amino acids 1–32 in the case of CD8 (MASPLTRFLSLNLLLLGESILGSGEAKPQAP (SEQ ID NO:65); Nakauchi et al., PNAS USA 82:5126 (1985) and 1–21 in the case of ICAM-2 (MSSFGYRTLTVALFTLICPG (SEQ ID NO:66); Staunton et al., Nature (London) 339:61 (1989)). These leader sequences deliver the construct to the membrane while the hydrophobic transmembrane domains, placed 3' of the random peptide region, serve to anchor the construct in the membrane. These transmembrane domains are encompassed by amino acids 145–195 from CD8 (PQRPEDCRPRGSVKGTGLDFACDIYIWAPLAGICVALLLSLIITLICYHSR (SEQ ID NO:67); Nakauchi, supra) and 224–256 from ICAM-2 (MVIIVTVVSVLLSLFVTSVLLCFIFGQHLRQQR (SEQ ID NO:68); Staunton, supra).

Alternatively, membrane anchoring sequences include the GPI anchor, which results in a covalent bond between the molecule and the lipid bilayer via a glycosyl-phosphatidylinositol bond for example in DAF (PNKGSGTTSGTTRLLSGHTCFTLTGLLGTLVTMGLLT (SEQ ID NO:69), with the bolded serine the site of the anchor; see Homans et al., Nature 333(6170):269–72 (1988), and Moran et al., J. Biol. Chem. 266:1250 (1991)). In order to do this, the GPI sequence from Thy-1 can be cassetted 3' of the variable region in place of a transmembrane sequence.

Similarly, myristylation sequences can serve as membrane anchoring sequences. It is known that the myristylation of c-src recruits it to the plasma membrane. This is a simple and effective method of membrane localization, given that the first 14 amino acids of the protein are solely responsible for this function: MGSSKSKPKDPSQR (SEQ ID NO:70) (see Cross et al., Mol. Cell. Biol. 4(9):1834 (1984); Spencer et al., Science 262:1019–1024 (1993), both of which are hereby incorporated by reference). This motif has already been shown to be effective in the localization of reporter genes and can be used to anchor the zeta chain of the TCR. This motif is placed 5' of the variable region in order to localize the construct to the plasma membrane. Other modifications such as palmitoylation can be used to anchor constructs in the plasma membrane; for example, palmitoylation sequences from the G protein-coupled receptor kinase GRK6 sequence (LLQRLFSRQDCCGNCSDSEEELPTRL (SEQ ID NO:71), with the bold cysteines being palmitolyated; Stoffel et al., J. Biol. Chem 269:27791 (1994)); from rhodopsin (KQFRNCMLTSLCCGKNPLGD (SEQ ID NO:72); Barnstable et al., J. Mol. Neurosci. 5(3):207 (1994)); and the p21H-ras 1 protein (LNPPDESGPGCMSCKCVLS (SEQ ID NO:73); Capon et al., Nature 302:33 (1983)).

In a preferred embodiment, the targeting sequence is a lysozomal targeting sequence, including, for example, a lysosomal degradation sequence such as Lamp-2 (KFERQ (SEQ ID NO:74); Dice, Ann. N.Y. Acad. Sci. 674:58 (1992); or lysosomal membrane sequences from Lamp-1 (MLIPIAGFFALAGLVLIVLIAYLI*GRKRSHAGYQTI* (SEQ ID NO:75), Uthayakumar et al., Cell. Mol. Biol. Res. 41:405 (1995)) or Lamp-2 (LVPIAVGAALAGVLILVLLAYFIG*LKHHHAGYEQF* (SEQ ID NO:76), Konecki et la., Biochem. Biophys. Res. Comm. 205:1–5 (1994), both of which show the transmembrane domains in italics and the cytoplasmic targeting signal underlined).

Alternatively, the targeting sequence may be a mitrochondrial localization sequence, including mitochondrial matrix sequences (e.g. yeast alcohol dehydrogenase III; MLRTSSLFTRRVQPSLFSRNILRLQST (SEQ ID NO:77); Schatz, Eur. J. Biochem. 165:1–6 (1987)); mitochondrial inner membrane sequences (yeast cytochrome c oxidase subunit IV; MLSLRQSIRFFKPATRTLCSSRYLL (SEQ ID NO:78); Schatz, supra); mitochondrial intermembrane space sequences (yeast cytochrome c1; MFSMLSKRWAQRTLSKSFYSTATGMSKSGKLTQKLVTAGVAAAGITASTLLYADSLTAEAMTA (SEQ ID NO:79); Schatz, supra) or mitochondrial outer membrane sequences (yeast 70 kD outer membrane protein; MKSFITRNKTAILATVAATGTAIGAYYYYNQLQQQQQRGKK (SEQ ID NO:80); Schatz, supra).

The target sequences may also be endoplasmic reticulum sequences, including the sequences from calreticulin (KDEL (SEQ ID NO:81); Pelham, Royal Society London Transactions B; 1–10 (1992)) or adenovirus E3/19K protein (LYLSRRSFIDEKKMP (SEQ ID NO:82); Jackson et al., EMBO J. 9:3153 (1990).

Furthermore, targeting sequences also include peroxisome sequences (for example, the peroxisome matrix sequence from Luciferase; SKL; Keller et al., PNAS USA 4:3264 (1987)); farnesylation sequences (for example, P21 H-ras 1; LNPPDESGPGCMSCKCVLS (SEQ ID NO:83), with the bold cysteine farnesylated; Capon, supra); geranylgeranylation sequences (for example, protein rab-5A; LTEPTQPTRNQCCSN (SEQ ID NO:84), with the bold cysteines geranylgeranylated; Farnsworth, PNAS USA 91:11963 (1994)); or destruction sequences (cyclin B1; RTALGDIGN (SEQ ID NO:85); Klotzbucher et al., EMBO J. 1:3053 (1996)).

In a preferred embodiment, the targeting sequence is a secretory signal sequence capable of effecting the secretion of the peptide. There are a large number of known secretory signal sequences which are placed 5' to the variable peptide region, and are cleaved from the peptide region to effect secretion into the extracellular space. Secretory signal sequences and their transferability to unrelated proteins are well known, e.g., Silhavy, et al. (1985) Microbiol. Rev. 49, 398–418. This is particularly useful to generate a peptide capable of binding to the surface of, or affecting the physiology of, a target cell that is other than the host cell, e.g., the cell infected with the retrovirus. In a preferred approach, a fusion polypeptide is configured to contain, in series, a secretion signal peptide-intein B motif-randomized library sequence-intein A. See FIG. 8. In this manner, target cells grown in the vicinity of cells caused to express the library of peptides, are bathed in secreted peptide. Target cells exhibiting a physiological change in response to the presence of a peptide, e.g., by the peptide binding to a surface receptor or by being internalized and binding to intracellular targets, and the secreting cells are localized by any of a variety of selection schemes and the peptide causing the effect determined. Exemplary effects include variously that of a designer cytokine (i.e., a stem cell factor capable of causing hematopoietic stem cells to divide and maintain their totipotential), a factor causing cancer cells to undergo spontaneous apoptosis, a factor that binds to the cell surface of target cells and labels them specifically, etc.

Suitable secretory sequences are known, including signals from IL-2 (MYRMQLLSCIALSLALVTNS (SEQ ID NO:86); Villinger et al., J. Immunol. 155:3946 (1995)), growth hormone (MATGSRTSLLLAFGLLCLP-WLQEGSA<u>FPT</u> (SEQ ID NO:87); Roskam et al., Nucleic Acids Res. 7:305 (1979)); preproinsulin (MALWMRLL-PLLALLALWGPDPAAA<u>FVN</u> (SEQ ID NO:88); Bell et al., Nature 284:26 (1980)); and influenza HA protein (MKAK-LLVLLYAFVAG<u>DQI</u> (SEQ ID NO:89); Sekikawa et al., PNAS 80:3563)), with cleavage between the non-under-lined-underlined junction. A particularly preferred secretory signal sequence is the signal leader sequence from the secreted cytokine IL-4, which comprises the first 24 amino acids of IL-4 as follows: MGLTSQLLPPLFFLLACAGN-FVHG (SEQ ID NO:90).

In a preferred embodiment, the fusion partner is a rescue sequence. A rescue sequence is a sequence which may be used to purify or isolate either the peptide or the nucleic acid encoding it. Thus, for example, peptide rescue sequences include purification sequences such as the $His_6$ tag for use with Ni affinity columns and epitope tags for detection, immunoprecipitation or FACS (fluorescence-activated cell sorting). Suitable epitope tags include myc (for use with the commercially available 9E10 antibody), the BSP biotinylation target sequence of the bacterial enzyme BirA, flu tags, lacZ, GST, and Strep tag I and I.

Alternatively, the rescue sequence may be a unique oligonucleotide sequence which serves as a probe target site to allow the quick and easy isolation of the retroviral construct, via PCR, related techniques, or hybridization.

While the discussion has been directed to the fusion of fusion partners to the intein portion of the fusion polypeptide, the fusion partners may be placed anywhere (i.e. N-terminal, C-terminal, internal) in the structure as the biology and activity permits. In addition, it is also possible to fuse one or more of these fusion partners to the intein portions of the fusion polypeptide. Thus, for example, a targeting sequence (either N-terminally, C-terminally, or internally, as described below) may be fused to intein A, and a rescue sequence fused to the same place or a different place on the molecule. Thus, any combination of fusion partners and peptides may be made.

In a preferred embodiment, the invention provides libraries of fusion polypeptides. By "library" herein is meant a sufficiently structurally diverse population of randomized expression products to effect a probabilistically sufficient range of cellular responses to provide one or more cells exhibiting a desired response. Accordingly, an interaction library must be large enough so that at least one of its members will have a structure that gives it affinity for some molecule, protein, or other factor whose activity is of interest. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as proposed here for expression in retroviruses, has the potential to code for $20^7$ ($10^9$) to $20^{20}$. Thus, with libraries of $10^7$ to $10^8$ per ml of retroviral particles the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different expression products are simultaneously analyzed in the subject methods. Preferred methods maximize library size and diversity.

In a preferred embodiment, libraries of all combinations of a peptide 3 to 30 amino acids in length are synthesized and analyzed as outlined herein. Libraries of smaller cyclic peptides, i.e., 3 to 4 amino acid in length, are advantageous because they are more constrained and thus there is a better chance that these libraries possess desirable pharmocokinetics properties as a consequence of their smaller size. Accordingly, the libraries of the present invention may be one of any of the following lengths: 3 amino acids, 4 amino acids, 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids, 25 amino acids, 26 amino acids, 27 amino acids, 28 amino acids, 29 amino acids and 30 amino acids in length.

The invention further provides fusion nucleic acids encoding the fusion polypeptides of the invention. As will be appreciated by those in the art, due to the degeneracy of the genetic code, an extremely large number of nucleic acids may be made, all of which encode the fusion proteins of the present invention. Thus, having identified a particular amino acid sequence, those skilled in the art could make any number of different nucleic acids, by simply modifying the sequence of one or more codons in a way which does not change the amino acid sequence of the fusion protein.

Using the nucleic acids of the present invention which encode a fusion protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the fusion protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The fusion nucleic acids are introduced into cells to screen for cyclic peptides capable of altering the phenotype of a cell. By "introduced into "or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The fusion nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

In a preferred embodiment, the fusion nucleic acids are part of a retroviral particle which infects the cells. Generally, infection of the cells is straightforward with the application of the infection-enhancing reagent polybrene, which is a polycation that facilitates viral binding to the target cell. Infection can be optimized such that each cell generally expresses a single construct, using the ratio of virus particles to number of cells. Infection follows a Poisson distribution.

In a preferred embodiment, the fusion nucleic acids are introduced into cells using retroviral vectors. Currently, the most efficient gene transfer methodologies harness the capacity of engineered viruses, such as retroviruses, to bypass natural cellular barriers to exogenous nucleic acid uptake. The use of recombinant retroviruses was pioneered by Richard Mulligan and David Baltimore with the Psi-2 lines and analogous retrovirus packaging systems, based on NIH 3T3 cells (see Mann et al., Cell 33:153–159 (1993), hereby incorporated by reference). Such helper-defective packaging lines are capable of producing all the necessary trans proteins-gag, pol, and env- that are required for packaging, processing, reverse transcription, and integration of recombinant genomes. Those RNA molecules that have in cis the ψ packaging signal are packaged into maturing virions. Retroviruses are preferred for a number of reasons. First, their derivation is easy. Second, unlike Adenovirus-mediated gene delivery, expression from retroviruses is long-term (adenoviruses do not integrate). Adeno-associated viruses have limited space for genes and regulatory units and there is some controversy as to their ability to integrate. Retroviruses therefore offer the best current compromise in terms of long-term expression, genomic flexibility, and stable integration, among other features. The main advantage of retroviruses is that their integration into the host genome allows for their stable transmission through cell division. This ensures that in cell types which undergo multiple independent maturation steps, such as hematopoietic cell progression, the retrovirus construct will remain resident and continue to express.

A particularly well suited retroviral transfection system is described in Mann et al., supra: Pear et al., PNAS USA 90(18):8392–6 (1993); Kitamura et al., PNAS USA 92:9146–9150 (1995); Kinsella et al., Human Gene Therapy 7:1405–1413; Hofmann et al., PNAS USA 93:5185–5190; Choate et al., Human Gene Therapy 7:2247 (1996); and WO 94/19478; and references cited therein, all of which are incorporated by reference.

In one embodiment of the invention, the library is generated in a intein-catalyzed cyclization scaffold. By "intein-catalyzed cyclization scaffold" herein is meant that the intein is engineered such that a cyclic peptide is generated upon intein-mediated splicing of the extein-intein junction points. Preferably, an intein cyclization scaffold includes the C-terminal intein motif, a library insert of 3 up to 30 amino acids in length, and the N-terminal intein motif. The C- and N-terminal intein motifs can be derived from any number of known inteins capable mediating protein splicing, including split-inteins.

Most wild-type inteins have requirements for a specific extein-encoded amino acid at the C-intein (IntB)/C-extein junction point. This varies depending on the intein, but most often consists of an cysteine, threonine or serine. Intein-generated cyclic peptide libraries may be generated in which this particular amino acid is fixed and corresponds to the amino acid present in the wild-type sequence. For example, the Ssp. DnaB intein utilizes an extein-encoded serine in this position.

A number of inteins have the ability to catalyze protein splicing when non-native amino acids are substituted at the C-intein (IntB)/C-extein junction point position. Degeneracy at the C-intein (IntB)/C-extein junction point position leads to cyclic peptide libraries of greater complexity and therefore added utility. The proposed degeneracy in this position most likely consists of a cysteine, serine or threonine but is not limited to these amino acids. The ability of a given intein-catalyzed cyclization scaffold to tolerate degeneracy at this position depends on the specific intein utilized and it's mechanism of protein splicing. Thus, isolation of intein cyclization scaffolds with a greater tolerance for degeneracy at the C-intein (IntB)/C-extein junction point is within the scope of this invention.

In one embodiment of the invention, the library is generated in a retrovirus DNA construct backbone, as is generally described in U.S. Ser. No. 08/789,333, filed Jan. 23, 1997, incorporated herein by reference. Standard oligonucleotide synthesis is done to generate the random portion of the candidate bioactive agent, using techniques well known in the art (see Eckstein, Oligonucleotides and Analogues, A Practical Approach, IRL Press at Oxford University Press, 1991); libraries may be commercially purchased. Libraries with up to $10^9$ to $10^{10}$ unique sequences can be readily generated in such DNA backbones. After generation of the DNA library, the library is cloned into a first primer. The first primer serves as a "cassette", which is inserted into the retroviral construct. The first primer generally contains a number of elements, including for example, the required regulatory sequences (e.g. translation, transcription, promoters, etc), fusion partners, restriction endonuclease (cloning and subcloning) sites, stop codons (preferably in all three frames), regions of complementarity for second strand priming (preferably at the end of the stop codon region as minor deletions or insertions may occur in the random region), etc. See U.S. Ser. No. 08/789,333, hereby incorporated by reference.

A second primer is then added, which generally consists of some or all of the complementarity region to prime the first primer and optional necessary sequences for a second unique restriction site for subcloning. DNA polymerase is added to make double-stranded oligonucleotides. The double-stranded oligonucleotides are cleaved with the appropriate subcloning restriction endonucleases and subcloned into the target retroviral vectors, described below.

Any number of suitable retroviral vectors may be used. Generally, the retroviral vectors may include: selectable marker genes under the control of internal ribosome entry sites (IRES), which allows for bicistronic operons and thus greatly facilitates the selection of cells expressing peptides at uniformly high levels; and promoters driving expression of a second gene, placed in sense or anti-sense relative to the 5' LTR. Suitable selection genes include, but are not limited to, neomycin, blastocidin, bleomycin, puromycin, and hygromycin resistance genes, as well as self-fluorescent markers such as green fluorescent protein, enzymatic markers such as lacZ, and surface proteins such as CD8, etc.

Figures 6, 13D:
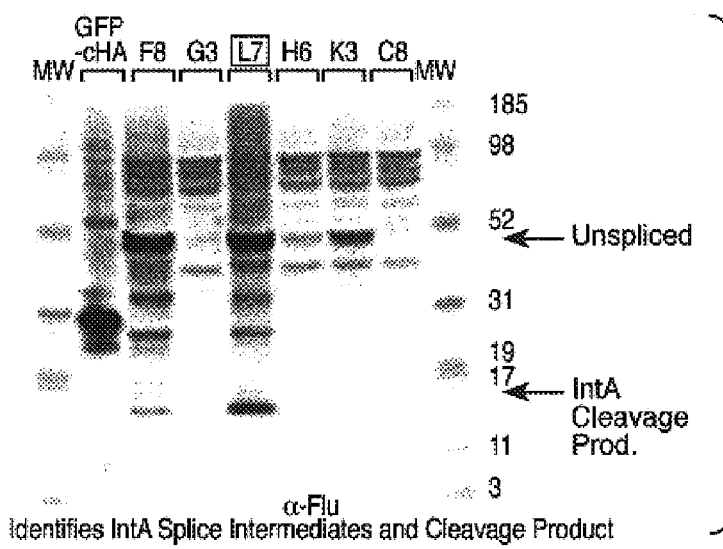

Preferred vectors include a vector based on the murine stem cell virus (MSCV) (see Hawley et al., Gene Therapy 1:136 (1994)) and a modified MFG virus (Rivere et al., Genetics 92:6733 (1995)), and pBABE, outlined in the examples. A general schematic of the retroviral construct is depicted in FIGS. 6 and 15A.

The retroviruses may include inducible and constitutive promoters. For example, there are situations wherein it is necessary to induce peptide expression only during certain phases of the selection process. For instance, a scheme to provide pro-inflammatory cytokines in certain instances must include induced expression of the peptides. This is because there is some expectation that over-expressed pro-inflammatory drugs might in the long-term be detrimental to cell growth. Accordingly, constitutive expression is undesirable, and the peptide is only turned on during that phase of the selection process when the phenotype is required, and then shut the peptide down by turning off the retroviral expression to confirm the effect or ensure long-term survival of the producer cells. A large number of both inducible and constitutive promoters are known.

In addition, it is possible to configure a retroviral vector to allow inducible expression of retroviral inserts after integration of a single vector in target cells; importantly, the entire system is contained within the single retrovirus. Tet-inducible retroviruses have been designed incorporating the Self-Inactivating (SIN) feature of 3' LTR enhancer/promoter retroviral deletion mutant (Hoffman et al., PNAS USA 93:5185 (1996)). Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population. A similar, related system uses a mutated Tet DNA-binding domain such that it bound DNA in the presence of Tet, and was removed in the absence of Tet. Either of these systems is suitable.

In this manner the primers create a library of fragments, each containing a different random nucleotide sequence that may encode a different peptide. The ligation products are then transformed into bacteria, such as *E. coli*, and DNA is prepared from the resulting library, as is generally outlined in Kitamura, PNAS USA 92:9146–9150 (1995), hereby expressly incorporated by reference.

Delivery of the library DNA into a retroviral packaging system results in conversion to infectious virus. Suitable retroviral packaging system cell lines include, but are not limited to, the Bing and BOSC23 cell lines described in WO 94/19478; Soneoka et al., Nucleic Acid Res. 23(4):628 (1995); Finer et al., Blood 83:43 (1994); Pheonix packaging lines such as PhiNX-eco and PhiNX-ampho, described below; 292T+gag-pol and retrovirus envelope; PA317; and cell lines outlined in Markowitz et al., Virology 167:400 (1988), Markowitz et al., J. Virol. 62:1120 (1988), Li et al., PNAS USA 93:11658 (1996), Kinsella et al., Human Gene Therapy 7:1405 (1996), all of which are incorporated by reference.

Preferred systems include PHEONIX-ECO and PHEONIX-AMPHO. Both PHEONIX-ECO and PHEONIX-AMPHO were tested for helper virus production and established as being helper-virus free. Both lines can carry episomes for the creation of stable cell lines which can be used to produce retrovirus. Both lines are readily testable by flow cytometry for stability of gag-pol (CD8) and envelope expression; after several months of testing the lines appear stable, and do not demonstrate loss of titre as did the first-generation lines BOSC23 and Bing (partly due to the choice of promoters driving expression of gag-pol and envelope). Both lines can also be used to transiently produce virus in a few days. Thus, these lines are fully compatible with transient, episomal stable, and library generation for retroviral gene transfer experiments. Finally, the titres produced by these lines have been tested. Using standard polybrene-enhanced retroviral infection, titres approaching or above $10^7$ per ml were observed for both PHEONIX-eco and PHEONIX-ampho when carrying episomal constructs. When transiently produced virus is made, titres are usually ½ to ⅓ that value.

These lines are helper-virus free, carry episomes for long-term stable production of retrovirus, stably produce gag-pol and env, and do not demonstrate loss of viral titre over time. In addition, PhiNX-eco and PhiNX-ampho are capable of producing titres approaching or above $10^7$ per ml when carrying episomal constructs, which, with concentration of virus, can be enhanced to $10^8$ to $10^9$ per ml.

In a preferred embodiment, the cell lines disclosed above, and the other methods for producing retrovirus, are useful for production of virus by transient transfection. The virus can either be used directly or be used to infect another retroviral producer cell line for "expansion" of the library.

Concentration of virus may be done as follows. Generally, retroviruses are titred by applying retrovirus-containing supernatant onto indicator cells, such as NIH3T3 cells, and then measuring the percentage of cells expressing phenotypic consequences of infection. The concentration of the virus is determined by multiplying the percentage of cells infected by the dilution factor involved, and taking into account the number of target cells available to obtain a relative titre. If the retrovirus contains a reporter gene, such as lacZ, then infection, integration, and expression of the recombinant virus is measured by histological staining for lacZ expression or by flow cytometry (FACS). In general, retroviral titres generated from even the best of the producer cells do not exceed $10^7$ per ml, unless concentration by relatively expensive or exotic apparatus. However, as it has been recently postulated that since a particle as large as a retrovirus will not move very far by brownian motion in liquid, fluid dynamics predicts that much of the virus never comes in contact with the cells to initiate the infection process. However, if cells are grown or placed on a porous filter and retrovirus is allowed to move past cells by gradual gravitometric flow, a high concentration of virus around cells can be effectively maintained at all times. Thus, up to a ten-fold higher infectivity by infecting cells on a porous membrane and allowing retrovirus supernatant to flow past them has been seen. This should allow titres of $10^9$ after concentration.

The fusion nucleic acids and polypeptides of the invention are used to make cyclic peptides. By "cyclic peptides" or grammatical equivalents herein is meant the intracellular catalysis of peptide backbone cyclization. Generally, backbone cyclization results in the joining of the N and C termini of a peptide together such that a cyclic product is generated inside cells.

Preferably, every member of a peptide library is tested for bioactivity using one of the assays described below. For example, a cyclic peptide with 7 random positions has a complexity of $20^7=1.28\times10^9$, all of which will be tested for biological activity.

In the event it is not possible to test every member of a library for bioactivity, the library may be deliberately biased. For example, a cyclic peptide can be biased to cellular entry by fixing one or more relatively hydrophobic amino acids, such as tyrosine or tryptophan. Other types of biased libraries which may be synthesized include libraries which primary contain cyclic peptides comprising amino acids with large side chains and libraries in which the number of cyclic peptide conformers is restricted.

Highly restrained cyclic peptide libraries are made by using codons which code mainly for amino acids with large side chains. That is, when several resides of a cyclic peptide encode amino acids with large side chains, the conformation space of the peptide is restricted. The result is to bias the peptide to a higher affinity by reducing peptide conformational entropy. For example, a library of cyclic peptides could be created by restricting the triplet nucleotides coding for each random amino acid in the library to C or T for the first position of the triplet, A, G or T for the second position in the triplet, and G, C or T for the third position in the triplet. This would result in a library biased to large amino acids, i.e., phenylalanine (F), leucine (L), tyrosine (Y), histidine (H), glutamine (Q), cysteine (C), tryptophan (W) and arginine (R). A library biased toward large amino acid side chains, combined with the loss of glycine, alanine, serine, threonine, aspartate, and glutamate results in a library coding for more rigid peptides. As this library lacks an acidic amino acid, a pre-synthesized triplet coding glutamate (i.e., GAG) or aspartate (GAC) may be added during the DNA synthesis of the library.

Alternatively, a large amino acid side chain (i.e.) residue library may be created by pre-synthesizing triplets for desired residues. These residues are then mixed together during the DNA synthesis of the library. An example of a pre-synthesized large residue library is a library coding tyrosine (Y), arginine (R), glutamic acid (E), histidine (H), leucine (L), glutamine (Q), and optionally proline (P) or threonine (T).

A biased library can be created by restricting the number of conformers in a cyclic peptide. This approach is useful for structure activity relationship optimization. The number of conformers may be restricted by fixing a proline in the cyclic peptide ring at one position and leaving all of the other residues random. A smaller number of conformers allows for higher affinity binding interactions with target molecules, and more selective interactions with target moleucles due to a diminution of the possibility of "induced fit" binding. "Induced fit" comes at the expense of binding affinity due to a loss upon binding of the higher conformational entropy of a multi-conformer peptide. Higher affinity and selectivity are desirable for the development of cyclic peptides drugs. This is achieved by reducing the conformational entropy by including a rigid amino acid in a fixed position in each library member. For example, fixing one proline in a 7mer peptide is sufficient to restrict the conformational space of the cyclic peptide. For 8 to 10 mers, two prolines may be fixed in the ring allowing a diversity of $(20)^6$ or $6.4 \times 10^7$ in the 6 unfixed position of a 10 mer ring. Such a library is large enough to give hits in most screens for candidate drugs (as described below).

As will be appreciated by those in the art, the type of cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a cyclic peptide. As is more fully described below, cell types implicated in a wide variety of disease conditions are particularly useful, so long as a suitable screen may be designed to allow the selection of cells that exhibit an altered phenotype as a consequence of the presence of a cyclic peptide within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be genetically engineered, that is, contain exogenous nucleic acid, for example, to contain target molecules.

Once made, the compositions of the invention find use in a number of applications. In particular, compositions with altered cyclization efficiency are made. The compositions of the invention also may be used to: (1) alter cellular phenotypes and/or physiology; (2) used in screening assays to identify target molecules associated with changes in cellular phenotype or phyisology; and, (3) used as drugs to treat a number of disease states, such as cancer, cardiovascular diseases, obesity, neurological disorders, etc.

In a preferred embodiment, inteins with altered cyclization activity are generated. Naturally occurring inteins are mutagenized and tested in vivo to determine whether the modified intein can catalyze protein or peptide cyclization in mammalian cells. Preferably, inteins so modified are characterized by more efficient cyclization kinetics in vivo or by the expression level of intein catalyzed cyclization scaffolds. Additional rounds of mutagenesis may be done to optimize in vivo function. Assays useful for measuring intein-catalyzed cyclization efficiency include fluorescent or gel based assays directly measuring cyclic peptide or protein levels, and functional assays based on the production of a functional cyclic peptide whose effects can be measured or selected for.

In a preferred embodiment, random mutagenesis (i.e. M13 primer mutagenesis and PCR mutagenesis), PCR shuffling or other directed evolution techniques are directed to a target codon or region and the resulting intein variants screened for altered cyclization activity. These techniques are well known and can be directed to predetermined sites, i.e., intein open reading frame or more specific regions or codons within.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the intein protein are desired, substitutions are generally made in accordance with the following chart:

Chart I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |

-continued

Chart I

| Original Residue | Exemplary Substitutions |
|---|---|
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

As outlined above, the variants typically exhibit the same qualitative biological activity (i.e. cyclization) although variants may be selected to modify other characteristics of the intein protein as needed. For example, endoplasmic reticulum/golgi directed intein libraries may be designed to operate in cellular environments more acidic than the cytoplasmic compartment.

In a preferred embodiment specific residues of an intein motif are substituted, resulting in proteins with modified characteristics. Such substitutions may occur at one or more residues, with 1–10 substitutions being preferred. Preferred characteristics to be modified include cyclization efficiency, half-life, stability, temperature sensitivity.

In a preferred embodiment, intein mutants are generated using PCR mutagenesis. The resulting mutants are screened for altered cyclization activity. By "altered" cyclization activity" refers to any characteristic or attribute of an intein that can be selected or detected and compared to the corresponding property of a naturally occurring intein. These properties include cyclization efficiency, stability, etc. Cyclization efficiency may be affected by the presence or absence of a given amino acid, the size of the peptide library, etc.

Unless otherwise specified, altered" cyclization activity, when comparing the cyclization efficiency of a mutant intein to the cyclization efficiency of wild-type or naturally occurring intein is preferably at least 1-fold, more preferably at least a 10-fold increase in activity.

Screens for mutants with improved cyclization efficiency can be done in procaryotes or eucaryotes. The mutants may be screened directly by assaying for the production of a cyclic peptide or indirectly by assaying a cyclic peptide's effects on a cell. Alternatively, the mutants may be screened indirectly by assaying the product of the cyclic peptide protein in vitro, e.g., enzyme inhibition assays, etc.

If the mutation prevents self-excision, no fluorescence is detected due to the interruption in the tertiary structure of GFP. If the mutation does not effect self-excision or enhances splicing efficiency, the degree of fluorescence may be quantified using a FACS analysis or other techniques known in the art. In addition, cyclization of the GFP reconstitutes the myc epitope which can be detected using Western analysis. T In a preferred embodiment, a first plurality of cells is screened. That is, the cells into which the fusion nucleic acids are introduced are screened for an altered phenotype. Thus, in this embodiment, the effect of the bioactive peptide is seen in the same cells in which it is made; i.e. an autocrine effect.

By a "plurality of cells" herein is meant roughly from about $10^3$ cells to $10^8$ or $10^9$, with from $10^6$ to $10^8$ being preferred. This plurality of cells comprises a cellular library, wherein generally each cell within the library contains a member of the peptide molecular library, i.e. a different peptide (or nucleic acid encoding the peptide), although as will be appreciated by those in the art, some cells within the library may not contain a peptide, and some may contain more than species of peptide. When methods other than retroviral infection are used to introduce the candidate nucleic acids into a plurality of cells, the distribution of candidate nucleic acids within the individual cell members of the cellular library may vary widely, as it is generally difficult to control the number of nucleic acids which enter a cell during electroporation, etc.

In a preferred embodiment, the fusion nucleic acids are introduced into a first plurality of cells, and the effect of the peptide is screened in a second or third plurality of cells, different from the first plurality of cells, i.e. generally a different cell type. That is, the effect of the bioactive peptide is due to an extracellular effect on a second cell; i.e. an endocrine or paracrine effect. This is done using standard techniques. The first plurality of cells may be grown in or on one media, and the media is allowed to touch a second plurality of cells, and the effect measured. Alternatively, there may be direct contact between the cells. Thus, "contacting" is functional contact, and includes both direct and indirect. In this embodiment, the first plurality of cells may or may not be screened.

If necessary, the cells are treated to conditions suitable for the expression of the peptide (for example, when inducible promoters are used).

Thus, the methods of the present invention comprise introducing a molecular library of fusion nucleic acids encoding randomized peptides fused to scaffold into a plurality of cells, a cellular library. Each of the nucleic acids comprises a different nucleotide sequence encoding scaffold with a random peptide. The plurality of cells is then screened, as is more fully outlined below, for a cell exhibiting an altered phenotype. The altered phenotype is due to the presence of a bioactive peptide.

By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e. half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptability, latency, adhesion, and uptake of viruses and bacterial pathogens; etc. By "capable of altering the phenotype" herein is meant that the bioactive peptide can change the phenotype of the cell in some detectable and/or measurable way.

The altered phenotype may be detected in a wide variety of ways, as is described more fully below, and will generally depend and correspond to the phenotype that is being changed. Generally, the changed phenotype is detected using, for example: microscopic analysis of cell morphology; standard cell viability assays, including both increased cell death and increased cell viability, for example, cells that are now resistant to cell death via virus, bacteria, or bacterial or synthetic toxins; standard labeling assays such as fluorometric indicator assays for the presence or level of a particular cell or molecule, including FACS or other dye staining techniques; biochemical detection of the expression of target compounds after killing the cells; etc. In some cases, as is more fully described herein, the altered phenotype is detected in the cell in which the fusion nucleic acid was introduced; in other embodiments, the altered phenotype is detected in a second cell which is responding to some molecular signal from the first cell.

An altered phenotype of a cell indicates the presence of a bioactive peptide, acting preferably in a transdominant way. By "transdominant" herein is meant that the bioactive peptide indirectly causes the altered phenotype by acting on a second molecule, which leads to an altered phenotype. That is, a transdominant expression product has an effect that is not in cis, i.e., a trans event as defined in genetic terms or biochemical terms. A transdominant effect is a distinguishable effect by a molecular entity (i.e., the encoded peptide or RNA) upon some separate and distinguishable target; that is, not an effect upon the encoded entity itself. As such, transdominant effects include many well-known effects by pharmacologic agents upon target molecules or pathways in cells or physiologic systems; for instance, the β-lactam antibiotics have a transdominant effect upon peptidoglycan synthesis in bacterial cells by binding to penicillin binding proteins and disrupting their functions. An exemplary transdominant effect by a peptide is the ability to inhibit NF-κB signaling by binding to IκB-α at a region critical for its function, such that in the presence of sufficient amounts of the peptide (or molecular entity), the signaling pathways that normally lead to the activation of NF-κB through phosphorylation and/or degradation of IκB-α are inhibited from acting at IκB-α because of the binding of the peptide or molecular entity. In another instance, signaling pathways that are normally activated to secrete IgE are inhibited in the presence of peptide. Or, signaling pathways in adipose tissue cells, normally quiescent, are activated to metabolize fat. Or, in the presence of a peptide, intracellular mechanisms for the replication of certain viruses, such as HIV-I, or Herpes viridae family members, or Respiratory Syncytia Virus, for example, are inhibited.

A transdominant effect upon a protein or molecular pathway is clearly distinguishable from randomization, change, or mutation of a sequence within a protein or molecule of known or unknown function to enhance or diminish a biochemical ability that protein or molecule already manifests. For instance, a protein that enzymatically cleaves β-lactam antibiotics, a β-lactamase, could be enhanced or diminished in its activity by mutating sequences internal to its structure that enhance or diminish the ability of this enzyme to act upon and cleave β-lactam antibiotics. This would be called a cis mutation to the protein. The effect of this protein upon β-lactam antibiotics is an activity the protein already manifests, to a distinguishable degree. Similarly, a mutation in the leader sequence that enhanced the export of this protein to the extracellular spaces wherein it might encounter β-lactam molecules more readily, or a mutation within the sequence that enhance the stability of the protein, would be termed cis mutations in the protein. For comparison, a transdominant effector of this protein would include an agent, independent of the β-lactamase, that bound to the β-lactamase in such a way that it enhanced or diminished the function of the β-lactamase by virtue of its binding to β-lactamase.

In a preferred embodiment, once a cell with an altered phenotype is detected, the presence of the fusion protein is verified, to ensure that the peptide was expressed and thus that the altered phenotype can be due to the presence of the peptide. As will be appreciated by those in the art, this verification of the presence of the peptide can be done either before, during or after the screening for an altered phenotype. This can be done in a variety of ways, although preferred methods utilize FACS techniques.

In a preferred embodiment, the devices of the invention comprise liquid handling components, including components for loading and unloading fluids at each station or sets of stations. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; holders with cartridges and/or caps; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In a preferred embodiment, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a preferred embodiment, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station.

In a preferred embodiment, thermocycler and thermoregulating systems are used for stabilizing the temperature of the heat exchangers such as controlled blocks or platforms to provide accurate temperature control of incubating samples from 4° C. to 100° C.; this is in addition to or in place of the station thermocontrollers.

In a preferred embodiment, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, for example when electronic detection is not done, the instrumentation will include a detector, which can be a wide variety of different detectors, depending on the labels and assay. In a preferred embodiment, useful detectors include a microscope(s) with multiple channels of fluorescence; plate readers to provide fluorescent, ultraviolet and visible spectrophotometric detection with single and dual wavelength endpoint and kinetics capability, fluroescence resonance energy transfer (FRET), luminescence, quenching, two-photon excitation, and intensity redistribution; CCD cameras to capture and transform data and images into quantifiable formats; and a computer workstation.

These instruments can fit in a sterile laminar flow or fume hood, or are enclosed, self-contained systems, for cell culture growth and transformation in multi-well plates or tubes and for hazardous operations. The living cells will be grown under controlled growth conditions, with controls for temperature, humidity, and gas for time series of the live cell assays. Automated transformation of cells and automated colony pickers will facilitate rapid screening of desired cells.

Flow cytometry or capillary electrophoresis formats can be used for individual capture of magnetic and other beads, particles, cells, and organisms.

The flexible hardware and software allow instrument adaptability for multiple applications. The software program modules allow creation, modification, and running of methods. The system diagnostic modules allow instrument alignment, correct connections, and motor operations. The customized tools, labware, and liquid, particle, cell and organism transfer patterns allow different applications to be performed. The database allows method and parameter storage. Robotic and computer interfaces allow communication between instruments.

In a preferred embodiment, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, samples, washes, assay components such as label probes, etc.

Once the presence of the fusion protein is verified, the cell with the altered phenotype is generally isolated from the plurality which do not have altered phenotypes. This may be done in any number of ways, as is known in the art, and will in some instances depend on the assay or screen. Suitable isolation techniques include, but are not limited to, FACS, lysis selection using complement, cell cloning, scanning by Fluorimager, expression of a "survival" protein, induced expression of a cell surface protein or other molecule that can be rendered fluorescent or taggable for physical isolation; expression of an enzyme that changes a non-fluorescent molecule to a fluorescent one; overgrowth against a background of no or slow growth; death of cells and isolation of DNA or other cell vitality indicator dyes, etc.

In a preferred embodiment, the fusion nucleic acid and/or the bioactive peptide (i.e. the fusion protein) is isolated from the positive cell. This may be done in a number of ways. In a preferred embodiment, primers complementary to DNA regions common to the retroviral constructs, or to specific components of the library such as a rescue sequence, defined above, are used to "rescue" the unique random sequence. Alternatively, the fusion protein is isolated using a rescue sequence. Thus, for example, rescue sequences comprising epitope tags or purification sequences may be used to pull out the fusion protein using immunoprecipitation or affinity columns. In some instances, as is outlined below, this may also pull out the primary target molecule, if there is a sufficiently strong binding interaction between the bioactive peptide and the target molecule. Alternatively, the peptide may be detected using mass spectroscopy.

Once rescued, the sequence of the bioactive peptide and/or fusion nucleic acid is determined. This information can then be used in a number of ways.

In a preferred embodiment, the bioactive peptide is resynthesized and reintroduced into the target cells, to verify the effect. This may be done using retroviruses, or alternatively using fusions to the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference.

In a preferred embodiment, the sequence of a bioactive peptide is used to generate more candidate peptides. For example, the sequence of the bioactive peptide may be the basis of a second round of (biased) randomization, to develop bioactive peptides with increased or altered activities. Alternatively, the second round of randomization may change the affinity of the bioactive peptide. Furthermore, it may be desirable to put the identified random region of the bioactive peptide into other presentation structures, or to alter the sequence of the constant region of the presentation structure, to alter the conformation/shape of the bioactive peptide. It may also be desirable to "walk" around a potential binding site, in a manner similar to the mutagenesis of a binding pocket, by keeping one end of the ligand region constant and randomizing the other end to shift the binding of the peptide around.

In a preferred embodiment, either the bioactive peptide or the bioactive nucleic acid encoding it is used to identify target molecules, i.e. the molecules with which the bioactive peptide interacts. As will be appreciated by those in the art, there may be primary target molecules, to which the bioactive peptide binds or acts upon directly, and there may be secondary target molecules, which are part of the signalling pathway affected by the bioactive peptide; these might be termed "validated targets".

In a preferred embodiment, the bioactive peptide is a drug. As will be appreciated by those in the art, the structure of the cyclic peptide may be modeled and used in rational drug design to synthesize agents that mimic the interaction of the cyclic peptide with its' target. Drugs may also be modeled based on the three dimensional structure of the peptide bound to its target. Drugs so modeled may have structures that are similar to or unrelated to the starting structure of the cyclic peptide or the cyclic peptide bound to its target. Alternatively, high throughput screens can be used to identify small molecules capable of competing with the cyclic peptide for its target.

In a preferred embodiment, the bioactive cyclic peptide may be used as the starting point for designing/synthesizing derivative molecules with similar or more favorable properties for use as a drug. For example, individual amino acids, specific chemical groups, etc., can be replaced and the derivative molecule tested for use as a drug. Both naturally occurring and synthetic amino acid analogs (see below for definition) can be introduced in to the derivative molecule to optimize properties such as binding, stability, pharmocokinectics. Preferably, the derivative molecule has one or more of the following properties: improved stability, higher binding affinity, improved specificity for the target, improved pharmocokinetics, i.e., absorption, distribution, resistance to degradation, etc.

In a preferred embodiment, the bioactive peptide is used to pull out target molecules. For example, as outlined herein, if the target molecules are proteins, the use of epitope tags, purification sequences, or affinity tags can allow the purification of primary target molecules via biochemical means (co-immunoprecipitation, affinity columns, etc.). Alternatively, the peptide, when expressed in bacteria and purified, can be used as a probe against a bacterial cDNA expression library made from mRNA of the target cell type. Or, peptides can be used as "bait" in either yeast or mammalian two or three hybrid systems. Such interaction cloning approaches have been very useful to isolate DNA-binding proteins and other interacting protein components. The peptide(s) can be combined with other pharmacologic activators to study the epistatic relationships of signal transduction pathways in question. It is also possible to synthetically prepare labeled peptide and use it to screen a cDNA library expressed in bacteriophage for those cDNAs which bind the peptide. Furthermore, it is also possible that one could use cDNA cloning via retroviral libraries to "complement" the effect induced by the peptide. In such a strategy, the peptide would be required to be stochiometrically titrating away some important factor for a specific signaling pathway. If this molecule or activity is replenished by over-expression of a cDNA from within a cDNA library, then one can clone the target. Similarly, cDNAs cloned by any of the above yeast or bacteriophage systems can be reintroduced to mammalian cells in this manner to confirm that they act to complement function in the system the peptide acts upon.

In a preferred embodiment, target molecules are identified by incorporating an affinity tagged amino acid residue into the sequence of the cyclic peptide. For example, incorporation of a cysteine alows for the chemical conjugation of the cyclic peptide to a solid support matrix via a disulfide bond. In particular, target molecules that bind to functional cyclic peptides are isolated and identified using affinity tagged amino acids.

In a preferred embodiment, the cysteine contributed by the extein is uniquely alkylated with an affinity reagent as part of the synthesis of the peptide to allow affinity extraction and identification of target molecules using HPLC-mass spectrometry methods. Cysteine-alkylated cyclic peptide analogs are tested for function, and if functional, target molecules are affinity extracted using methods well known in the art. If the cysteine-alkylated peptide analogs are not functional, synthetic cyclic peptide analogs are constructed with cysteine-affinity tag amino acid analogs in other positions and tested for function. In alternative embodiments, lysine affinity tagged amino acids are used.

Alternatively, if an affinity tagged amino acid cannot be produced in vivo, the tag can be introduced in vitro and tested in vivo for function.

Any amino acid which can be used as a affinity tag may be used in the methods of the invention. This includes both naturally occurring and synthetic amino acid analogs which can be introduced into the cyclic peptide to facilitate chemical conjugation or binding to a solid support matrix. Thus "amino acid", or "peptide residue", as used herein means both naturally occurring and synthetic amino acids. For example, homo-phenylalanine, citrulline, and noreleucine are considered amino acids for the purposes of the invention. "Amino acid" also includes imino acid residues such as proline and hydroxyproline. In addition, any amino acid can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Such derivatives have the property of greatly increased stability, and therefore are advantageous in the formulation of compounds which may have longer in vivo half lives, when administered by oral, intravenous, intramuscular, intraperitoneal, topical, rectal, intraocular, or other routes.

In the preferred embodiment, the amino acids are in the (S) or L-configuration. If non-naturally occurring side chains are used, non-amino acid substituents may be used, for example to prevent or retard in vivo degradations. Proteins including non-naturally occurring amino acids may be synthesized or in some cases, made recombinantly; see van Hest et al., FEBS Lett 428:(1–2) 68–70 May 22, 1998 and Tang et al., Abstr. Pap Am. Chem. S218:U138–U138 Part 2 Aug. 22, 1999, both of which are expressly incorporated by reference herein.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3- thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole (alkyl)alanines, and D- or L-alkylainines where alkyl may be substituted or unsubstituted methyl, ethyl, propyl, hexyl, butyl, pentyl, isopropyl, iso-butyl, sec-isotyl, iso-pentyl, non-acidic amino acids, of C1–C20.

Acidic amino acids can be substituted with non-carboxylate amino acids while maintaining a negative charge, and derivatives or analogs thereof, such as the non-limiting examples of (phosphono)alanine, glycine, leucine, isoleucine, threonine, or serine; or sulfated (e.g., —SO$_3$H) threonine, serine, tyrosine.

Other substitutions may include unnatural hyroxylated amino acids may made by combining "alkyl" with any natural amino acid. The term "alkyl" as used herein refers to a branched or unbranched saturated hydrocarbon group of 1 to 24 carbon atoms, such as methyl, ethyl, n-propyl, isoptopyl, n-butyl, isobutyl, t-butyl, octyl, decyl, tetradecyl, hexadecyl, eicosyl, tetracisyl and the like. Alkyl includes heteroalkyl, with atoms of nitrogen, oxygen and sulfur. Preferred alkyl groups herein contain 1 to 12 carbon atoms. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage can be replaced by a ketomethylene moiety. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Additional amino acid modifications of amino acids of to the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/ e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

Examples of affinity labeled amino acids useful for extraction of target molecules include lysine-epsilon amino biotin, or lysine reacted with amine-specific biotinylation reagents such as biotin-NHS ester and sulfo-NHS biotin.

Spacers may be incorporated between the affinity element and the peptide to relieve steric restraints between the affinity tag and a cyclic peptide bound to a target molecule. A spacer which may be used with affinity tagged lysine is NHS-LC-biotin (Pierce Checmical CO., Rockford Ill.), although other spacers as are known in the art also may be used.

Examples of spacers which can be used with affinity tagged cysteines include cysteine reacted with iodoacetamido-biotin, biotin-hexyl-3'-(2'-pyridyldithio) propionamide (a 29 Å spacer from Pierce Chemical), iodoacetyl-LC-biotin (27 Å spacer) or biotin-BMCC with a 32 Å spacer (Pierce Chemical). An example of a spacer used with affinity tagged cysteine is shown in Structure 1:

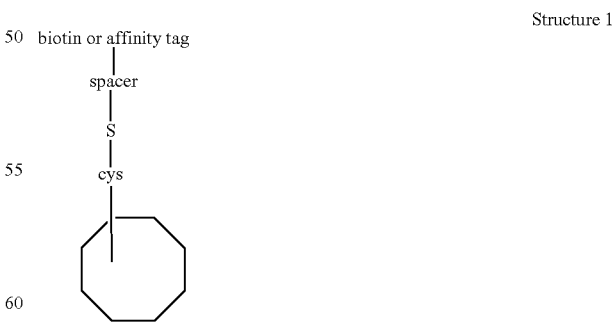

Structure 1

Alternatively, as part of the solid phase synthesis of the peptide, affinity tags may be synthesized branching off from the cysteine or lysine. In this case, the spacer consists of a defined number (i.e. n) of amino acids branching off the side chain of the cysteine or lysine or another residue of the cyclic peptide. Preferably, n=1 to 40. This allows for spacers of variable length, ranging from 3 Å to 100 Å or more. Gycines, because of their flexibility, are preferred because a sterically bulky target molecules bound to the cyclic peptide can be accommodated. The affinity tag is inserted at the end of the side chain as illustrated in Structure 2:

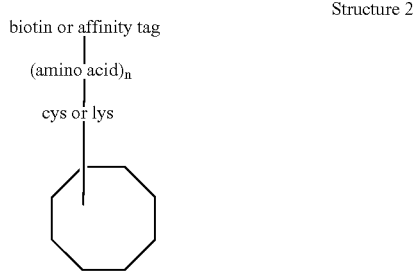

Structure 2

In a preferred embodiment, the spacer is at least one protein diameter long (20–40 Å). When the interacting target molecule is part of a large complex, the spacer is up to at least two protein diameters (40–80 Å).

Once primary target molecules have been identified, secondary target molecules may be identified in the same manner, using the primary target as the "bait". In this manner, signaling pathways may be elucidated. Similarly, bioactive peptides specific for secondary target molecules may also be discovered, to allow a number of bioactive peptides to act on a single pathway, for example for combination therapies.

The screening methods of the present invention may be useful to screen a large number of cell types under a wide variety of conditions. Generally, the host cells are cells that are involved in disease states, and they are tested or screened under conditions that normally result in undesirable consequences on the cells. When a suitable bioactive peptide is found, the undesirable effect may be reduced or eliminated. Alternatively, normally desirable consequences may be reduced or eliminated, with an eye towards elucidating the cellular mechanisms associated with the disease state or signalling pathway.

In a preferred embodiment, the present methods are useful in cancer applications. The ability to rapidly and specifically kill tumor cells is a cornerstone of cancer chemotherapy. In general, using the methods of the present invention, random libraries can be introduced into any tumor cell (primary or cultured), and peptides identified which by themselves induce apoptosis, cell death, loss of cell division or decreased cell growth. This may be done de novo, or by biased randomization toward known peptide agents, such as angiostatin, which inhibits blood vessel wall growth. Alternatively, the methods of the present invention can be combined with other cancer therapeutics (e.g. drugs or radiation) to sensitize the cells and thus induce rapid and specific apoptosis, cell death, loss of cell division or decreased cell growth after exposure to a secondary agent. Similarly, the present methods may be used in conjunction with known cancer therapeutics to screen for agonists to make the therapeutic more effective or less toxic. This is particularly preferred when the chemotherapeutic is very expensive to produce such as taxol.

Known oncogenes such as v-Abl, v-Src, v-Ras, and others, induce a transformed phenotype leading to abnormal cell growth when transfected into certain cells. This is also a major problem with micro-metastases. Thus, in a preferred embodiment, non-transformed cells can be transfected with these oncogenes, and then random libraries introduced into these cells, to select for bioactive peptides which reverse or correct the transformed state. One of the signal features of oncogene transformation of cells is the loss of contact inhibition and the ability to grow in soft-agar. When transforming viruses are constructed containing v-Abl, v-Src, or v-Ras in IRES-puro retroviral vectors, infected into target 3T3 cells, and subjected to puromycin selection, all of the 3T3 cells hyper-transform and detach from the plate. The cells may be removed by washing with fresh medium. This can serve as the basis of a screen, since cells which express a bioactive peptide will remain attached to the plate and form colonies.

Similarly, the growth and/or spread of certain tumor types is enhanced by stimulatory responses from growth factors and cytokines (PDGF, EGF, Heregulin, and others) which bind to receptors on the surfaces of specific tumors. In a preferred embodiment, the methods of the invention are used to inhibit or stop tumor growth and/or spread, by finding bioactive peptides capable of blocking the ability of the growth factor or cytokine to stimulate the tumor cell. The introduction of random libraries into specific tumor cells with the addition of the growth factor or cytokine, followed by selection of bioactive peptides which block the binding, signaling, phenotypic and/or functional responses of these tumor cells to the growth factor or cytokine in question.

Similarly, the spread of cancer cells (invasion and metastasis) is a significant problem limiting the success of cancer therapies. The ability to inhibit the invasion and/or migration of specific tumor cells would be a significant advance in the therapy of cancer. Tumor cells known to have a high metastatic potential (for example, melanoma, lung cell carcinoma, breast and ovarian carcinoma) can have random libraries introduced into them, and peptides selected which in a migration or invasion assay, inhibit the migration and/or invasion of specific tumor cells. Particular applications for inhibition of the metastatic phenotype, which could allow a more specific inhibition of metastasis, include the metastasis suppressor gene NM23, which codes for a dinucleoside diphosphate kinase. Thus intracellular peptide activators of this gene could block metastasis, and a screen for its upregulation (by fusing it to a reporter gene) would be of interest. Many oncogenes also enhance metastasis. Peptides which inactivate or counteract mutated RAS oncogenes, v-MOS, v-RAF, A-RAF, v-SRC, v-FES, and v-FMS would also act as anti-metastatics. Peptides which act intracellularly to block the release of combinations of proteases required for invasion, such as the matrix metalloproteases and urokinase, could also be effective antimetastatics.

In a preferred embodiment, the random libraries of the present invention are introduced into tumor cells known to have inactivated tumor suppressor genes, and successful reversal by either reactivation or compensation of the knockout would be screened by restoration of the normal phenotype. A major example is the reversal of p53-inactivating mutations, which are present in 50% or more of all cancers. Since p53's actions are complex and involve its action as a transcription factor, there are probably numerous potential ways a peptide or small molecule derived from a peptide could reverse the mutation. One example would be upregulation of the immediately downstream cyclin-dependent kinase p21 CIP1/WAF1. To be useful such reversal would have to work for many of the different known p53 mutations. This is currently being approached by gene therapy; one or more small molecules which do this might be preferable.

Another example involves screening of bioactive peptides which restore the constitutive function of the brca-1 or brca-2 genes, and other tumor suppressor genes important in breast cancer such as the adenomatous polyposis *coli* gene (APC) and the *Drosophila* discs-large gene (Dig), which are components of cell-cell junctions. Mutations of brca-1 are important in hereditary ovarian and breast cancers, and constitute an additional application of the present invention.

In a preferred embodiment, the methods of the present invention are used to create novel cell lines from cancers from patients. A retrovirally delivered short peptide which inhibits the final common pathway of programmed cell death should allow for short- and possibly long-term cell lines to be established. Conditions of in vitro culture and infection of human leukemia cells will be established. There is a real need for methods which allow the maintenance of certain tumor cells in culture long enough to allow for physiological and pharmacological studies. Currently, some human cell lines have been established by the use of transforming agents such as Epstein-Barr virus that considerably alters the existing physiology of the cell. On occasion, cells will grow on their own in culture but this is a random event. Programmed cell death (apoptosis) occurs via complex signaling pathways within cells that ultimately activate a final common pathway producing characteristic changes in the cell leading to a non-inflammatory destruction of the cell. It is well known that tumor cells have a high apoptotic index, or propensity to enter apoptosis in vivo. When cells are placed in culture, the in vivo stimuli for malignant cell growth are removed and cells readily undergo apoptosis. The objective would be to develop the technology to establish cell lines from any number of primary tumor cells, for example primary human leukemia cells, in a reproducible manner without altering the native configuration of the signaling pathways in these cells. By introducing nucleic acids encoding peptides which inhibit apoptosis, increased cell survival in vitro, and hence the opportunity to study signalling transduction pathways in primary human tumor cells, is accomplished. In addition, these methods may be used for culturing primary cells, i.e. non-tumor cells.

In a preferred embodiment, the present methods are useful in cardiovascular applications. In a preferred embodiment, cardiomyocytes may be screened for the prevention of cell damage or death in the presence of normally injurious conditions, including, but not limited to, the presence of toxic drugs (particularly chemotherapeutic drugs), for example, to prevent heart failure following treatment with adriamycin; anoxia, for example in the setting of coronary artery occlusion; and autoimmune cellular damage by attack from activated lymphoid cells (for example as seen in post viral myocarditis and lupus). Candidate bioactive peptides are inserted into cardiomyocytes, the cells are subjected to the insult, and bioactive peptides are selected that prevent any or all of: apoptosis; membrane depolarization (i.e. decrease arrythmogenic potential of insult); cell swelling; or leakage of specific intracellular ions, second messengers and activating molecules (for example, arachidonic acid and/or lysophosphatidic acid).

In a preferred embodiment, the present methods are used to screen for diminished arrhythmia potential in cardiomyocytes. The screens comprise the introduction of the candidate nucleic acids encoding candidate bioactive peptides, followed by the application of arrythmogenic insults, with screening for bioactive peptides that block specific depolarization of cell membrane. This may be detected using patch clamps, or via fluorescence techniques). Similarly, channel activity (for example, potassium and chloride channels) in cardiomyocytes could be regulated using the present methods in order to enhance contractility and prevent or diminish arrhythmias.

In a preferred embodiment, the present methods are used to screen for enhanced contractile properties of cardiomyocytes and diminish heart failure potential. The introduction of the libraries of the invention followed by measuring the rate of change of myosin polymerization/depolymerization using fluorescent techniques can be done. Bioactive peptides which increase the rate of change of this phenomenon can result in a greater contractile response of the entire myocardium, similar to the effect seen with digitalis.

In a preferred embodiment, the present methods are useful to identify agents that will regulate the intracellular and sarcolemmal calcium cycling in cardiomyocytes in order to prevent arrhythmias.

Bioactive peptides are selected that regulate sodium-calcium exchange, sodium proton pump function, and regulation of calcium-ATPase activity.

In a preferred embodiment, the present methods are useful to identify agents that diminish embolic phenomena in arteries and arterioles leading to strokes (and other occlusive events leading to kidney failure and limb ischemia) and angina precipitating a myocardial infarct are selected. For example, bioactive peptides which will diminish the adhesion of platelets and leukocytes, and thus diminish the occlusion events. Adhesion in this setting can be inhibited by the libraries of the invention being inserted into endothelial cells (quiescent cells, or activated by cytokines, i.e. IL-1, and growth factors, i.e. PDGF/EGF) and then screening for peptides that either: 1) down regulate adhesion molecule expression on the surface of the endothelial cells (binding assay); 2) block adhesion molecule activation on the surface of these cells (signaling assay); or 3) release in an autocrine manner peptides that block receptor binding to the cognate receptor on the adhering cell.

Embolic phenomena can also be addressed by activating proteolytic enzymes on the cell surfaces of endothelial cells, and thus releasing active enzyme which can digest blood clots. Thus, delivery of the libraries of the invention to endothelial cells is done, followed by standard fluorogenic assays, which will allow monitoring of proteolytic activity on the cell surface towards a known substrate. Bioactive peptides can then be selected which activate specific enzymes towards specific substrates.

In a preferred embodiment, arterial inflammation in the setting of vasculitis and post-infarction can be regulated by decreasing the chemotactic responses of leukocytes and mononuclear leukocytes. This can be accomplished by blocking chemotactic receptors and their responding pathways on these cells. Candidate bioactive libraries can be inserted into these cells, and the chemotactic response to diverse chemokines (for example, to the IL-8 family of chemokines, RANTES) inhibited in cell migration assays.

In a preferred embodiment, arterial restenosis following coronary angioplasty can be controlled by regulating the proliferation of vascular intimal cells and capillary and/or arterial endothelial cells. Candidate bioactive peptide libraries can be inserted into these cell types and their proliferation in response to specific stimuli monitored. One application may be intracellular peptides which block the expression or function of c-myc and other oncogenes in smooth muscle cells to stop their proliferation. A second application may involve the expression of libraries in vascular smooth muscle cells to selectively induce their apoptosis. Application of small molecules derived from these peptides may require targeted drug delivery; this is available with stents, hydrogel coatings, and infusion-based catheter systems. Peptides which downregulate endothelin-1A receptors or which block the release of the potent vasoconstrictor and vascular smooth muscle cell mitogen endothelin-1 may also be candidates for therapeutics. Peptides can be isolated from these libraries which inhibit growth of these cells, or which prevent the adhesion of other cells in the circulation known to release autocrine growth factors, such as platelets (PDGF) and mononuclear leukocytes.

The control of capillary and blood vessel growth is an important goal in order to promote increased blood flow to ischemic areas (growth), or to cut-off the blood supply (angiogenesis inhibition) of tumors. Candidate bioactive peptide libraries can be inserted into capillary endothelial cells and their growth monitored. Stimuli such as low oxygen tension and varying degrees of angiogenic factors can regulate the responses, and peptides isolated that produce the appropriate phenotype. Screening for antagonism of vascular endothelial cell growth factor, important in angiogenesis, would also be useful.

In a preferred embodiment, the present methods are useful in screening for decreases in atherosclerosis producing mechanisms to find peptides that regulate LDL and HDL metabolism. Candidate libraries can be inserted into the appropriate cells (including hepatocytes, mononuclear leukocytes, endothelial cells) and peptides selected which lead to a decreased release of LDL or diminished synthesis of LDL, or conversely to an increased release of HDL or enhanced synthesis of HDL. Bioactive peptides can also be isolated from candidate libraries which decrease the production of oxidized LDL, which has been implicated in atherosclerosis and isolated from atherosclerotic lesions. This could occur by decreasing its expression, activating reducing systems or enzymes, or blocking the activity or production of enzymes implicated in production of oxidized LDL, such as 15-lipoxygenase in macrophages.

In a preferred embodiment, the present methods are used in screens to regulate obesity via the control of food intake mechanisms or diminishing the responses of receptor signaling pathways that regulate metabolism. Bioactive peptides that regulate or inhibit the responses of neuropeptide Y (NPY), cholecystokinin and galanin receptors, are particularly desirable. Candidate libraries can be inserted into cells that have these receptors cloned into them, and inhibitory peptides selected that are secreted in an autocrine manner that block the signaling responses to galanin and NPY. In a similar manner, peptides can be found that regulate the leptin receptor.

In a preferred embodiment, the present methods are useful in neurobiology applications. Candidate libraries may be used for screening for anti-apoptotics for preservation of neuronal function and prevention of neuronal death. Initial screens would be done in cell culture. One application would include prevention of neuronal death, by apoptosis, in cerebral ischemia resulting from stroke. Apoptosis is known to be blocked by neuronal apoptosis inhibitory protein (NAIP); screens for its upregulation, or effecting any coupled step could yield peptides which selectively block neuronal apoptosis. Other applications include neurodegenerative diseases such as Alzheimer's disease and Huntington's disease.

In a preferred embodiment, the present methods are useful in bone biology applications. Osteoclasts are known to play a key role in bone remodeling by breaking down "old" bone, so that osteoblasts can lay down "new" bone. In osteoporosis one has an imbalance of this process. Osteoclast overactivity can be regulated by inserting candidate libraries into these cells, and then looking for bioactive peptides that produce:

1) a diminished processing of collagen by these cells; 2) decreased pit formation on bone chips; and 3) decreased release of calcium from bone fragments.

The present methods may also be used to screen for agonists of bone morphogenic proteins, hormone mimetics to stimulate, regulate, or enhance new bone formation (in a manner similar to parathyroid hormone and calcitonin, for example). These have use in osteoporosis, for poorly healing fractures, and to accelerate the rate of healing of new fractures. Furthermore, cell lines of connective tissue origin can be treated with candidate libraries and screened for their growth, proliferation, collagen stimulating activity, and/or proline incorporating ability on the target osteoblasts. Alternatively, candidate libraries can be expressed directly in osteoblasts or chondrocytes and screened for increased production of collagen or bone.

In a preferred embodiment, the present methods are useful in skin biology applications. Keratinocyte responses to a variety of stimuli may result in psoriasis, a proliferative change in these cells. Candidate libraries can be inserted into cells removed from active psoriatic plaques, and bioactive peptides isolated which decrease the rate of growth of these cells.

In a preferred embodiment, the present methods are useful in the regulation or inhibition of keloid formation (i.e. excessive scarring). Candidate libraries inserted into skin connective tissue cells isolated from individuals with this condition, and bioactive peptides isolated that decrease proliferation, collagen formation, or proline incorporation. Results from this work can be extended to treat the excessive scarring that also occurs in burn patients. If a common peptide motif is found in the context of the keloid work, then it can be used widely in a topical manner to diminish scarring post burn.

Similarly, wound healing for diabetic ulcers and other chronic "failure to heal" conditions in the skin and extremities can be regulated by providing additional growth signals to cells which populate the skin and dermal layers. Growth factor mimetics may in fact be very useful for this condition. Candidate libraries can be inserted into skin connective tissue cells, and bioactive peptides isolated which promote the growth of these cells under "harsh" conditions, such as low oxygen tension, low pH, and the presence of inflammatory mediators.

Cosmeceutical applications of the present invention include the control of melanin production in skin melanocytes. A naturally occurring peptide, arbutin, is a tyrosine hydroxylase inhibitor, a key enzyme in the synthesis of melanin. Candidate libraries can be inserted into melanocytes and known stimuli that increase the synthesis of melanin applied to the cells. Bioactive peptides can be isolated that inhibit the synthesis of melanin under these conditions.

In a preferred embodiment, the present methods are useful in endocrinology applications. The retroviral peptide library technology can be applied broadly to any endocrine, growth factor, cytokine or chemokine network which involves a signaling peptide or protein that acts in either an endocrine, paracrine or autocrine manner that binds or dimerizes a receptor and activates a signaling cascade that results in a known phenotypic or functional outcome. The methods are applied so as to isolate a peptide which either mimics the desired hormone (i.e., insulin, leptin, calcitonin, PDGF, EGF, EPO, GMCSF, IL1-17, mimetics) or inhibits its action by either blocking the release of the hormone, blocking its binding to a specific receptor or carrier protein (for example, CRF binding protein), or inhibiting the intracellular responses of the specific target cells to that hormone. Selection of peptides which increase the expression or release of hormones from the cells which normally produce them could have broad applications to conditions of hormonal deficiency.

In a preferred embodiment, the present methods are useful in infectious disease applications. Viral latency (herpes viruses such as CMV, EBV, HBV, and other viruses such as HIV) and their reactivation are a significant problem, particularly in immunosuppressed patients (patients with AIDS and transplant patients). The ability to block the reactivation and spread of these viruses is an important goal. Cell lines known to harbor or be susceptible to latent viral infection can be infected with the specific virus, and then stimuli applied to these cells which have been shown to lead to reactivation and viral replication. This can be followed by measuring viral titers in the medium and scoring cells for phenotypic changes. Candidate libraries can then be inserted into these cells under the above conditions, and peptides isolated which block or diminish the growth and/or release of the virus. As with chemotherapeutics, these experiments can also be done with drugs which are only partially effective towards this outcome, and bioactive peptides isolated which enhance the virucidal effect of these drugs. Bioactive peptides may also be tested for the ability to block some aspect of viral assembly, viral replication, entry or infectious cycle.

One example of many is the ability to block HIV-1 infection. HIV-1 requires CD4 and a co-receptor which can be one of several seven transmembrane G-protein coupled receptors. In the case of the infection of macrophages, CCR-5 is the required co-receptor, and there is strong evidence that a block on CCR-5 will result in resistance to HIV-1 infection. There are two lines of evidence for this statement. First, it is known that the natural ligands for CCR-5, the CC chemokines RANTES, MIP1a and MIP1b are responsible for CD8+ mediated resistance to HIV. Second, individuals homozygous for a mutant allele of CCR-5 are completely resistant to HIV infection. Thus, an inhibitor of the CCR-5/HIV interaction would be of enormous interest to both biologists and clinicians. The extracellular anchored constructs offer superb tools for such a discovery. Into the transmembrane, epitope tagged, glycine-serine tethered constructs (ssTM V G20 E TM), one can place a random, cyclized peptide library of the general sequence CNNNNNNNNNNC or C—(X)$_n$—C. Then one infects a cell line that expresses CCR-5 with retroviruses containing this library. Using an antibody to CCR-5 one can use FACS to sort desired cells based on the binding of this antibody to the receptor. All cells which do not bind the antibody will be assumed contain inhibitors of this antibody binding site. These inhibitors, in the retroviral construct can be further assayed for their ability to inhibit HIV-1 entry.

Viruses are known to enter cells using specific receptors to bind to cells (for example, HIV uses CD4, coronavirus uses CD13, murine leukemia virus uses transport protein, and measles virus uses CD44) and to fuse with cells (HIV uses chemokine receptor). Candidate libraries can be inserted into target cells known to be permissive to these viruses, and bioactive peptides isolated which block the ability of these viruses to bind and fuse with specific target cells.

Intein libraries may also be used to screen for cyclic peptides which block HIV-1 infection. For example, inteins can be designed such that cyclized peptides are secreted from cells where they can bind to CCR5 and antagonize HIV-1 binding.

In a preferred embodiment, the present invention finds use with infectious organisms. Intracellular organisms such as mycobacteria, *listeria, salmonella, pneumocystis, yersinia, leishmania, T. cruzi*, can persist and replicate within cells, and become active in immunosuppressed patients. There are currently drugs on the market and in development which are either only partially effective or ineffective against these organisms. Candidate libraries can be inserted into specific cells infected with these organisms (pre- or post-infection), and bioactive peptides selected which promote the intracellular destruction of these organisms in a manner analogous to intracellular "antibiotic peptides" similar to magainins. In addition peptides can be selected which enhance the cidal properties of drugs already under investigation which have insufficient potency by themselves, but when combined with a specific peptide from a candidate library, are dramatically more potent through a synergistic mechanism. Finally, bioactive peptides can be isolated which alter the metabolism of these intracellular organisms, in such a way as to terminate their intracellular life cycle by inhibiting a key organismal event.

Antibiotic drugs that are widely used have certain dose dependent, tissue specific toxicities. For example renal toxicity is seen with the use of gentamicin, tobramycin, and amphotericin; hepatotoxicity is seen with the use of INH and rifampin; bone marrow toxicity is seen with chloramphenicol; and platelet toxicity is seen with ticarcillin, etc. These toxicities limit their use. Candidate libraries can be introduced into the specific cell types where specific changes leading to cellular damage or apoptosis by the antibiotics are produced, and bioactive peptides can be isolated that confer protection, when these cells are treated with these specific antibiotics.

Furthermore, the present invention finds use in screening for bioactive peptides that block antibiotic transport mechanisms. The rapid secretion from the blood stream of certain antibiotics limits their usefulness. For example penicillins are rapidly secreted by certain transport mechanisms in the kidney and choroid plexus in the brain. Probenecid is known to block this transport and increase serum and tissue levels. Candidate agents can be inserted into specific cells derived from kidney cells and cells of the choroid plexus known to have active transport mechanisms for antibiotics. Bioactive peptides can then be isolated which block the active transport of specific antibiotics and thus extend the serum halflife of these drugs.

In a preferred embodiment, the present methods are useful in drug toxicities and drug resistance applications. Drug toxicity is a significant clinical problem. This may manifest itself as specific tissue or cell damage with the result that the drug's effectiveness is limited. Examples include myeloablation in high dose cancer chemotherapy, damage to epithelial cells lining the airway and gut, and hair loss. Specific examples include adriamycin induced cardiomyocyte death, cisplatinin-induced kidney toxicity, vincristine-induced gut motility disorders, and cyclosporin-induced kidney damage. Candidate libraries can be introduced into specific cell types with characteristic drug-induced phenotypic or functional responses, in the presence of the drugs, and agents isolated which reverse or protect the specific cell type against the toxic changes when exposed to the drug. These effects may manifest as blocking the drug induced apoptosis of the cell of interest, thus initial screens will be for survival of the cells in the presence of high levels of drugs or combinations of drugs used in combination chemotherapy.

Drug toxicity may be due to a specific metabolite produced in the liver or kidney which is highly toxic to specific cells, or due to drug interactions in the liver which block or enhance the metabolism of an administered drug. Candidate libraries can be introduced into liver or kidney cells following the exposure of these cells to the drug known to produce the toxic metabolite. Bioactive peptides can be isolated which alter how the liver or kidney cells metabolize the drug, and specific agents identified which prevent the generation of a specific toxic metabolite. The generation of the metabolite can be followed by mass spectrometry, and phenotypic changes can be assessed by microscopy. Such a screen can also be done in cultured hepatocytes, cocultured with readout cells which are specifically sensitive to the toxic metabolite. Applications include reversible (to limit toxicity) inhibitors of enzymes involved in drug metabolism.

Multiple drug resistance, and hence tumor cell selection, outgrowth, and relapse, leads to morbidity and mortality in cancer patients. Candidate libraries can be introduced into tumor cell lines (primary and cultured) that have demonstrated specific or multiple drug resistance. Bioactive peptides can then be identified which confer drug sensitivity when the cells are exposed to the drug of interest, or to drugs used in combination chemotherapy. The readout can be the onset of apoptosis in these cells, membrane permeability changes, the release of intracellular ions and fluorescent markers. The cells in which multidrug resistance involves membrane transporters can be preloaded with fluorescent transporter substrates, and selection carried out for peptides which block the normal efflux of fluorescent drug from these cells. Candidate libraries are particularly suited to screening for peptides which reverse poorly characterized or recently discovered intracellular mechanisms of resistance or mechanisms for which few or no chemosensitizers currently exist, such as mechanisms involving LRP (lung resistance protein). This protein has been implicated in multidrug resistance in ovarian carcinoma, metastatic malignant melanoma, and acute myeloid leukemia. Particularly interesting examples include screening for agents which reverse more than one important resistance mechanism in a single cell, which occurs in a subset of the most drug resistant cells, which are also important targets. Applications would include screening for peptide inhibitors of both MRP (multidrug resistance related protein) and LRP for treatment of resistant cells in metastatic melanoma, for inhibitors of both p-glycoprotein and LRP in acute myeloid leukemia, and for inhibition (by any mechanism) of all three proteins for treating pan-resistant cells.

In a preferred embodiment, the present methods are useful in improving the performance of existing or developmental drugs. First pass metabolism of orally administered drugs limits their oral bioavailability, and can result in diminished efficacy as well as the need to administer more drug for a desired effect. Reversible inhibitors of enzymes involved in first pass metabolism may thus be a useful adjunct enhancing the efficacy of these drugs. First pass metabolism occurs in the liver, thus inhibitors of the corresponding catabolic enzymes may enhance the effect of the cognate drugs. Reversible inhibitors would be delivered at the same time as, or slightly before, the drug of interest. Screening of candidate libraries in hepatocytes for inhibitors (by any mechanism, such as protein downregulation as well as a direct inhibition of activity) of particularly problematical isozymes would be of interest. These include the CYP3A4 isozymes of cytochrome P450, which are involved in the first pass metabolism of the anti-HIV drugs saquinavir and indinavir. Other applications could include reversible inhibitors of UDP-glucuronyltransferases, sulfotransferases, N-acetyltransferases, epoxide hydrolases, and glutathione S-transferases, depending on the drug. Screens would be done in cultured hepatocytes or liver microsomes, and could involve antibodies recognizing the specific modification performed in the liver, or co-cultured readout cells, if the metabolite had a different bioactivity than the untransformed drug. The enzymes modifying the drug would not necessarily have to be known, if screening was for lack of alteration of the drug.

In a preferred embodiment, the present methods are useful in immunobiology, inflammation, and allergic response applications. Selective regulation of T lymphocyte responses is a desired goal in order to modulate immune-mediated diseases in a specific manner. Candidate libraries can be introduced into specific T cell subsets (TH1, TH2, CD4+, CD8+, and others) and the responses which characterize those subsets (cytokine generation, cytotoxicity, proliferation in response to antigen being presented by a mononuclear leukocyte, and others) modified by members of the library. Agents can be selected which increase or diminish the known T cell subset physiologic response. This approach will be useful in any number of conditions, including: 1) autoimmune diseases where one wants to induce a tolerant state (select a peptide that inhibits T cell subset from recognizing a self-antigen bearing cell); 2) allergic diseases where one wants to decrease the stimulation of IgE producing cells (select peptide which blocks release from T cell subsets of specific B-cell stimulating cytokines which induce switch to IgE production); 3) in transplant patients where one wants to induce selective immunosuppression (select peptide that diminishes proliferative responses of host T cells to foreign antigens); 4) in lymphoproliferative states where one wants to inhibit the growth or sensitize a specific T cell tumor to chemotherapy and/or radiation; 5) in tumor surveillance where one wants to inhibit the killing of cytotoxic T cells by Fas ligand bearing tumor cells; and 5) in T cell mediated inflammatory diseases such as Rheumatoid arthritis, Connective tissue diseases (SLE), Multiple sclerosis, and inflammatory bowel disease, where one wants to inhibit the proliferation of disease-causing T cells (promote their selective apoptosis) and the resulting selective destruction of target tissues (cartilage, connective tissue, oligodendrocytes, gut endothelial cells, respectively).

Regulation of B cell responses will permit a more selective modulation of the type and amount of immunoglobulin made and secreted by specific B cell subsets. Candidate libraries can be inserted into B cells and bioactive peptides selected which inhibit the release and synthesis of a specific immunoglobulin. This may be useful in autoimmune diseases characterized by the overproduction of auto antibodies and the production of allergy causing antibodies, such as IgE. Agents can also be identified which inhibit or enhance the binding of a specific immunoglobulin subclass to a specific antigen either foreign of self. Finally, agents can be selected which inhibit the binding of a specific immunoglobulin subclass to its receptor on specific cell types.

Similarly, agents which affect cytokine production may be selected, generally using two cell systems. For example, cytokine production from macrophages, monocytes, etc. may be evaluated. Similarly, agents which mimic cytokines, for example erythropoetin and IL1-17, may be selected, or agents that bind cytokines such as TNF-α, before they bind their receptor.

Antigen processing by mononuclear leukocytes (ML) is an important early step in the immune system's ability to recognize and eliminate foreign proteins. Candidate agents can be inserted into ML cell lines and agents selected which alter the intracellular processing of foreign peptides and sequence of the foreign peptide that is presented to T cells by MLs on their cell surface in the context of Class II MHC. One can look for members of the library that enhance immune responses of a particular T cell subset (for example, the peptide would in fact work as a vaccine), or look for a library member that binds more tightly to MHC, thus displacing naturally occurring peptides, but nonetheless the agent would be less immunogenic (less stimulatory to a specific T cell clone). This agent would in fact induce immune tolerance and/or diminish immune responses to foreign proteins. This approach could be used in transplantation, autoimmune diseases, and allergic diseases.

The release of inflammatory mediators (cytokines, leukotrienes, prostaglandins, platelet activating factor, histamine, neuropeptides, and other peptide and lipid mediators) is a key element in maintaining and amplifying aberrant immune responses. Candidate libraries can be inserted into MLs, mast cells, eosinophils, and other cells participating in a specific inflammatory response, and bioactive peptides selected which inhibit the synthesis, release and binding to the cognate receptor of each of these types of mediators.

In a preferred embodiment, the present methods are useful in biotechnology applications. Candidate library expression in mammalian cells can also be considered for other pharmaceutical-related applications, such as modification of protein expression, protein folding, or protein secretion. One such example would be in commercial production of protein pharmaceuticals in CHO or other cells. Candidate libraries resulting in bioactive peptides which select for an increased cell growth rate (perhaps peptides mimicking growth factors or acting as agonists of growth factor signal transduction pathways), for pathogen resistance (see previous section), for lack of sialylation or glycosylation (by blocking glycotransferases or rerouting trafficking of the protein in the cell), for allowing growth on autoclaved media, or for growth in serum free media, would all increase productivity and decrease costs in the production of protein pharmaceuticals.

Random peptides displayed on the surface of circulating cells can be used as tools to identify organ, tissue, and cell specific peptide targeting sequences. Any cell introduced into the bloodstream of an animal expressing a library targeted to the cell surface can be selected for specific organ and tissue targeting. The bioactive peptide sequence identified can then be coupled to an antibody, enzyme, drug, imaging agent or substance for which organ targeting is desired.

Other agents which may be selected using the present invention include: 1) agents which block the activity of transcription factors, using cell lines with reporter genes; 2) agents which block the interaction of two known proteins in cells, using the absence of normal cellular functions, the mammalian two hybrid system or fluorescence resonance energy transfer mechanisms for detection; and 3) agents may be identified by tethering a random peptide to a protein binding region to allow interactions with molecules sterically close, i.e. within a signalling pathway, to localize the effects to a functional area of interest.

In a preferred embodiment, the bioactive peptide may also be used in gene therapy. In gene therapy applications, genes encoding the peptide are introduced into cells in order to achieve in vivo synthesis of a therapeutically effective genetic product. "Gene therapy" includes both conventional gene therapy where a lasting effect is achieved by a single treatment, and the administration of gene therapeutic agents, which involves the one time or repeated administration of a therapeutically effective DNA or mRNA.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection [Dzau et al., Trends in Biotechnology 11:205–210 (1993)]. In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262:4429–4432 (1987); and Wagner et al., Proc. Natl. Acad. Sci. U.S.A. 87:3410–3414 (1990). For review of gene marking and gene therapy protocols see Anderson et al., Science 256:808–813 (1992).

Alternatively, an ex vivo approach can be used in which a cell excreting a therapeutically effective peptide may be transplanted into an individual, for the constant or regulated systemic delivery of the peptide.

The pharmaceutical compositions of the present invention comprise a compound in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The compounds can be formulated using pharmaceutically acceptable carriers into dosages suitable for oral administration. Such carriers enable the compounds of the invention to be formulated as tablets, pills, capsules, liquids, gels, syrups, slurries, and the like for oral ingestion.

The administration of the bioactive peptides of the present invention, preferably in the form of a sterile aqueous solution, can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds, inflammation, etc., the peptide may be directly applied as a solution or spray. Depending upon the manner of introduction, the pharmaceutical composition may be formulated in a variety of ways. The concentration of the therapeutically active peptide in the formulation may vary from about 0.1 to 100 weight %.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Isolation of Inteins with Altered Cyclization Activity

A fluorescent reporter system was designed for quantifying intein cyclization. GFP was split at the loop 3 junction and the translational order of the N and C-terminal fragments were reversed (FIG. 12A). The termini were held together by a glycine-serine linker. In some constructs, one-half of the myc epitope was fused onto either side of the loop 3 junction (FIG. 12A). The resulting GFP molecules were positioned with an intein scaffold comprising either wild-type or a mutant intein (FIG. 12C).

Mutant intein sequences obtained using PCR mutagenesis were screened for activity by FACS sorting for increases in fluorescence. Western blot analysis of several other mutants is shown in FIG. 13. In FIG. 13, several of the mutants had cyclization efficiencies greater than the parental starting intein, J3.

Example 2

Biasing a Cyclic Peptide to Reduce the Number of Conformers

To test the effects of a fixed proline in a cyclic 7mer, the conformation space of the 7mer cyclic peptide RGDGWS (SEQ ID NO:57), containing two flexible glycines was compared with that of cyclic RGPGWS (SEQ ID NO:59) using quenched molecular dynamics calculations (O'Connor, et al., (1992) J. Med. Chem., 35:2870–81; Mackay, et al., (1989) "The role of energy minimization in simulation strategies of biomolecular systems", In Prediction of Protein Structure and the Principles of Protein Conformation, Fasman, G., ed., New York, Plenum Press, pp. 317–358.

The lowest 5 kcal energy conformers were collected from a total of at least 10,000 individual conformers obtained from multiple molecular dynamics trajectories, and compared with each other using the backbone amino acids by overlaying the structures and calculating the root mean square deviation of these atoms in the best fit overlay using InsightII (Molecular Simulations Inc.).

An example of the cluster graph of the lowest energy conformers for each peptide is shown in FIGS. 16 and 17. The root mean square deviation (RMSD, Å) is coded by color, with very similar conformers (RMSD<Å) in yellow, still highly similar conformers (RMSD between 1–2 Å) in white, similar conformers (RMSD between 2–3 Å) in blue, less similar conformers (RMSD between 3–4 Å) in red, and dissimilar conformers in black (not shown).

For the cyclic peptide SRGDGWS (SEQ ID NO:57), shown in FIG. 16 (srgdgwsLowest5A.ps), there were 62 low energy conformers. There was one family of very similar conformers (yellow square at bottom left) and two families of quite similar conformers in yellow/white, one roughly in the middle of the graph, and one (with only moderately similar conformers) near the top right corner. These comprised approximately 20 of the 62 conformers. The rest of the low energy conformers were not very similar to each other, and much of the graph is red or black. Backbone overlaid conformers from most similar family, No. 1, are shown at the lower left. In the lower middle, is family No. 2. These conformers, when overlaid are clearly not similar. Conformers in family No. 3 (lower right) are rather heterogeneous, although not as much as those from the red and black regions of the graph.

For the cyclic peptide SRGPGWS (SEQ ID NO:57), representing the substitution of Pro for Asp 4, the graph of the lowest energy conformers looks quite different (FIG. 17; srgpgwsLowest5B.ps). There is a much larger family of very similar conformers (lower left of graph, family No. 1, conformers 1–26). Family No. 2 also has very similar conformers, although they are all different from family No. 1. Even family No. 3, representing over two thirds of all low energy conformers (frames 1–59) contains conformers that are similar enough to give a blurred donut appearance. Thus, substitution of a single pro for another residue (asp in this case) clearly freezes out two additional families of conformers. As this peptide has two glycines, the effect of proline on conformational narrowing of cyclic peptides with 1 or 0 glycines may be more profound.

I claim:

1. A retroviral vector comprising a nucleotide sequence encoding a fusion polypeptide comprising, from N-terminus to C-terminus:
   a) a C-terminal domain of an intein;
   b) a random peptide;
   c) an N-terminal domain of an intein;
   wherein the amino acid sequence of said intein or a region thereof is obtained from *Synechocystis* and wherein said fusion protein is capable of undergoing a reaction to cyclize said peptide to produce a cyclic peptide in a mammalian cell.

2. The retroviral vector of claim 1, in which the encoded fusion polypeptide has altered splicing activity as compared to a wild-type *Synechocystis* intein.

3. The retroviral vector of claim 1, wherein said intein is a *Synechocystis* DnaB intein.

4. The retroviral vector of claim 1, wherein said intein is a *Synechocystis* DnaE intein.

5. The retroviral vector of claim 1, wherein said nucleotide sequence further encodes a reporter protein.

6. The retroviral vector of claim 5 in which the reporter protein is a fluorescent protein.

7. The retroviral vector of claim 6 in which the fluorescent protein is a green fluorescent protein, a blue fluorescent protein, a yellow fluorescent protein or a red fluorescent protein.

* * * * *